US009345831B2

(12) United States Patent
Raday et al.

(10) Patent No.: US 9,345,831 B2
(45) Date of Patent: May 24, 2016

(54) AUTOMATIC INJECTION DEVICE

(75) Inventors: Lior Raday, M.P. Hof Ashkelon (IL); David Daily, Herzilia (IL); Ehoud Carmel, Ganey Tikva (IL); Uriel Ronen, Tel Aviv (IL)

(73) Assignee: E3D AGRICULTURAL COOPERATIVE ASSOCIATION LTD, Merom Hagalil (IL)

( * ) Notice: Subject to any disclaimer, the term of this patent is extended or adjusted under 35 U.S.C. 154(b) by 106 days.

(21) Appl. No.: 12/446,168

(22) PCT Filed: Oct. 18, 2007

(86) PCT No.: PCT/IL2007/001258
§ 371 (c)(1),
(2), (4) Date: Aug. 24, 2009

(87) PCT Pub. No.: WO2008/047372
PCT Pub. Date: Apr. 24, 2008

(65) Prior Publication Data
US 2010/0036318 A1 Feb. 11, 2010

Related U.S. Application Data

(60) Provisional application No. 60/853,411, filed on Oct. 19, 2006.

(51) Int. Cl.
*A61M 5/20* (2006.01)
*A61M 5/50* (2006.01)
(Continued)

(52) U.S. Cl.
CPC ......... *A61M 5/2033* (2013.01); *A61M 5/31571* (2013.01); *A61M 5/50* (2013.01);
(Continued)

(58) Field of Classification Search
CPC . A61M 5/2033; A61M 5/1782; A61M 5/326; A61M 2005/3258; A61M 2005/206; A61M 2005/208; A61M 2005/2013; A61M 2005/2073
USPC ................................ 604/218, 192, 134–139
See application file for complete search history.

(56) References Cited

U.S. PATENT DOCUMENTS 4,333,457 A 6/1982 Margulies
4,592,742 A 6/1986 Landau
(Continued)

FOREIGN PATENT DOCUMENTS

CA 2 356 614 4/2000
EP 1 034 809 9/2000
(Continued)

OTHER PUBLICATIONS

A Supplementary European Search Report dated Mar. 15, 2010, which issued during the prosecution of Applicant's European Patent Application No. EP 04 77 0523.
(Continued)

*Primary Examiner* — Bhisma Mehta
*Assistant Examiner* — Jenna Zhang
(74) *Attorney, Agent, or Firm* — Sughrue Mion, PLLC

(57) ABSTRACT

An injection device for injecting a fluid into an object, the injection device including a plunger assembly for operative engagement with a syringe adapted to contain the fluid and permit ejection of the fluid therefrom via a syringe outlet, the plunger assembly being displaceable in a first direction which causes at least some of the fluid contained in the syringe to be ejected from the syringe via the syringe outlet and an inadvertent fluid ejection prevention assembly coupled to the plunger assembly for preventing ejection of fluid from the syringe in situations where the syringe outlet is neither in operative engagement with a vial adaptor suitable for providing fluid communication with the interior of a vial nor in fluid communication with an injection site within the object.

8 Claims, 178 Drawing Sheets

(51) Int. Cl.
*A61M 5/315* (2006.01)
*A61M 5/32* (2006.01)
*A61M 5/24* (2006.01)
*A61M 5/178* (2006.01)

(52) U.S. Cl.
CPC ............ *A61M 5/1782* (2013.01); *A61M 5/326* (2013.01); *A61M 2005/206* (2013.01); *A61M 2005/208* (2013.01); *A61M 2005/2013* (2013.01); *A61M 2005/2073* (2013.01); *A61M 2005/3258* (2013.01); *A61M 2205/27* (2013.01); *A61M 2205/276* (2013.01)

(56) References Cited

U.S. PATENT DOCUMENTS

| | | | |
|---|---|---|---|
| 4,623,332 | A | 11/1986 | Lindmayer et al. |
| 4,902,279 | A | 2/1990 | Schmidtz et al. |
| 4,998,918 | A | 3/1991 | Nimura |
| 5,092,842 | A | 3/1992 | Bechtold et al. |
| 5,137,516 | A | 8/1992 | Rand et al. |
| 5,215,536 | A | 6/1993 | Lampropoulos et al. |
| 5,267,963 | A | 12/1993 | Bachynsky |
| 5,295,965 | A | 3/1994 | Wilmot |
| 5,300,030 | A | 4/1994 | Crossman et al. |
| 5,320,609 | A | 6/1994 | Haber et al. |
| 5,478,316 | A | 12/1995 | Bitdinger et al. |
| 5,527,287 | A | 6/1996 | Miskinyar |
| 5,540,664 | A | 7/1996 | Wyrick |
| 5,584,815 | A | 12/1996 | Pawelka et al. |
| 5,599,309 | A | 2/1997 | Marshall et al. |
| 5,616,128 | A | 4/1997 | Meyer |
| 5,665,071 | A | 9/1997 | Wyrick |
| 5,681,291 | A | 10/1997 | Galli |
| 5,695,472 | A | 12/1997 | Wyrick |
| 5,779,677 | A | 7/1998 | Frezza |
| 5,823,998 | A | 10/1998 | Yamagata |
| 5,851,197 | A | 12/1998 | Marano |
| 5,957,897 | A | 9/1999 | Jeffrey |
| 5,975,355 | A * | 11/1999 | Cecala .............. A61M 5/31591 222/283 |
| 6,015,396 | A | 1/2000 | Buttgen et al. |
| 6,070,623 | A | 6/2000 | Aneas |
| 6,099,503 | A | 8/2000 | Stradella |
| 6,099,504 | A | 8/2000 | Gross et al. |
| 6,149,626 | A | 11/2000 | Bachynsky et al. |
| 6,159,181 | A | 12/2000 | Crossman et al. |
| 6,241,708 | B1 | 6/2001 | Reilly et al. |
| 6,270,479 | B1 | 8/2001 | Bergens et al. |
| 6,280,421 | B1 | 8/2001 | Kirchhofer et al. |
| 6,319,233 | B1 | 11/2001 | Jansen et al. |
| 6,364,865 | B1 | 4/2002 | Lavi et al. |
| 6,371,939 | B2 | 4/2002 | Bergents et al. |
| 6,387,078 | B1 | 5/2002 | Gillespie, III |
| 6,530,903 | B2 | 3/2003 | Wang et al. |
| 6,544,234 | B1 | 4/2003 | Gabriel |
| 6,565,553 | B2 | 5/2003 | Sadowski et al. |
| 6,572,590 | B1 | 6/2003 | Stevens et al. |
| 6,585,690 | B1 | 7/2003 | Hoeck et al. |
| 6,592,555 | B1 | 7/2003 | Wen-Pi et al. |
| 6,595,962 | B1 | 7/2003 | Perthu |
| 6,605,058 | B1 | 8/2003 | Wich |
| 6,605,067 | B1 | 8/2003 | Larsen |
| 6,607,508 | B2 * | 8/2003 | Knauer .................. A61M 5/204 604/131 |
| 6,613,019 | B2 | 9/2003 | Munk |
| 6,620,137 | B2 | 9/2003 | Kirchhofer et al. |
| 6,638,255 | B1 | 10/2003 | Weber |
| 6,673,049 | B2 | 1/2004 | Hommann et al. |
| 6,685,676 | B2 | 2/2004 | Jansen et al. |
| 6,971,999 | B2 | 12/2005 | Py et al. |
| 7,097,634 | B2 | 8/2006 | Gilbert |
| 7,128,728 | B2 | 10/2006 | Kirchhofer |
| 7,300,420 | B2 | 11/2007 | Doyle |
| 7,357,790 | B2 | 4/2008 | Hommann et al. |
| 7,357,791 | B2 | 4/2008 | Kirchhofer et al. |
| 7,442,185 | B2 | 10/2008 | Amark |
| 7,442,186 | B2 | 10/2008 | Blomquist |
| 7,476,217 | B2 | 1/2009 | Martin et al. |
| 7,569,035 | B1 | 8/2009 | Wilmot |
| 7,717,877 | B2 | 5/2010 | Lavi |
| 7,905,866 | B2 | 3/2011 | Haider |
| 7,931,625 | B2 | 4/2011 | Kirchhofer |
| 7,931,626 | B2 | 4/2011 | Kirchhofer |
| 7,976,499 | B2 | 7/2011 | Grunhut et al. |
| 2001/0037087 | A1 | 11/2001 | Knauer |
| 2002/0133122 | A1 | 9/2002 | Giambattista et al. |
| 2003/0040697 | A1 * | 2/2003 | Pass .................... A61M 5/1782 604/21 |
| 2003/0093036 | A1 | 5/2003 | Crossman et al. |
| 2003/0105430 | A1 * | 6/2003 | Lavi .................... A61M 5/2033 604/136 |
| 2007/0118081 | A1 | 5/2007 | Daily et al. |
| 2009/0204076 | A1 | 8/2009 | Liversidge |
| 2011/0098641 | A1 | 4/2011 | Haider |

FOREIGN PATENT DOCUMENTS

| | | |
|---|---|---|
| EP | 0666084 | 4/2004 |
| EP | 1349590 | 5/2006 |
| EP | 1654020 | 3/2010 |
| EP | 0620748 | 7/2010 |
| EP | 1518575 | 11/2010 |
| EP | 1590023 | 5/2011 |
| FR | 2 770 404 | 5/1999 |
| WO | WO 99/03529 | 1/1999 |
| WO | WO 02/47746 | 6/2002 |
| WO | WO 03/011378 | 2/2003 |
| WO | 03/041763 A2 | 5/2003 |
| WO | WO 03/047663 | 6/2003 |
| WO | WO 2004/060445 | 7/2004 |
| WO | WO 2005/025636 | 3/2005 |
| WO | WO 2005/025637 | 3/2005 |
| WO | WO 2005/086587 | 9/2005 |
| WO | WO 2005025636 A3 * | 4/2006 .......... A61M 5/2033 |
| WO | 2005/021070 | 5/2006 |
| WO | WO 2008/047372 | 4/2008 |

OTHER PUBLICATIONS

A Supplementary European Search Report dated Feb. 12, 2010, which issued during the prosecution of Applicant's European Patent Application No. EP 04 77 0522.
An Office Action dated Jun. 29, 2010, which issued during the prosecution of Applicant's U.S. Appl. No. 10/572,215.
An Office Action dated Jul. 19, 2013, which issued during the prosecution of U.S. Appl. No. 13/611,899.
An Office Action dated Feb. 10, 2012, which issued during the prosecution of European Patent Application No. 04770522.
A Hearing Notice in Reference dated Jan. 19, 2012, which issued during the prosecution of Indian Patent Application No. 426/MUMNP/2006.
An Office Action dated Jul. 7, 2011, which issued during the prosecution of Canadian Patent Application No. 2,539,315.
A Search Report dated Nov. 6, 2013 which issued during the prosecution of Applicant's European Application No. 13 17 5764.3.
An Office Action dated Feb. 27, 2014, which issued during the prosecution of U.S. Appl. No. 12/741,628.
An Office Action dated Mar. 24 2014, which issued during the prosecution of U.S. Appl. No. 13/611,899.
An Office Action dated Oct. 18, 2013, which issued during the prosecution of U.S. Appl. No. 12/741,628.
Communication dated Jun. 27, 2014 from the United States Patent Office in counterpart U.S. Appl. No. 13/611,899.
US 5,954,699, 09/1999, Jost et al. (withdrawn)

* cited by examiner

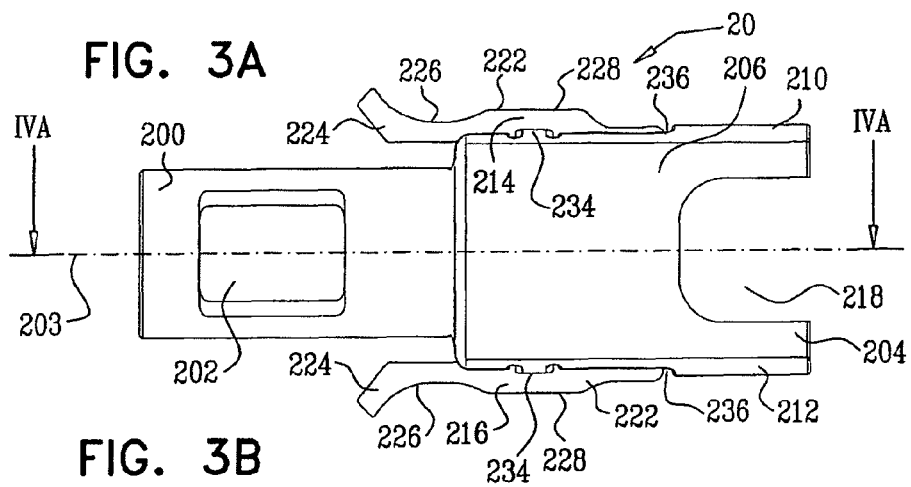
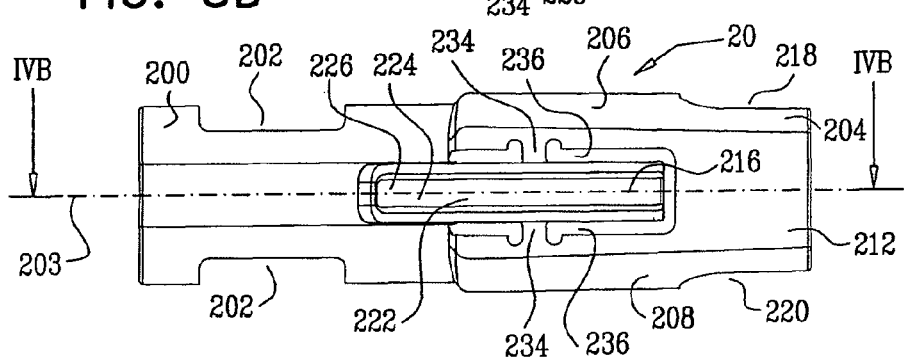
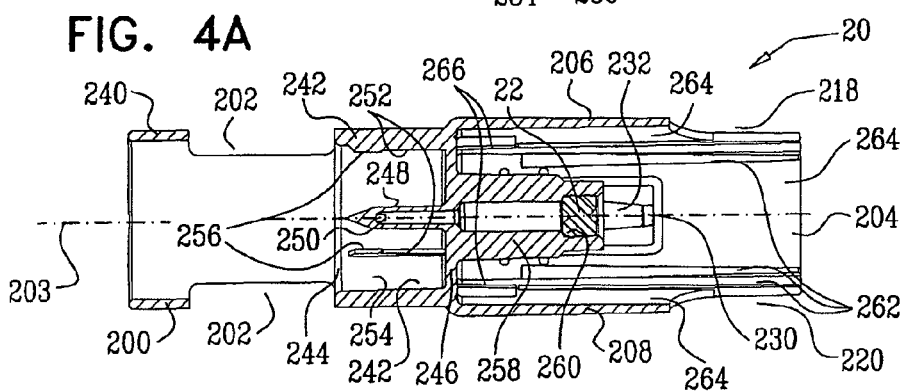
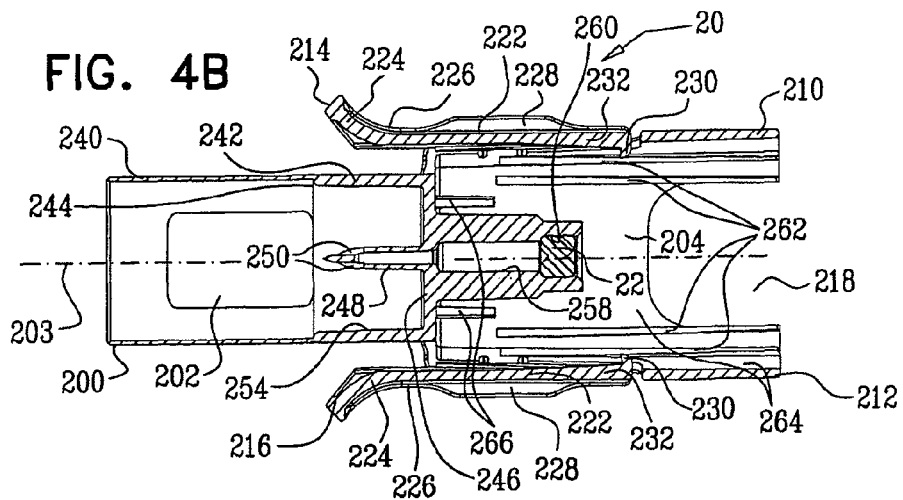

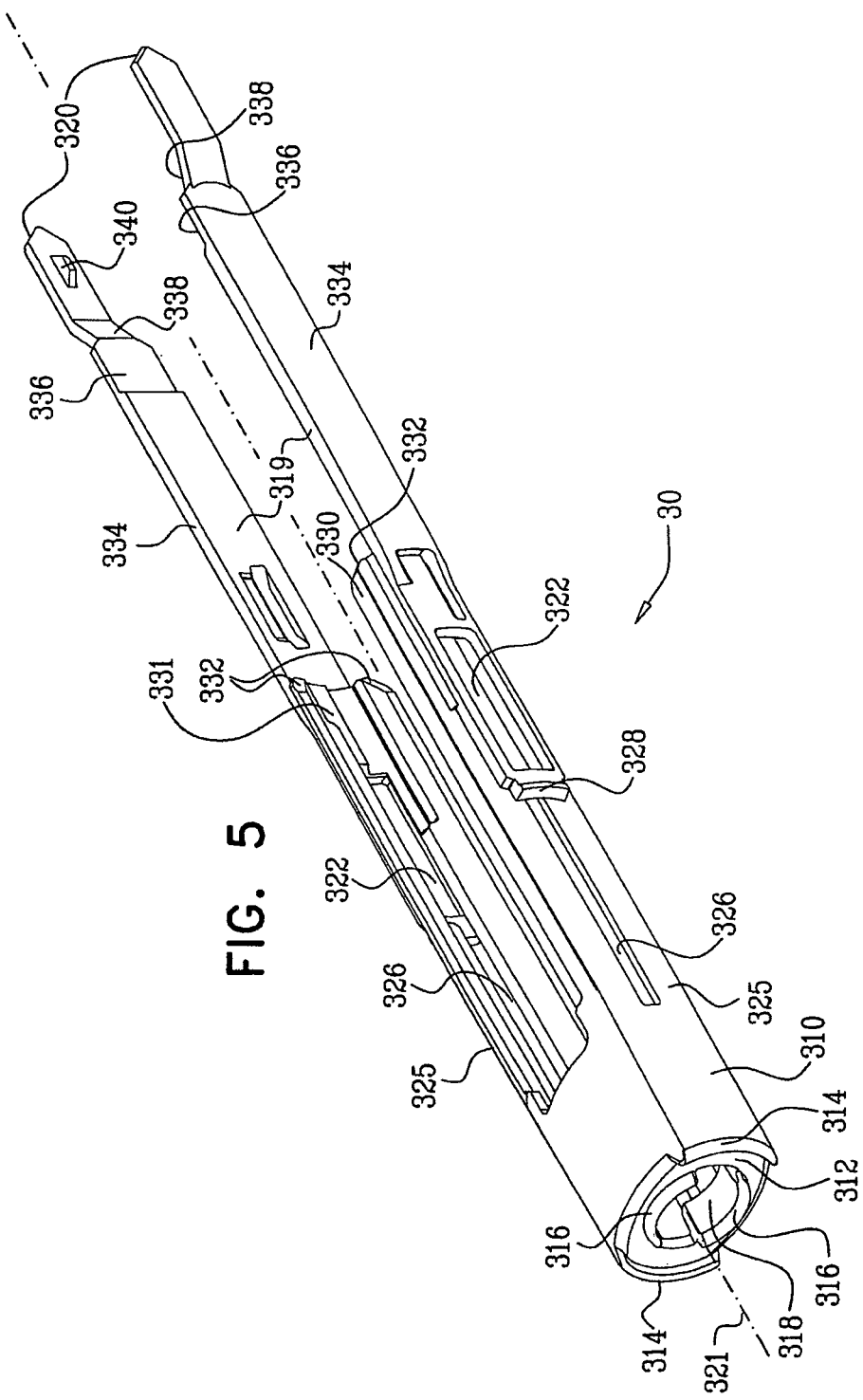

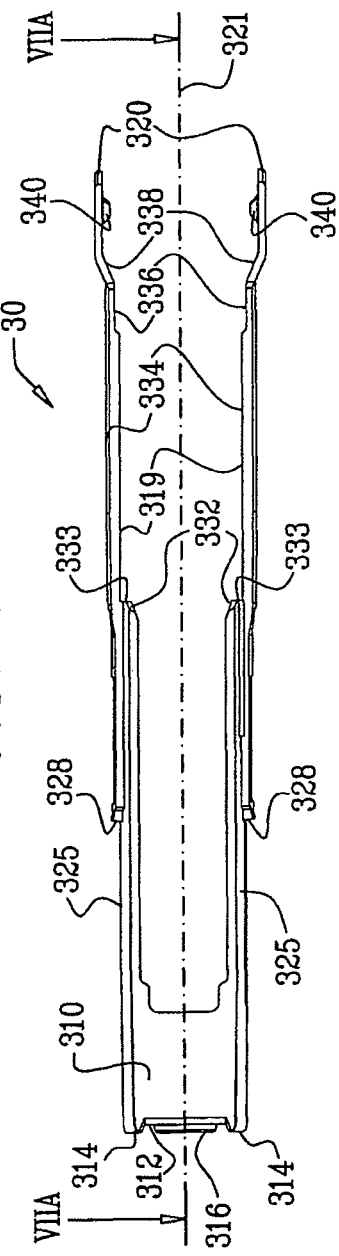
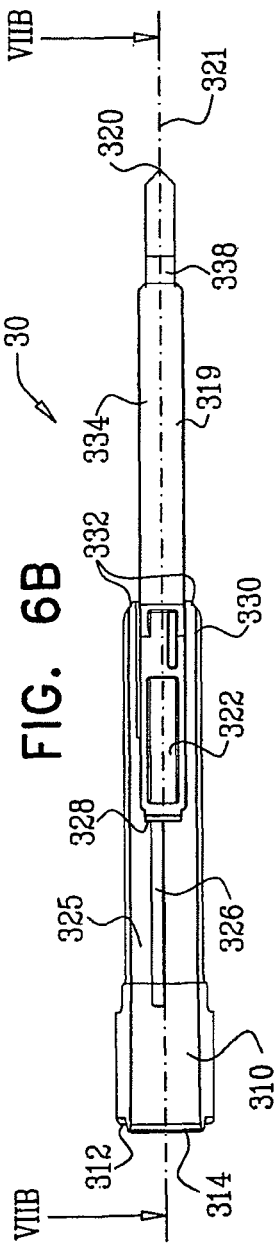

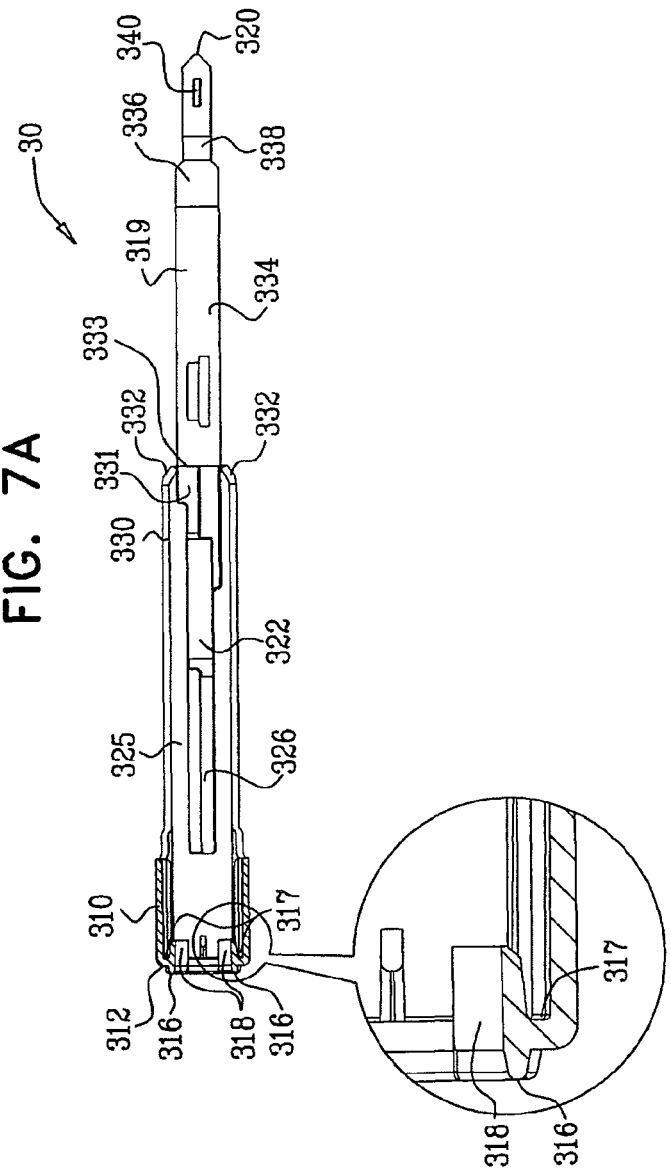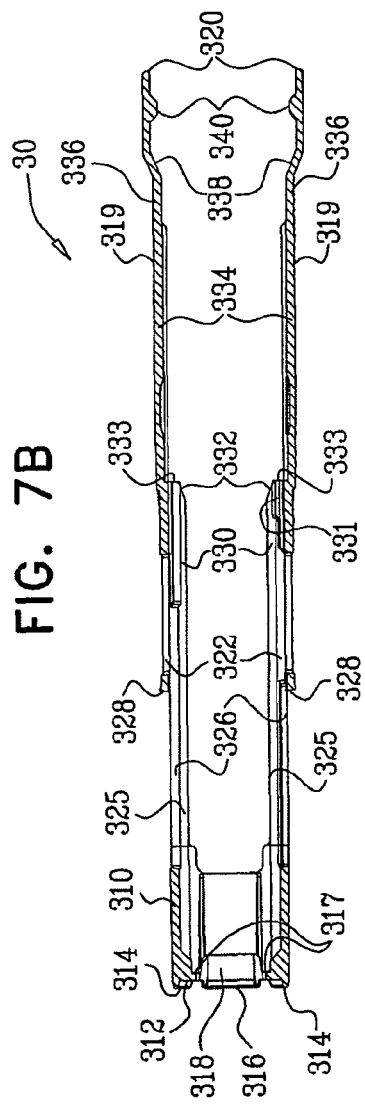

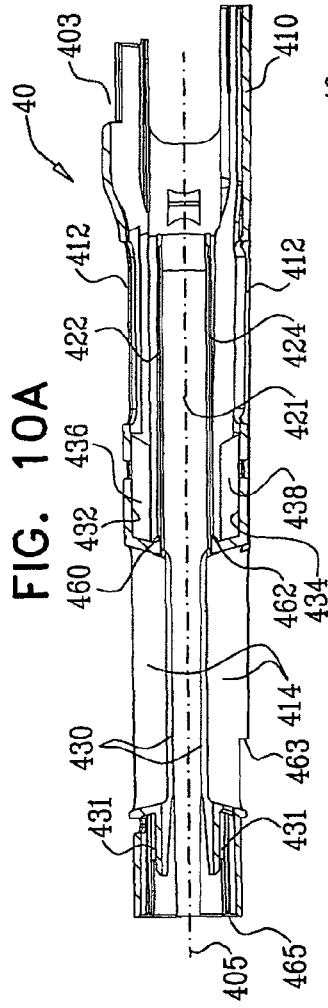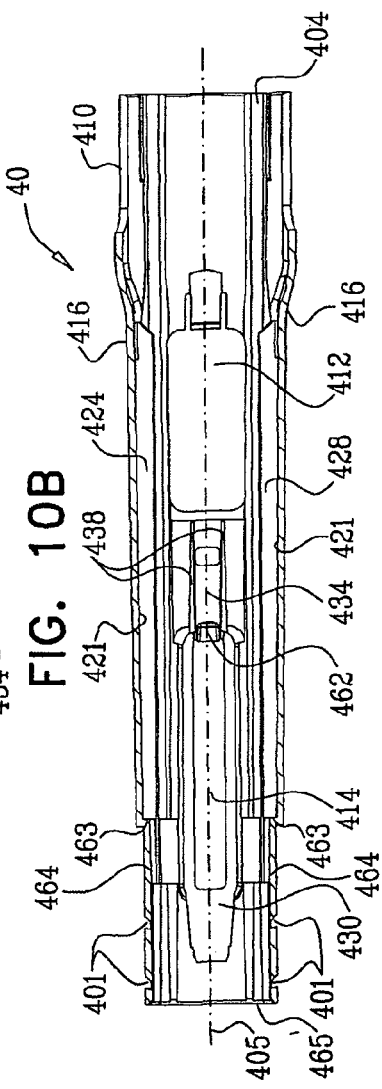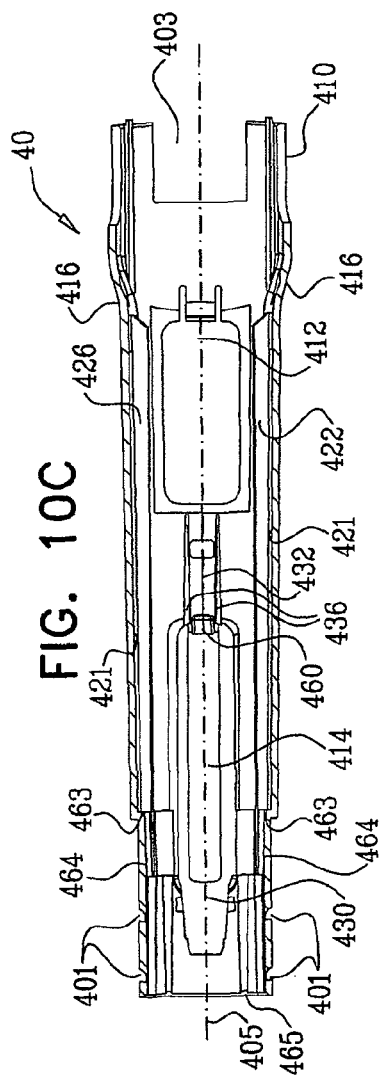

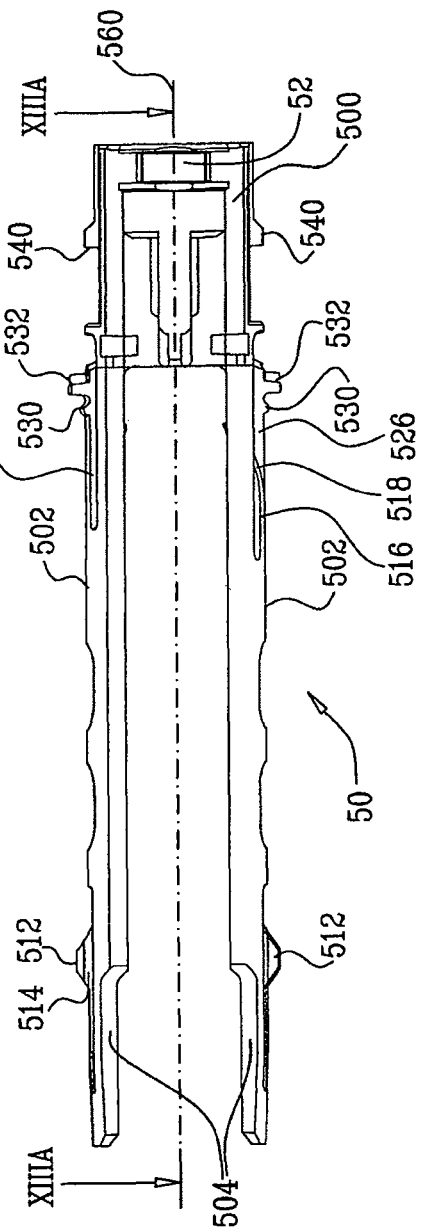
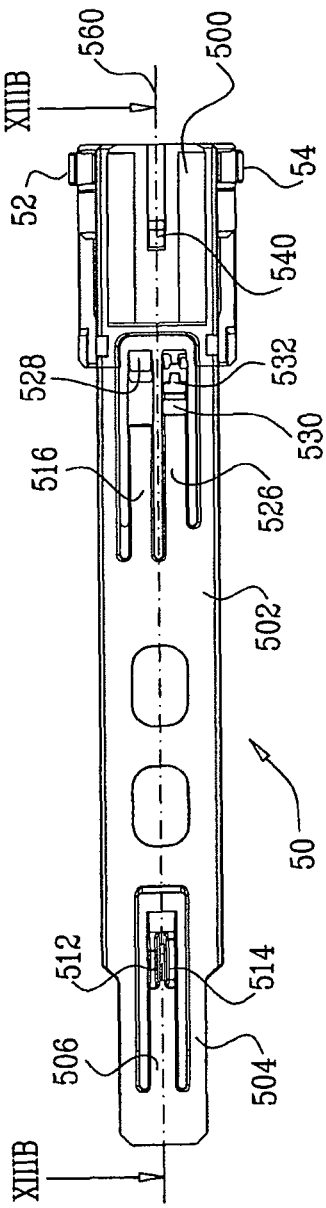

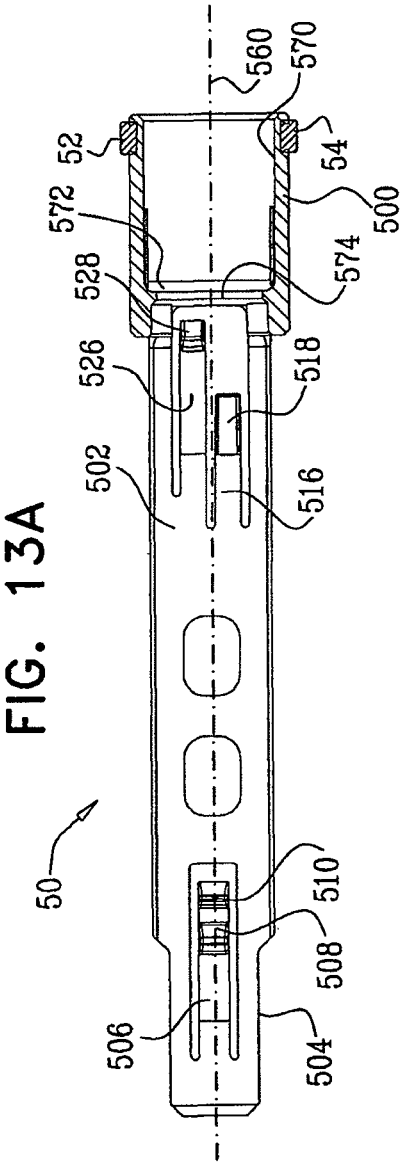
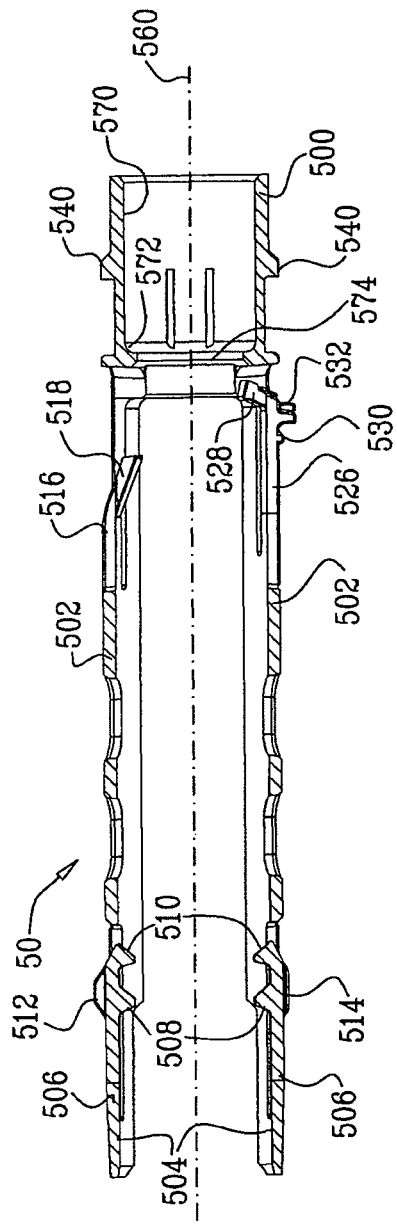

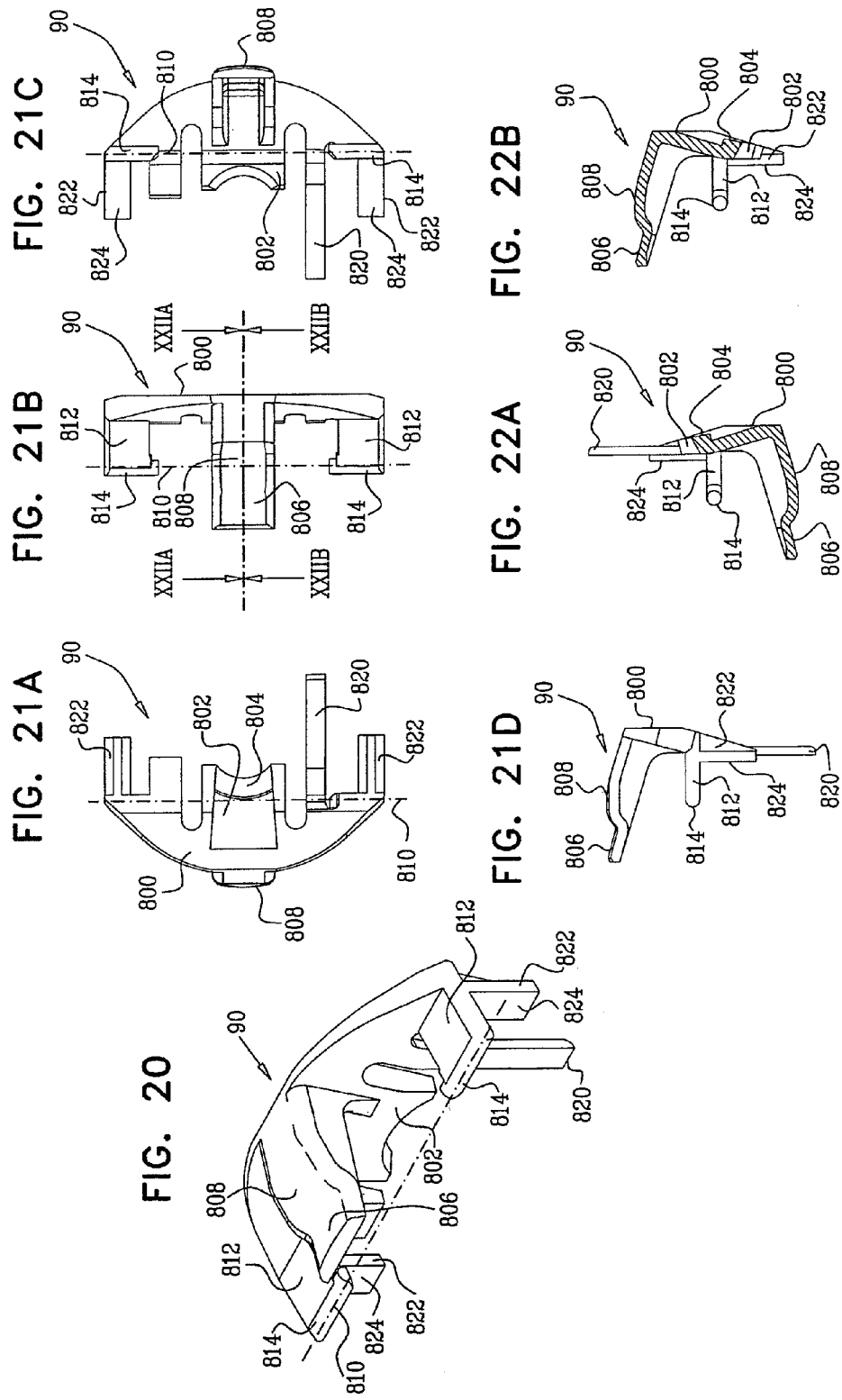

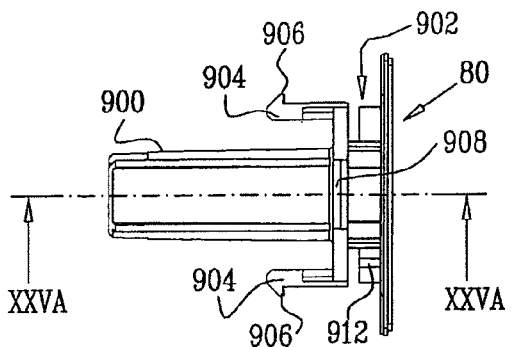
FIG. 24A
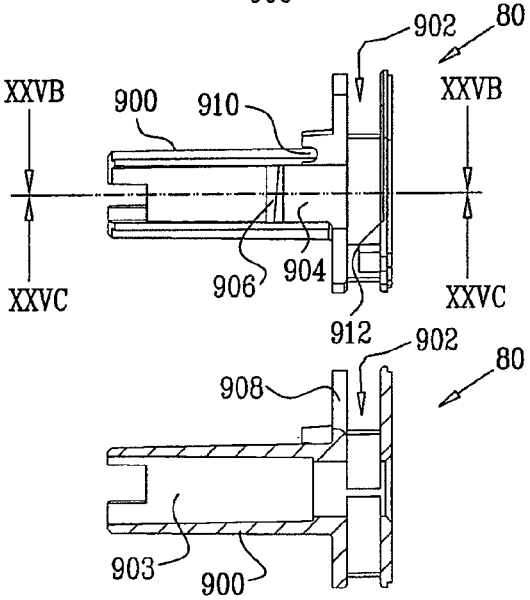
FIG. 24B
FIG. 25A
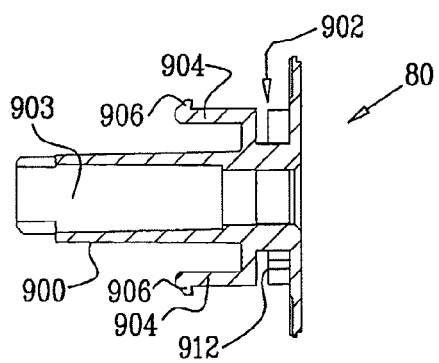
FIG. 25B
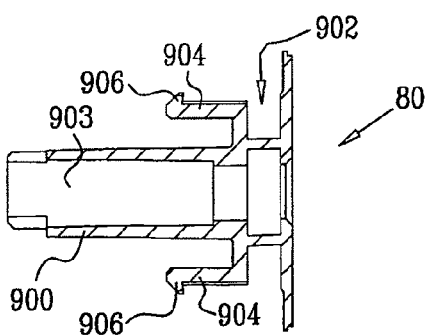
FIG. 25C

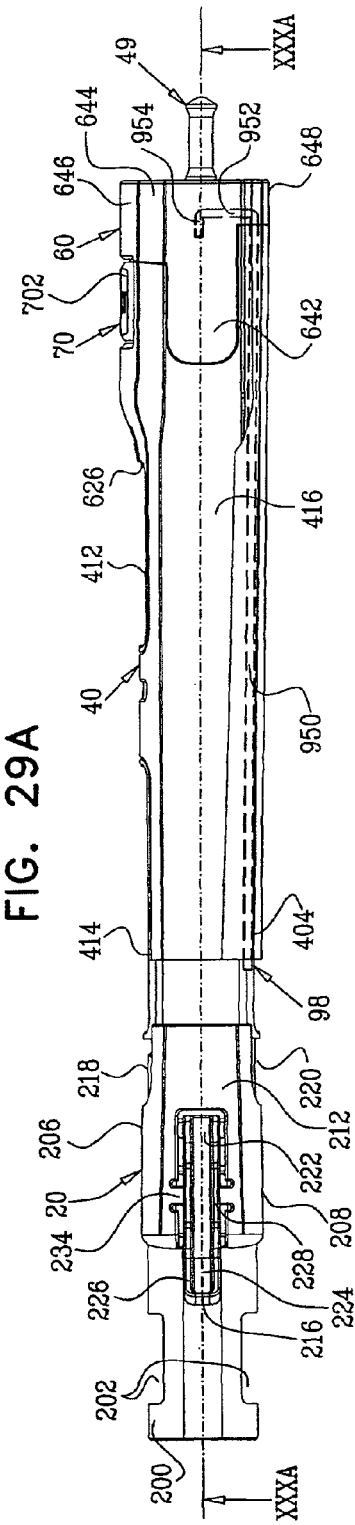
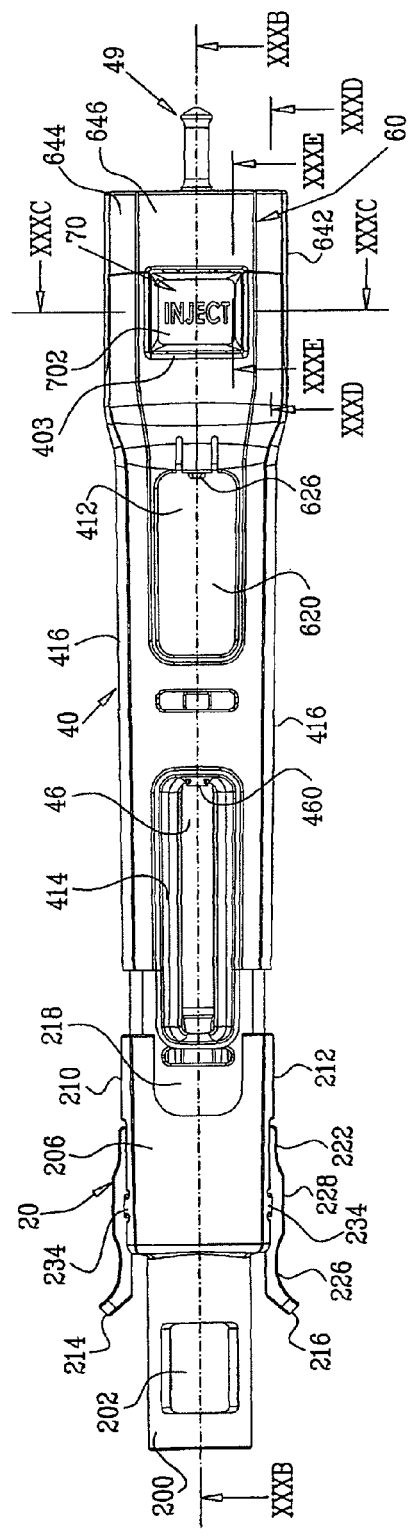
FIG. 29A
FIG. 29B

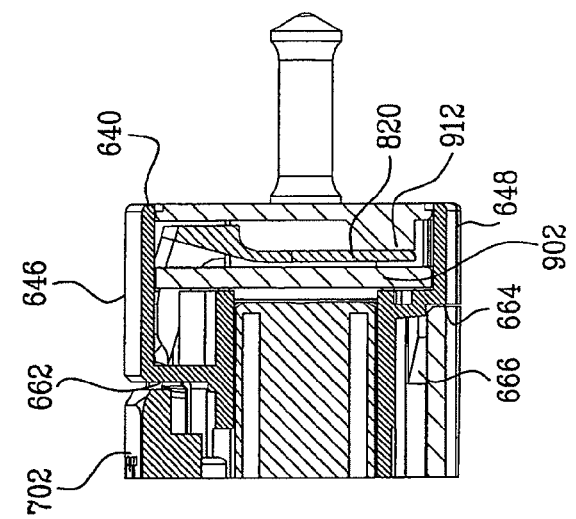
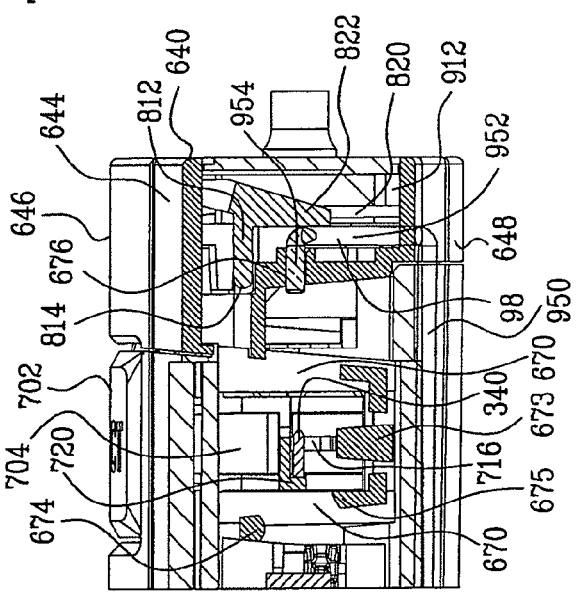
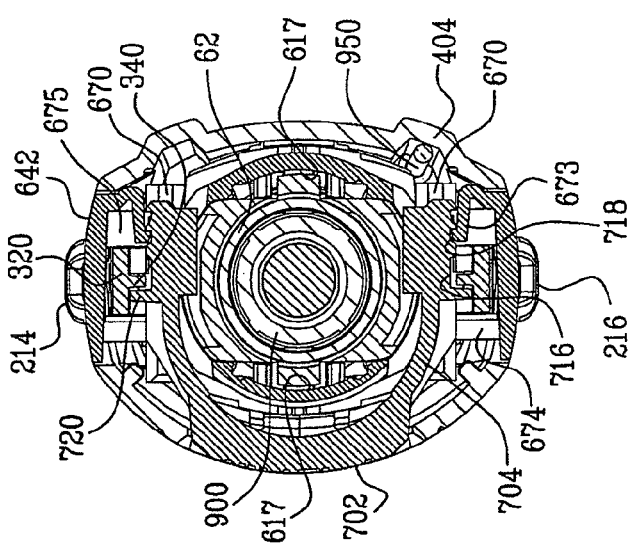
FIG. 30C
FIG. 30D
FIG. 30E

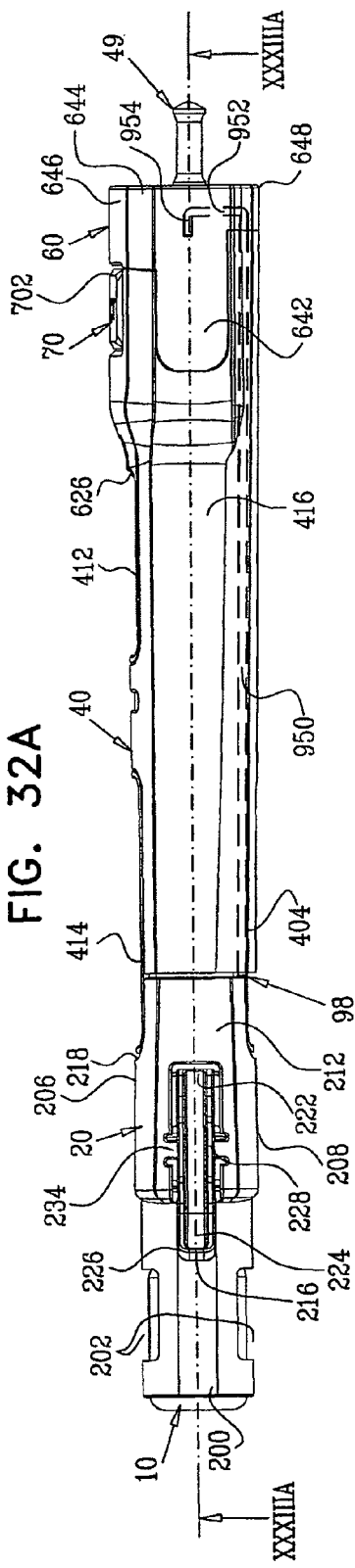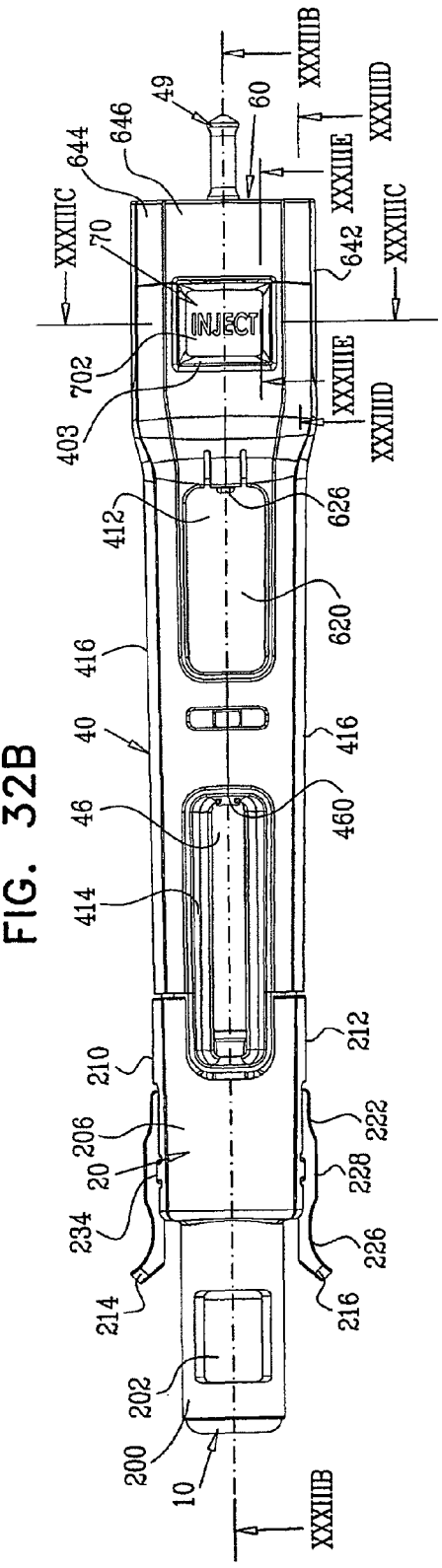

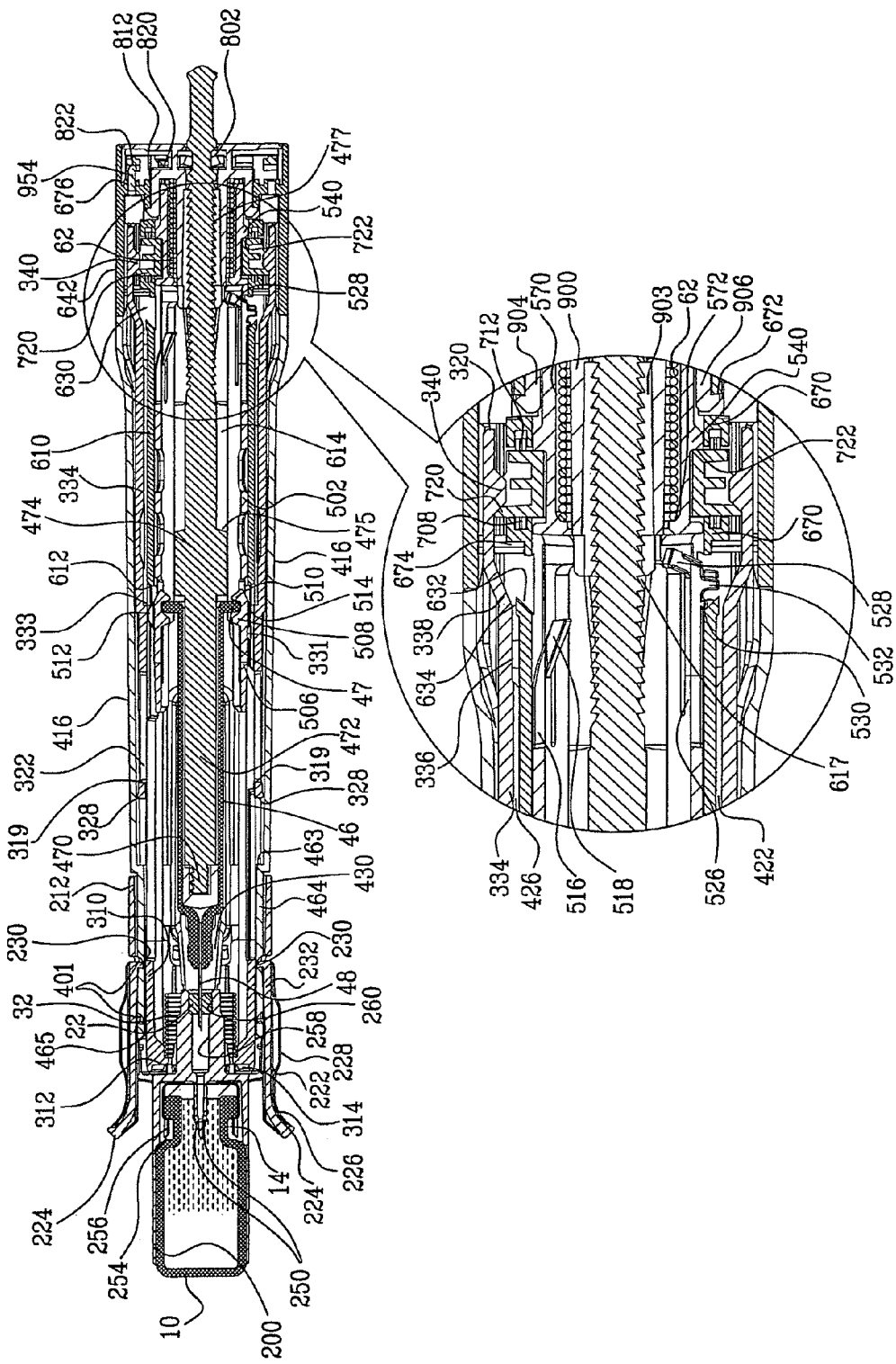

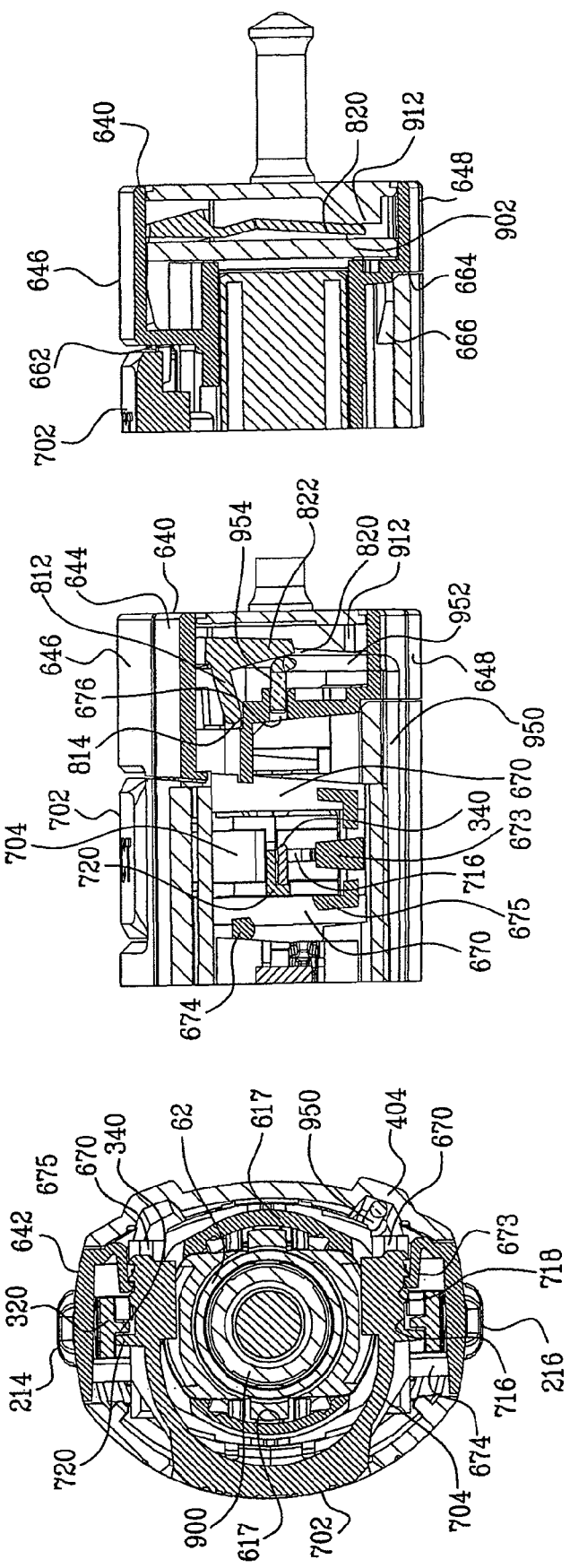

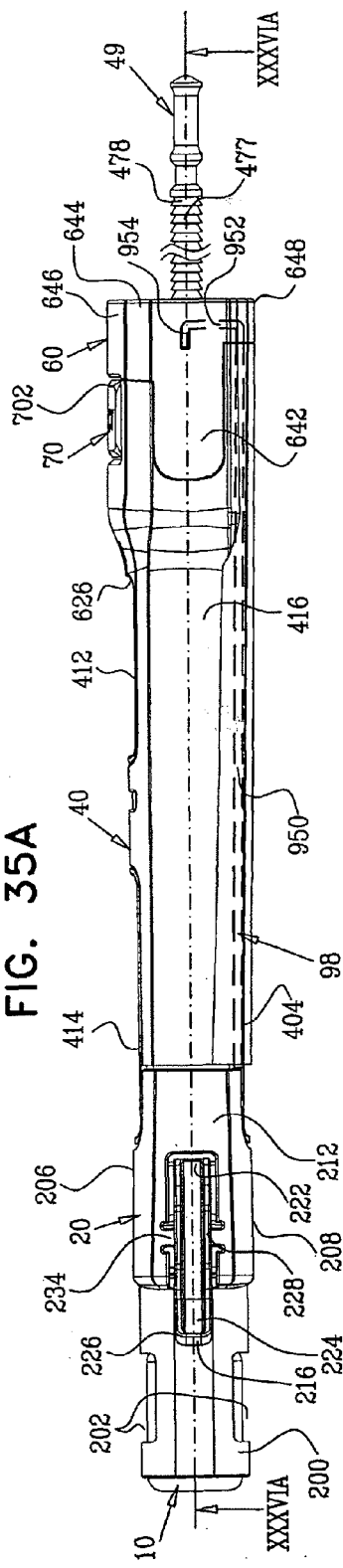
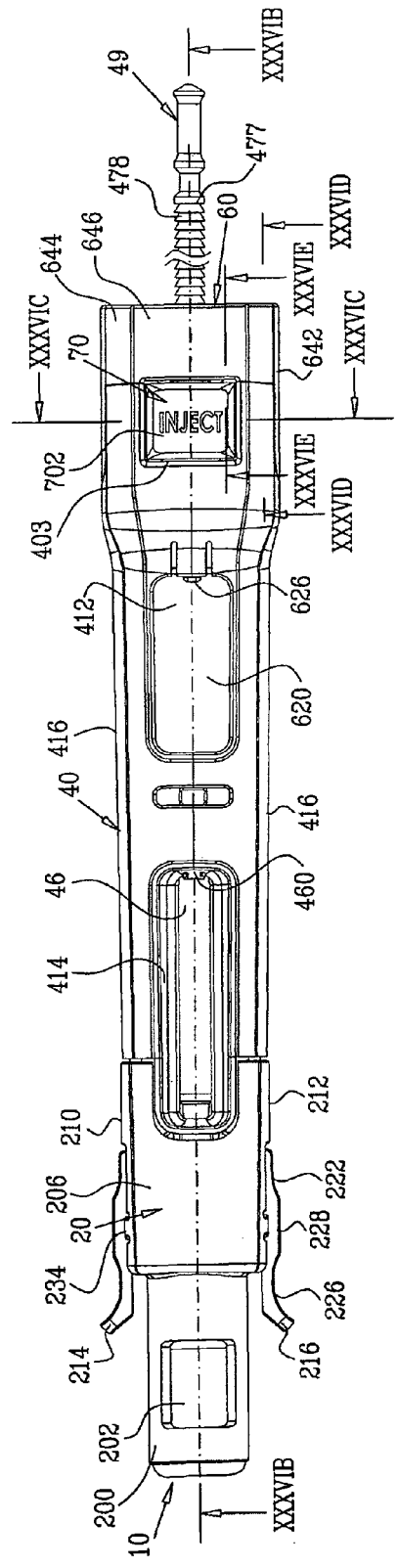
FIG. 35A
FIG. 35B

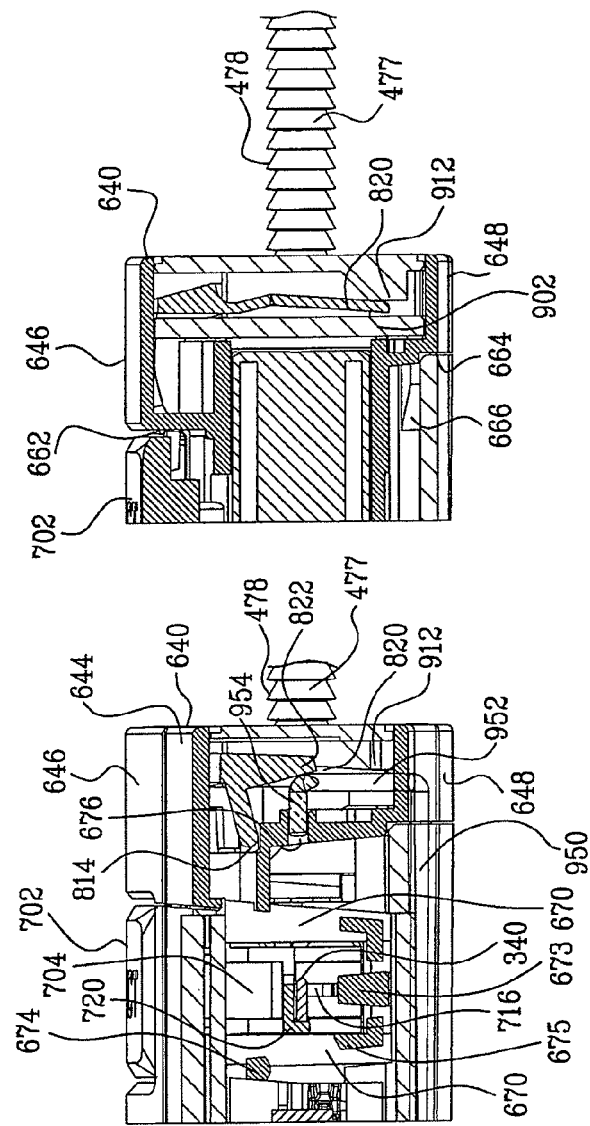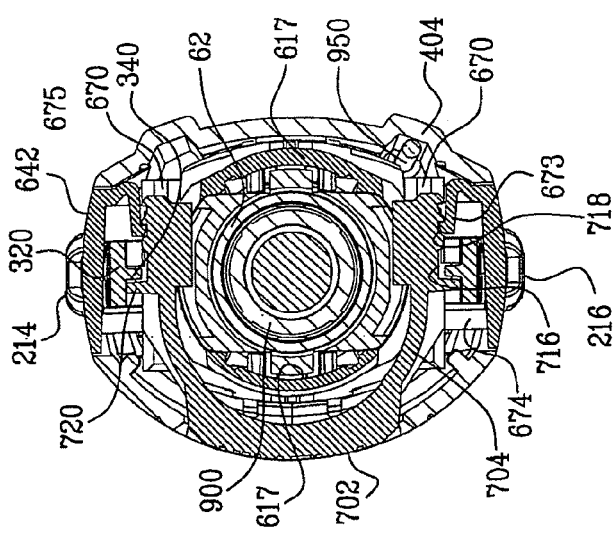

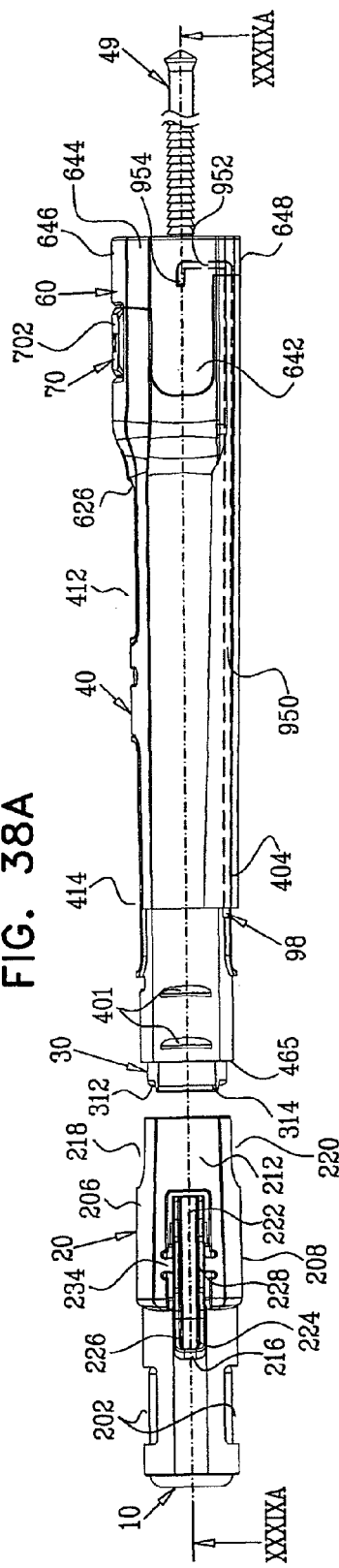
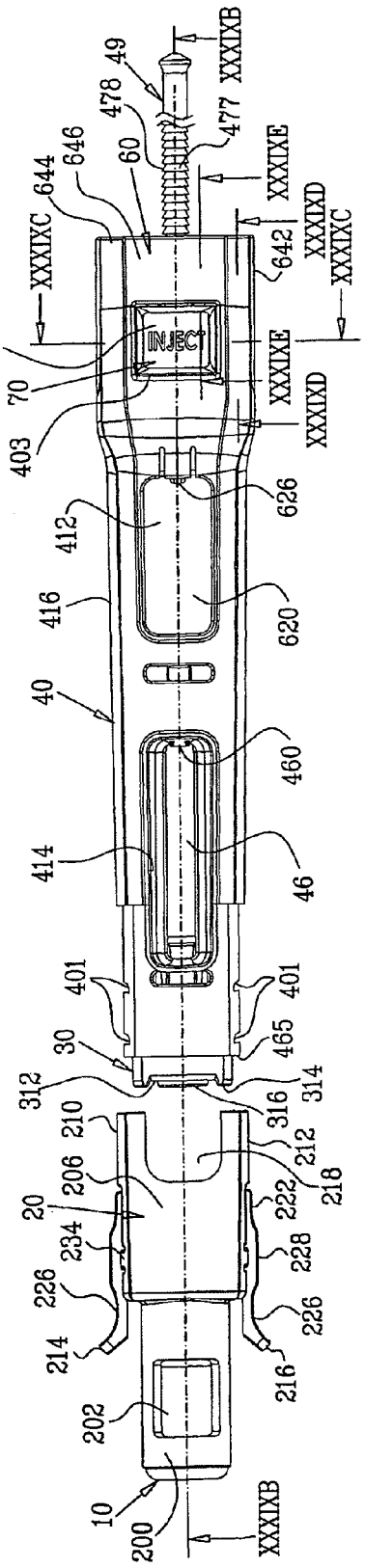

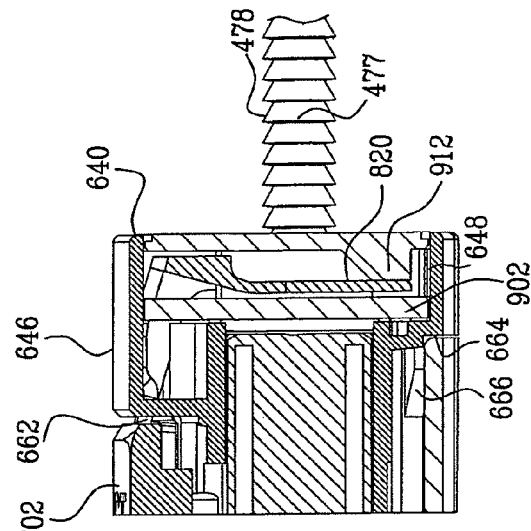
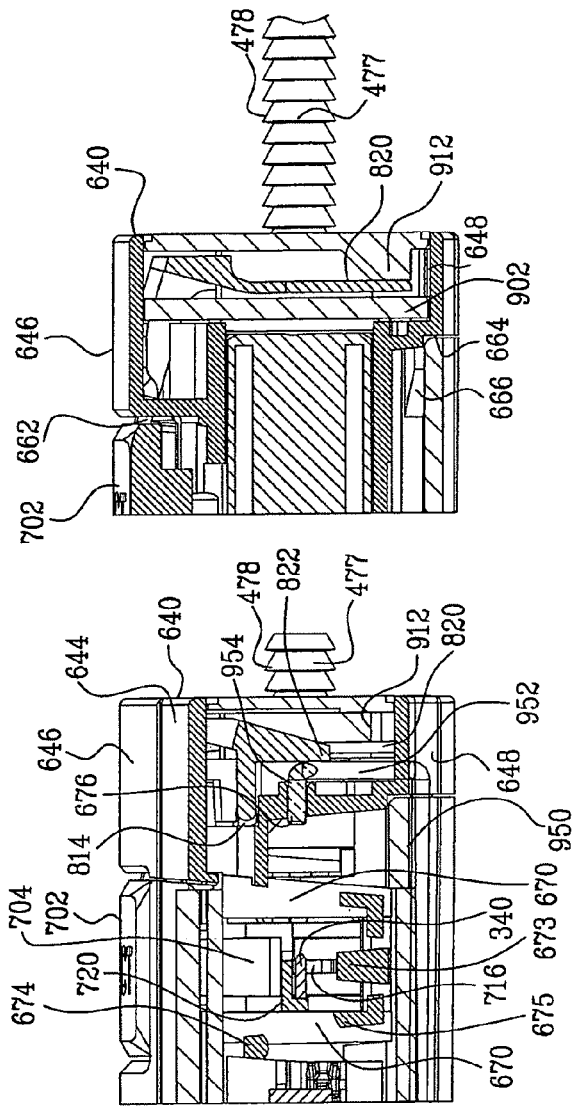
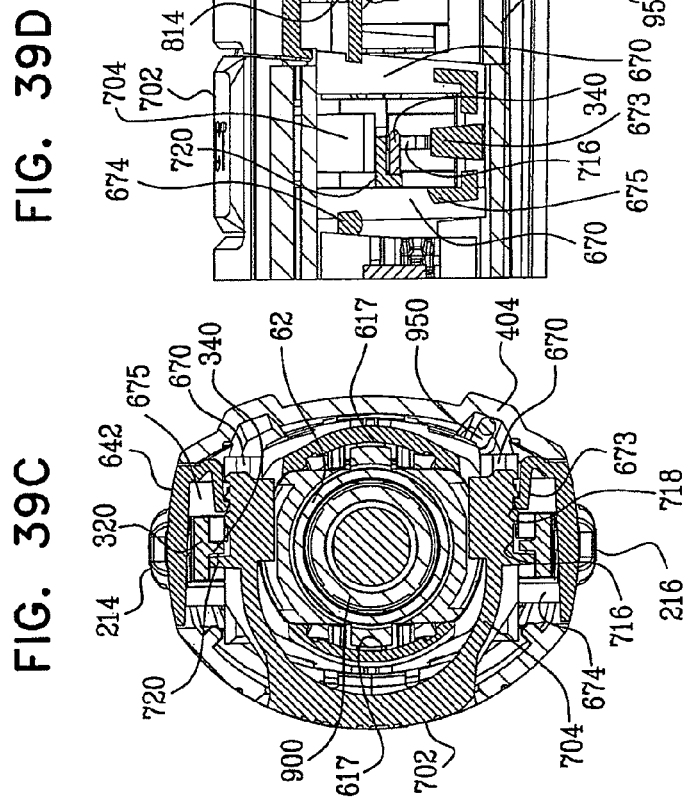
FIG. 39C
FIG. 39D
FIG. 39E

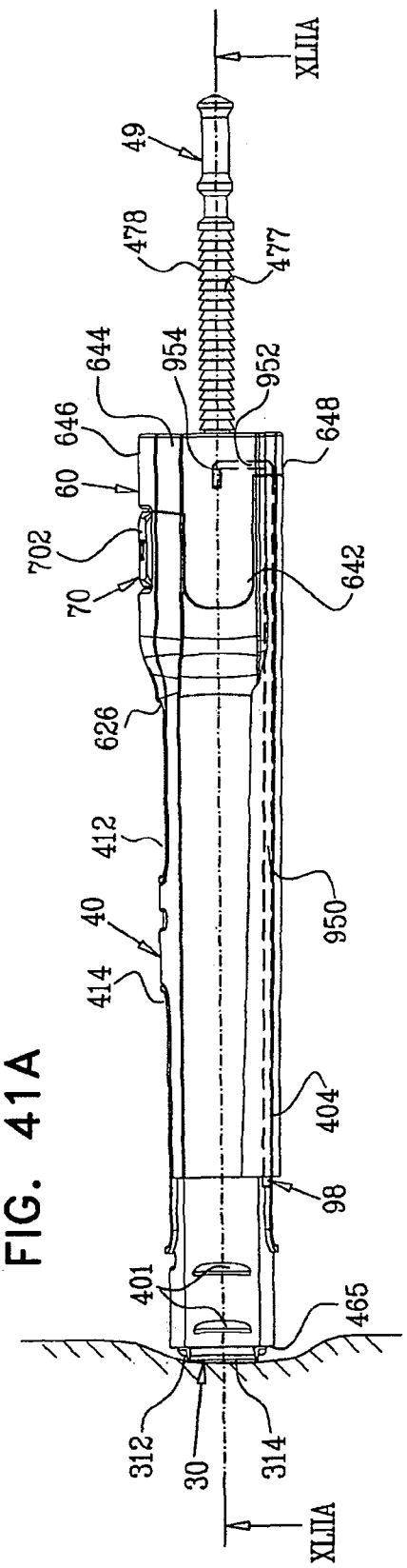
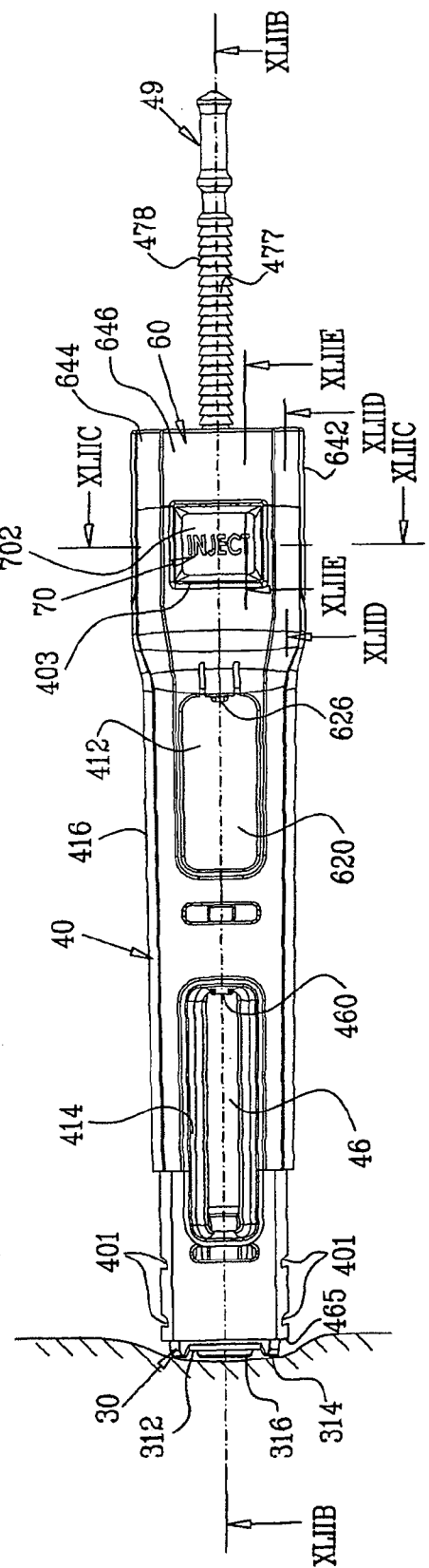
FIG. 41A
FIG. 41B

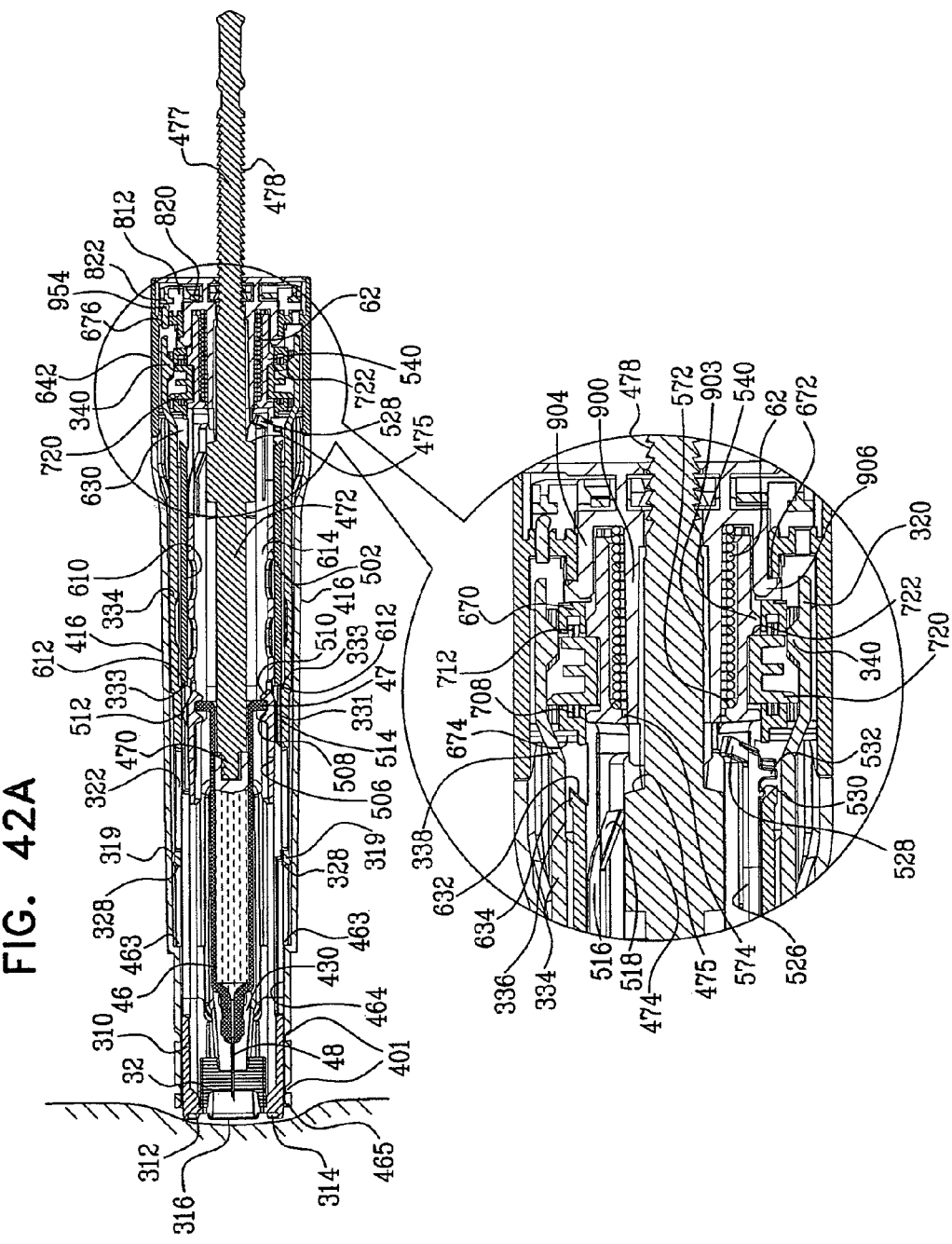

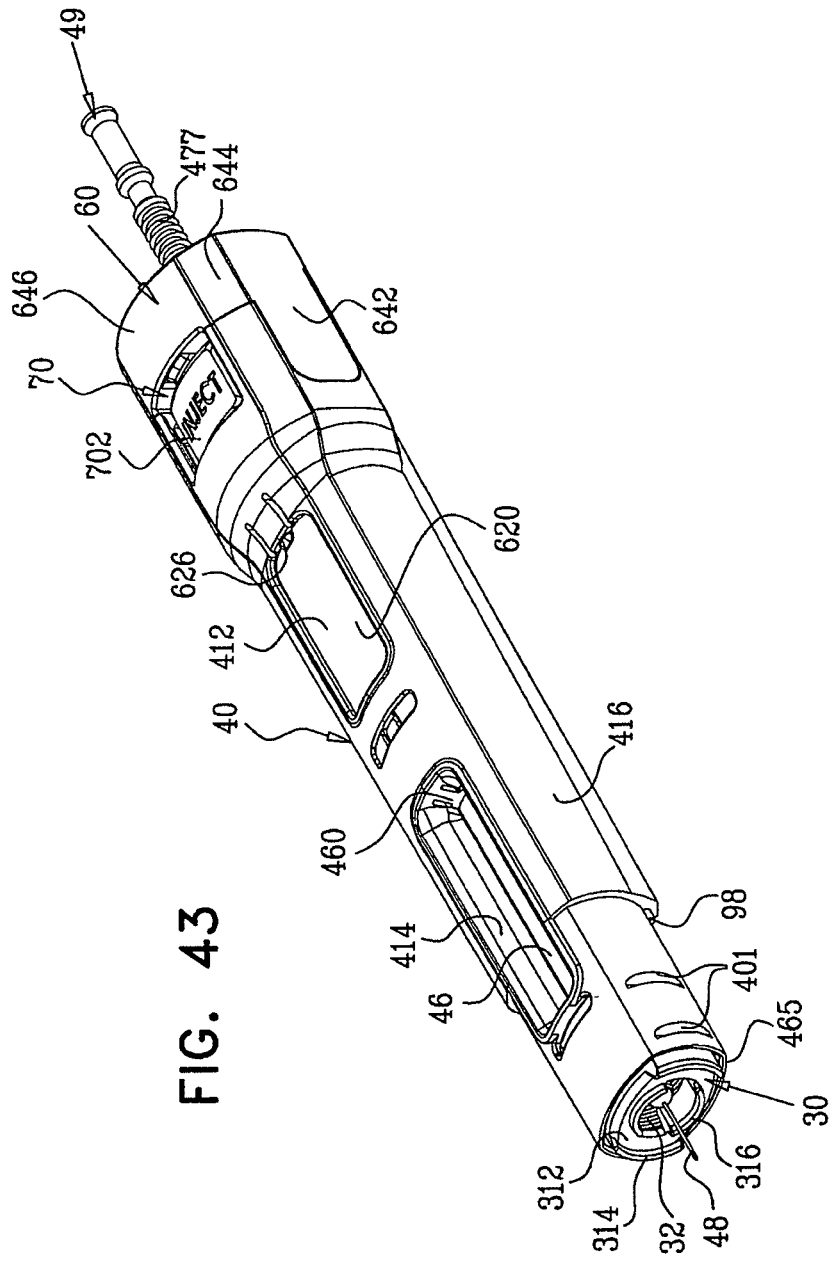

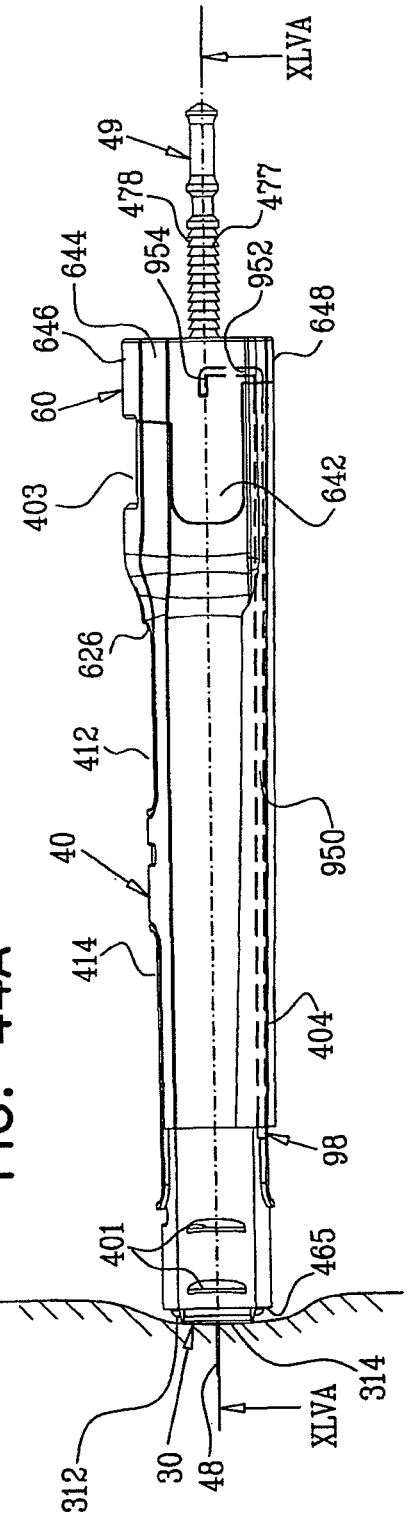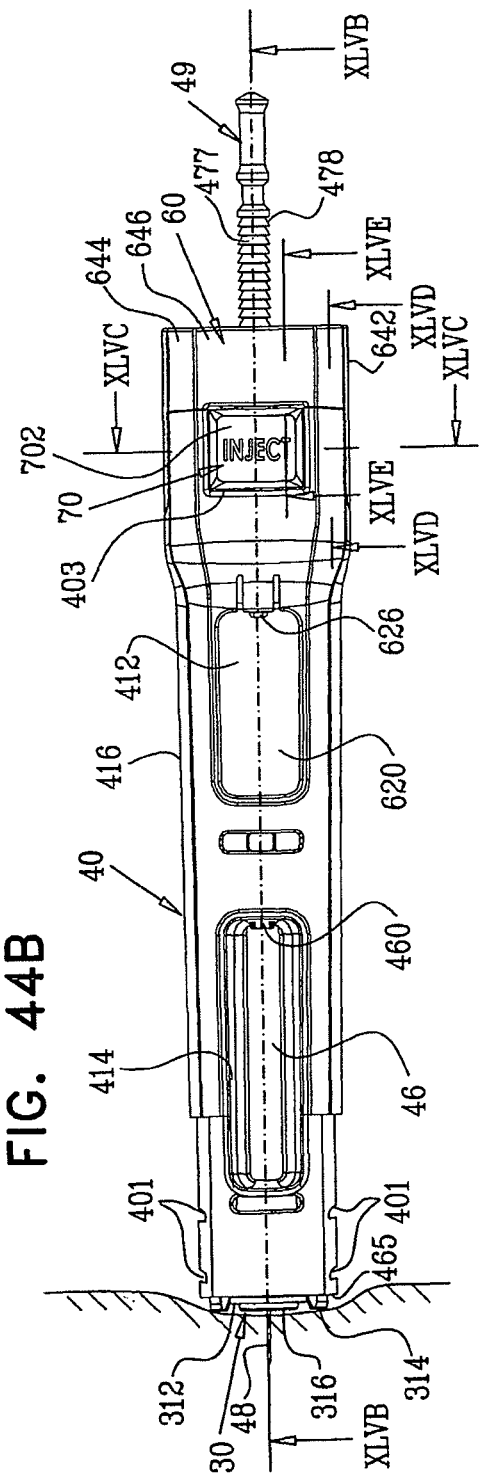
FIG. 44A
FIG. 44B

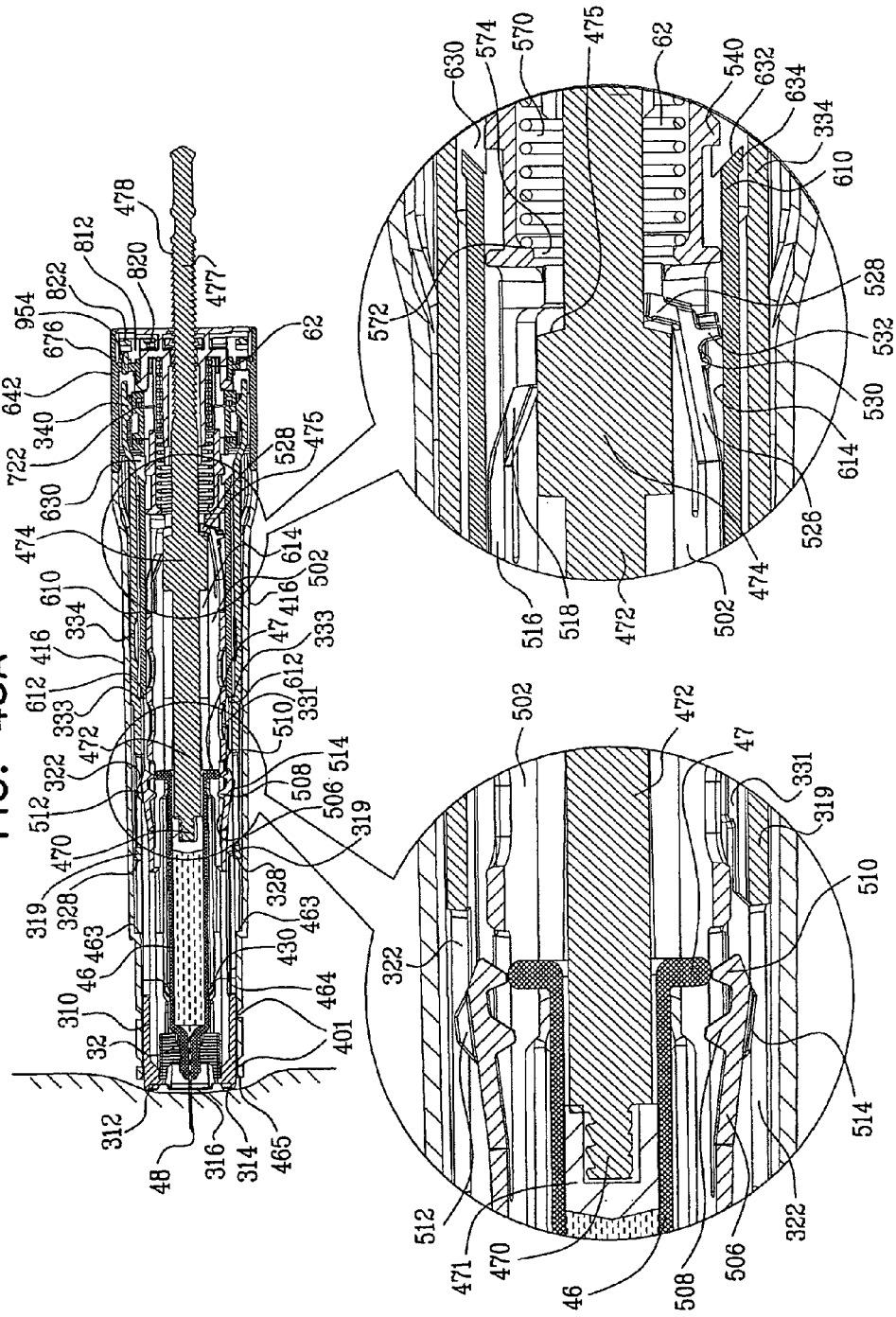

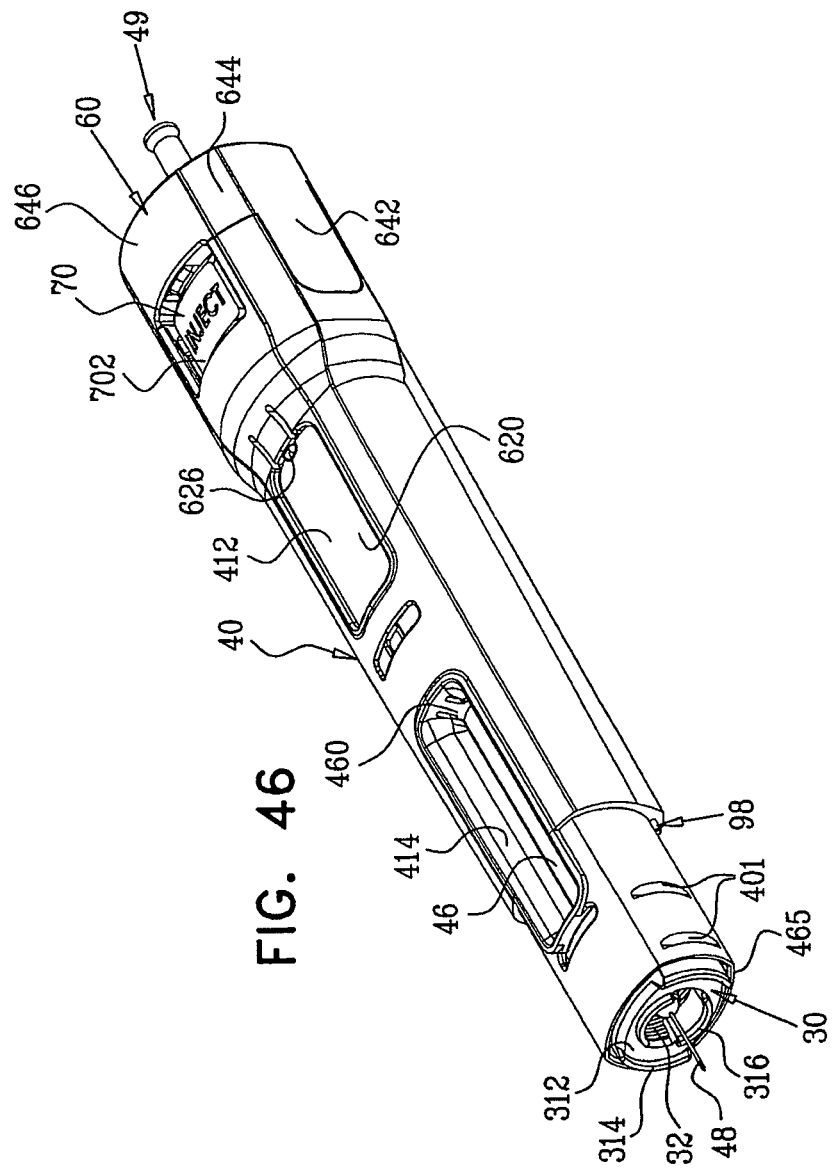

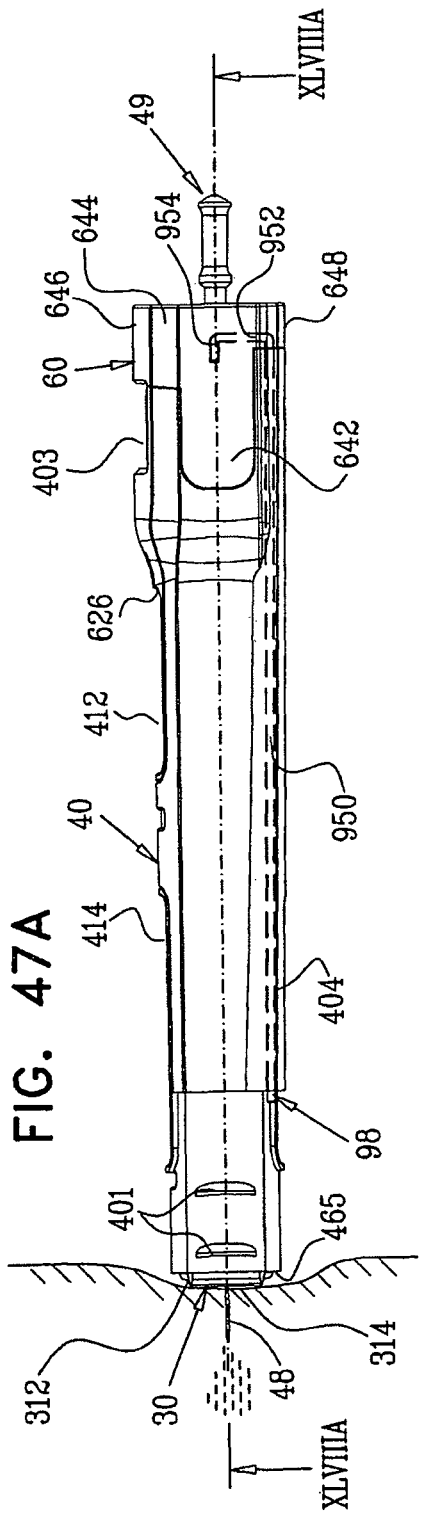
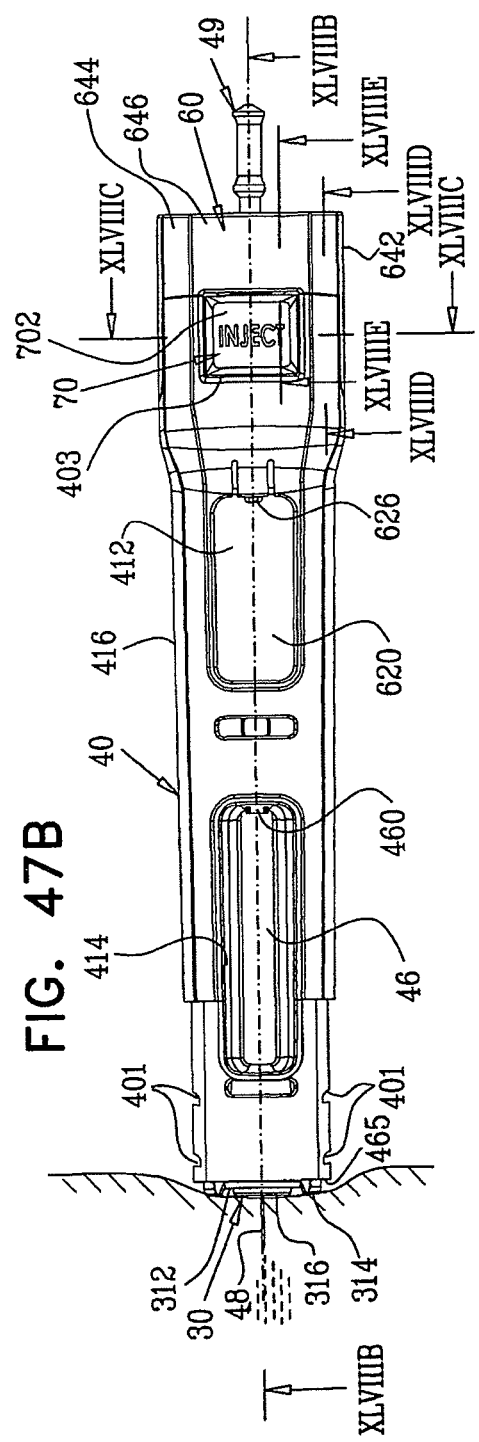
FIG. 47A
FIG. 47B

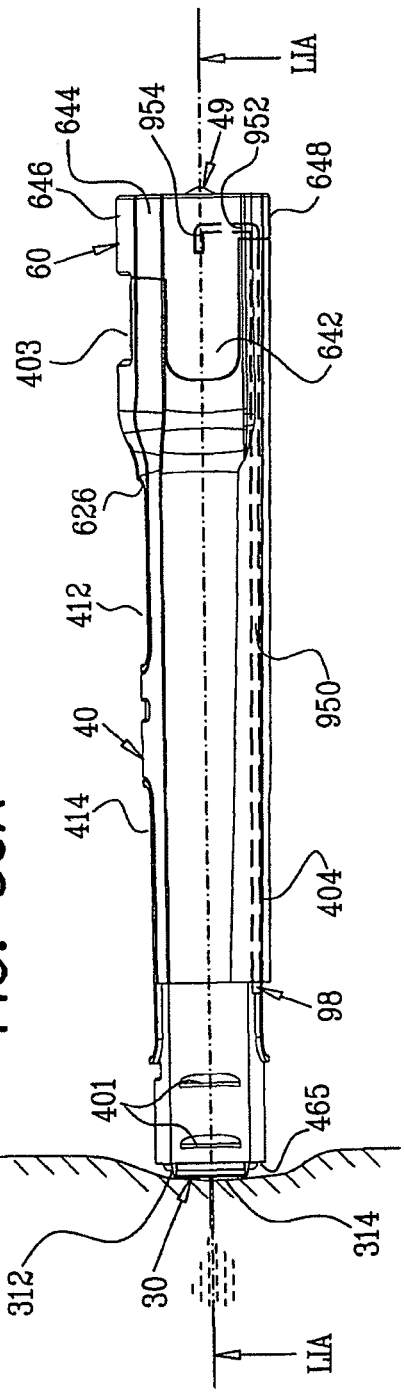
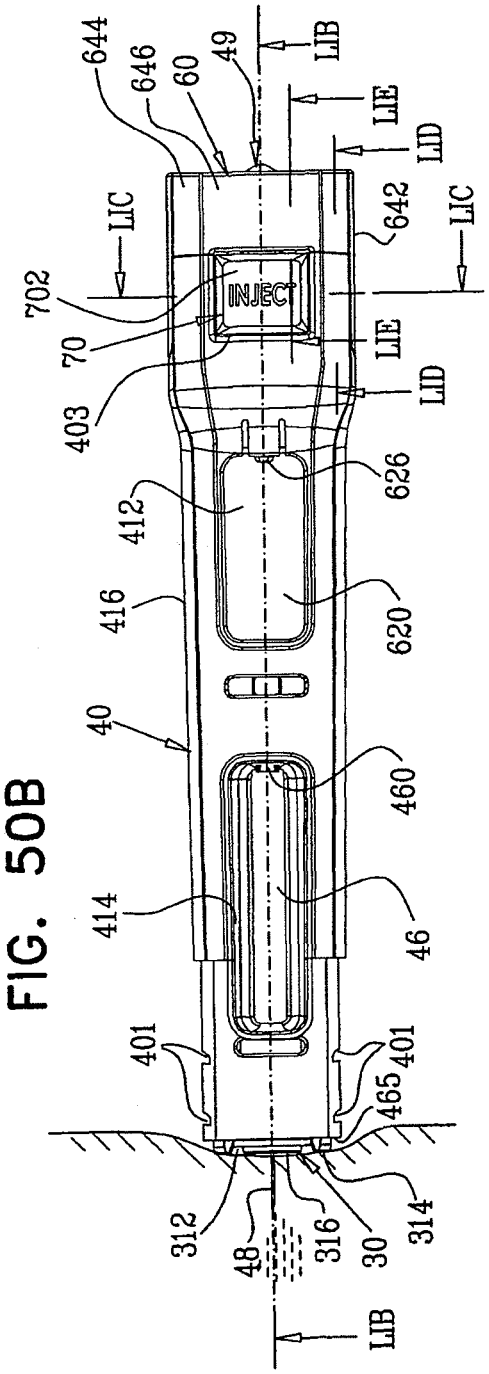

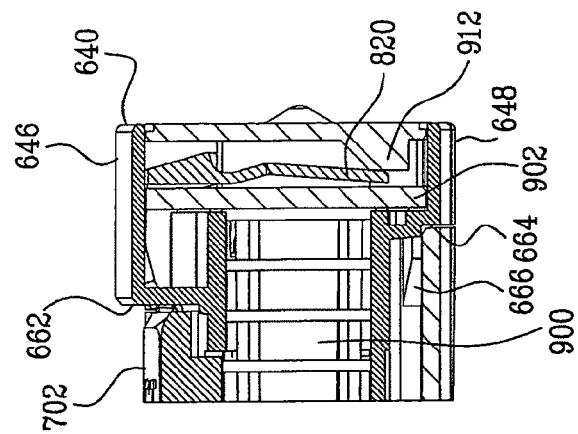
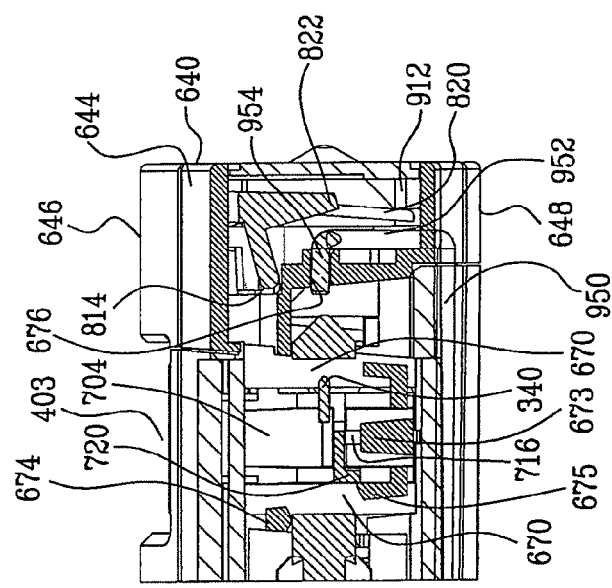
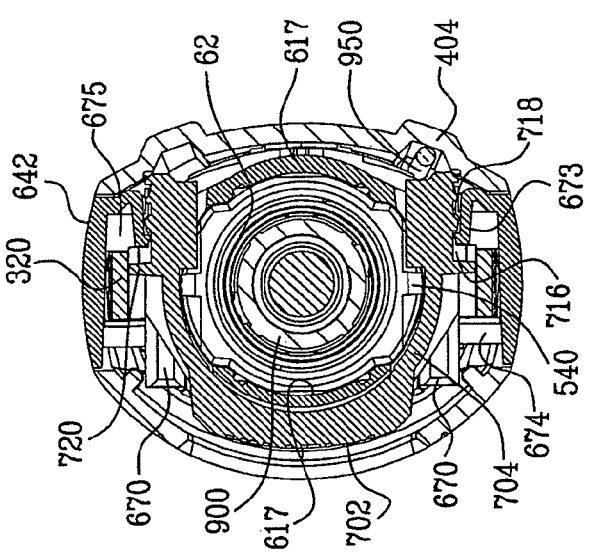

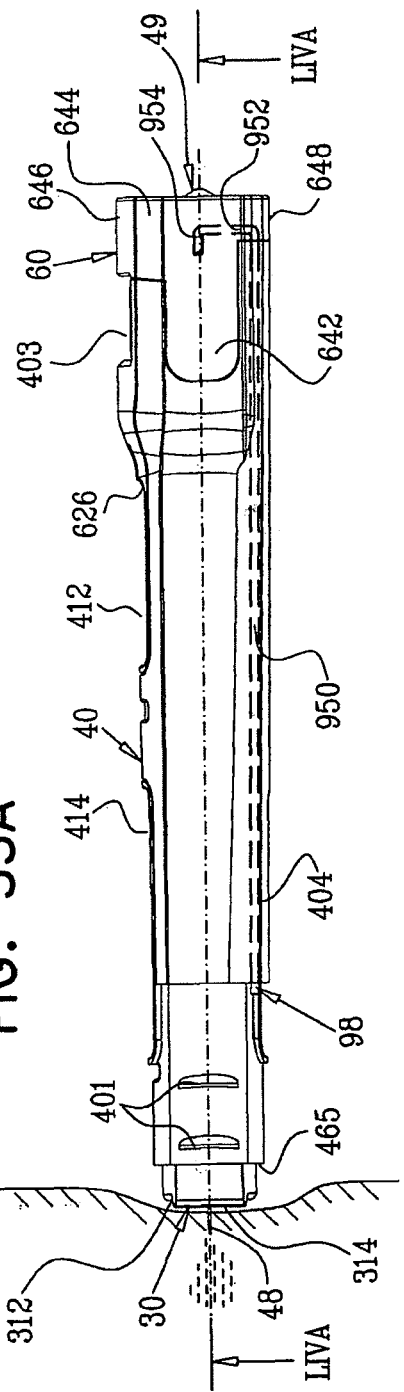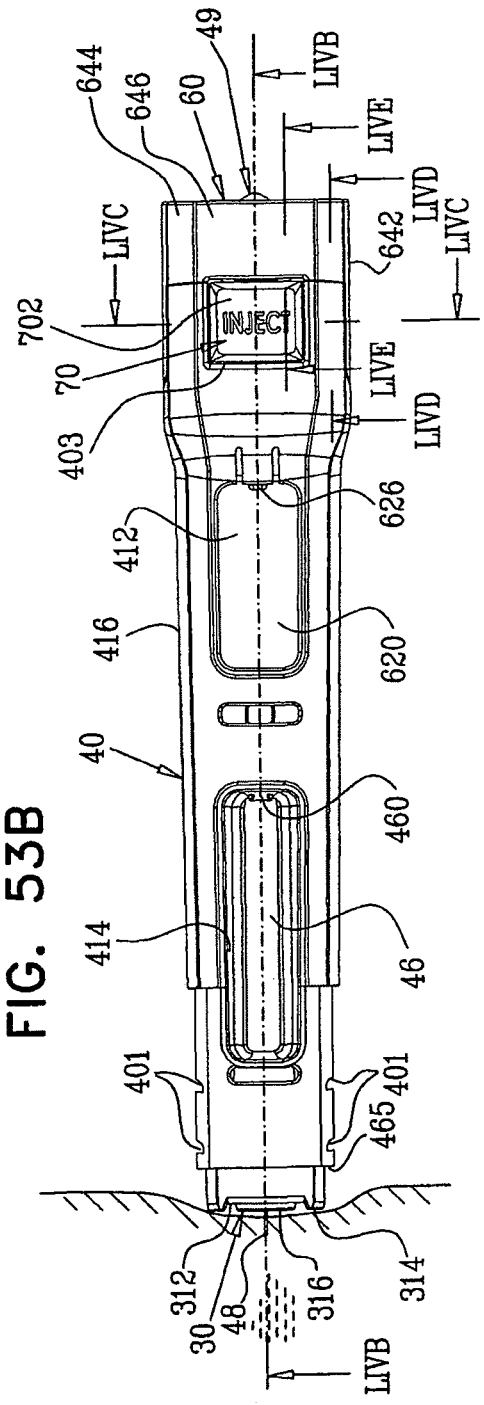

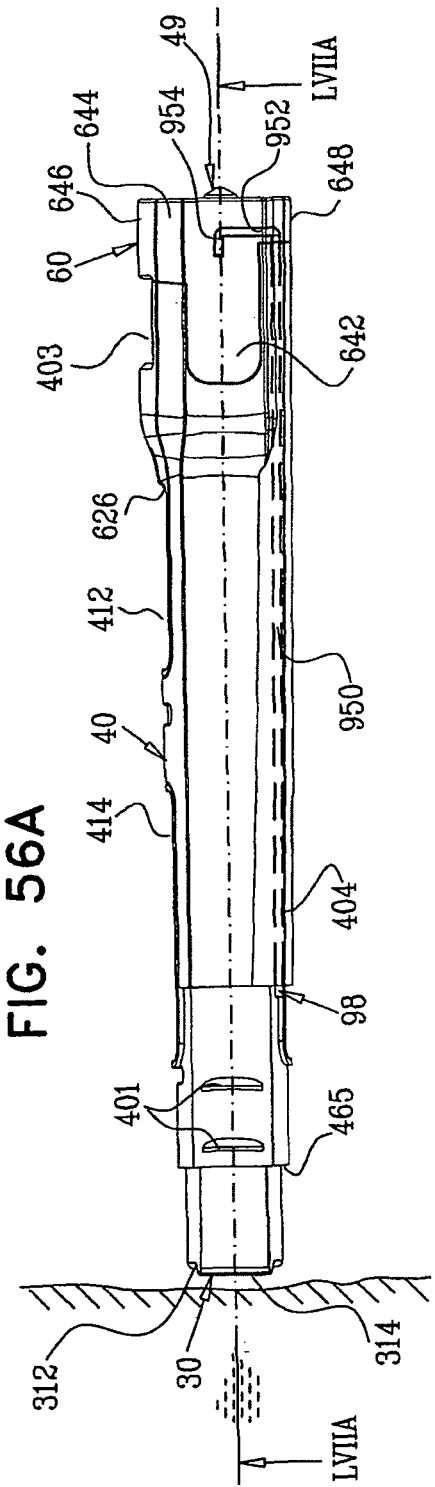
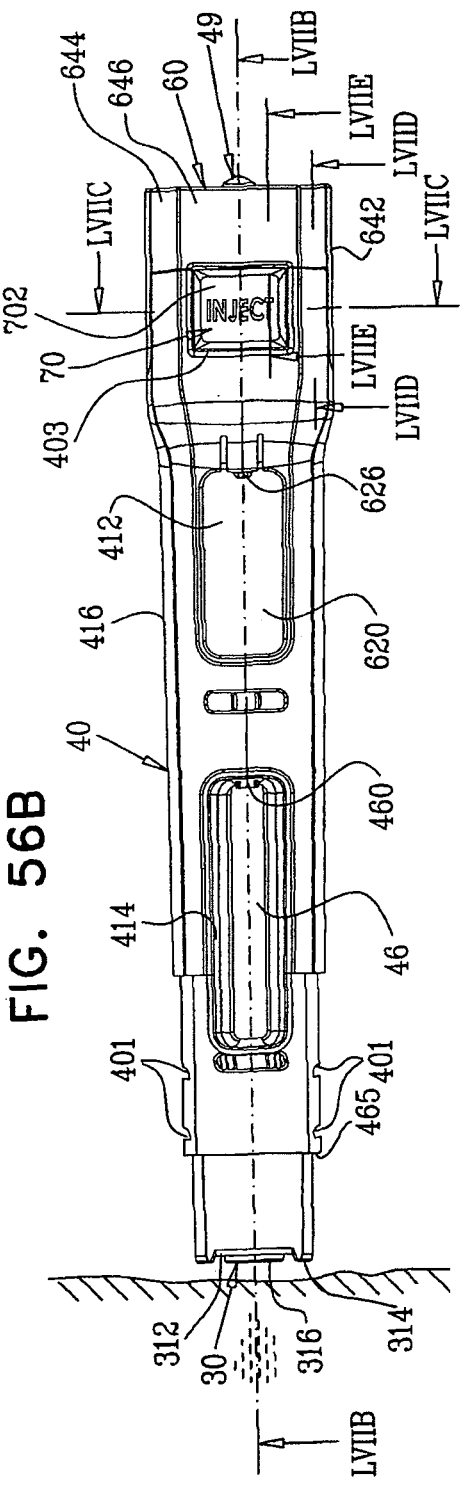
FIG. 56A
FIG. 56B

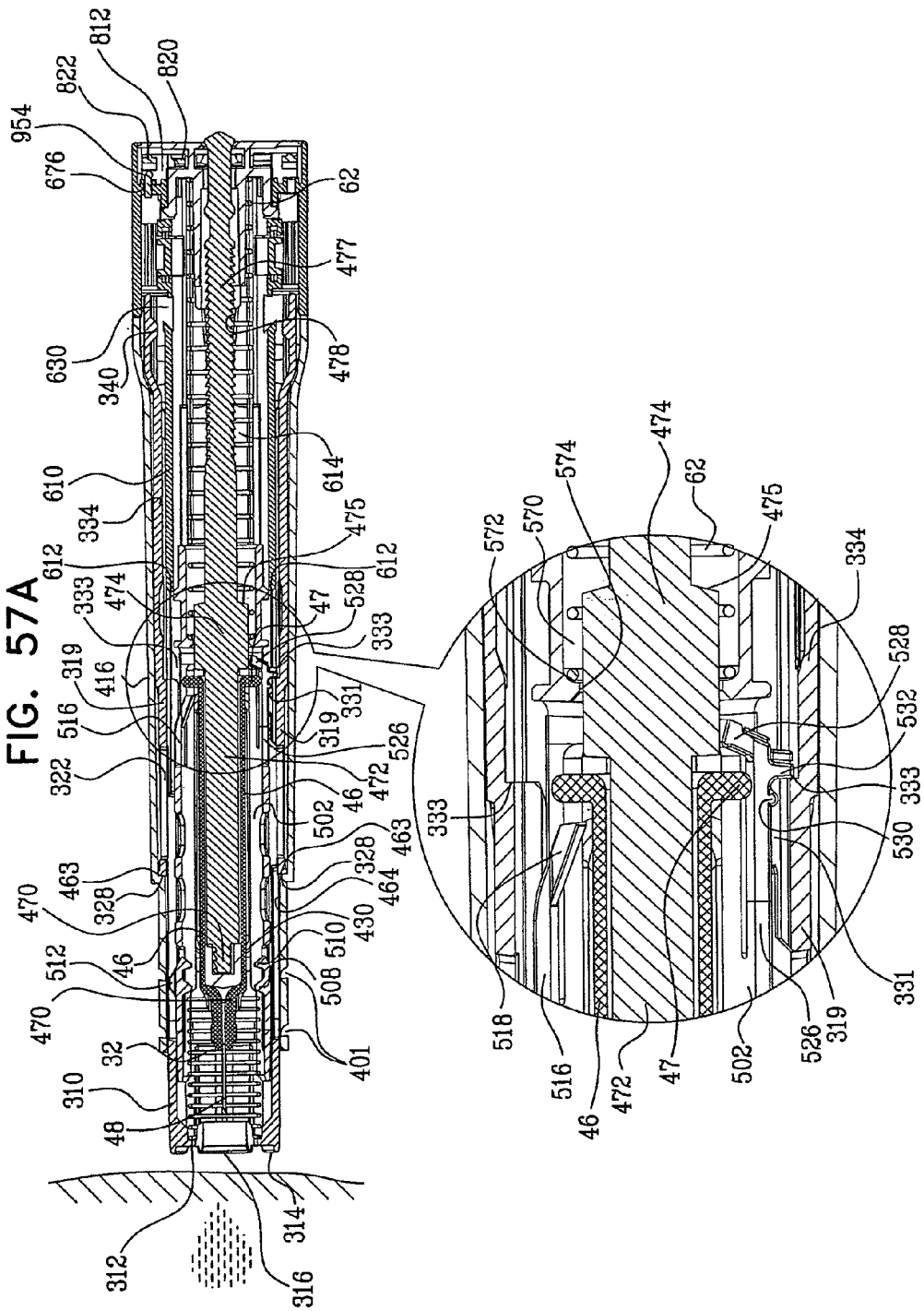

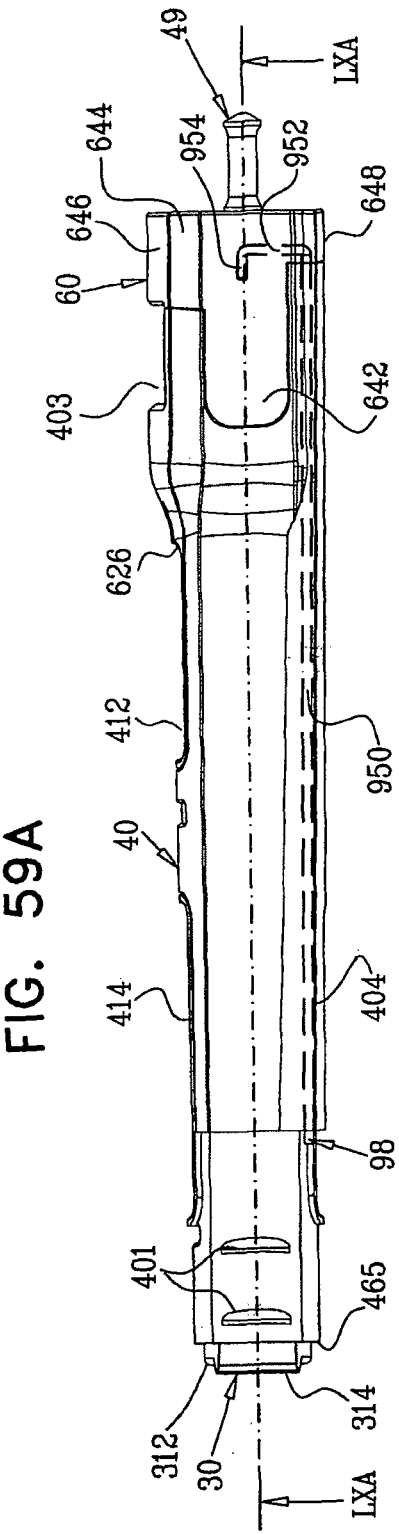
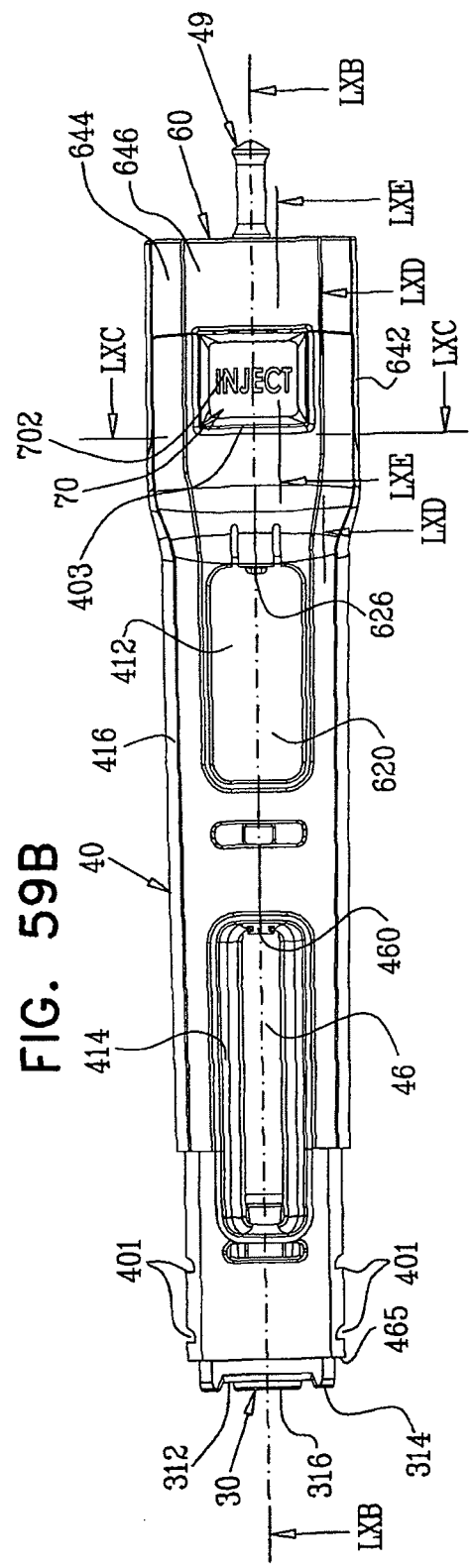
FIG. 59A
FIG. 59B

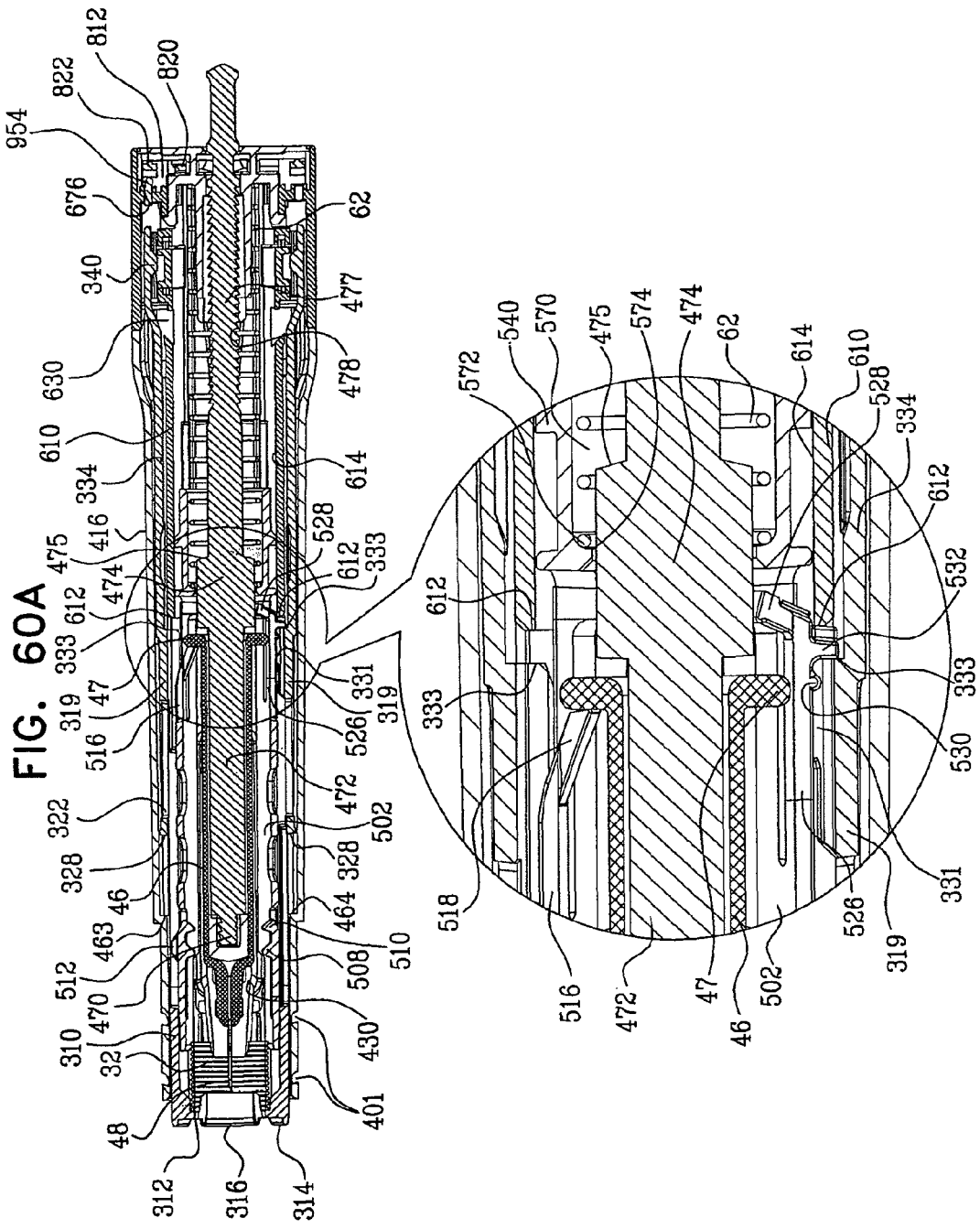

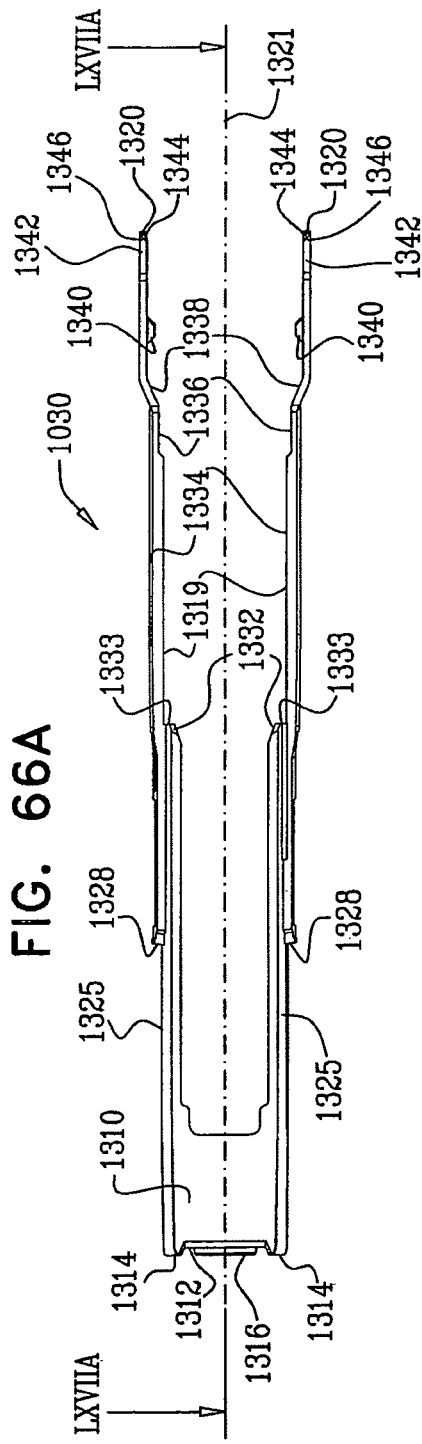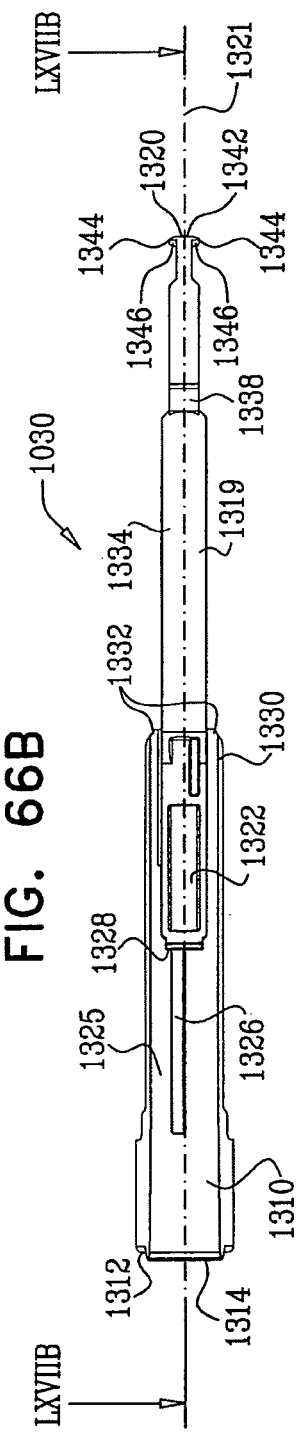

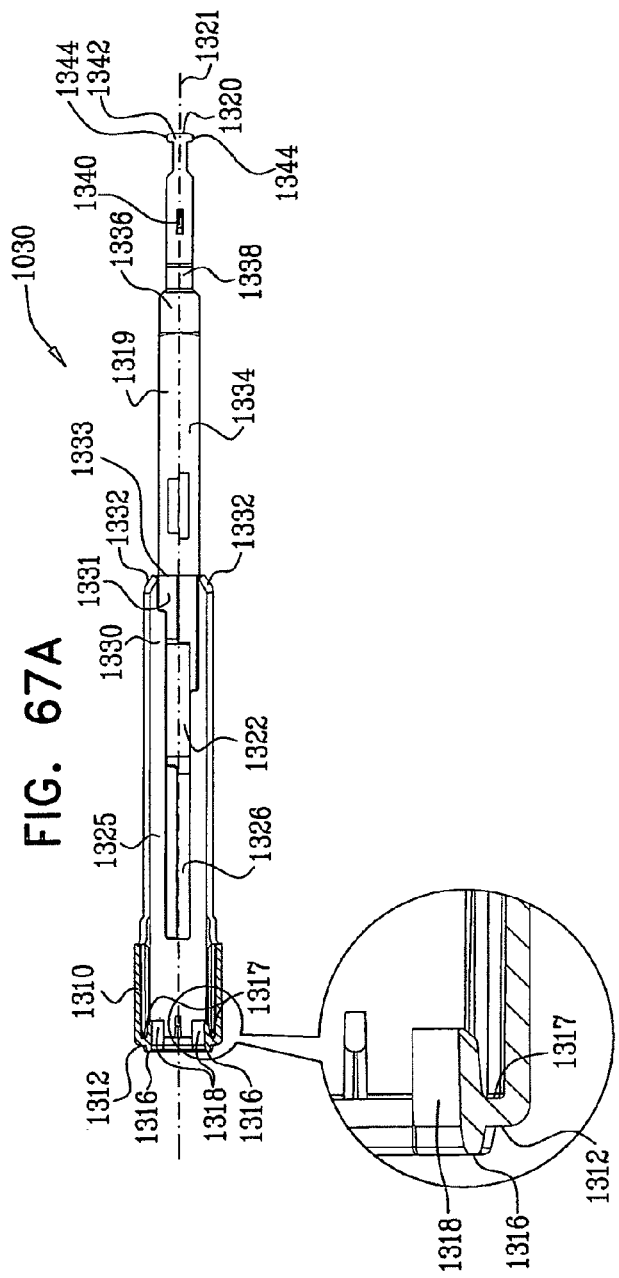

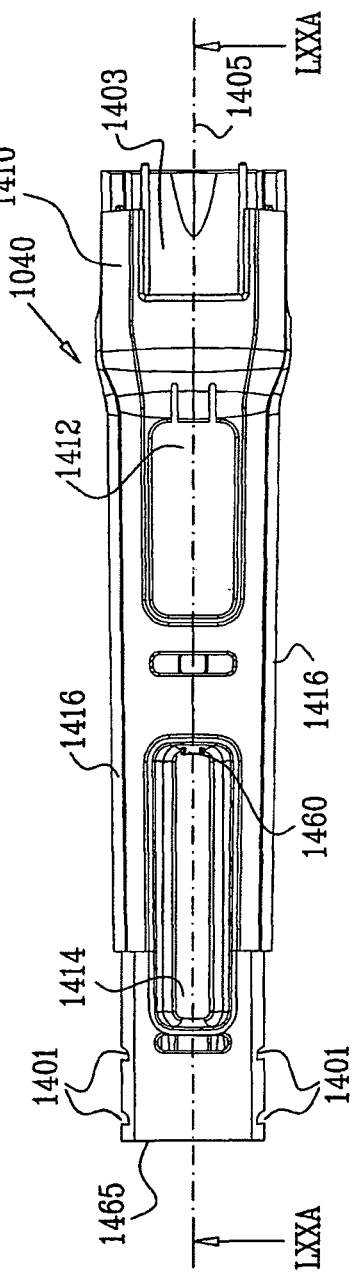
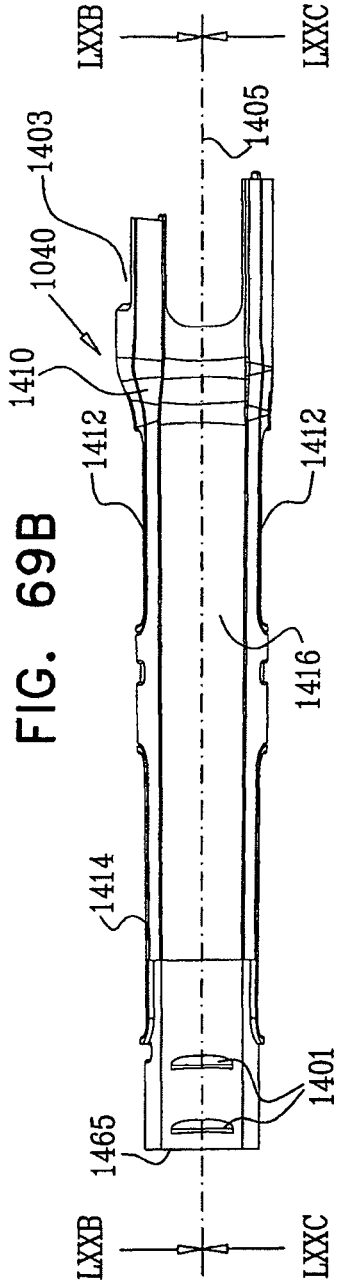

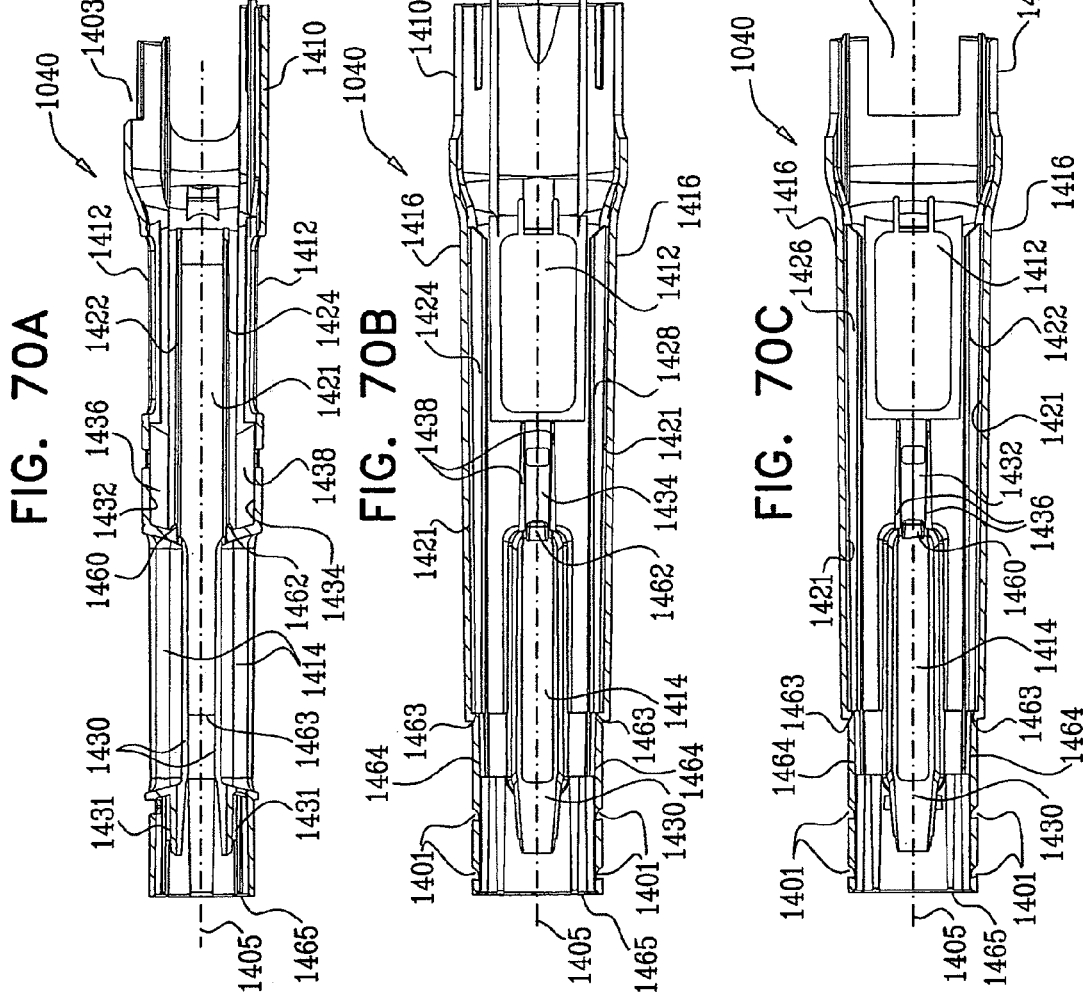

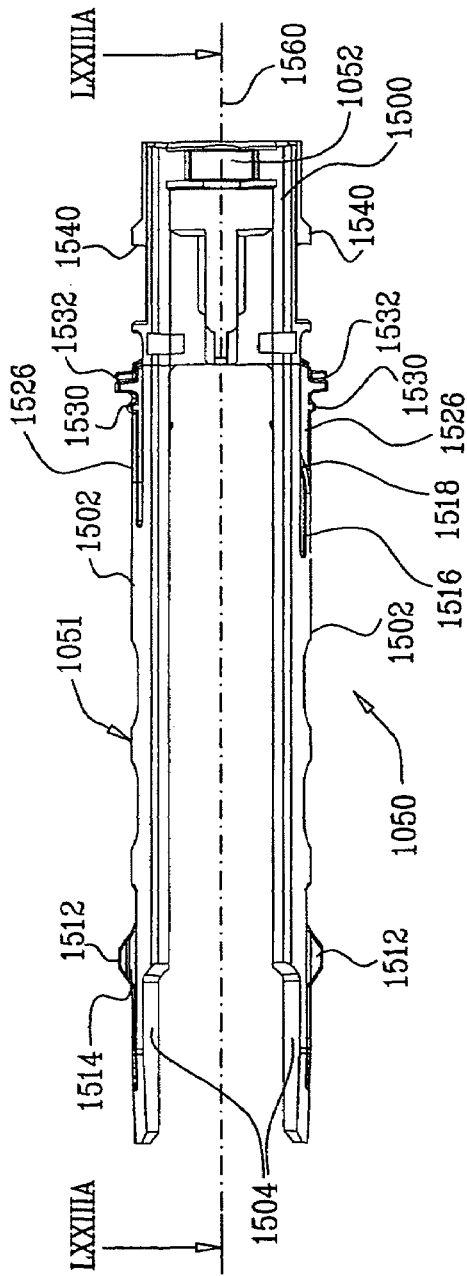
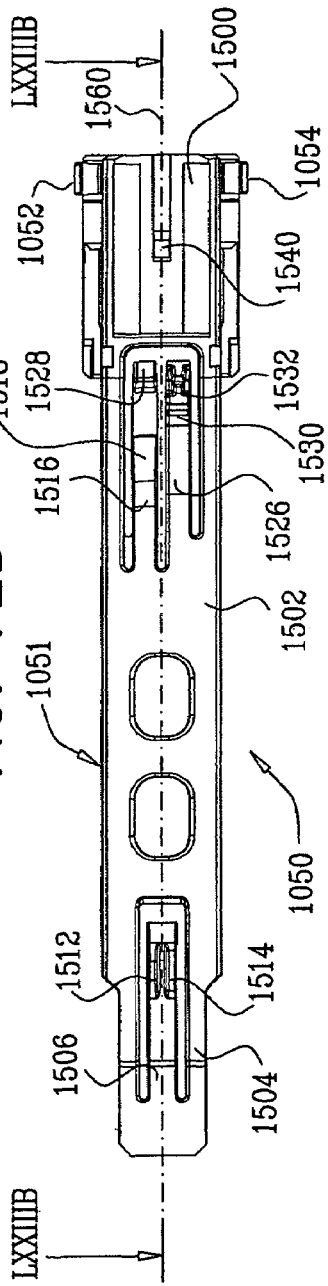

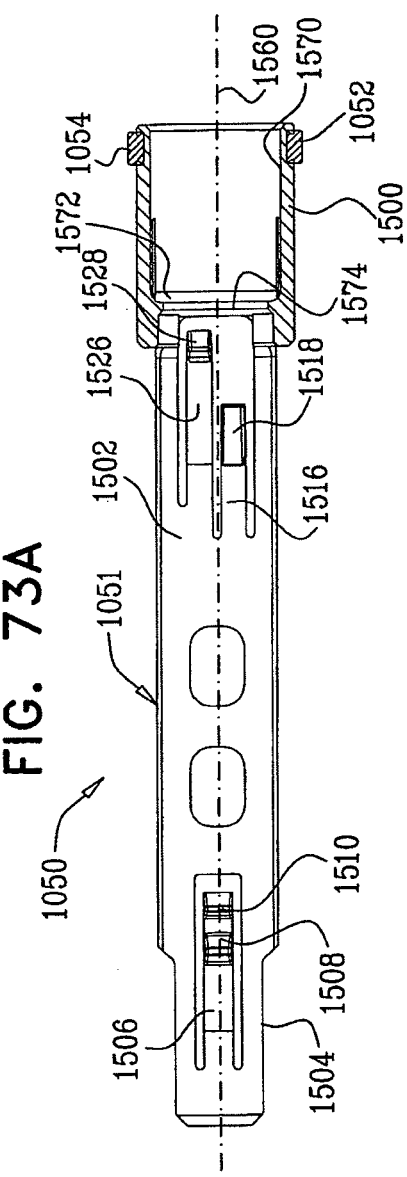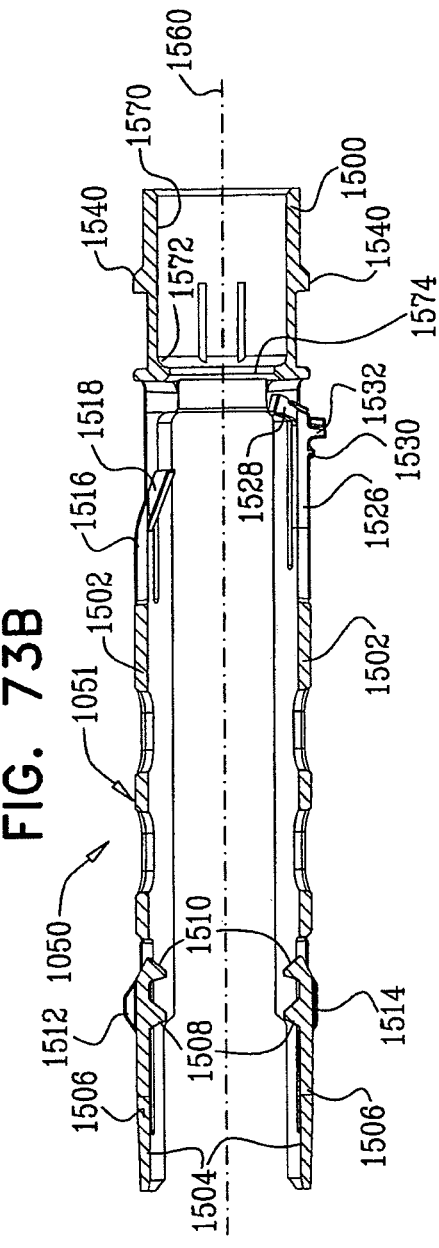

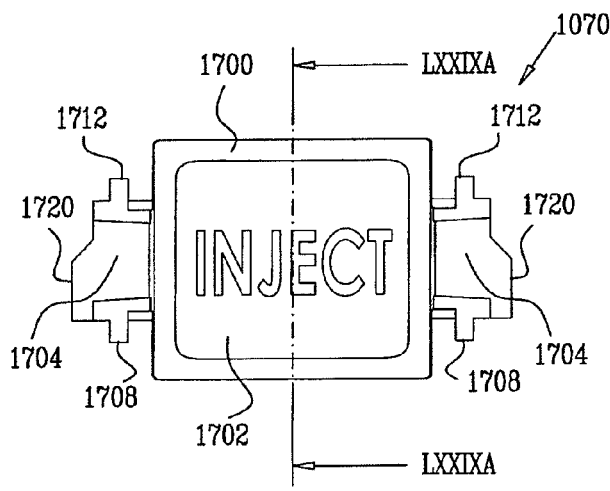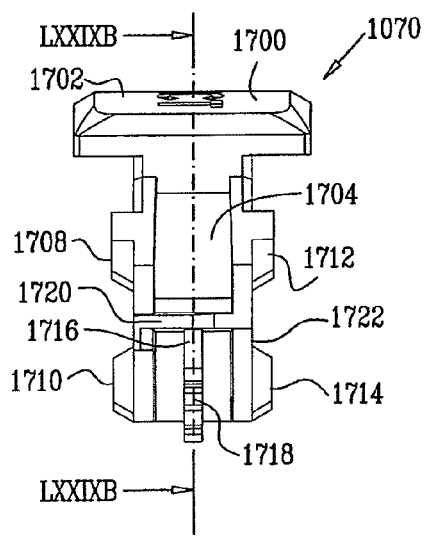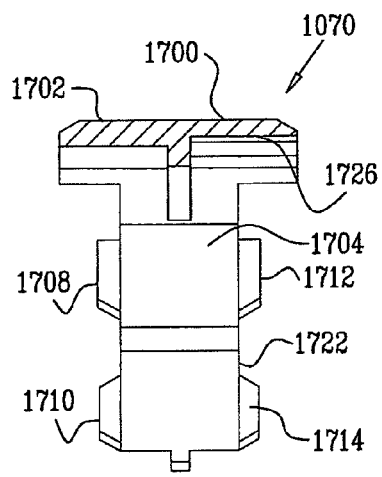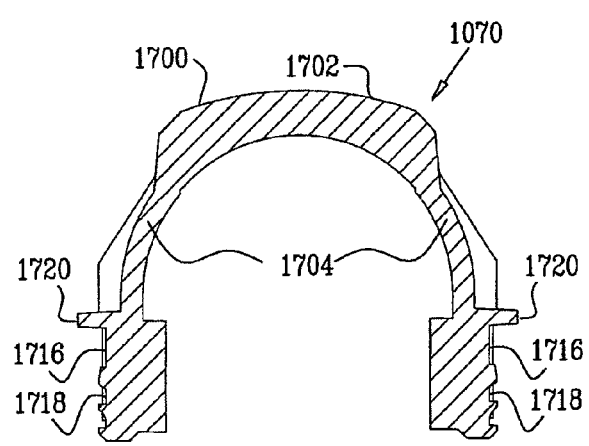

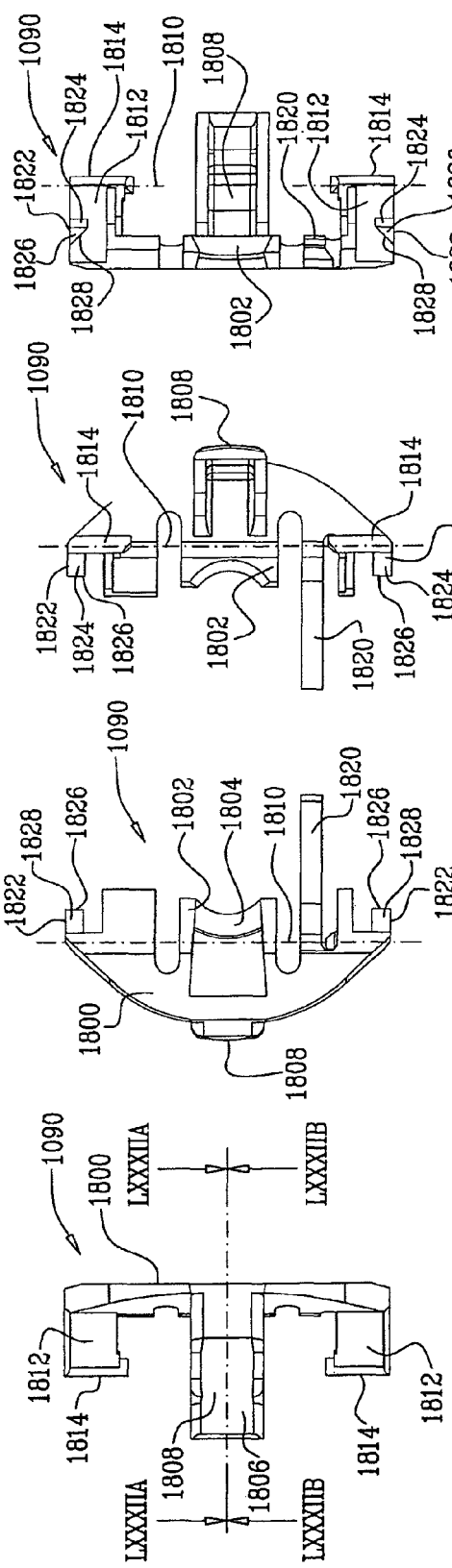

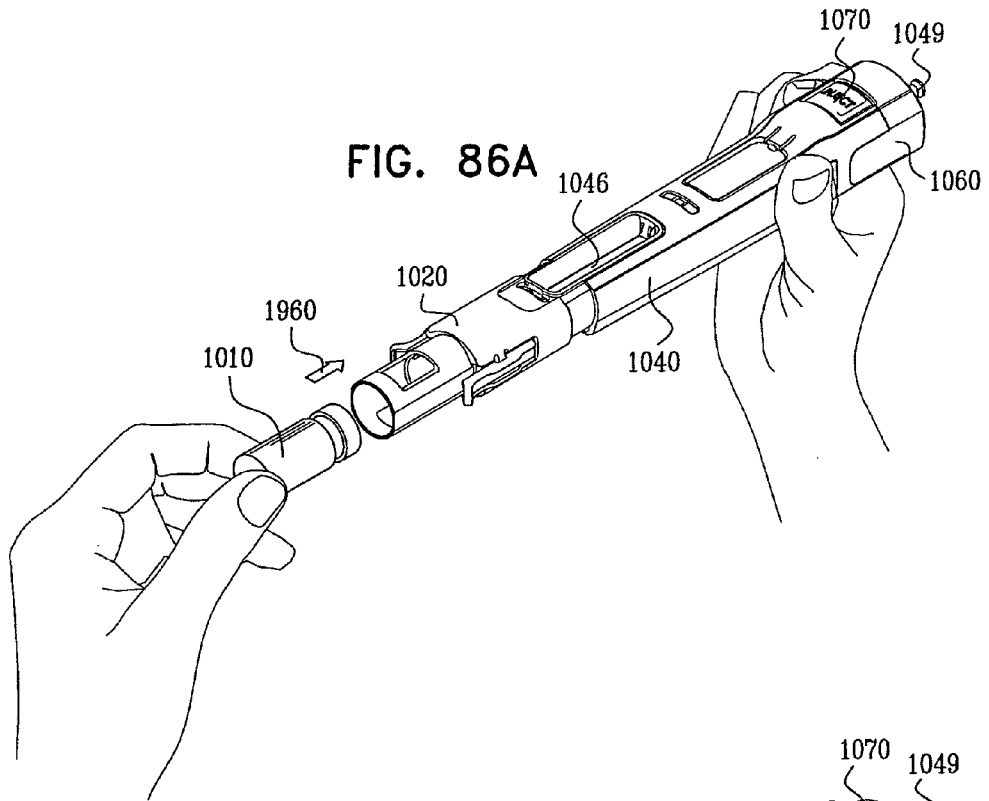
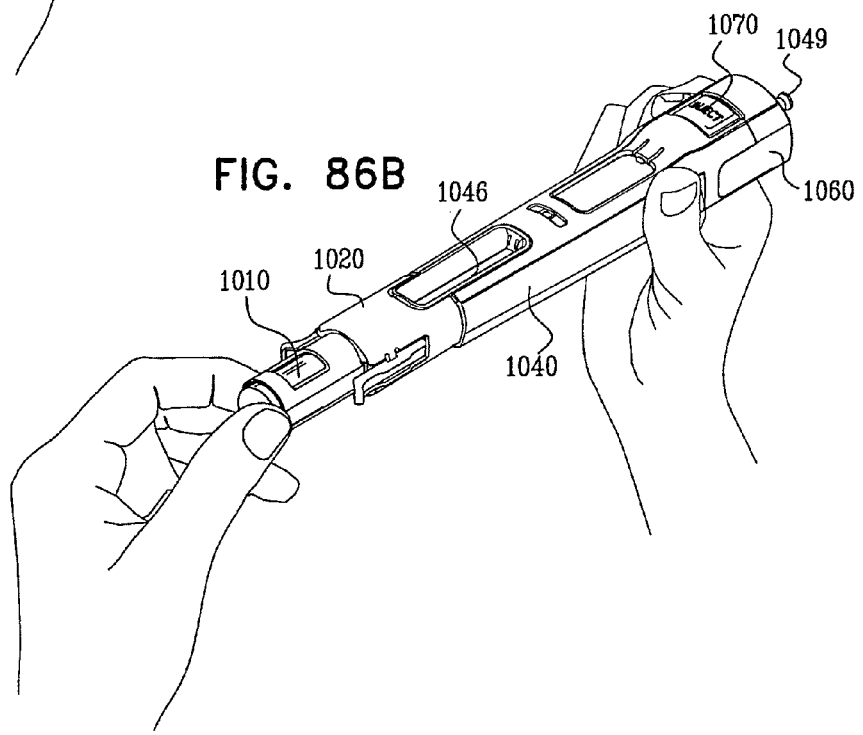

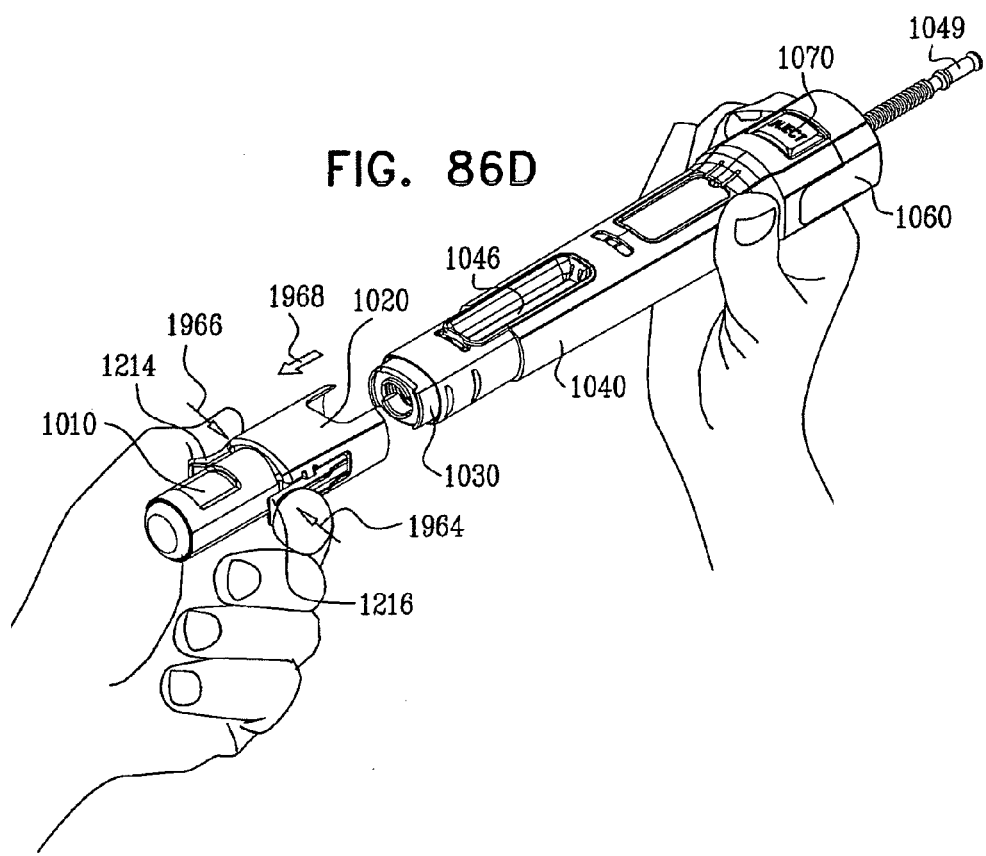

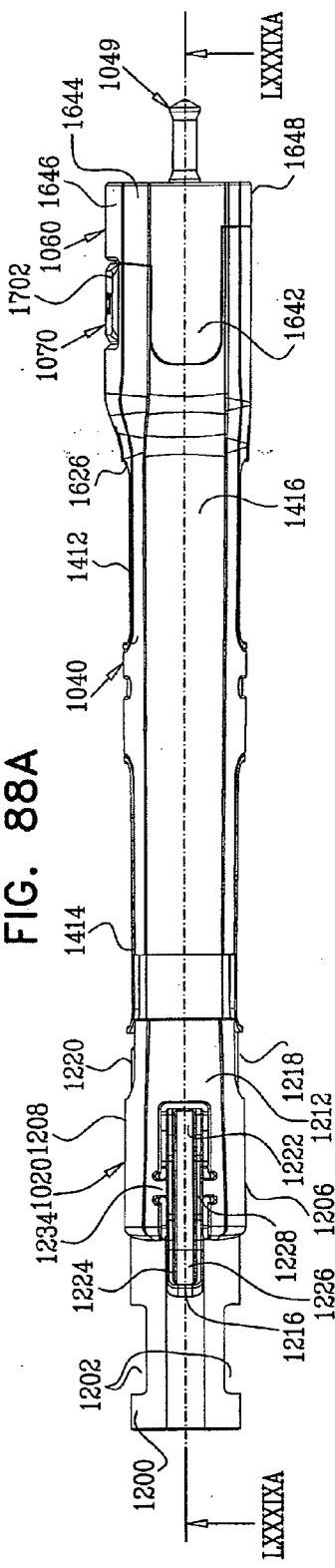
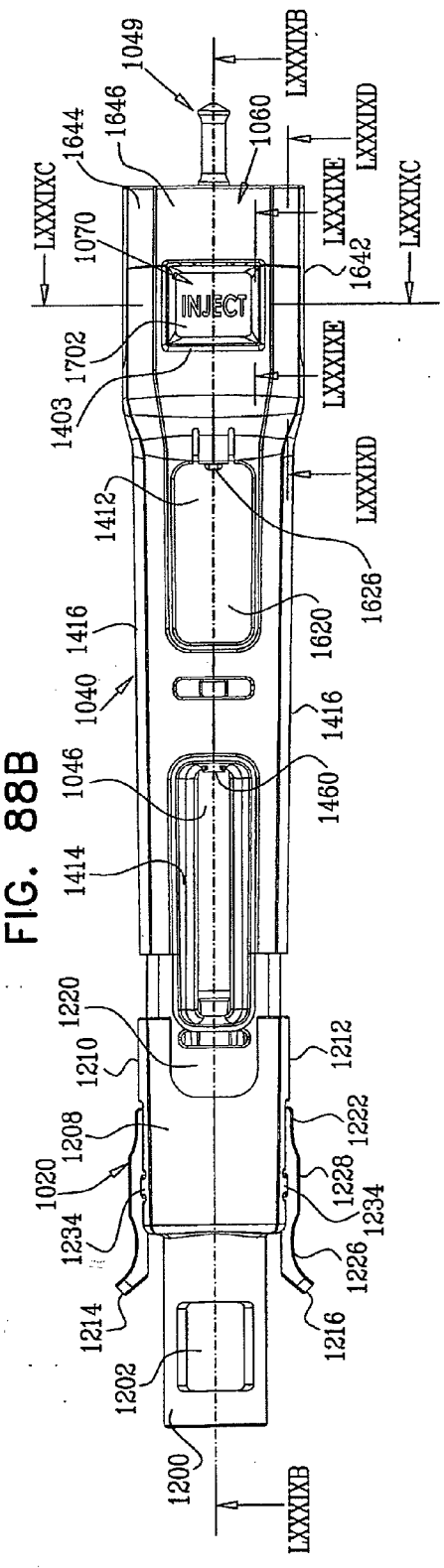
FIG. 88A
FIG. 88B

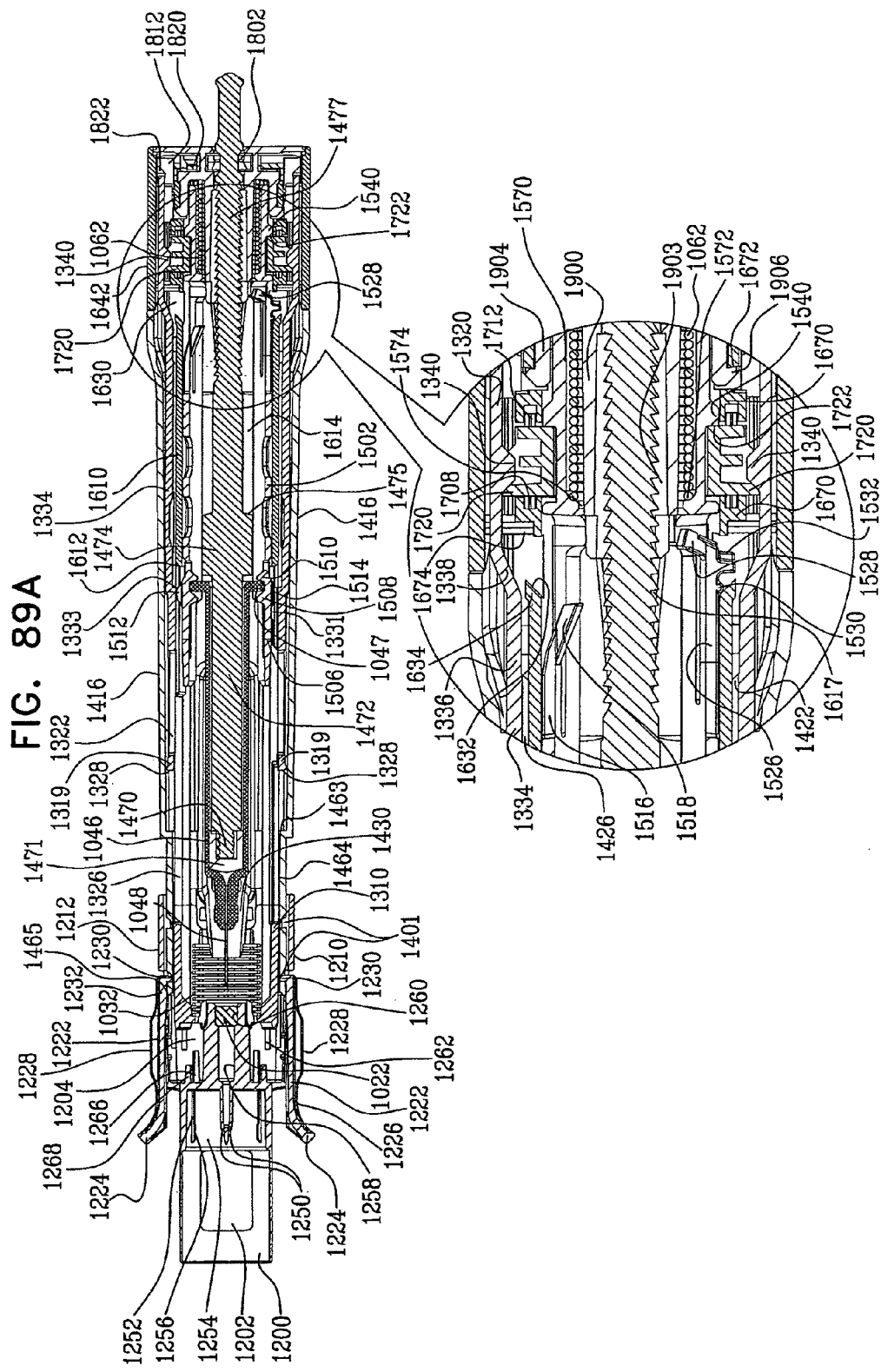

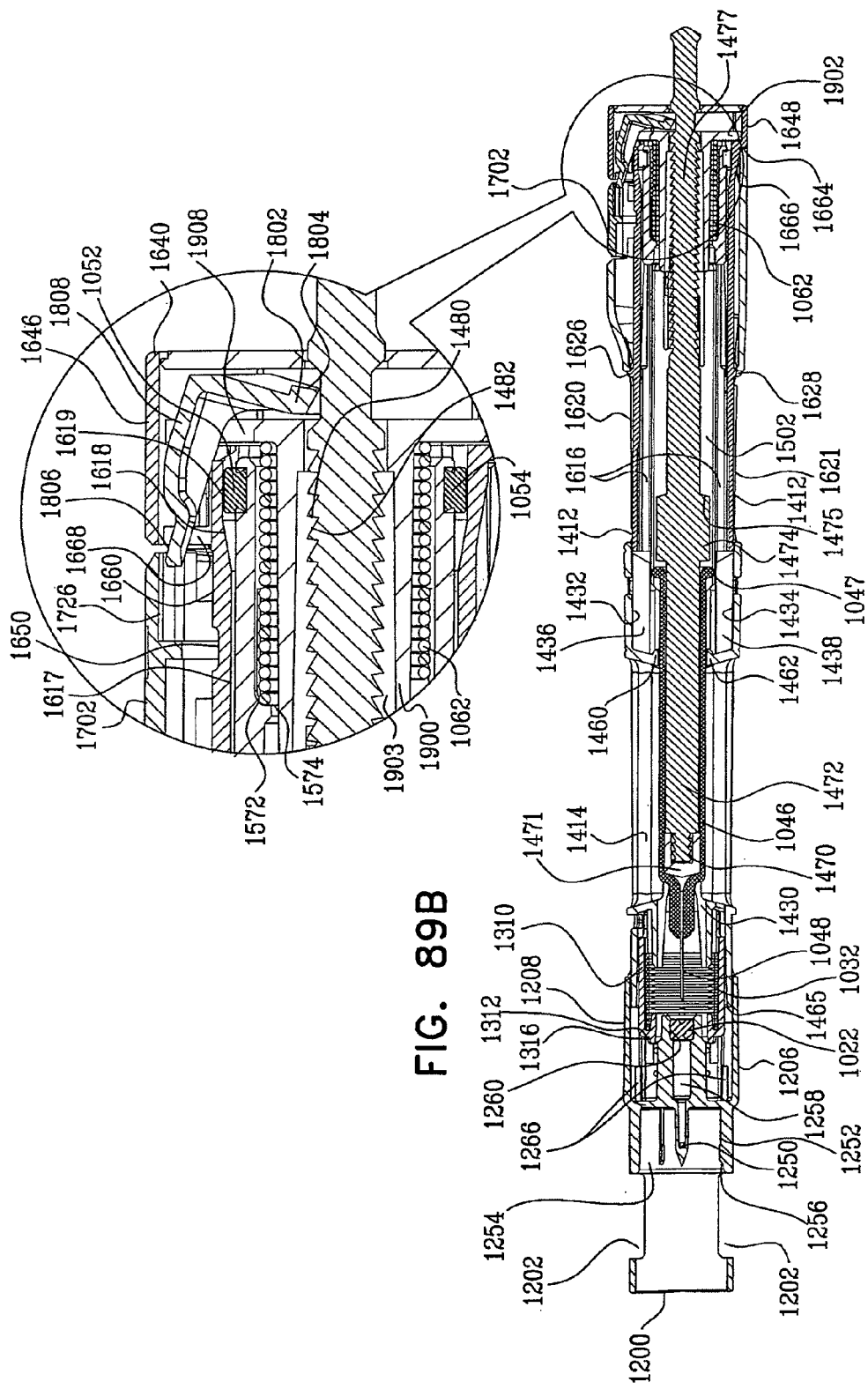

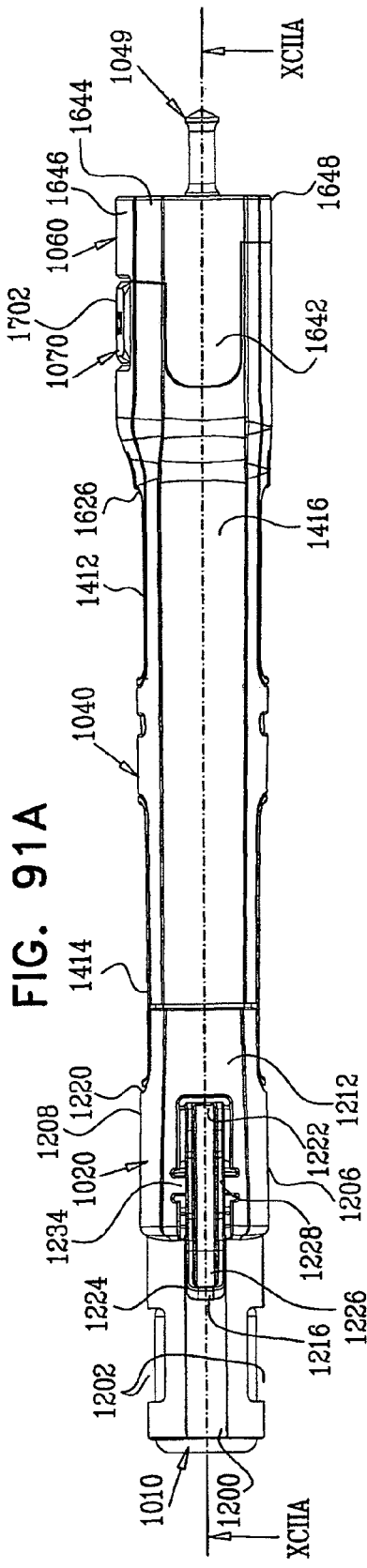
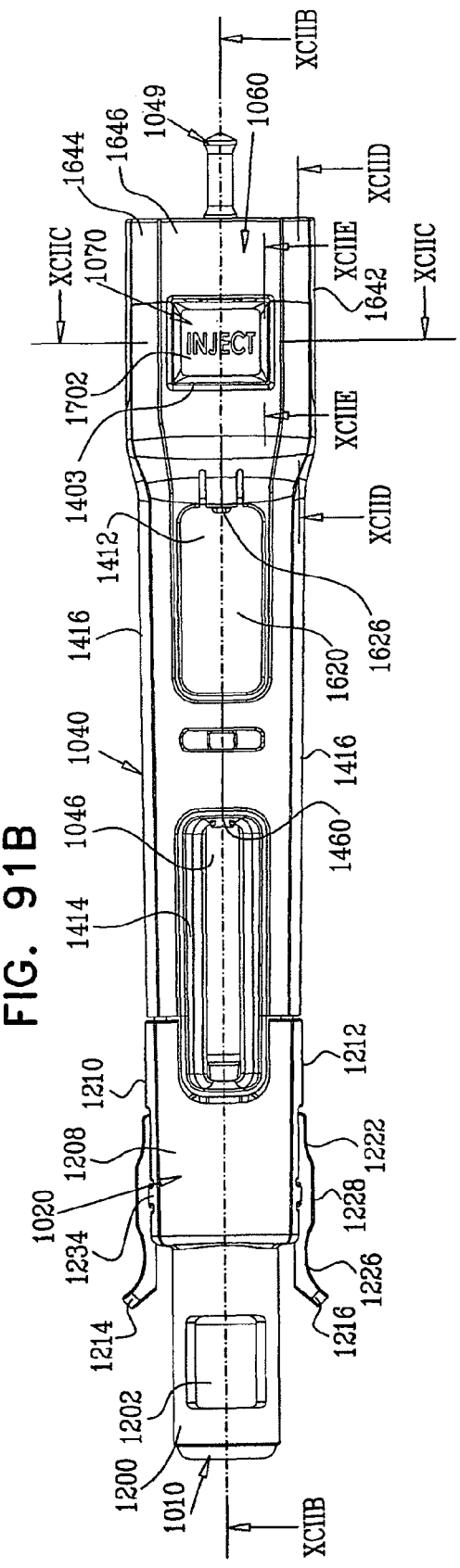
FIG. 91A
FIG. 91B

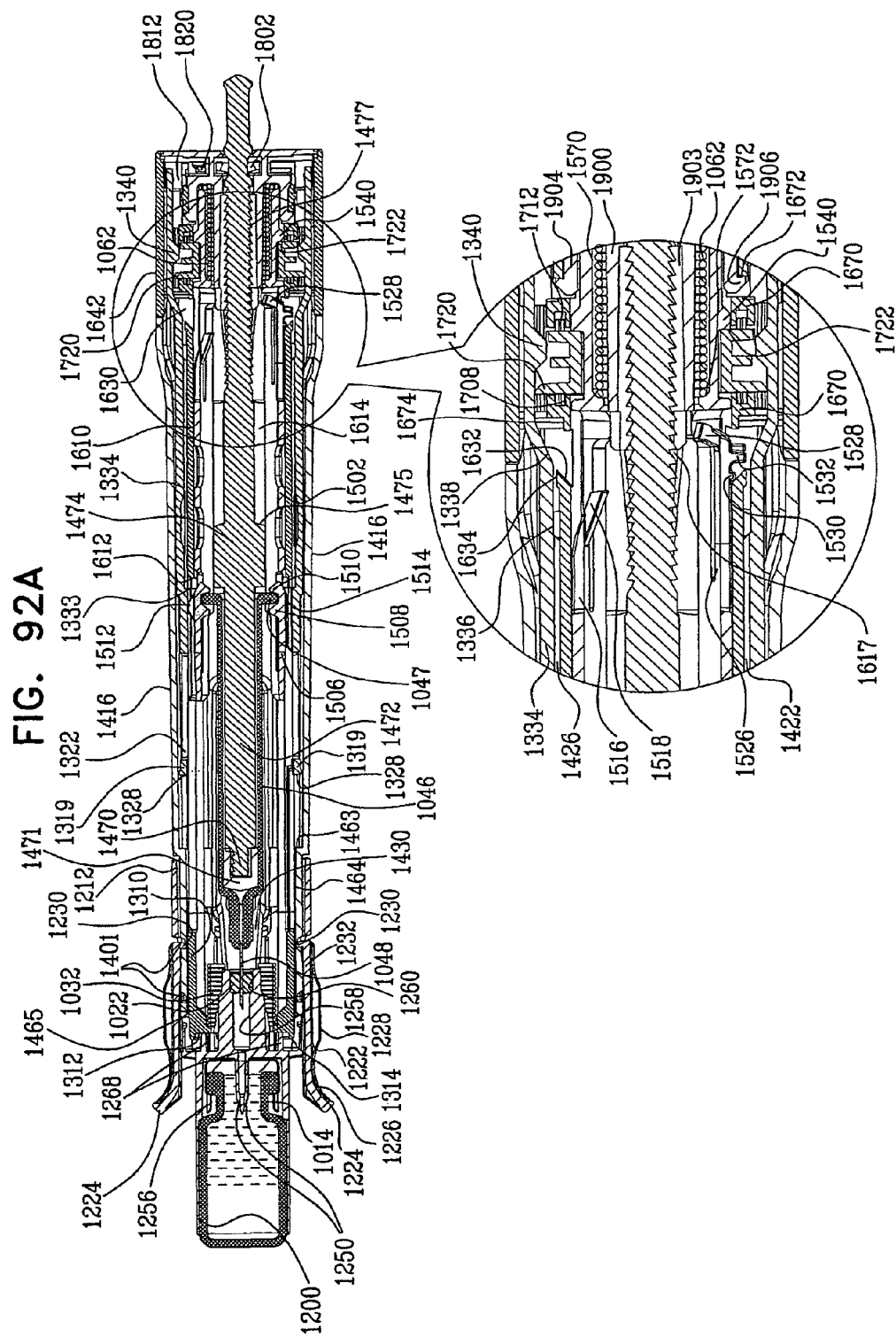

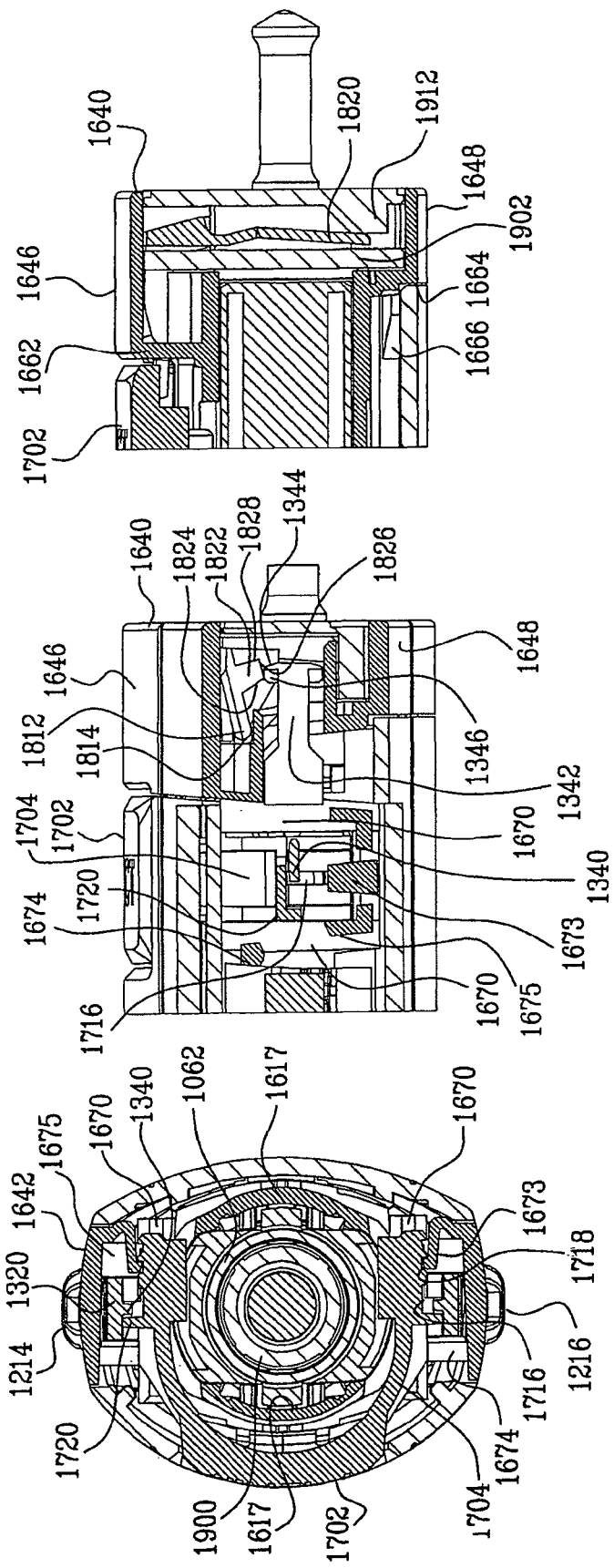

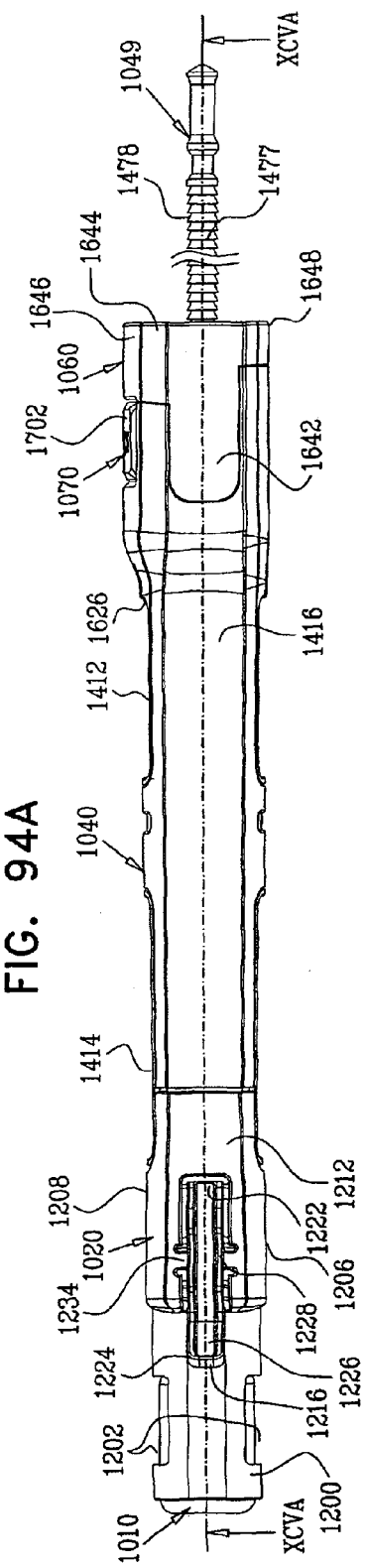
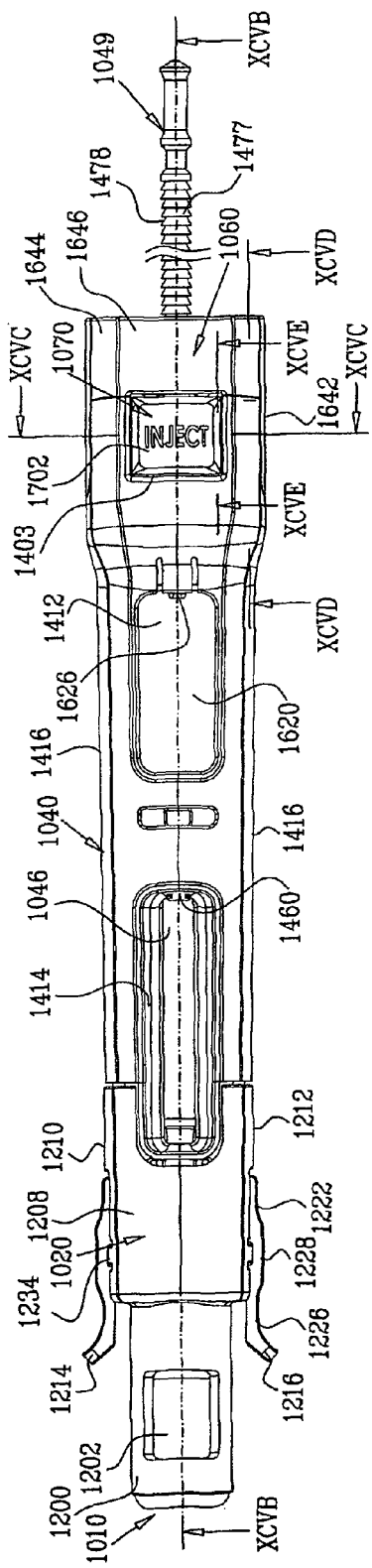

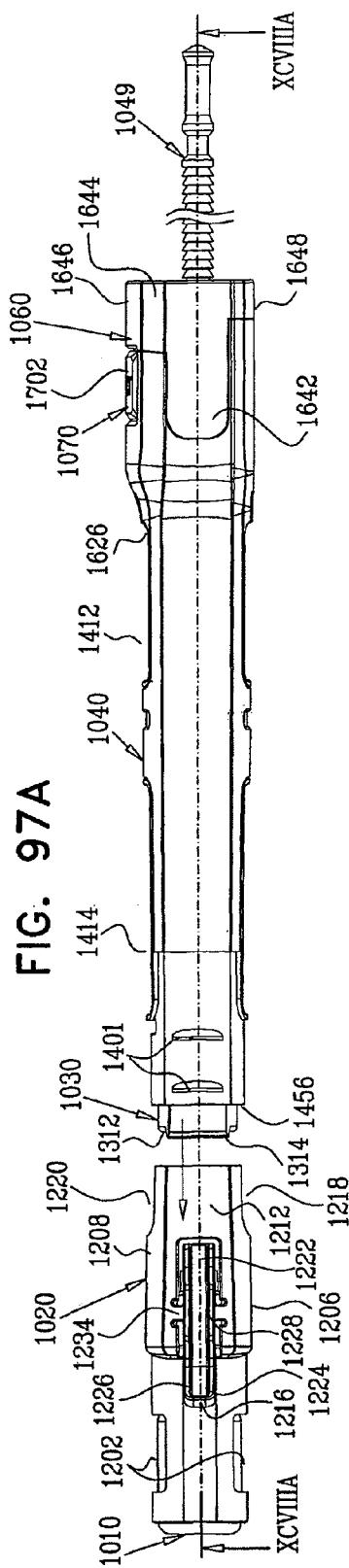
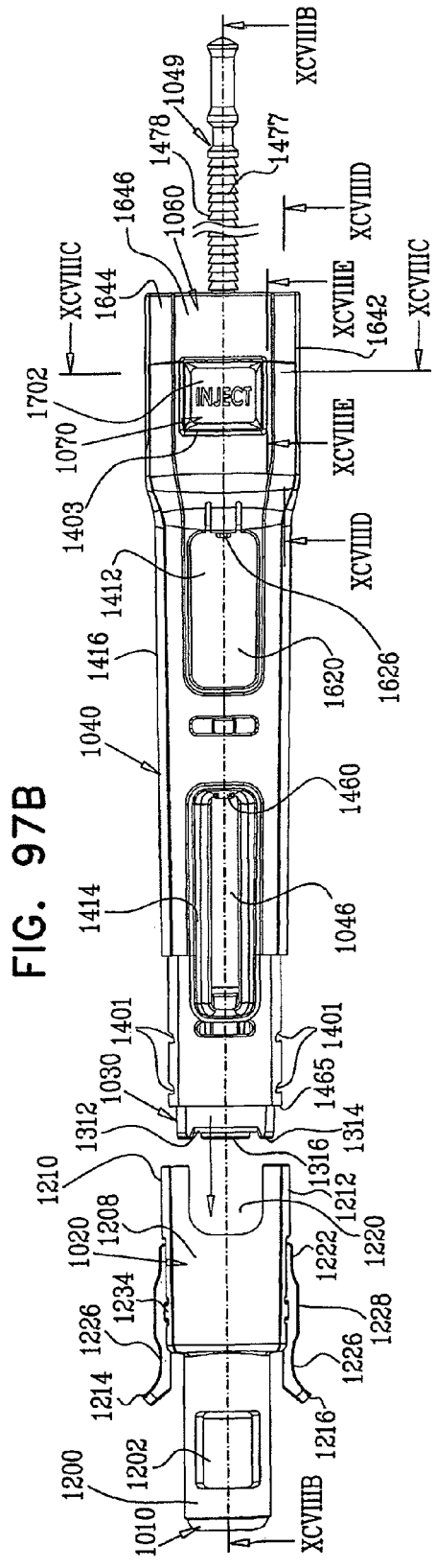
FIG. 97A
FIG. 97B

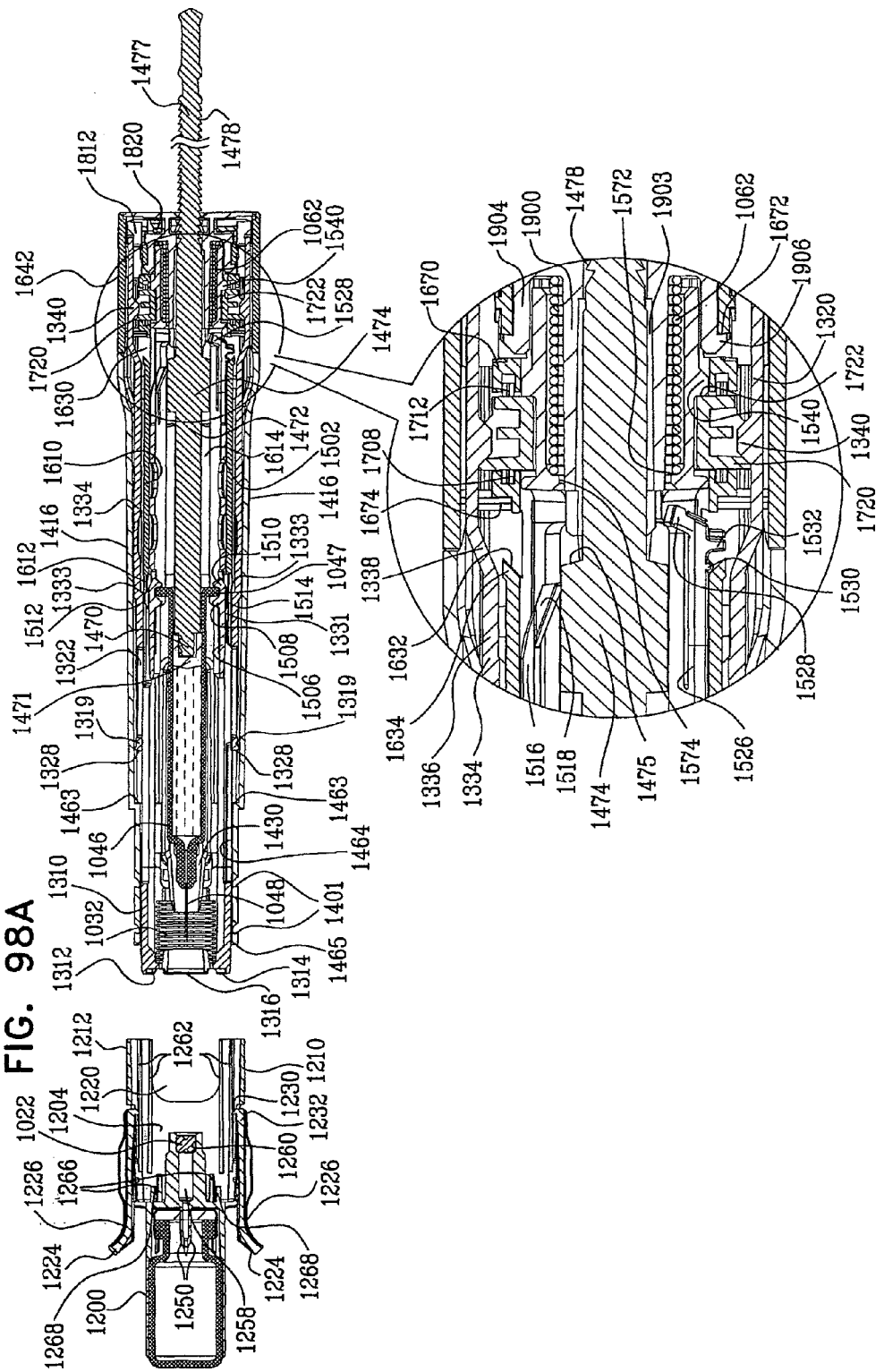

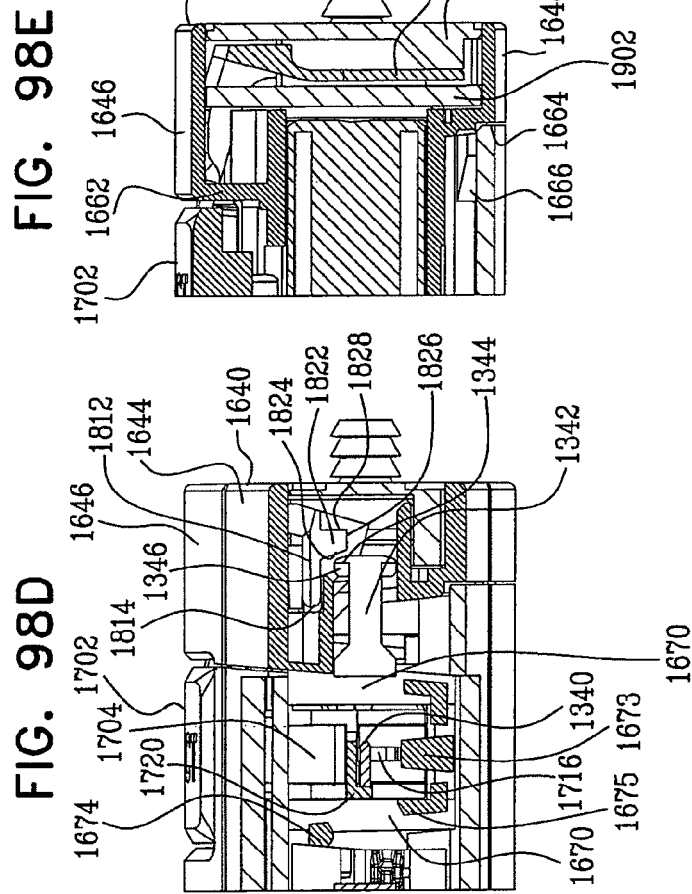
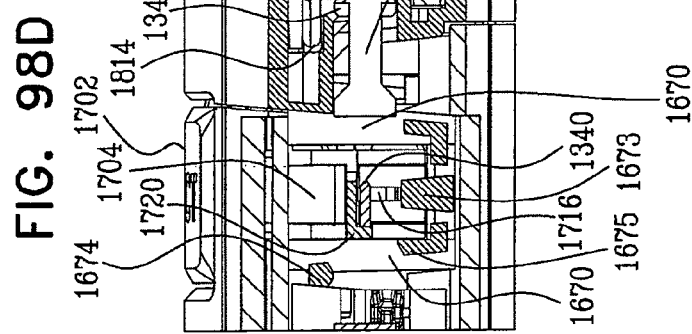
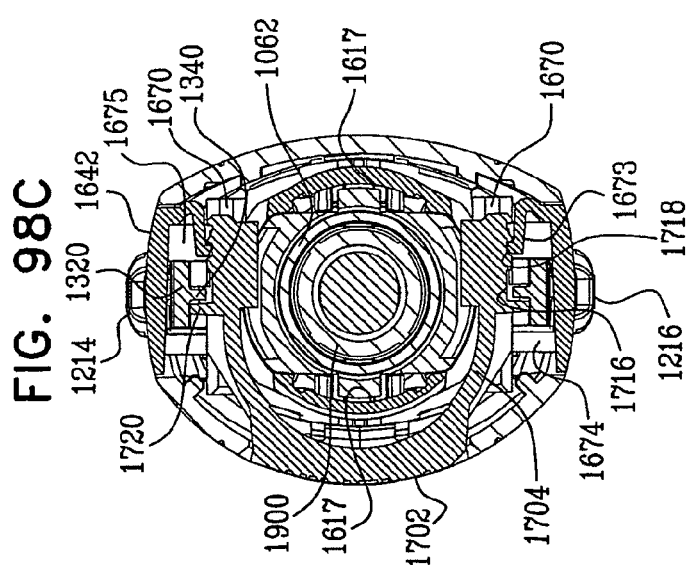

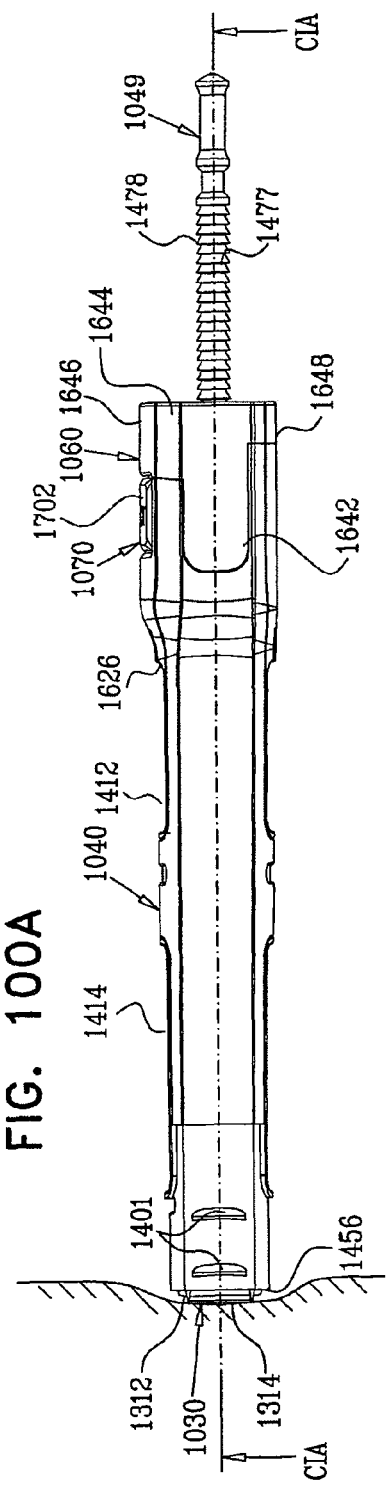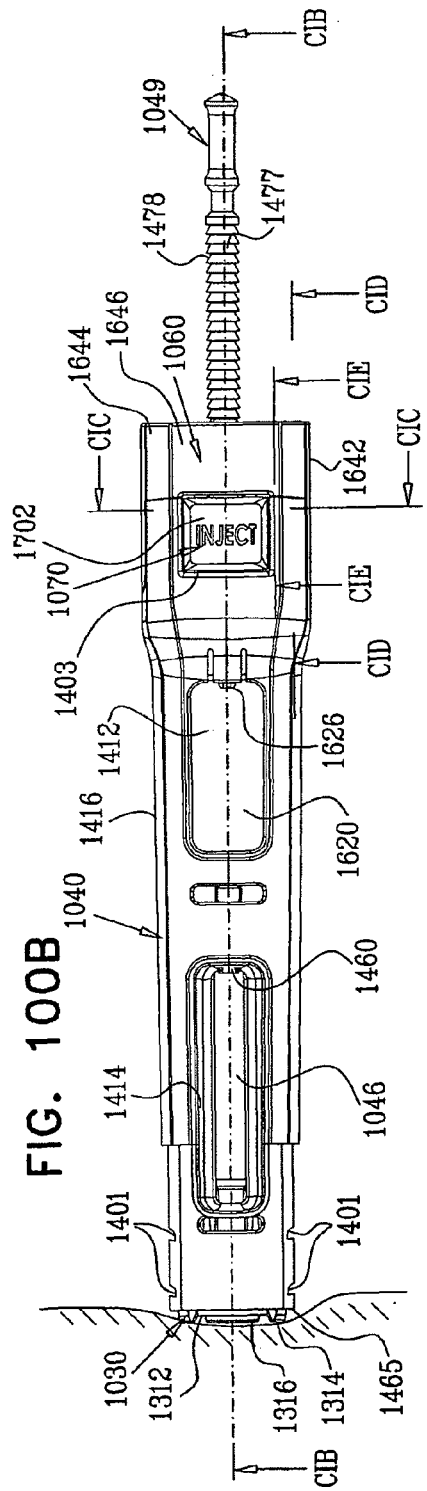

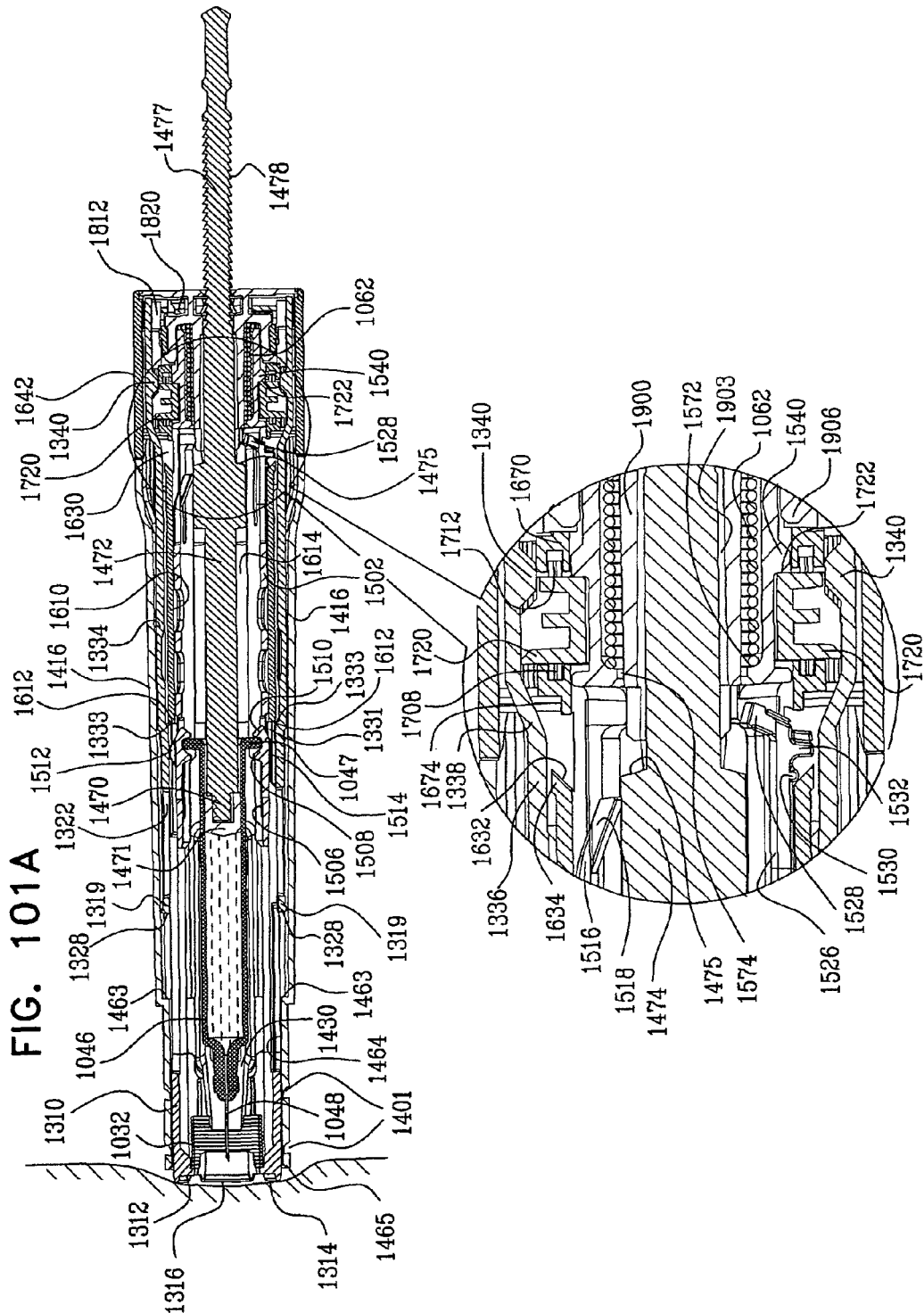

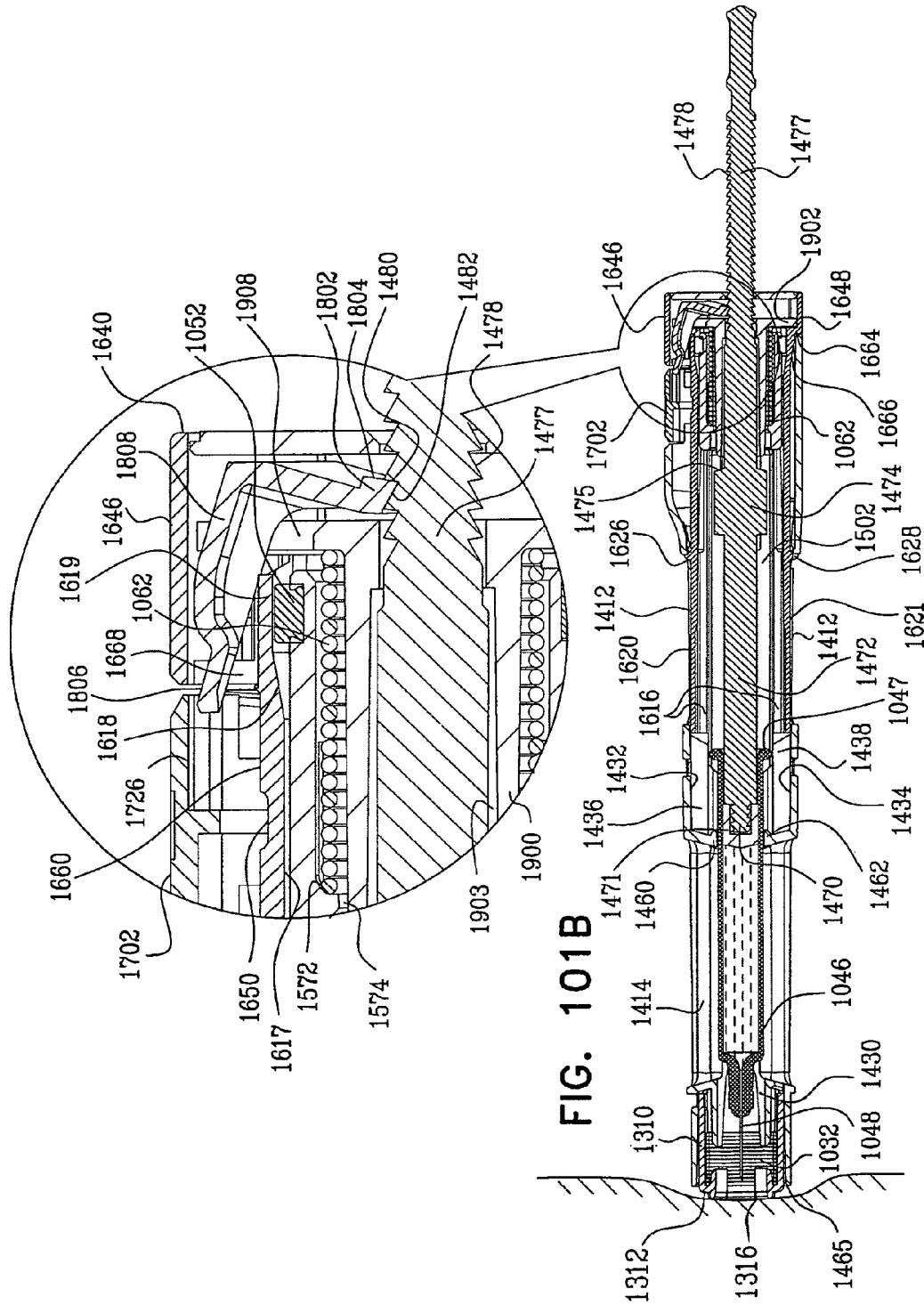

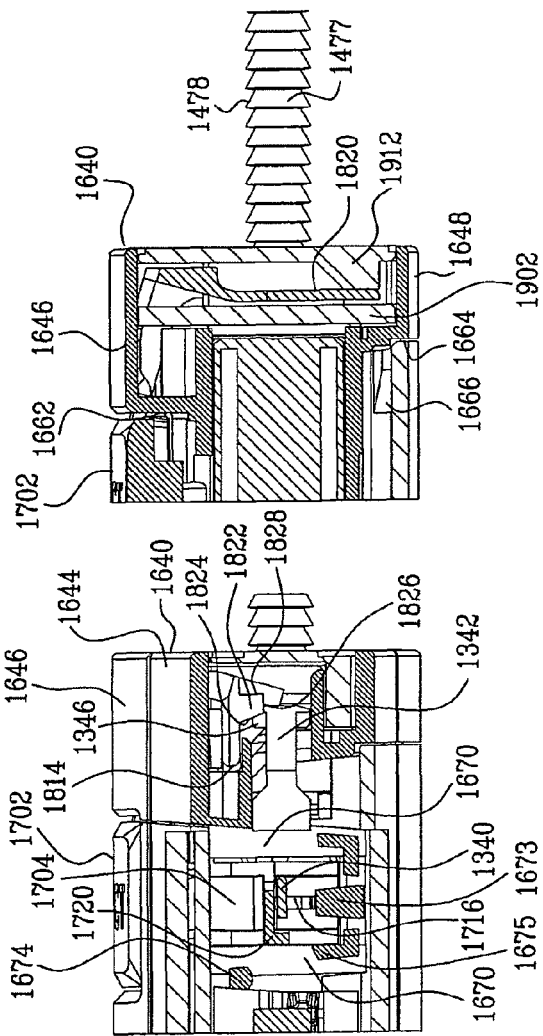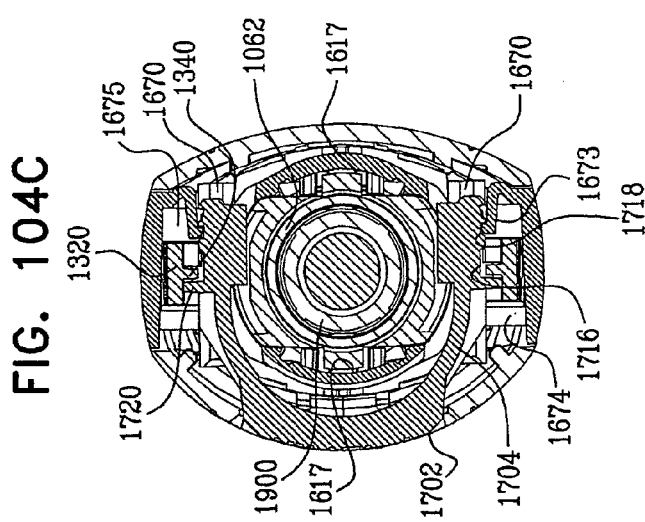

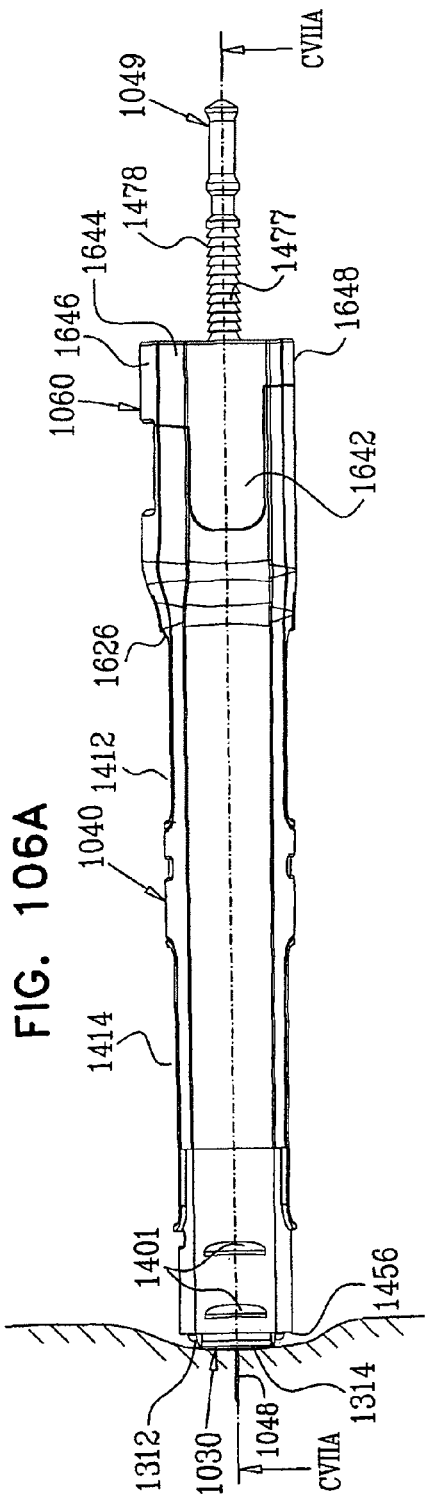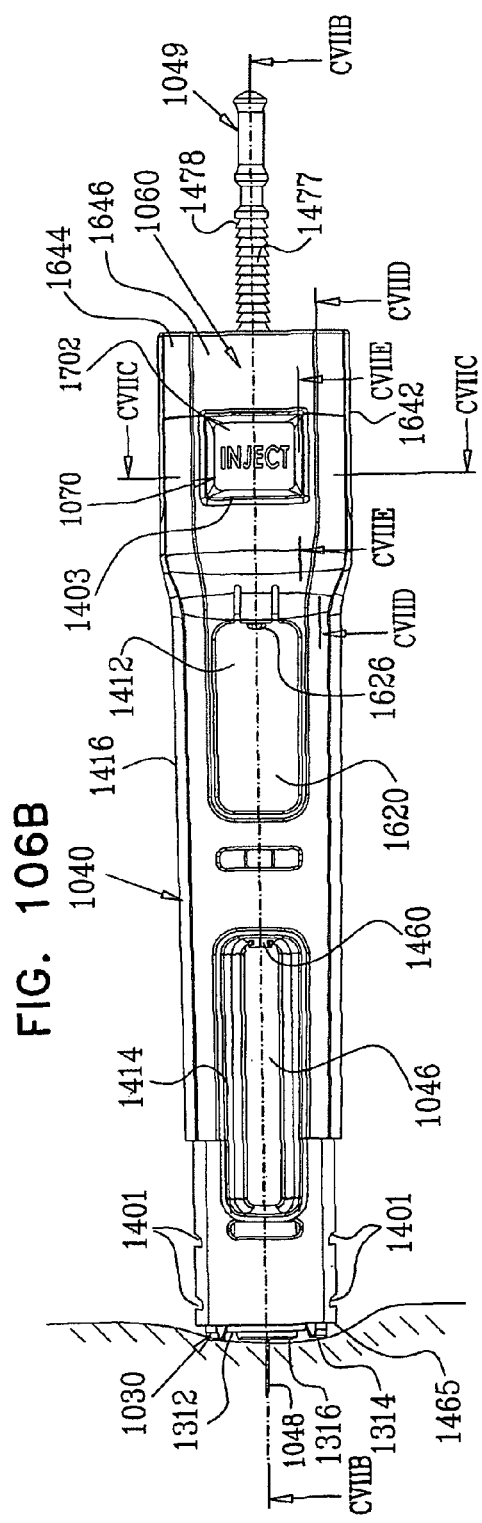

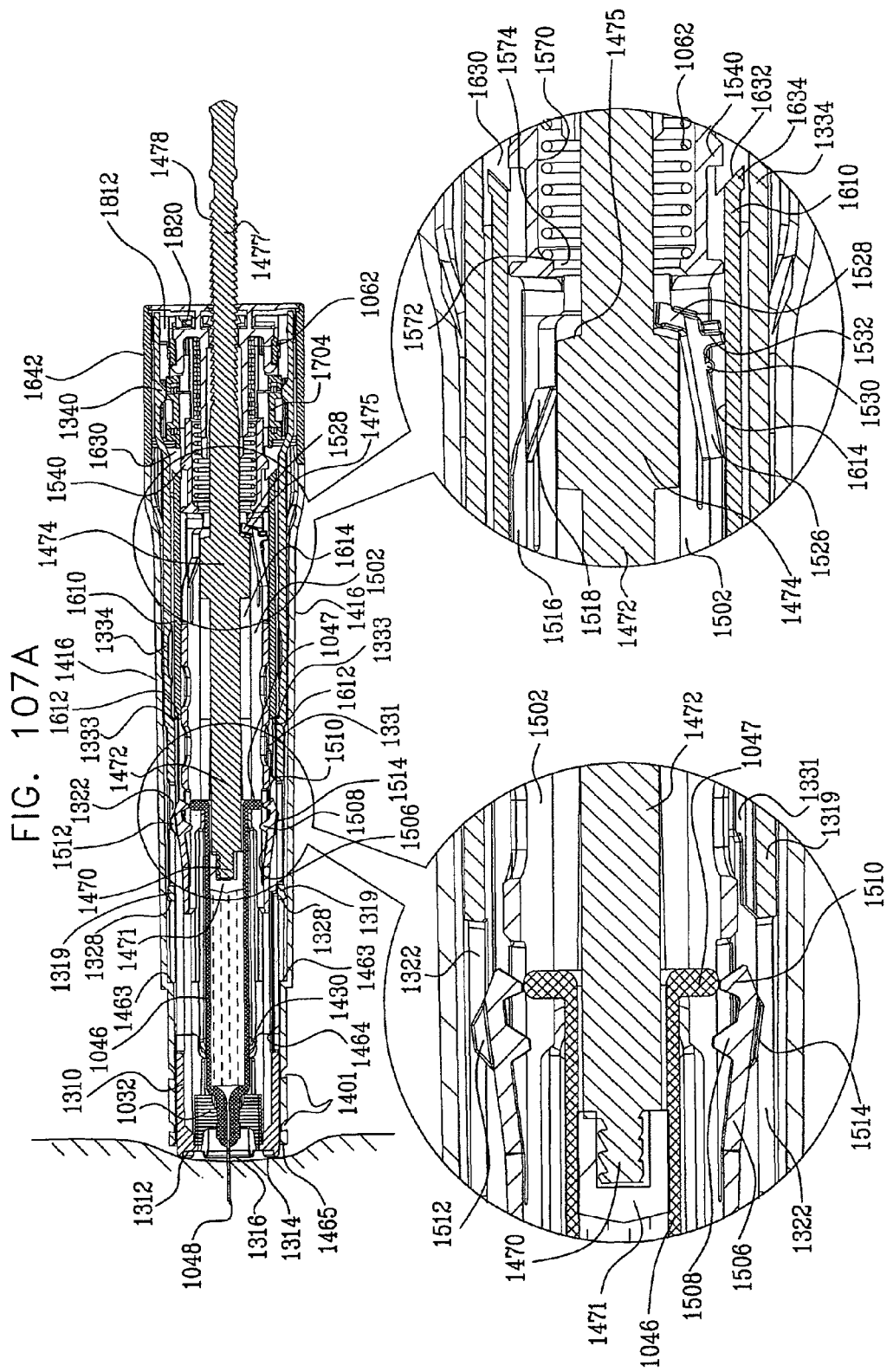

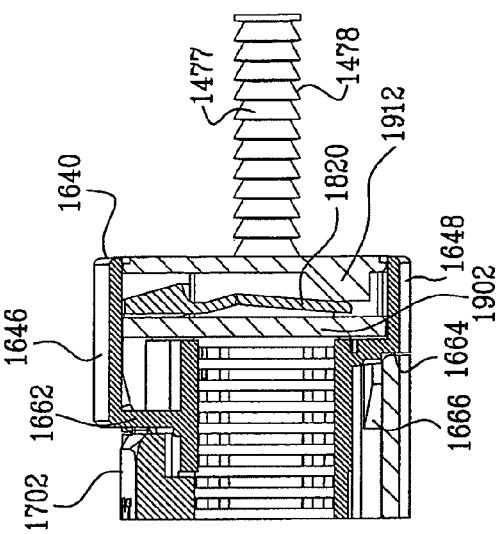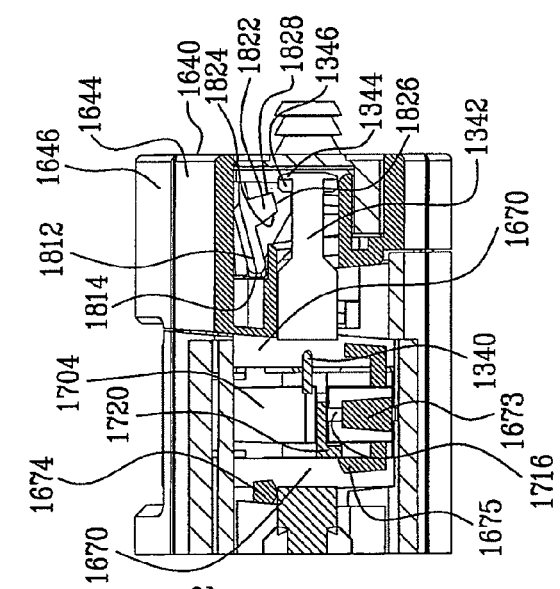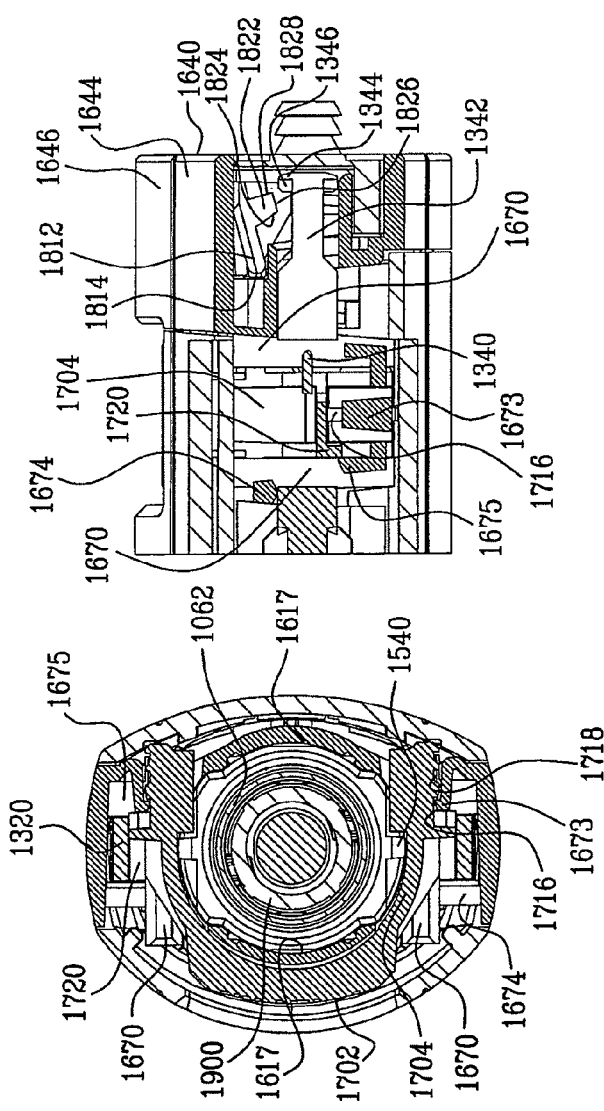

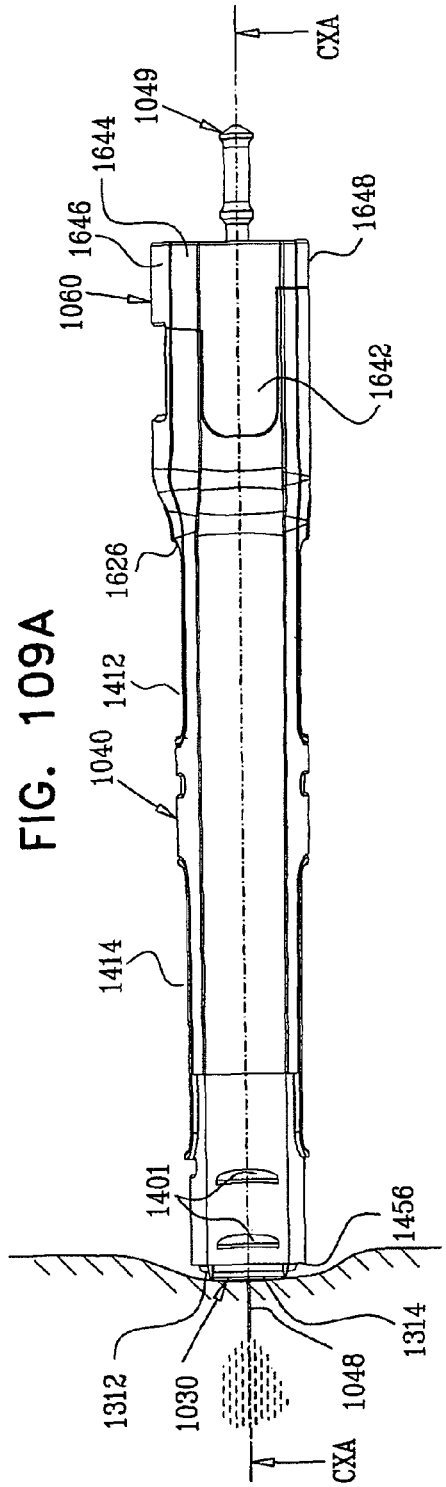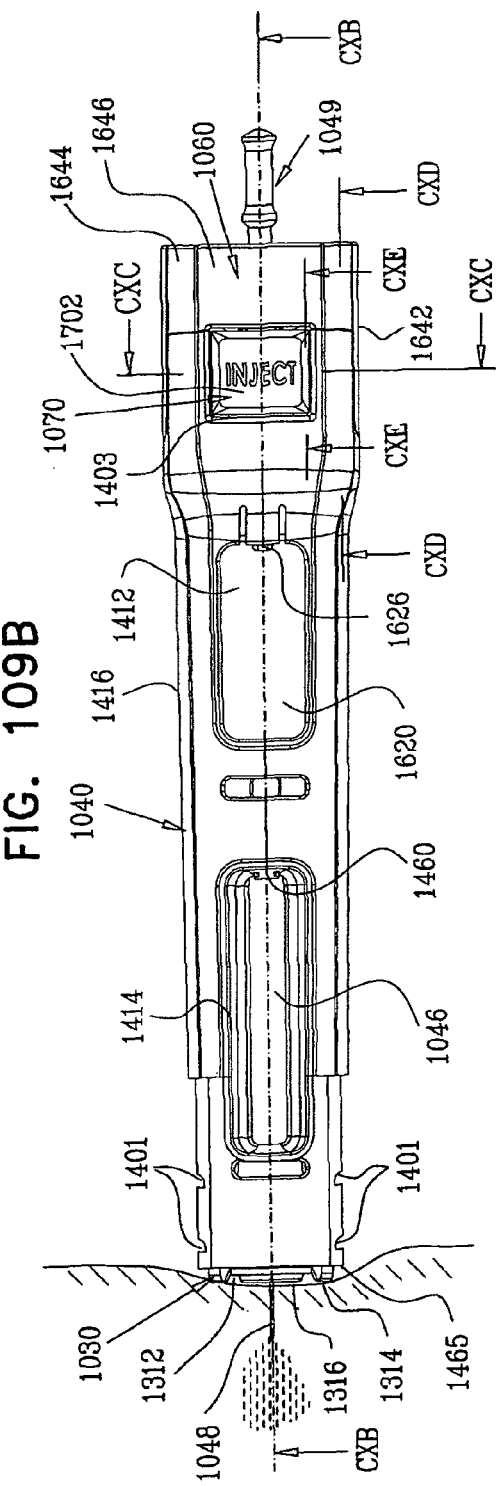

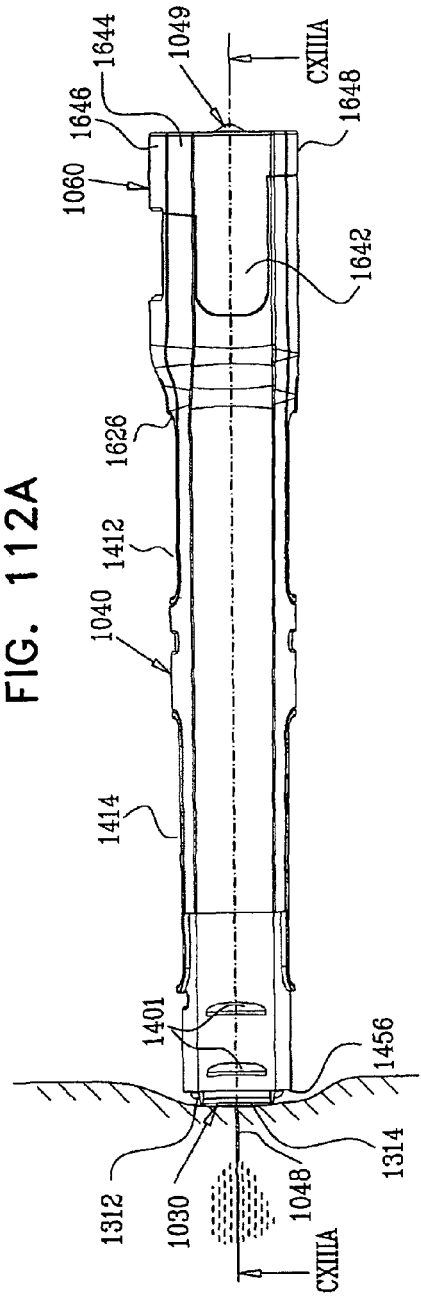
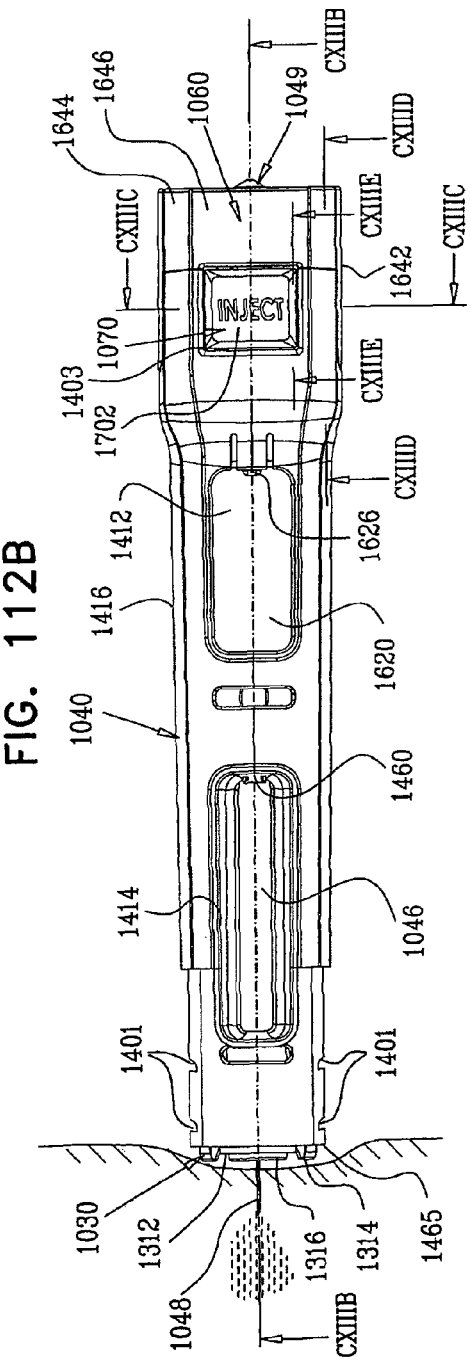
FIG. 112A
FIG. 112B

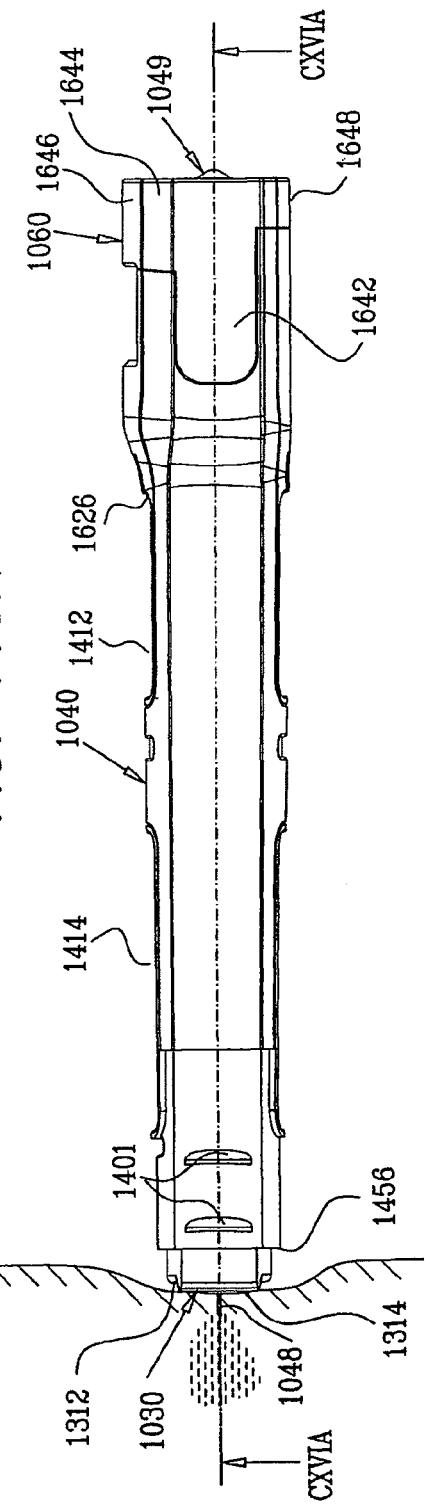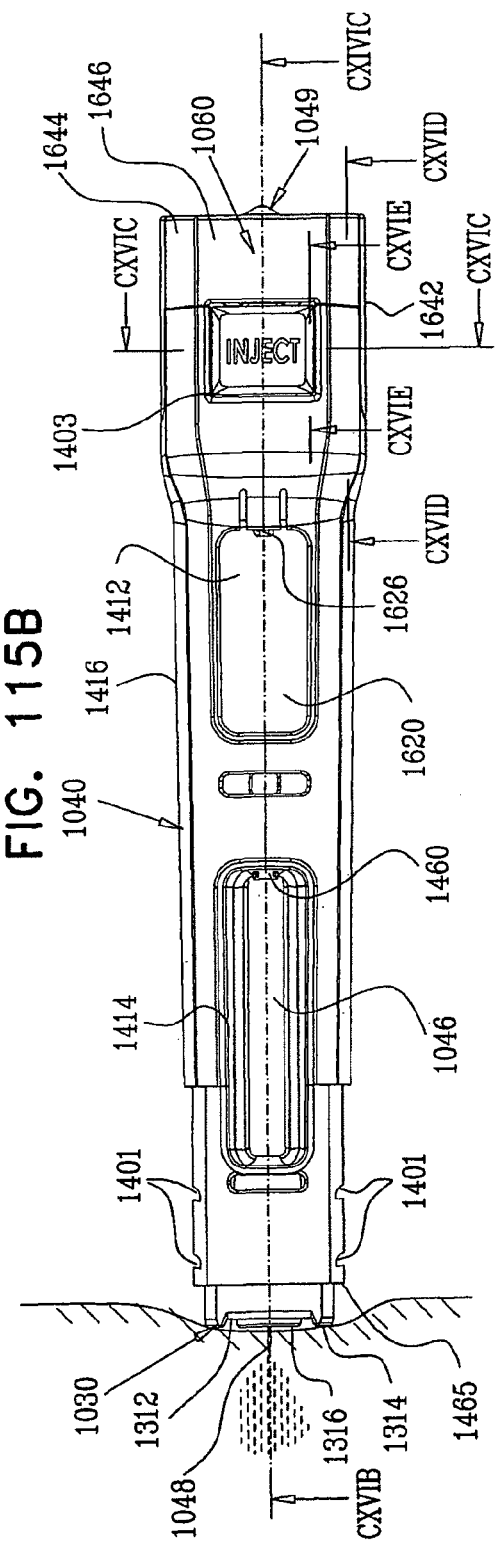

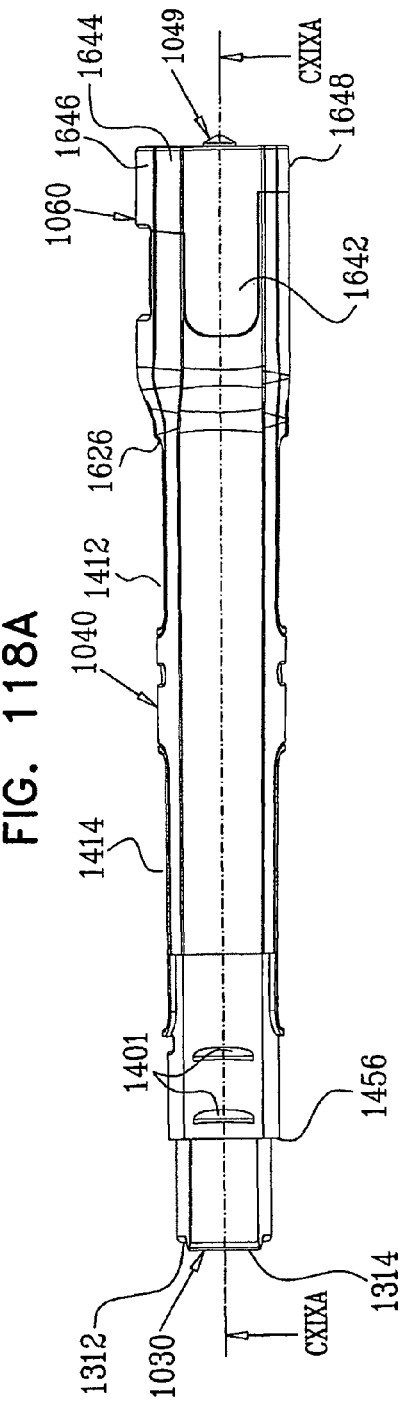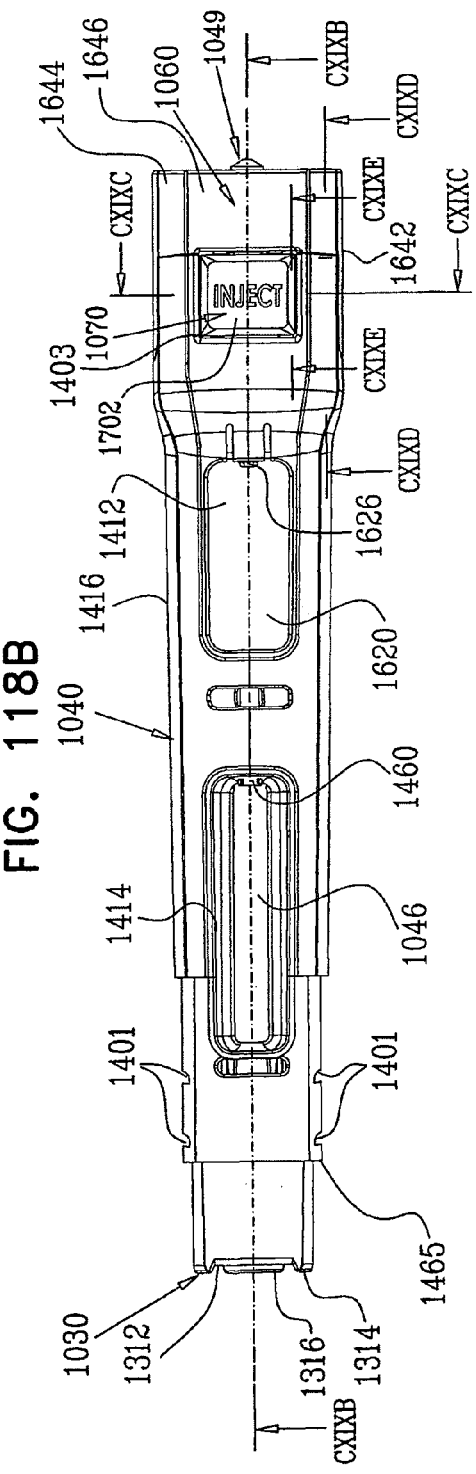

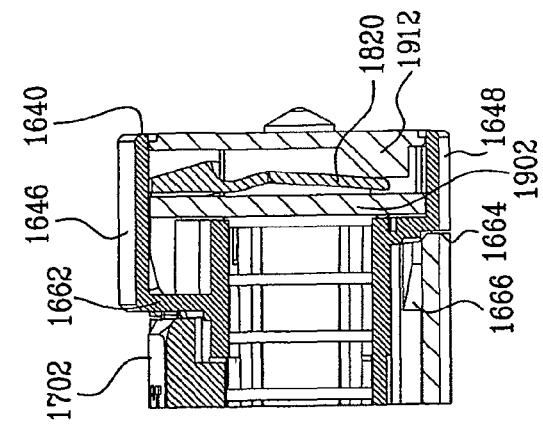
FIG. 119E  FIG. 119D
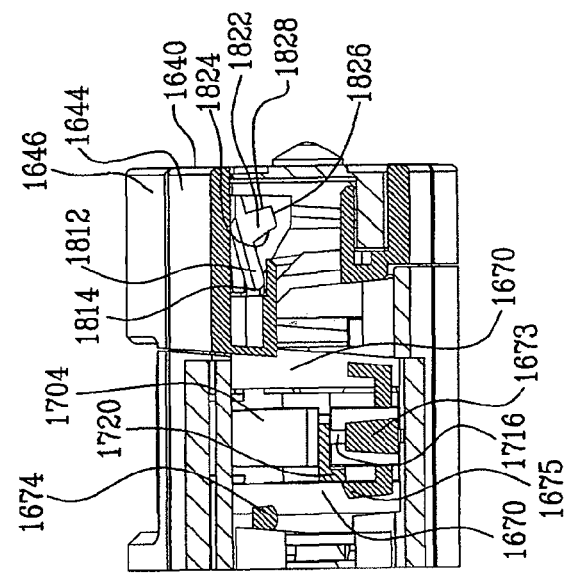
FIG. 119C
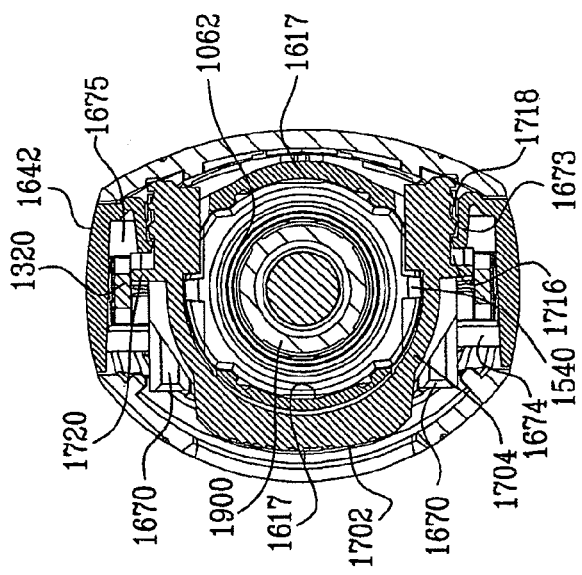

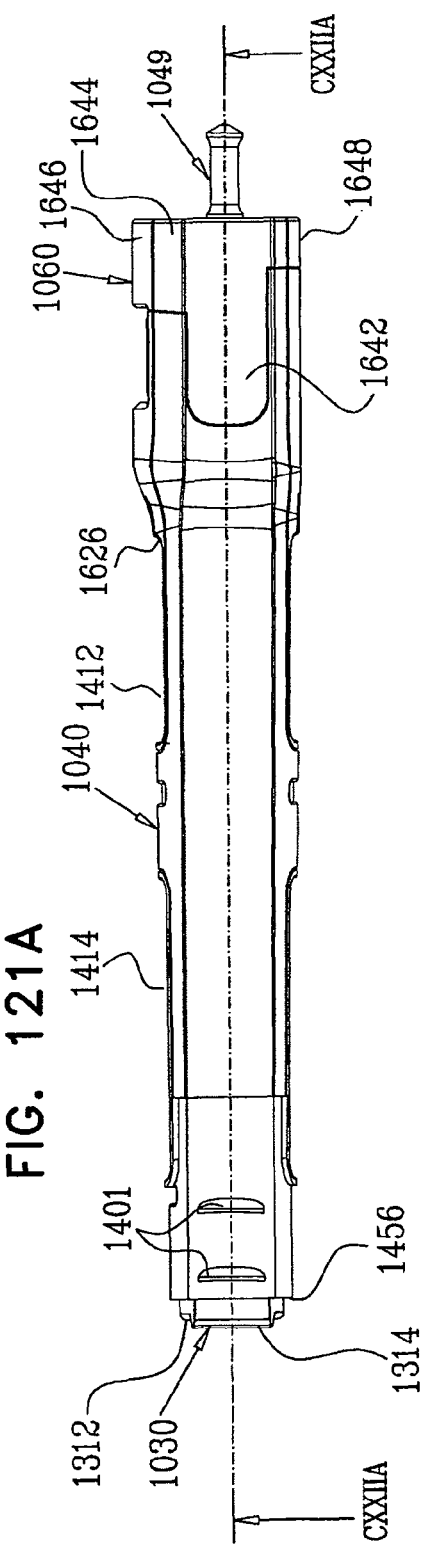
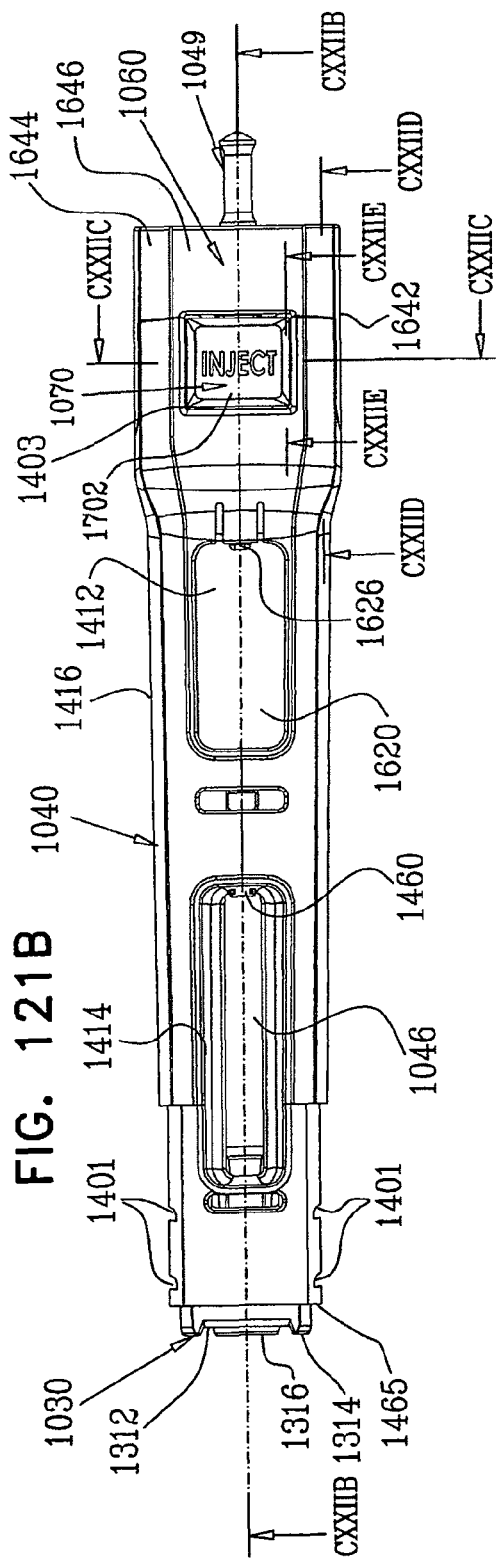
FIG. 121A
FIG. 121B

AUTOMATIC INJECTION DEVICE

REFERENCE TO RELATED APPLICATIONS

Reference is hereby made to U.S. Provisional Patent Application Ser. No. 60/853,411, filed Oct. 19, 2006, entitled AUTOMATIC INJECTION DEVICE, the contents of which are hereby incorporated by reference and priority of which is hereby claimed pursuant to 37 CFR 1.78(a) (4) and (5)(i).

FIELD OF THE INVENTION

The present invention relates to automatic injection devices for hypodermic syringes generally.

BACKGROUND OF THE INVENTION

The following U.S. patents are believed to represent the current state of the art: U.S. Pat. Nos. 4,474,572; 4,475,906; 4,484,910; 4,487,602; 4,505,710; 4,512,767; 4,515,590; 4,518,387; 4,529,401; 4,529,403; 4,530,695; 4,534,759; 4,547,189; 4,553,962; 4,573,970; 4,573,976; 4,578,061; 4,578,064; 4,580,561; 4,592,744; 4,594,073; 4,596,558; 4,597,753; 4,600,403; 4,601,708; 4,613,328; 4,620,540; 4,620,847; 4,624,660; 4,650,468; 4,658,830; 4,659,326; 4,664,651; 4,664,654; 4,666,436; 4,672,967; 4,681,565; 4,687,465; 4,687,467; 4,689,042; 4,699,614; 4,710,170; 4,723,937; 4,735,618; 4,738,663; 4,743,234; 4,744,955; 4,745,907; 4,747,829; 4,747,831; 4,753,636; 4,755,169; 4,758,227; 4,758,230; 4,758,231; 4,766,908; 4,767,407; 4,767,413; 4,770,655; 4,781,683; 4,781,685; 4,781,688; 4,784,640; 4,787,384; 4,787,893; 4,790,823; 4,790,827; 4,795,432; 4,795,433; 4,798,587; 4,799,921; 4,804,370; 4,808,169; 4,813,937; 4,813,940; 4,820,275; 4,820,286; 4,826,484; 4,826,489; 4,826,490; 4,828,548; 4,832,682; 4,832,693; 4,834,704; 4,834,718; 4,842,598; 4,846,811; 4,850,961; 4,850,968; 4,850,971; 4,850,976; 4,850,977; 4,850,994; 4,861,338; 4,863,427; 4,863,435; 4,863,436; 4,865,592; 4,874,372; 4,874,382; 4,883,466; 4,883,472; 4,886,499; 4,887,998; 4,892,107; 4,892,523; 4,894,054; 4,894,055; 4,898,589; 4,900,303; 4,900,307; 4,900,311; 4,902,279; 4,904,242; 4,906,236; 4,908,022; 4,909,794; 4,909,795; 4,911,706; 4,913,702; 4,915,702; 4,917,672; 4,919,146; 4,919,657; 4,923,443; 4,923,445; 4,927,414; 4,929,237; 4,929,241; 4,931,040; 4,932,944; 4,932,946; 4,932,947; 4,935,013; 4,935,014; 4,936,830; 4,941,879; 4,944,723; 4,944,725; 4,946,441; 4,950,240; 4,950,241; 4,950,250; 4,950,252; 4,955,866; 4,955,868; 4,955,869; 4,955,870; 4,961,728; 4,966,589; 4,966,592; 4,966,593; 4,973,310; 4,973,317; 4,976,704; 4,988,335; 4,988,339; 4,994,045; 4,998,921; 4,998,922; 5,000,736; 5,000,737; 5,002,548; 5,007,903; 5,011,475; 5,015,240; 5,017,187; 5,019,043; 5,019,044; 5,019,047; 5,019,048; 5,021,059; 5,024,665; 5,026,349; 5,030,208; 5,034,003; 5,037,306; 5,037,382; 5,037,393; 5,037,400; 5,041,094; 5,042,977; 5,045,066; 5,047,016; 5,049,133; 5,049,136; 5,053,010; 5,053,018; 5,055,102; 5,057,086; 5,057,089; 5,059,180; 5,059,185; 5,061,249; 5,061,251; 5,064,419; 5,067,490; 5,067,948; 5,071,353; 5,080,104; 5,084,027; 5,084,029; 5,084,030; 5,085,640; 5,085,641; 5,085,642; 5,088,986; 5,088,988; 5,092,843; 5,092,851; 5,092,852; 5,092,853; 5,098,382; 5,098,400; 5,098,401; 5,102,393; 5,102,397; 5,104,378; 5,104,380; 5,104,384; 5,104,385; 5,106,370; 5,106,372; 5,106,379; 5,108,378; 5,108,379; 5,112,307; 5,112,316; 5,114,404; 5,120,310; 5,120,314; 5,120,321; 5,122,118; 5,122,124; 5,125,898; 5,125,899; 5,127,910; 5,135,507; 5,135,510; 5,137,515; 5,137,516; 5,141,496; 5,143,414; 5,147,311; 5,147,326; 5,147,327; 5,149,323; 5,152,751; 5,156,599; 5,160,326; 5,163,916; 5,163,917; 5,163,918; 5,167,632; 5,167,641; 5,169,389; 5,169,392; 5,176,641; 5,176,655; 5,176,656; 5,176,657; 5,183,468; 5,183,469; 5,188,614; 5,190,526; 5,193,552; 5,195,982; 5,195,983; 5,195,985; 5,199,952; 5,201,708; 5,201,710; 5,205,826; 5,205,827; 5,207,646; 5,207,699; 5,209,739; 5,211,628; 5,211,629; 5,215,524; 5,215,533; 5,215,534; 5,215,535; 5,215,536; 5,217,437; 5,219,338; 5,221,262; 5,222,943; 5,222,947; 5,222,974; 5,224,936; 5,226,882; 5,228,883; 5,232,457; 5,232,458; 5,238,654; 5,242,388; 5,242,401; 5,242,416; 5,242,420; 5,246,428; 5,250,031; 5,256,152; 5,257,976; 5,261,894; 5,263,933; 5,267,961; 5,267,963; 5,269,761; 5,269,762; 5,269,766; 5,273,532; 5,273,538; 5,273,539; 5,273,541; 5,273,544; 5,279,554; 5,279,566; 5,279,577; 5,279,579; 5,279,581; 5,279,582; 5,279,583; 5,279,590; 5,282,793; 5,282,822; 5,282,827; 5,284,479; 5,290,233; 5,290,239; 5,290,240; 5,290,254; 5,292,314; 5,295,963; 5,295,965; 5,295,972; 5,295,973; 5,295,974; 5,295,975; 5,300,029; 5,300,030; 5,300,040; 5,300,045; 5,304,137; 5,304,138; 5,306,251; 5,306,258; 5,308,332; 5,311,841; 5,312,353; 5,312,366; 5,312,368; 5,312,370; 5,312,371; 5,312,372; 5,314,503; 5,318,538; 5,320,609; 5,322,517; 5,324,265; 5,328,475; 5,328,482; 5,328,484; 5,330,430; 5,334,149; 5,334,158; 5,334,173; 5,336,180; 5,336,187; 5,336,199; 5,338,303; 5,338,311; 5,342,310; 5,342,320; 5,344,407; 5,344,408; 5,346,475; 5,346,480; 5,346,481; 5,348,544; 5,352,200; 5,352,202; 5,352,203; 5,354,287; 5,356,387; 5,358,489; 5,360,410; 5,364,362; 5,364,370; 5,366,447; 5,368,568; 5,368,570; 5,368,571; 5,370,619; 5,370,626; 5,374,250; 5,378,240; 5,383,857; 5,385,550; 5,385,551; 5,385,557; 5,389,076; 5,389,085; 5,391,151; 5,391,183; 5,395,317; 5,395,337; 5,399,163; 5,401,246; 5,401,249; 5,401,251; 5,403,286; 5,403,287; 5,405,326; 5,405,327; 5,407,436; 5,409,466; 5,411,487; 5,415,638; 5,415,645; 5,415,648; 5,419,766; 5,419,773; 5,423,746; 5,425,715; 5,425,722; 5,429,611; 5,429,612; 5,429,613; 5,431,631; 5,431,632; 5,433,712; 5,445,618; 5,445,620; 5,451,210; 5,458,576; 5,458,580; 5,460,611; 5,462,531; 5,466,223; 5,468,227; 5,474,687; 5,478,314; 5,478,316; 5,478,328; 5,480,385; 5,480,387; 5,480,390; 5,482,039; 5,484,414; 5,486,163; 5,486,164; 5,487,732; 5,487,733; 5,487,734; 5,489,272; 5,492,536; 5,496,278; 5,501,672; 5,512,048; 5,512,050; 5,514,097; 5,514,107; 5,520,639; 5,520,649; 5,522,797; 5,522,812; 5,527,283; 5,527,284; 5,527,307; 5,529,189; 5,531,691; 5,531,692; 5,531,694; 5,531,704; 5,531,706; 5,533,975; 5,533,984; 5,536,243; 5,536,253; 5,536,257; 5,538,506; 5,538,508; 5,540,664; 5,540,666; 5,542,920; 5,542,927; 5,549,558; 5,549,568; 5,549,570; 5,549,572; 5,549,708; 5,558,648; 5,562,623; 5,562,624; 5,562,626; 5,562,631; 5,569,202; 5,569,203; 5,573,513; 5,575,770; 5,578,011; 5,578,014; 5,578,015; 5,582,591; 5,586,976; 5,591,133; 5,591,134; 5,591,138; 5,593,387; 5,593,390; 5,599,309; 5,599,313; 5,599,316; 5,599,318; 5,601,532; 5,601,535; 5,605,544; 5,609,577; 5,611,781; 5,611,782; 5,613,500; 5,613,951; 5,613,952; 5,615,771; 5,616,123; 5,616,132; 5,616,134; 5,616,135; 5,620,422; 5,620,425; 5,624,401; 5,624,405; 5,628,765; 5,630,803; 5,632,730; 5,632,733; 5,634,906; 5,634,909; 5,634,937; 5,637,092; 5,637,094; 5,643,220; 5,643,222; 5,647,851; 5,649,622; 5,651,774; 5,653,687; 5,653,688; 5,653,693; 5,656,031; 5,658,256; 5,658,257; 5,658,258; 5,658,259; 5,662,610; 5,662,617; 5,665,071; 5,665,075; 5,669,889; 5,672,155; 5,672,161; 5,681,291; 5,681,295; 5,688,240; 5,688,251; 5,693,016; 5,693,022; 5,693,023; 5,695,472; 5,704,911; 5,704,921; 5,707,393; 5,709,662; 5,709,667; 5,709,668;

5,713,866; 5,713,871; 5,713,872; 5,720,727; 5,725,498;
5,738,655; 5,741,223; 5,743,879; 5,743,887; 5,743,888;
5,743,891; 5,746,718; 5,749,854; 5,749,860; 5,755,692;
5,769,822; 5,769,827; 5,779,675; 5,779,677; 5,779,684;
5,788,677; 5,788,713; 5,792,107; 5,792,121; 5,792,122;
5,795,336; 5,797,885; 5,800,403; 5,807,334; 5,807,345;
5,807,352; 5,810,775; 5,810,784; 5,817,054; 5,817,070;
5,820,602; 5,823,997; 5,823,998; 5,827,293; 5,830,130;
5,836,911; 5,836,920; 5,843,036; 5,843,047; 5,848,990;
5,851,197; 5,853,390; 5,853,393; 5,855,839; 5,858,000;
5,865,227; 5,865,804; 5,868,711; 5,879,337; 5,882,342;
5,885,257; 5,891,052; 5,891,092; 5,891,097; 5,891,105;
5,897,508; 5,899,885; 5,899,886; 5,908,404; 5,908,408;
5,910,131; 5,911,706; 5,919,166; 5,921,959; 5,921,960;
5,921,961; 5,921,963; 5,921,964; 5,925,019; 5,928,188;
5,928,194; 5,928,205; 5,931,813; 5,938,638; 5,938,639;
5,941,850; 5,944,692; 5,944,693; 5,951,522; 5,954,699;
5,957,892; 5,957,895; 5,957,897; 5,960,797; 5,961,491;
5,971,953; 5,976,111; 5,980,487; 5,980,488; 5,980,491;
5,980,494; 5,984,899; 5,984,900; 5,989,219; 5,989,221;
5,993,417; 5,993,418; 5,997,500; 5,997,511; 5,997,513;
6,001,080; 6,007,474; 6,010,486; 6,010,487; 6,015,396;
6,015,438; 6,017,325; 6,022,337; 6,033,386; 6,033,387;
6,036,674; 6,039,713; 6,050,974; 6,050,977; 6,056,716;
6,056,724; 6,056,734; 6,063,040; 6,063,053; 6,066,115;
6,068,616; 6,074,360; 6,074,369; 6,074,370; 6,077,245;
6,080,135; 6,083,199; 6,083,200; 6,086,562; 6,086,569;
6,090,077; 6,090,078; 6,090,080; 6,093,172; 6,099,500;
6,099,503; 6,099,504; 6,102,844; 6,113,574; 6,117,112;
6,117,113; 6,126,637; 6,129,710; 6,142,972; 6,149,626;
6,149,629; 6,156,008; 6,156,010; 6,156,013; 6,156,015;
6,159,161; 6,159,181; 6,159,185; 6,171,284; 6,179,812;
6,183,444; 6,183,446; 6,186,980; 6,192,891; 6,193,695;
6,206,856; 6,206,857; 6,210,369; 6,217,550; 6,217,559;
6,221,044; 6,221,051; 6,221,052; 6,224,576; 6,228,054;
6,228,055; 6,235,006; 6,241,707; 6,241,708; 6,254,575;
6,254,580; 6,258,056; 6,261,264; 6,261,265; 6,267,748;
6,270,472; 6,270,481; 6,273,870; 6,280,399; 6,280,420;
6,280,421; 6,283,941; 6,293,925; 6,299,601; 6,309,374;
6,309,375; 6,312,409; 6,315,113; 6,319,233; 6,319,234;
6,322,536; 6,325,781; 6,325,789; 6,331,173; 6,332,875;
6,344,031; 6,356,783; 6,361,525; 6,368,303; 6,371,938;
6,379,336; 6,387,078; 6,402,716; 6,409,701; 6,409,703;
6,409,706; 6,412,490; 6,413,236; 6,413,237; 6,416,323;
6,416,497; 6,419,658; 6,428,463; 6,428,517; 6,432,035;
6,432,082; 6,432,087; 6,436,068; 6,440,098; 6,443,929;
6,447,480; 6,454,743; 6,458,105; 6,461,331; 6,461,333;
6,468,247; 6,475,194; 6,478,780; 6,482,176; 6,485,469;
6,485,474; 6,494,863; 6,500,155; 6,508,755; 6,511,454;
6,514,230; 6,517,516; 6,517,517; 6,524,278; 6,527,734;
6,527,742; 6,530,896; 6,530,904; 6,537,249; 6,537,252;
6,544,234; 6,547,764; 6,551,275; 6,551,276; 6,551,278;
6,554,798; 6,558,351; 6,558,357; 6,565,533; 6,565,538;
6,569,115; 6,572,584; 6,572,585; 6,575,939; 6,579,256;
6,582,405; 6,584,910; 6,585,690; 6,585,693; 6,585,702;
6,589,158; 6,592,508; 6,592,555; 6,592,556; 6,595,962;
6,599,268; 6,599,269; 6,599,272; 6,605,058; 6,605,067;
6,605,073; 6,607,508; 6,607,509; 6,613,019; 6,613,022;
6,616,630; 6,616,638; 6,616,639; 6,620,136; 6,620,137;
6,620,138; 6,623,455; 6,623,458; 6,623,459; 6,626,864;
6,629,957; 6,629,959; 6,632,198; 6,637,587; 6,638,248;
6,638,255; 6,641,561; 6,645,181; 6,652,482; 6,656,164;
6,659,975; 6,659,982; 6,663,593; 6,669,666; 6,673,034;
6,673,044; 6,673,049; 6,678,550; 6,679,863; 6,679,864;
6,685,676; 6,685,677; 6,689,091; 6,689,106; 6,689,107;
6,689,108; 6,692,470; 6,692,471; 6,699,218; 6,702,784;
6,706,011; 6,706,015; 6,706,019; 6,709,416; 6,712,787;
6,712,788; 6,716,191; 6,716,197; 6,716,198; 6,719,721;
6,719,728; 6,719,730; 6,723,068; 6,723,072; 6,726,655;
6,726,658; 6,726,661; 6,726,662; 6,730,059; 6,736,800;
6,740,059; 6,743,203; 6,749,833; 6,752,782; 6,752,784;
6,752,798; 6,761,706; 6,767,336; RE 33,585; RE 34,335; RE 34,936; RE 36,398; RE 36,447; RE 37,110; RE 37,252 and RE 37,487.

SUMMARY OF THE INVENTION

The present invention seeks to provide an improved automatic injection device.

There is thus provided in accordance with a preferred embodiment of the present invention an injection device for injecting a fluid into an object, the injection device including a plunger assembly for operative engagement with a syringe adapted to contain the fluid and permit ejection of the fluid therefrom via a syringe outlet, the plunger assembly being displaceable in a first direction which causes at least some of the fluid contained in the syringe to be ejected from the syringe via the syringe outlet and an inadvertent fluid ejection prevention assembly coupled to the plunger assembly for preventing ejection of fluid from the syringe in situations where the syringe outlet is neither in operative engagement with a vial adaptor suitable for providing fluid communication with the interior of a vial nor in fluid communication with an injection site within the object.

In accordance with a preferred embodiment of the present invention the plunger assembly is adapted for displacement also in a second direction opposite to the first direction. Preferably, the injection device also includes a user operable actuator button, which, when displaced in a button displacement direction, is operable to enable displacement of the plunger assembly in the first direction, the user operable actuator button normally being displaceable in the button displacement direction only when the syringe outlet is in operative engagement with the injection site. Additionally or alternatively, the inadvertent fluid ejection prevention assembly includes a vial adaptor engagement assembly which is displaceable responsive to operative engagement with the vial adaptor to an operative orientation which enables the plunger assembly to be displaced in the first direction.

There is further provided in accordance with a further preferred embodiment of the present invention an automatic injection device for injecting a fluid into an object, the automatic injection device including a plunger assembly for operative engagement with a syringe adapted to contain the fluid and permit ejection of the fluid therefrom via a syringe outlet, the plunger assembly being displaceable in a first direction which causes at least some of the fluid contained in the syringe to be ejected from the syringe via the syringe outlet and a user operable actuator button which, when displaced in a button displacement direction, is operable to cause displacement of the plunger assembly in the first direction, the user operable actuator button being mechanically locked against displacement in the button displacement direction when the syringe outlet is in operative engagement with a vial adaptor.

In accordance with a preferred embodiment of the present invention the plunger assembly is adapted for displacement also in a second direction opposite to the first direction. Preferably, the automatic injection device also includes a vial adaptor engagement assembly which is displaceable responsive to operative engagement with the vial adaptor to an operative orientation which enables the plunger assembly to be displaced in the first direction.

There is additionally provided in accordance with an additional preferred embodiment of the present invention an automatic injection device for injecting a fluid into an object, the automatic injection device including a plunger assembly for operative engagement with a syringe adapted to contain the fluid and permit ejection of the fluid therefrom via a syringe outlet, the plunger assembly being displaceable in a first direction which causes at least some of the fluid contained in the syringe to be ejected from the syringe via the syringe outlet and an inadvertent fluid ejection prevention assembly coupled to the plunger assembly and including a vial adaptor engagement assembly which is displaceable responsive to operative engagement with a vial adaptor to an operative orientation which enables the plunger assembly to be displaced in the first direction.

In accordance with a preferred embodiment of the present invention the vial adaptor engagement assembly includes a needle guard. Preferably, the automatic injection device also includes a selectable driving assembly operative, when actuated by a user, to drive the plunger assembly in the first direction, and wherein the inadvertent fluid ejection prevention assembly includes a locking assembly operative to lock the plunger assembly against displacement in the first direction and to permit displacement of the plunger assembly in a second direction, opposite to the first direction.

In accordance with another preferred embodiment of the present invention, the automatic injection device also includes a user operable actuation button operative when pressed by a user to generally simultaneously unlock the plunger assembly and unlock the selectable driving assembly. Additionally or alternatively, the vial adaptor engagement assembly includes a connector rod which provides mechanical interaction between the vial adaptor and the locking assembly. Preferably, the plunger assembly is adapted for displacement also in a second direction opposite to the first direction.

There is also provided in accordance with another preferred embodiment of the present invention an injection device for injecting a fluid into an object, the injection device including a plunger assembly for operative engagement with a syringe adapted to contain the fluid and permit ejection of the fluid therefrom via a syringe outlet, the plunger assembly being displaceable in a first direction, which causes at least some of the fluid contained in the syringe to be ejected from the syringe via the syringe outlet, and in a second direction opposite to the first direction, a selectable driving assembly operative, when actuated by a user, to drive the plunger assembly in the first direction, a first locking assembly operative to lock the plunger assembly against displacement in the first direction and to permit displacement of the plunger assembly in the second direction and a second locking assembly operative to lock the selectable driving assembly against displacement in the first direction.

In accordance with a preferred embodiment of the present invention, the injection device also includes a user operable actuation button operative when pressed by the user to generally simultaneously unlock the plunger assembly and unlock the selectable driving assembly. Preferably, the injection device also includes a vial adaptor engagement assembly which is displaceable responsive to operative engagement with a vial adaptor to an operative orientation which enables the plunger assembly to be displaced in the first direction.

In accordance with another preferred embodiment of the present invention the vial adaptor engagement assembly includes a connector rod which provides mechanical interaction between the vial adaptor and the first locking assembly. Additionally or alternatively, the vial adaptor engagement assembly includes a needle guard which provides mechanical interaction between the vial adaptor and the first locking assembly.

BRIEF DESCRIPTION OF THE DRAWINGS

The present invention will be understood and appreciated more fully from the following detailed description, taken in conjunction with the drawings in which:

FIGS. 3A and 3B are respective top and side view simplified planar illustrations of the drug vial adaptor of FIG. 2;

FIGS. 4A and 4B are sectional illustrations taken along respective section lines and directions IVA-IVA and IVB-IVB in FIGS. 3A and 3B;

FIG. 5 is a simplified pictorial illustration of a needle guard element which forms part of the automatic injection device of FIG. 1;

FIGS. 6A and 6B are respective top and side view simplified planar illustrations of the needle guard element of FIG. 5;

FIGS. 7A and 7B are sectional illustrations taken along respective section lines and directions VIIA-VIIA and VIIB-VIIB in FIGS. 6A and 6B;

FIGS. 10A, 10B and 10C are sectional illustrations taken along respective section lines and directions XA-XA, XB-XB and XC-XC in FIGS. 9A and 9B;

FIGS. 12A and 12B are respective top and side view simplified planar illustrations of the selectable driving assembly of FIG. 11;

FIGS. 13A and 13B are sectional illustrations taken along respective section lines and directions XIIIA-XIIIA and XIIIB-XIIIB in FIGS. 12A and 12B;

FIG. 20 is a simplified pictorial illustration of a plunger locking element which forms part of the automatic injection device of FIG. 1;

FIGS. 21A, 21B, 21C and 21D are respective rear, top, front and side view simplified planar illustrations of the plunger locking element of FIG. 20;

FIGS. 22A and 22B are sectional illustrations taken along respective section lines and directions XXIIA-XXIIA and XXIIB-XXIIB in FIG. 211B;

FIGS. 24A and 24B are respective top and side view simplified planar illustrations of the rear end element of FIG. 23;

FIGS. 25A, 25B and 25C are sectional illustrations taken along respective section lines and directions XXVA-XXVA, XXVB-XXVB and XXVC-XXVC in FIGS. 24A and 24B;

FIGS. 29A and 29B are respective side and top view simplified planar illustrations of the automatic injection device of FIG. 28;

FIGS. 30A, 30B, 30C, 30D and 30E are sectional illustrations taken along respective section lines and directions XXXA-XXXA, XXXB-XXXB, XXXC-XXXC, XXXD-XXXD and XXXE-XXXE in FIGS. 29A and 29B;

FIGS. 32A and 32B are respective side and top view simplified planar illustrations of the automatic injection device of FIG. 31;

FIGS. 33A, 33B, 33C, 33D and 33E are sectional illustrations taken along respective section lines and directions XXXIIIA-XXXIIIA, XXXIIIB-XXXIIIB, XXXIIIC-XXXIIIC, XXXIIID-XXXIIID and XXXIIIE-XXXIIIE in FIGS. 32A and 32B;

FIGS. 35A and 35B are respective side and top view simplified planar illustrations of the automatic injection device of FIG. 34;

FIGS. 36A, 36B, 36C, 36D and 36E are sectional illustrations taken along respective section lines and directions XXXVIA-XXXVIA, XXXVIB-XXXVIB, XXXVIC-XXXVIC, XXXVID-XXXVID and XXXVIE-XXXVIE in FIGS. 35A and 35B;

FIGS. 38A and 38B are respective side and top view simplified planar illustrations of the automatic injection device of FIG. 37;

FIGS. 39A, 39B, 39C, 39D and 39E are sectional illustrations taken along respective section lines and directions XXXIXA-XXXIXA, XXXIXB-XXXIXB, XXXIXC-XXXIXC, XXXIXD-XXXIXD and XXXIXE-XXXIXE in FIGS. 38A and 38B;

FIGS. 41A and 41B are respective side and top view simplified planar illustrations of the automatic injection device of FIG. 40;

FIGS. 42A, 42B, 42C, 42D and 42E are sectional illustrations taken along respective section lines and directions XLIIA-XLIIA, XLIIB-XLIIB, XLIIC-XLIIC, XLIID-XLIID and XLIIE-XLIIE in FIGS. 41A and 41B;

FIG. 43 is a simplified assembled view illustration of the automatic injection device of FIGS. 1 and 27F in a needle penetration, pre-drug delivery operative orientation;

FIGS. 44A and 44B are respective side and top view simplified planar illustrations of the automatic injection device of FIG. 43;

FIGS. 45A, 45B, 45C, 45D and 45E are sectional illustrations taken along respective section lines and directions XLVA-XLVA, XLVB-XLVB, XLVC-XLVC, XLVD-XLVD and XLVE-XLVE in FIGS. 44A and 44B;

FIG. 46 is a simplified assembled view illustration of the automatic injection device of FIGS. 1 and 27G in a drug delivery operative orientation;

FIGS. 47A and 47B are respective side and top view simplified planar illustrations of the automatic injection device of FIG. 46;

FIGS. 50A and 50B are respective side and top view simplified planar illustrations of the automatic injection device of FIG. 49;

FIGS. 51A, 51B, 51C, 51D and 51E are sectional illustrations taken along respective section lines and directions LIA-LIA, LIB-LIB, LIC-LIC, LID-LID and LIE-LIE in FIGS. 50A and 50B;

FIGS. 53A and 53B are respective side and top view simplified planar illustrations of the automatic injection device of FIG. 52;

FIGS. 56A and 56B are respective side and top view simplified planar illustrations of the automatic injection device of FIG. 55;

FIGS. 57A, 57B, 57C, 57D and 57E are sectional illustrations taken along respective section lines and directions LVIIA-LVIIA, LVIIB-LVIIB, LVIIC-LVIIC, LVIID-LVIID and LVIIE-LVIIE in FIGS. 56A and 56B;

FIGS. 59A and 59B are respective side and top view simplified planar illustrations of the automatic injection device of FIG. 58;

FIGS. 60A, 60B, 60C, 60D and 60E are sectional illustrations taken along respective section lines and directions LXA-LXA, LXB-LXB, LXC-LXC, LXD-LXD and LXE-LXE in FIGS. 59A and 59B;

FIGS. 66A and 66B are respective top and side view simplified planar illustrations of the needle guard element of FIG. 65;

FIGS. 67A and 67B are sectional illustrations taken along respective section lines and directions LXVIIA-LXVIIA and LXVIIB-LXVIIB in FIGS. 66A and 66B;

FIGS. 69A and 69B are respective top and side view simplified planar illustrations of the forward housing of FIG. 68;

FIGS. 70A, 70B and 70C are sectional illustrations taken along respective section lines and directions LXXA-LXXA, LXXB-LAB and LXXC-LXXC in FIGS. 69A and 69B;

FIGS. 72A and 72B are respective top and side view simplified planar illustrations of the selectable driving assembly of FIG. 71;

FIGS. 73A and 73B are sectional illustrations taken along respective section lines and directions LXXIIIA-LXXIIIA and LXXIIIB-LXXIIIB in FIGS. 72A and 72B;

FIGS. 78A and 78B are respective top and side view simplified planar illustrations of the actuation button of FIG. 77;

FIGS. 79A and 79B are sectional illustrations taken along respective section lines and directions LXXIXA-LXXIXA and LXXIXB-LXXIXB in FIGS. 78A and 78B;

FIGS. 81A, 81B, 81C, 81D and 81E are respective top, left side, right side, bottom and front view simplified planar illustrations of the plunger locking element of FIG. 80;

FIGS. 82A and 82B are sectional illustrations taken along respective section lines and directions LXXXIIA-LXXXIIA and LXXXIIB-LXXXIIB in FIGS. 82A and 82B;

FIGS. 86A, 86B, 86C, 86D, 86E, 86F, 86G, 86H, 86I, 86J, 86K and 86L are simplified pictorial illustration of various stages of typical use of the automatic injection device of FIG. 61;

FIGS. 88A and 88B are respective side and top view simplified planar illustrations of the automatic injection device of FIG. 87;

FIGS. 89A, 89B, 89C, 89D and 89E are sectional illustrations taken along respective section lines and directions LXXXIXA-LXXXIXA, LXXXIXB-LXXXIXB, LXXXIXC-LXXXIXC, LXXXIXD-LXXXIXD and LXXXIXE-LXXXIXE in FIGS. 88A and 88B;

FIGS. 91A and 91B are respective side and top view simplified planar illustrations of the automatic injection device of FIG. 90;

FIGS. 92A, 92B, 92C, 92D and 92E are sectional illustrations taken along respective section lines and directions XCIIA-XCIIA, XCIIB-XCIIB, XCIIC-XCIIC, XCIID-XCIID and XCIIE-XCIIE in FIGS. 91A and 91B;

FIGS. 94A and 94B are respective side and top view simplified planar illustrations of the automatic injection device of FIG. 93;

FIGS. 97A and 97B are respective side and top view simplified planar illustrations of the automatic injection device of FIG. 96;

FIGS. 98A, 98B, 98C, 98D and 98E are sectional illustrations taken along respective section lines and directions XCVIIIA-XCVIIIA, XCVIIIB-XCVIIIB, XCVIIIC-XCVIIIC, XCVIIID-XCVIIID and XCVIIIE-XCVIIIE in FIGS. 97A and 97B;

FIGS. 100A and 100B are respective side and top view simplified planar illustrations of the automatic injection device of FIG. 99;

FIGS. 101A, 101B, 101C, 101D and 101E are sectional illustrations taken along respective section lines and directions CIA-CIA, CIB-CIB, CIC-CIC, CID-CID and CIE-CIE in FIGS. 100A and 100B;

FIGS. 104A, 104B, 104C, 104D and 104E are sectional illustrations taken along respective section lines and directions CIVA-CIVA, CIVB-CIVB, CIVC-CIVC, CIVD-CIVD and CIVE-CIVE in FIGS. 103A and 103B;

FIGS. 106A and 106B are respective side and top view simplified planar illustrations of the automatic injection device of FIG. 105;

FIGS. 107A, 107B, 107C, 107D and 107E are sectional illustrations taken along respective section lines and directions CVIIA-CVIIA, CVIIB-CVIIB, CVIIC-CVIIC, CVIID-CVIID and CVIIE-CVIIE in FIGS. 106A and 106B;

FIGS. 109A and 109B are respective side and top view simplified planar illustrations of the automatic injection device of FIG. 108;

FIGS. 112A and 112B are respective side and top view simplified planar illustrations of the automatic injection device of FIG. 111;

FIGS. 115A and 115B are respective side and top view simplified planar illustrations of the automatic injection device of FIG. 114;

FIGS. 118A and 118B are respective side and top view simplified planar illustrations of the automatic injection device of FIG. 117;

FIGS. 119A, 119B, 119C, 119D and 119E are sectional illustrations taken along respective section lines and directions CXIXA-CXIXA, CXIXB-CXIXB, CXIXC-CXIXC, CXIXD-CXIXD and CXIXE-CXIXE in FIGS. 118A and 118B;

FIG. 120 is a simplified assembled view illustration of the automatic injection device of FIGS. 61 and 86L in a needleshield push back misuse operative orientation;

FIGS. 121A and 121B are respective side and top view simplified planar illustrations of the automatic injection device of FIG. 120; and FIGS. 122A, 122B, 122C, 122D and 122E are sectional illustrations taken along respective section lines and directions CXXIIA-CXXIIA, CXXIIB-CXXIIB, CXXIIC-CXXIIC, CXXIID-CXXIID and CXXIIE-CXXIIE in FIGS. 121A and 121B.

DETAILED DESCRIPTION OF PREFERRED EMBODIMENTS

Reference is now made to FIGS. 1-26, which illustrate the constituent elements of an automatic injection device constructed and operative in accordance with a preferred embodiment of the present invention.

Figure 1:
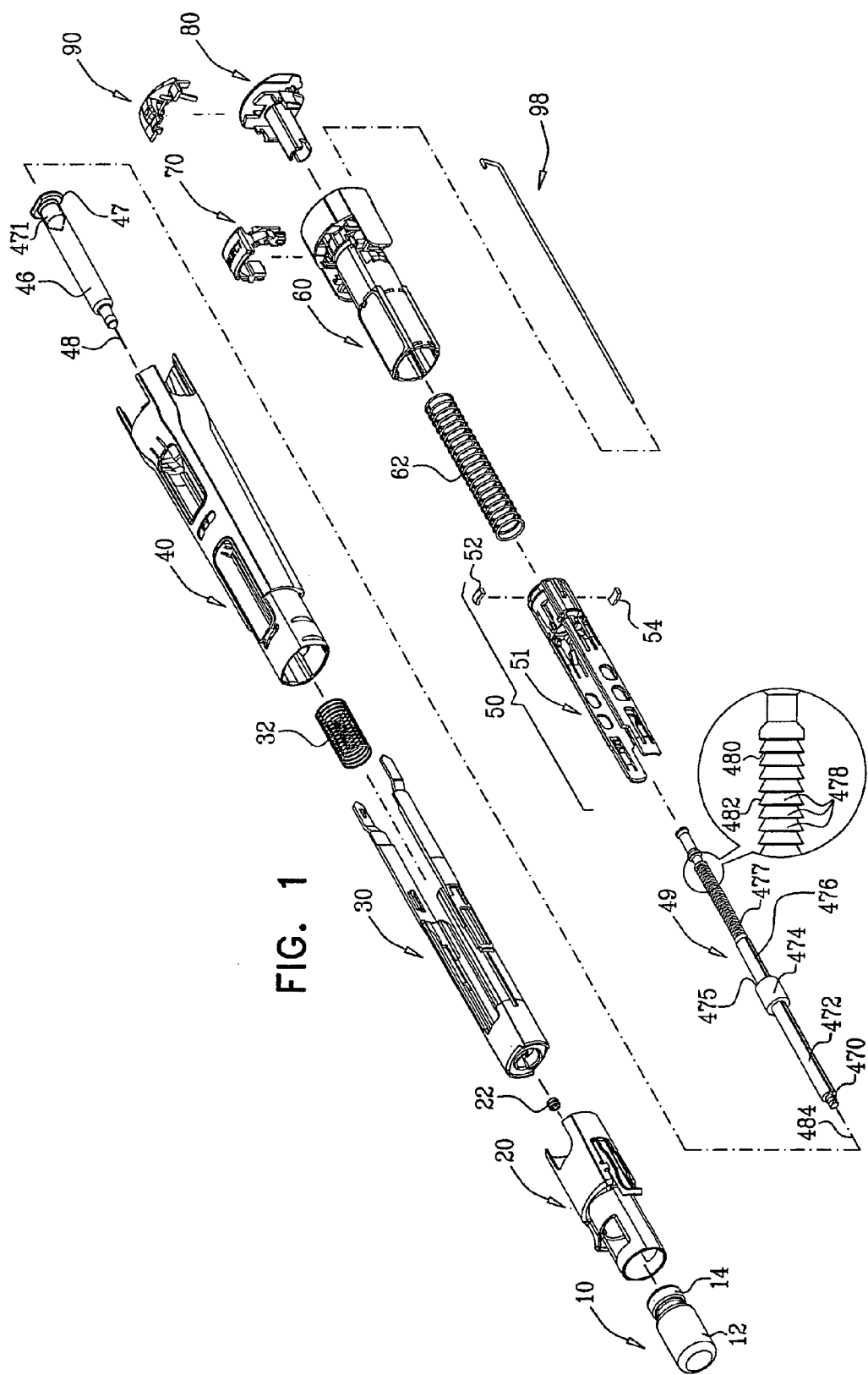
FIG. 1 is a simplified exploded view illustration of an automatic injection device constructed and operative in accordance with a preferred embodiment of the present invention.

As seen with particular clarity in FIG. 1, the automatic injection device comprises a drug vial 10, including a body portion 12, a neck portion 14 and an elastomeric seal (not shown). The term "vial" is used throughout to describe any suitable container. The drug vial 10 is seated in a drug vial adaptor 20 having a septum 22 associated therewith. A needle guard element 30, which is positioned by a compression spring 32 within a forward end of a forward housing 40, is operative to engage, at a front end thereof, the drug vial adaptor 20.

A syringe 46, including a rear flange 47 and having a hypodermic needle 48 integrally formed therewith, is operatively engaged by a plunger 49. The term "syringe" is used throughout to refer to a container having an elongate bore along which a plunger and piston may travel. Syringe 46 and plunger 49 are preferably located within the forward housing 40. Syringe 46 may be a conventional syringe, such as a commercially available syringe sold under the catalog designation BD-Hypak™ or may be any other suitable syringe or cartridge.

Plunger 49 selectably engages a selectable driving assembly 50, which includes a selectable driving element 51 and a pair of elastomeric motion damping elements 52 and 54. Selectable driving assembly 50 is preferably at least partially seated within a rear housing 60, forward of a main compression spring 62, also seated within rear housing 60. The main compression spring 62 provides selectable forward displacement to the selectable driving assembly 50. Selectable operation of plunger 49 by selectable driving assembly 50 causes the plunger 49 to inject liquid contents of syringe 46 through hypodermic needle 48.

The rear housing 60 has associated therewith an actuation button 70, operative to selectably actuate operation of selectable driving assembly 50. Within rear housing 60 are seated a rear end element 80, operative to seal the rear end of the rear housing 60, and a plunger locking element 90, cooperative with rear end element 80 and operative to lock the plunger 49 when liquid contents of the syringe 46 should not be injected through needle 48. A locking rod 98 is operative to selectably engage the plunger locking element 90 thereby unlocking the plunger 49.

Figure 2:
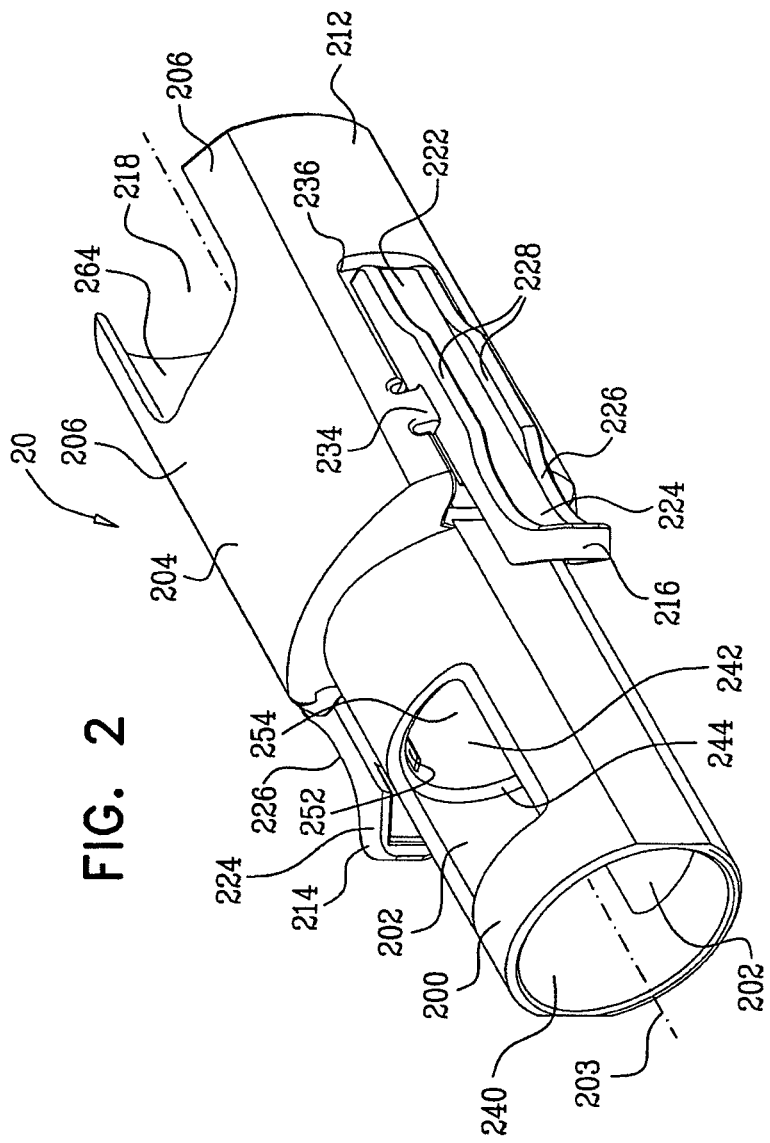
FIG. 2 is a simplified pictorial illustration of a drug vial adaptor which forms part of the automatic injection device of FIG. 1.

Reference is now made to FIG. 2, which is a simplified pictorial illustration of drug vial adaptor 20 which forms part of the automatic injection device of FIG. 1, to FIGS. 3A and 3B, which are respective top and side view simplified planar illustrations of the drug vial adaptor of FIG. 2, and to FIGS. 4A and 4B, which are sectional illustrations thereof taken along respective section lines and directions IVA-IVA and IVB-IVB in FIGS. 3A and 3B.

As seen in FIGS. 2-4B, the drug vial adaptor 20 includes a generally circular cylindrical forward facing sleeve 200, which is configured to generally enclose drug vial 10 (FIG. 1) and is sized such as to render it difficult, if not impossible, to remove drug vial 10 from sleeve 200, following full insertion of the drug vial 10 into the sleeve 200. Sleeve 200 is preferably formed with a pair of oppositely placed windows 202 to enable a user to view the contents of the vial 10 following insertion thereof into sleeve 200.

It is seen that drug vial adaptor 20 is preferably side-to-side symmetric about a longitudinal axis 203.

Integrally formed with sleeve 200 is a generally rectangular cylindrical rearward facing sleeve 204 having first and second curved side walls 206 and 208 and first and second curved edge walls 210 and 212. Hinged finger engagement portions 214 and 216 are integrally formed with edge walls 210 and 212 respectively. Side walls 206 and 208 are formed with respective rearward facing cut outs 218 and 220.

Hinged finger engagement portions 214 and 216 each include a generally planar portion 222 having an outwardly curved forward end 224, defining a finger engagement surface 226, and raised side edges 228 extending along both sides of portion 222. An inwardly facing retaining protrusion 230 is located on an inwardly facing surface of a rearward end 232 of generally planar portion 222. A pair of integrally formed side hinges 234 supports planar portion 222 in an elongate cut out 236 formed in each of edge walls 210 and 212.

The forward facing sleeve 200 includes a forward-most portion 240 having a first inner diameter and, rearward thereof, an intermediate portion 242 having a second inner diameter, less than the first inner diameter. A shoulder 244 is defined between portions 240 and 242. Intermediate portion 242 is defined by a bulkhead 246 having defined at its center a hollow spike 248 which extends forwardly nearly to shoulder 244. In use, spike 248 punctures the elastomeric seal of drug vial 10 (FIG. 1), thereby to enable fluid communication between the interior of drug vial 10 and the interior of syringe 46 (FIG. 1), via apertures 250 formed at a forward end of spike 248. This takes place only after the vial adaptor 20 moves rearwardly along axis 203, enabling fluid communication between the interior of syringe 46 and apertures 250.

Preferably, a plurality of centering and retaining ribs 252 are provided along an interior facing surface 254 of intermediate portion 242. Ribs 252 preferably include a forwardly located interiorly facing protrusion 256 for engaging neck portion 14 of drug vial 10 (FIG. 1).

Extending rearwardly from bulkhead 246 into the interior of rearward facing sleeve 204 is a generally cylindrical fluid passageway defining lumen 258 which defines, at a rearward end thereof, a septum receiving recess 260 in which septum 22 is located.

Preferably, a plurality of guiding ribs 262 are provided along interior facing surfaces 264 of side walls 206 and 208 and edge walls 210 and 212. Additionally, a plurality of positioning ribs 266 extend rearwardly from bulkhead 246 along surfaces 264 of side walls 206 and 208.

Reference is now made to FIG. 5, which is a simplified pictorial illustration of needle guard element 30 which forms part of the automatic injection device of FIG. 1, to FIGS. 6A and 6B, which are respective top and side view simplified planar illustrations of the needle guard element of FIG. 5, and to FIGS. 7A and 7B, which are sectional illustrations thereof taken along respective section lines and directions VIIA-VIIA and VIIB-VIIB in FIGS. 6A and 6B.

As will be described hereinbelow in detail, needle guard element 30 includes a pair of restriction elements, which prevent actuation of the device when a user presses actuation button 70 (FIG. 1) when the device is not pressed against the user's body. At a forward part of the needle guard element there is provided a cylindrical portion having a front end including a generally circular bore, through which the needle passes during injection of the drug. Following injection, the cylindrical portion is displaced forwardly relative to the needle, thereby covering the needle and preventing inadvertent needle pricks.

As seen in FIGS. 5-7B, the needle guard element 30 is preferably an integrally formed element, preferably injection molded of plastic and preferably has a generally cylindrical configuration including a generally tubular portion 310, having a forward facing body engaging surface 312 including pairs of concentrically located ribbed circumferential forward facing ring portions 314 and 316. A rearward facing internal surface 317, facing opposite from body engaging surface 312, forms a spring-seat for spring 32 (FIG. 1) in cooperation with rearward extensions 318 of ring portions 316 which assist in locating the spring 32 on surface 317.

Needle guard element 30 includes a pair of symmetric mounting arms 319 having rearwardmost ends 320, arranged symmetrically about a longitudinal axis 321, which, when the automatic injection device is assembled, is coaxial with the longitudinal axis 203 of drug vial adaptor 20 (FIGS. 2-4B). Mounting arms 319 are symmetric upon rotation about axis 321 and extend parallel thereto along and rearwardly of tubular portion 310. Each of arms 319 is formed with a rectangular window 322.

Each of symmetric mounting arms 319 is formed with a forward portion 325 having formed therein an elongated slot 326, which extends rearwardly of generally tubular portion 310 to a somewhat curved stop surface 328. Stop surface 328 is disposed adjacent a forward edge of rectangular window 322. A widened arm portion 330, having an interiorly facing surface 331, is formed on each of arms 319. The widened arm portion 330 extends rearwardly along generally tubular portion 310 to a location rearwardly of rectangular window 322 and terminates in an inclined surface 332 adjacent a shoulder 333.

Extending further rearwardly from a location slightly forwardly of inclined surface 332, is an intermediate arm portion 334, having an outer surface which is disposed slightly radially outwardly with respect to longitudinal axis 321 as compared with forward portion 325. At a rearward end 336 of intermediate arm portion 334, the thickness of intermediate arm portion 334 is reduced, and arm 319 continues rearwardly at an outwardly inclined portion 338. Outwardly inclined portion 338 is followed by rearwardmost end 320 of arm 319, which has an inwardly facing generally trapezoidal protrusion 340. As will be described hereinbelow, generally trapezoidal protrusion 340 serves as a restriction element, which prevents actuation of the device when a user presses actuation button 70 (FIG. 1) when the device is not pressed against the user's body.

Figure 8:
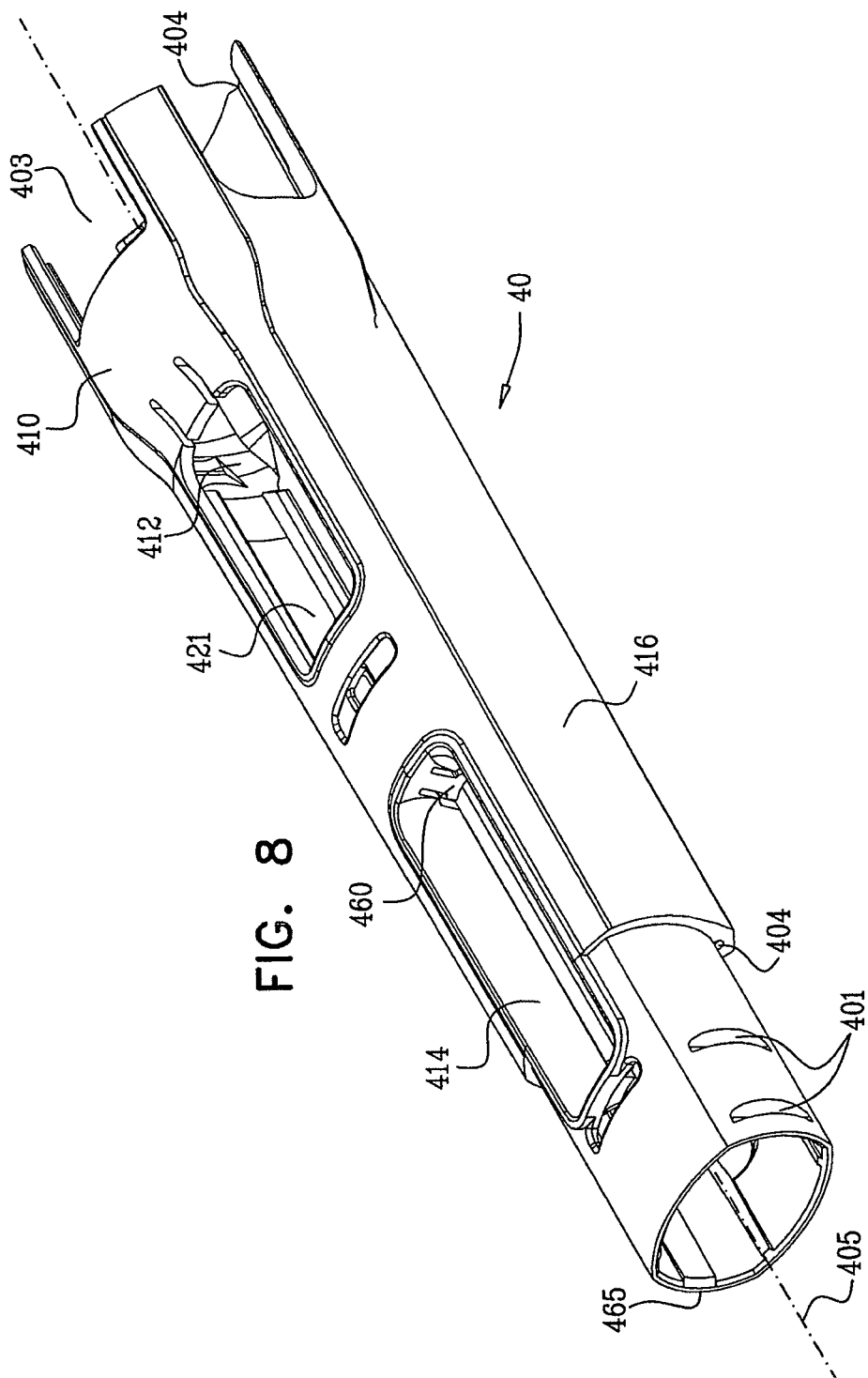
FIG. 8 is a simplified pictorial illustration of a forward housing which forms part of the automatic injection device of FIG. 1.
Figure 9A:
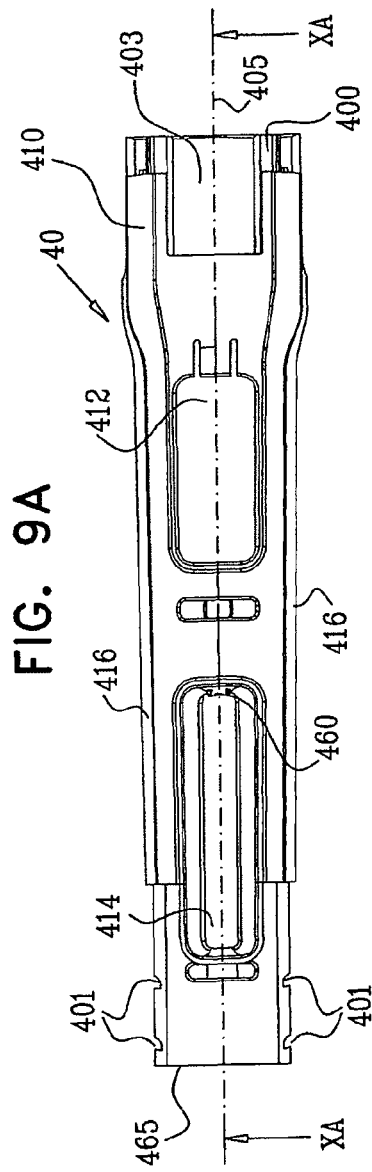
FIGS. 9A, 9B and 9C are respective top, side and front view simplified planar illustrations of the forward housing of FIG. 8.
Figure 9B:
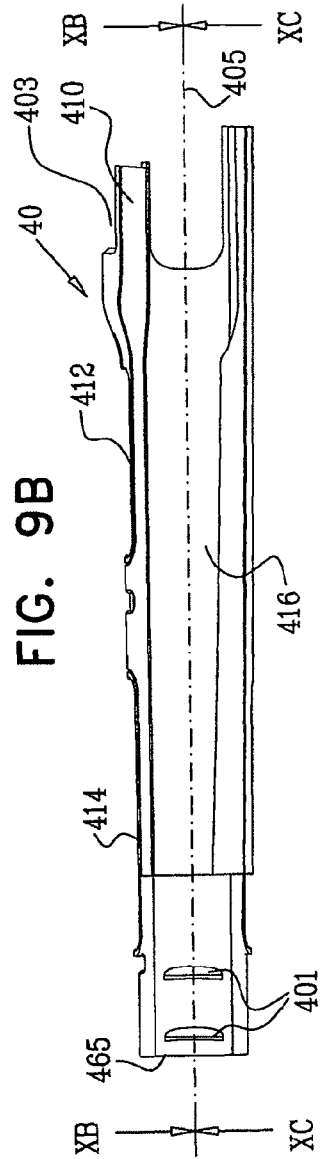
Figure 9C:
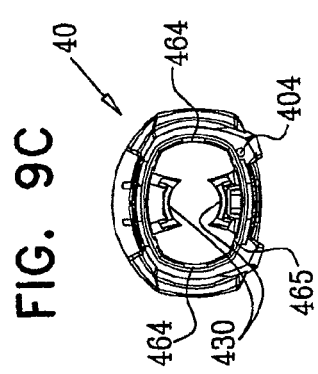

Reference is now made to FIG. 8, which is a simplified pictorial illustration of forward housing 40 which forms part of the automatic injection device of FIG. 1, to FIGS. 9A, 9B and 9C, which are respective top, side and front view simplified planar illustrations of the forward housing of FIG. 8, and to FIGS. 10A, 10B and 10C, which are sectional illustrations taken along respective section lines and directions XA-XA, XB-XB and XC-XC in FIGS. 9A and 9B.

As will be described hereinbelow in detail, the forward housing 40 includes, at a forward portion thereof, two pairs of recesses 401, adapted to receive the retaining protrusions 230 of the finger engagement portions 214 and 216 of the drug vial adaptor (FIGS. 2-4B). At a rear end of the forward housing 40 is a cutout portion 403 adapted to accommodate the actuation button 70 (FIG. 1). As seen with particular clarity in FIGS. 8 and 9C, the forward housing 40 includes a longitudinal recess or channel 404 which is adapted to accommodate the locking rod 98 (FIG. 1).

As seen in FIGS. 8-10C, the forward housing 40 is preferably an integrally formed element, preferably injection molded of plastic and preferably has a generally cylindrical configuration arranged along a longitudinal axis 405, which, when the automatic injection device is assembled, is coaxial with longitudinal axes 203 (FIGS. 2-4B) and 321 (FIGS. 5-7B). Forward housing 40 includes a generally tubular rear portion 410, having an open back and formed with a pair of top-to-bottom symmetric snap fit engagement sockets 412 which receive protrusions of the rear housing 60 (FIG. 1) during factory assembly of the automatic injection device.

Forward of tubular rear portion 410 and rearwardly of the recesses 401 are formed a pair of top-to-bottom symmetric windows 414, which allow the syringe 46 (FIG. 1) and drug content thereof to be viewed when the automatic injection device is assembled, during use thereof and otherwise. A pair of outer side surfaces 416 of forward housing 40 have corresponding inner side surfaces 421, each of which defines a plurality of longitudinally extending ribs 422, 424, 426 and 428 which are used to slidably guide the needle guard element 30 (FIGS. 5-7B) during axial movement thereof.

Inner facing protrusions 430 define a rearward facing spring seat 431 for spring 32 (FIG. 1). Inner facing protrusions 430 are also operative to slidably support syringe 46 (FIG. 1) and to slidably guide actuation arms of selectable driving assembly 50 (FIG. 1).

Inner top and bottom surfaces 432 and 434 define respective pairs of ribs 436 and 438 which are operative to slidably rotationally orient the syringe 46 (FIG. 1) about axis 405 during axial movement of the syringe 46. As best seen in FIG. 10A, inner facing protrusions 430 define, at rearward facing portions thereof, protrusions 460 and 462 which form a stop for flange 47 (FIG. 1), thus limiting the forward movement of the syringe 46 (FIG. 1).

Inner side surface 421 extends forwardly to an inwardly extending shoulder 463 from which extends an inner surface 464 which extends to a forward edge 465 of forward housing 40. Shoulder 463 defines a stop which limits the forward movement of needle guard element 30 (FIGS. 5-7B) relative to forward housing 40.

As seen in FIG. 1, plunger 49 includes a threaded protrusion 470, which threadably engages a corresponding threaded socket (not shown) formed in a rear surface of a resilient piston 471 which sealingly engages the interior of syringe 46. Rearwardly of threaded protrusion 470 is a generally circular cylindrical portion 472 having a first cross sectional radius, followed by a relatively short circular cylindrical portion 474 having a second cross sectional radius greater than the first radius and defining a rearward facing shoulder 475.

Rearward of portion 474 is a third generally circular cylindrical portion 476 having a third cross sectional radius, generally equal to the first radius. Rearwardly of portion 476 is formed a toothed portion 477, each tooth 478 thereof having a generally transverse forwardly facing portion 480 and a slanted rearwardly facing portion 482. The particular shape of the teeth of toothed portion 477 enables rearward movement of the plunger 49 at any time, and requires a specific configuration of the device in order to enable forward movement of the plunger 49.

Plunger 49 is preferably symmetrically disposed about a longitudinal axis 484, which, when the automatic injection device is assembled, is coaxial with longitudinal axes 203 (FIGS. 2-4B), 321 (FIGS. 5-7B) and 405 (FIGS. 8-10C).

Figure 11:
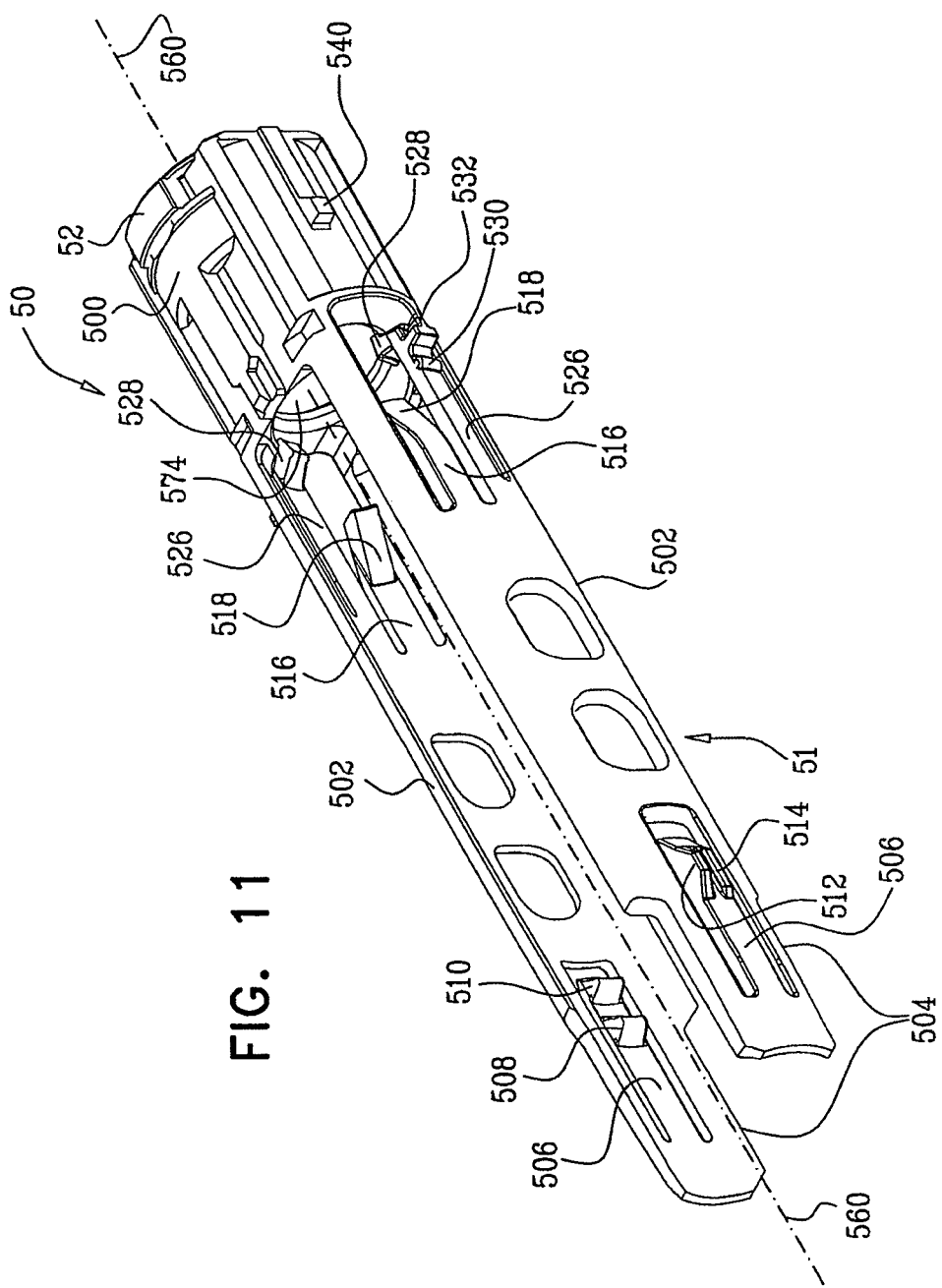
FIG. 11 is a simplified pictorial illustration of a selectable driving assembly which forms part of the automatic injection device of FIG. 1.

Reference is now made to FIG. 11, which is a simplified pictorial illustration of selectable driving assembly 50 which forms part of the automatic injection device of FIG. 1, to FIGS. 12A and 12B, which are respective top and side view simplified planar illustrations of the selectable driving assembly of FIG. 11, and to FIGS. 13A and 13B, which are sectional illustrations taken along respective section lines and directions XIIIA-XIIIA and XIIIB-XIIIB in FIGS. 12A and 12B.

The selectable driving assembly 50 includes selectable driving element 51 and elastomeric motion damping elements 52 and 54. Selectable driving element 51 includes a rearward facing generally cylindrical portion 500 and a pair of longitudinal arms 502. At a forward end 504 of each of the longitudinal arms 502 there is provided a first hinged finger 506 having formed thereon a pair of inwardly facing protrusions 508 and 510. The inwardly facing protrusions 508 and 510 are adapted to engage the flange 47 of syringe 46 (FIG. 1) to retain it in position during the stages shown in FIGS. 27A-27E and to control its forward movement during actuation of the device. Opposite protrusions 508 and 510, on an outer facing surface of first hinged finger 506, are formed a pair of outwardly facing generally trapezoidal protrusions 512 and 514. It is seen that protrusion 512 extends outwardly to a greater degree than does protrusion 514.

Rearwardly of first hinged finger 506 on each of longitudinal arms 502 is a second hinged finger 516, having an inwardly facing protrusion 518, which is adapted to rearwardly displace the syringe 46 (FIG. 1) following injection, when the needle guard element 30 (FIGS. 5-7B) is rearwardly displaced.

Generally alongside and parallel to second hinged fingers 516 there are formed third hinged fingers 526, each including an inwardly facing slanted protrusion 528, operative to forwardly displace the plunger 49 (FIG. 1) during injection, and a pair of outwardly facing protrusions 530 and 532, which are operative to inwardly bend the third hinged fingers 526 during actuation and which engage the needle-guard element 30 (FIGS. 5-7B) and are operative to displace it forwardly as soon as the device disengages the user's body.

The cylindrical portion 500 of the selectable driving assembly 50 includes protrusions 540 on opposite sides thereof, which are adapted to maintain the selectable driving assembly 50 in place when the device is in its storage position, by abutting against the actuation button 70 (FIG. 1). The cylindrical portion 500 also has seated therein motion damping elements 52 and 54 which engage an internal surface of the rear housing 60 (FIG. 1), and thus are operative to slow the forward movement of the selectable driving assembly, thereby slowing the forward movement of the syringe 46 (FIG. 1) and plunger 49 (FIG. 1) during injection.

As seen in FIGS. 11-13B, the selectable driving element 51 is preferably an integrally formed element, preferably injection molded of plastic and preferably has a generally cylindrical configuration including generally cylindrical portion 500, which has an open back. Longitudinal arms 502 are preferably symmetric actuation arms and extend forwardly of cylindrical portion 500 parallel to a longitudinal axis 560, which, when the automatic injection device is assembled, is coaxial with longitudinal axes 203 (FIGS. 2-4B), 321 (FIGS. 5-7B), 405 (FIGS. 8-10C) and 484 (FIG. 1). Arms 502 are symmetric upon rotation about axis 560, and each has a generally curved cross section.

An interior generally cylindrical surface 570 of cylindrical portion 500 terminates at a forward end of cylindrical portion 500 at a shoulder 572, forwardly of which is an opening 574 through which extends plunger 49 (FIG. 1). Shoulder 572 defines a spring seat for spring 62 (FIG. 1).

Figure 14:
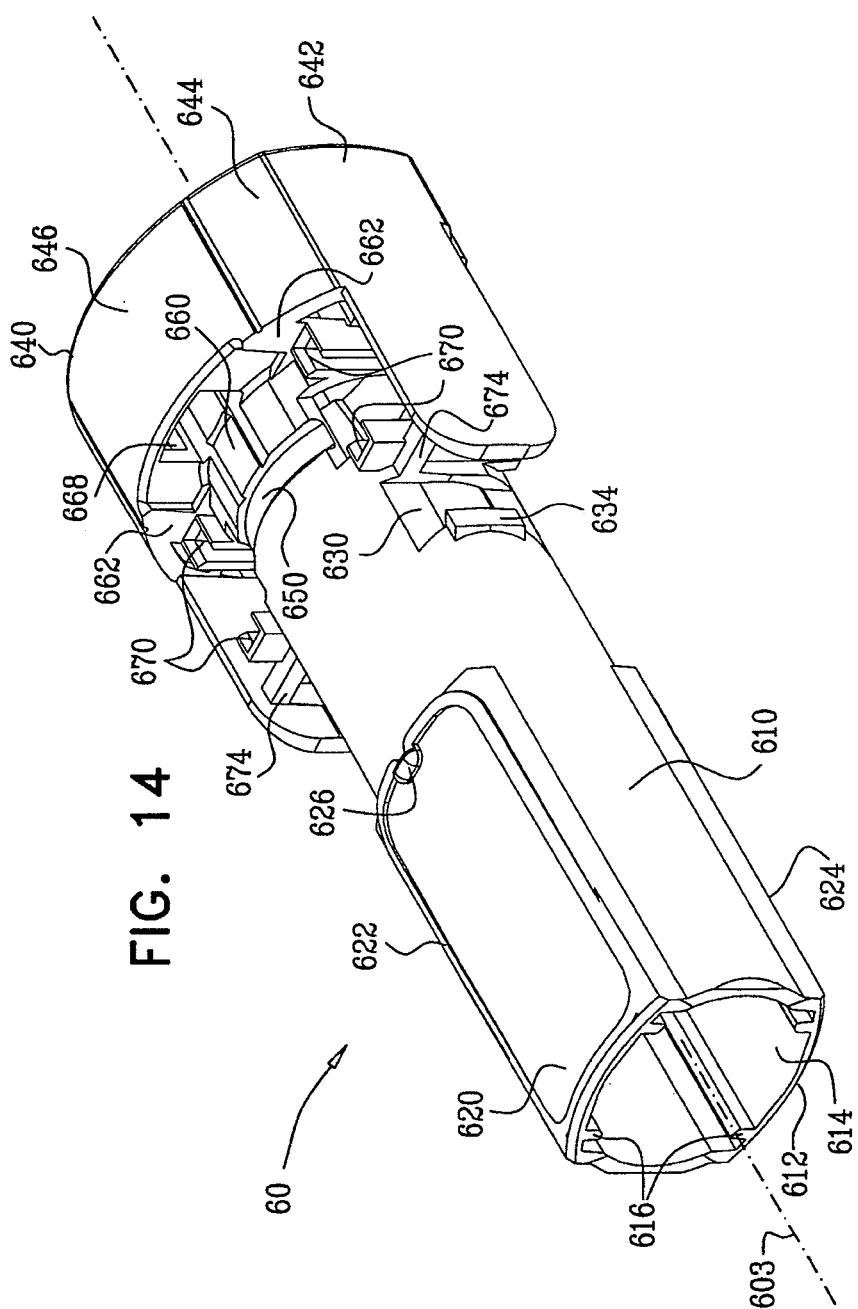
FIG. 14 is a simplified pictorial illustration of a rear housing which forms part of the automatic injection device of FIG. 1.
Figure 15A:
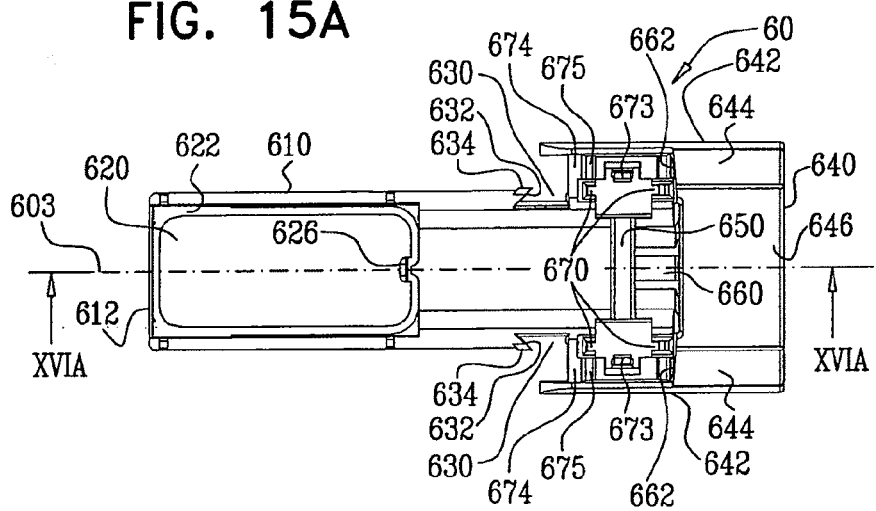
FIGS. 15A, 15B and 15C are respective top, side and rear view simplified planar illustrations of the rear housing of FIG. 14.
Figure 15B:
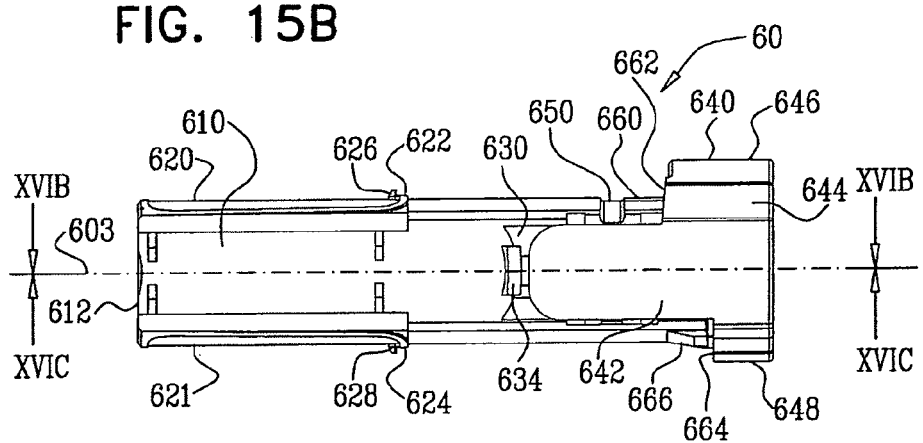
Figure 15C:
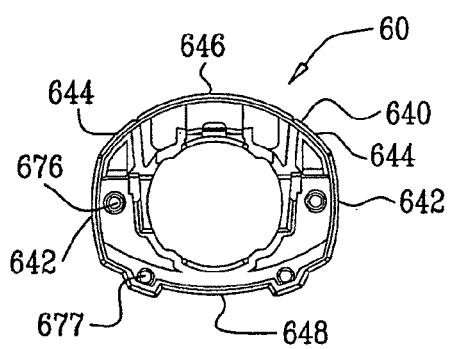
Figure 16A:
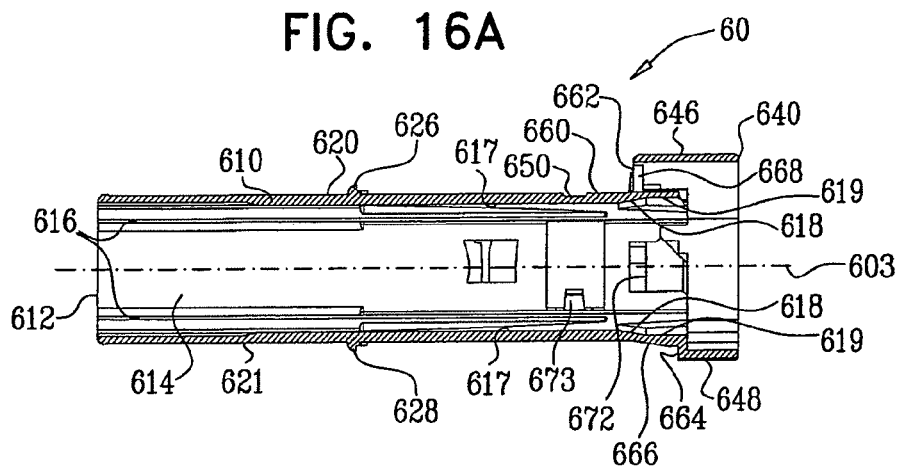
FIGS. 16A, 16B and 16C are sectional illustrations taken along respective section lines and directions XVIA-XVIA, XVIB-XVIB and XVIC-XVIC in FIGS. 15A and 15B.
Figure 16B:
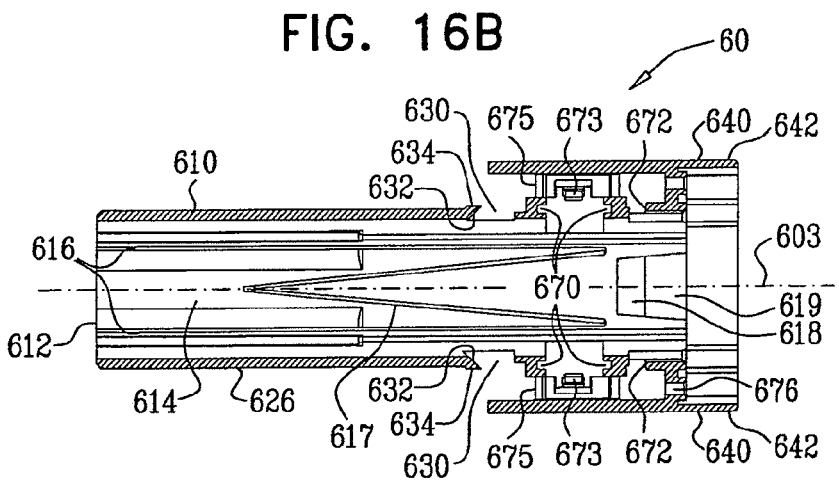
Figure 16C:
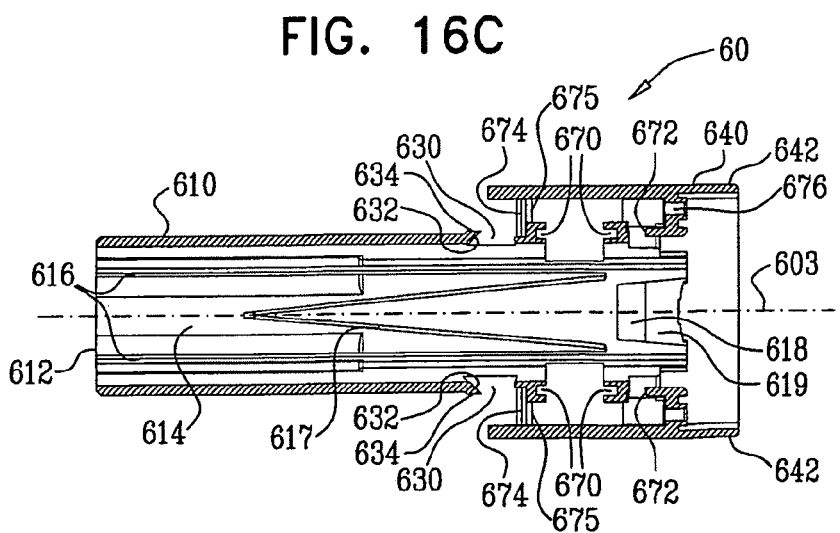

Reference is now made to FIG. 14, which is a simplified pictorial illustration of rear housing 60, which forms part of the automatic injection device of FIG. 1, to FIGS. 15A, 15B and 15C, which are respective top, side and rear view simplified planar illustrations of the rear housing of FIG. 14, and to FIGS. 16A, 16B and 16C, which are sectional illustrations taken along respective section lines and directions XVIA-XVIA, XVIB-XVIB and XVIC-XVIC in FIGS. 15A and 15B.

As seen in FIGS. 14-16C, the rear housing 60 is preferably an integrally formed element, preferably injection molded of plastic and preferably has a generally cylindrical configuration arranged about a longitudinal axis 603, which, when the automatic injection device is assembled, is coaxial with longitudinal axes 203 (FIGS. 2-4B), 321 (FIGS. 5-7B), 405 (FIGS. 8-10C), 484 (FIG. 1) and 560 (FIGS. 11-13B). The rear housing 60 includes a tube 610, which includes a forward portion 612 having an interiorly facing surface 614 including four generally equally spaced, longitudinally extending, guiding ribs 616. Also formed on interiorly facing surface 614 are a pair of interiorly facing protrusions 617 whose width tapers in a forwardly facing direction to a point, thus defining a generally triangular engagement surface for elastomeric motion damping elements 52 and 54 (FIG. 1). Disposed adjacent the wide end of each of protrusions 617 are an inclined recess 618 and a cylindrical recess 619, which serve to guide elastomeric motion damping elements 52 and 54 upstream of their engagement with protrusions 617.

Formed on a pair of generally equally spaced exteriorly facing surfaces 620 and 621 of tube 610 are respective generally rectangular outwardly protruding frames 622 and 624. Further protrusions 626 and 628 are located interiorly of frames 622 and 624 respectively and centered adjacent rearward ends thereof. Protrusions 626 and 628 are accommodated in snap fit engagement sockets 412 of the forward housing 40 (FIGS. 8-10C) during factory assembly of the device, and thereby maintain the connection of the rear housing 60 to the forward housing 40.

Formed in tube 610 adjacent a rearward end thereof are a pair of side cutouts 630 each having an undercut forward edge 632. Disposed forwardly of each of edges 632 is a generally rectangular outwardly facing protrusion 634.

Integrally formed with tube 610 and partially overlapping a rearward portion thereof is a generally cylindrical rearward housing surface portion 640 including first and second generally rectangular side surface portions 642, intermediate surface portions 644, a top surface portion 646 and a bottom surface portion 648. At its rearward end, tube 610 is formed with a transverse curved recess 650. Rearwardly of recess 650 is a generally cylindrical portion 660.

Disposed rearwardly of portion 660 is a wall 662 which connects tube 610 to surface 646. Adjacent surfaces 644 and 646, the wall 662 is generally perpendicular to tube 610 and to surfaces 644 and 646. Adjacent surface 648, the wall includes a perpendicular portion 664 and a tapered portion 666. An opening 668 in wall 662 communicates with a volume disposed between cylindrical portion 660 and surface 646.

Four elongate tracks 670, disposed alongside curved recess 650 between tube 610 and surfaces 642, preferably each having a generally U-shaped cross section, define a pair of guiding tracks for actuation button 70 (FIG. 1). A pair of rear end element retaining portions 672 are located rearwardly of tracks 670 for engagement with rear end element 80.

Between each pair of tracks 670 there is disposed a flexible biasing finger 673 for engagement with actuation button 70.

Extending between each of forwardly disposed tracks 670 and a corresponding rectangular side surface 642 are a pair of transverse portions 674 and 675 which guide a corresponding arm 319 (FIGS. 5-7B) of needle guard element 30.

As seen with particular clarity in FIG. 15C, there are provided longitudinally extending bores 676 and 677 for accommodating locking rod 98 (FIG. 1)

Figure 17A:
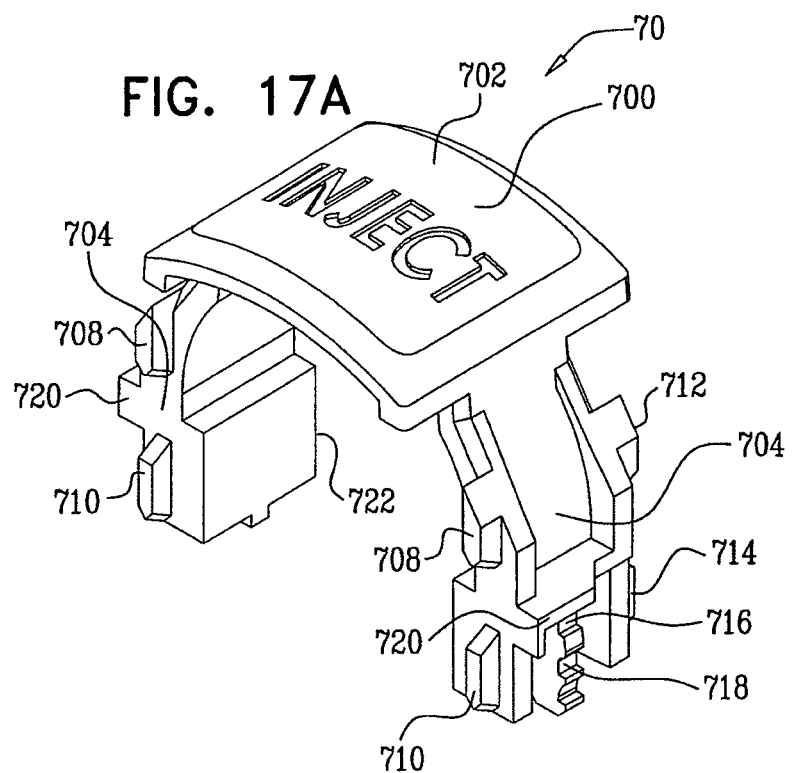
FIGS. 17A and 17B are respective front and back view simplified pictorial illustrations of an actuation button which forms part of the automatic injection device of FIG. 1.
Figure 17B:
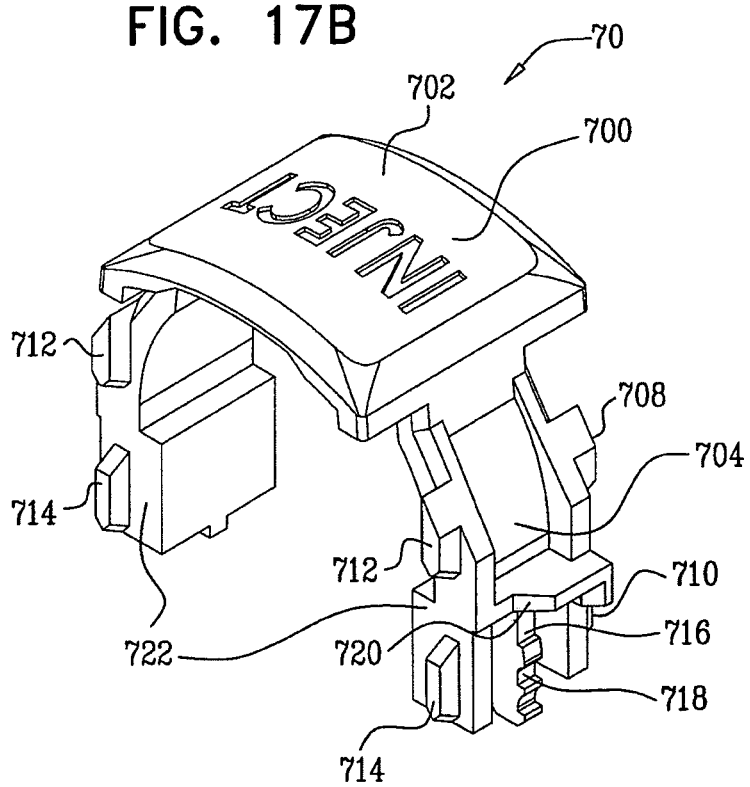
Figure 18A:
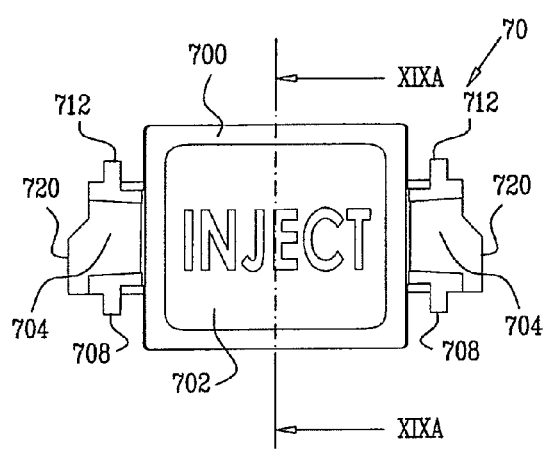
FIGS. 18A and 18B are respective top and side view simplified planar illustrations of the actuation button of FIGS. 17A and 17B.
Figure 18B:
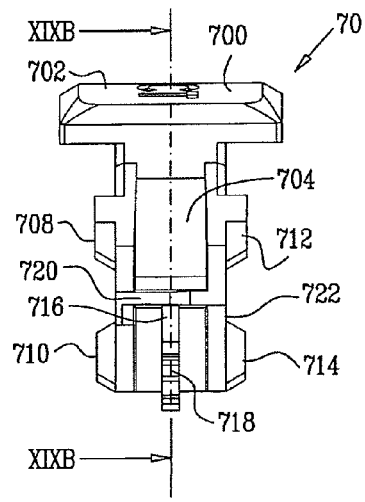
Figure 19A:
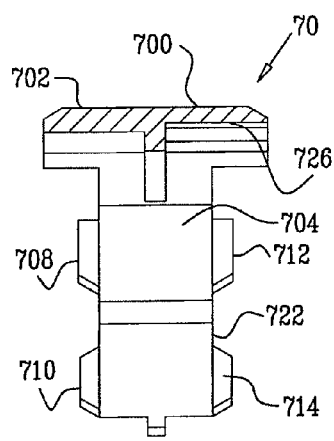
FIGS. 19A and 19B are sectional illustrations taken along respective section lines and directions XIXA-XIXA and XIXB-XIXB in FIGS. 18A and 18B.
Figure 19B:
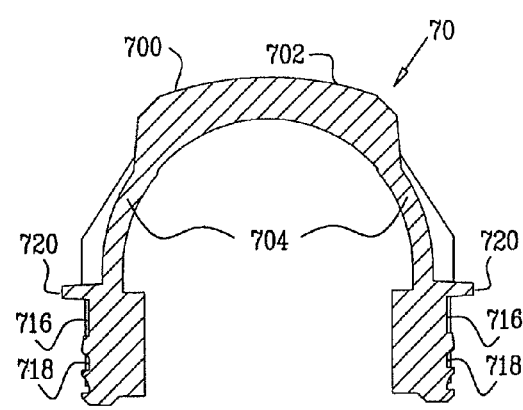

Reference is now made to FIGS. 17A and 17B, which are respective front and back view simplified pictorial illustrations of actuation button 70 which forms part of the automatic injection device of FIG. 1, to FIGS. 18A and 18B, which are respective top and side view simplified planar illustrations of the actuation button of FIGS. 17A and 17B, and to FIGS. 19A and 19B, which are sectional illustrations taken along respective section lines and directions XIXA-XIXA and XIXB-XIXB in FIGS. 18A and 18B.

The actuation button 70 has the general configuration of a side-to-side symmetric arch and includes a central portion 700 having a top finger engagement surface 702, a pair of generally rectangular legs 704, and a bottom surface 726. Each of legs 704 includes first and second generally trapezoidal forwardly directed protrusions 708 and 710 and first and second generally trapezoid rearwardly directed protrusions 712 and 714, which are adapted to be seated in correspondingly configured tracks 670 (FIGS. 14-16C) of the rear housing 60. Intermediate the forwardly directed protrusions 708 and 710 and rearwardly directed protrusions 712 and 714, each leg 704 includes first and second outwardly facing recesses 716 and 718, which are adapted to engage the flexible biasing fingers 673 (FIGS. 14-16C) of the rear housing 60 and thereby maintain the actuation button 70 in either its storage state or its activated state.

Adjacent the forwardly directed protrusions 708 and 710 and rearwardly directed protrusions 712 and 714 on each leg 704 there is provided a generally L-shaped transverse outwardly facing protrusion 720 with respect to which the generally trapezoidal protrusions 340 (FIGS. 5-7B) of the needle guard element 30 are oriented prior to actuation of the device, so as to prevent premature actuation of the device. The L-shaped transverse outwardly facing protrusions 720 additionally prevent the inward displacement of the actuation button 70 when the device is not pressed against the user's body and the needle guard element 30 (FIGS. 5-7B) is not rearwardly displaced.

Each of the legs 704 additionally includes a rearward facing surface 722, against which protrusion 540 (FIG. 11-13B) of the selectable driving assembly 50 abuts prior to actuation of the device.

During inward displacement of the actuation button 70 and resulting actuation of the device, the plunger locking element 90 (FIG. 1) abuts against bottom surface 726 of the central portion 700, generally underlying the top finger engagement surface 702.

Reference is now made to FIG. 20, which is a simplified pictorial illustration of plunger locking element 90 which forms-part of the automatic injection device of FIG. 1, to FIGS. 21A, 21B, 21C and 21D, which are respective rear, top, front and side view simplified planar illustrations of the plunger locking element of FIG. 20, and to FIGS. 22A and 22B, which are sectional illustrations taken along respective section lines and directions XXIIA-XXIIA and XXIIB-XXIIB in FIG. 21B.

The plunger locking element 90 is preferably an integrally formed element, preferably injection molded of plastic and includes an upright back portion 800 having, at a central bottom region thereof, a plunger engaging protrusion 802 having a curved bottom facing edge surface 804 which engages the teeth 478 of toothed portion 477 (FIG. 1) of the plunger 49 and thus prevents the plunger 49 from moving forward. An actuation button engagement surface 806 is provided on a forwardly extending protrusion 808 of the top portion of the plunger locking element 90. The actuation button engagement surface 806 is engaged by the actuation button 70 (FIGS. 17A-19B) and is rotated thereby about an axis 810, extending perpendicular to axis 603 of rear housing 60 (FIGS. 14-16B), during actuation of the device, thereby releasing the locking of the plunger 49 (FIG. 1).

A pair of forwardly facing protrusions 812, each having a curved forward end 814, define axis 810 about which the plunger locking element 90 rotates during actuation of the device. These protrusions are seated in corresponding hemispherical recesses of the rear end element 80 (FIG. 1). A resilient leg 820 extends downwardly from back portion 800, generally alongside one of the forwardly facing protrusions 812 and constantly urges the plunger locking element 90 to rotate about axis 810 to a configuration in which the plunger 49 (FIG. 1) is locked. When the plunger locking element 90 is rotated about axis 810, the resilient leg 820 abuts against the rear end element 80 (FIG. 1) and the plunger 49 is released.

A pair of downward facing protrusions 822, each having a generally planar forwardly facing surface 824, are formed on either side of the back portion 800 of the plunger locking element 90. When the drug vial adaptor 20 (FIGS. 2-4B) is connected to the forward housing 40 (FIGS. 8-10C), drug vial adaptor 20 rearwardly pushes a forward portion of the locking rod 98 (FIG. 1) which extends forwardly out of the forward housing 40, thereby rearwardly displacing the locking rod 98. When the locking rod 98 is rearwardly displaced, a rearward portion thereof abuts against protrusions 822 and causes rotation of the plunger locking element 90, about axis 810, thereby releasing the plunger 49 (FIG. 1).

Figure 23:
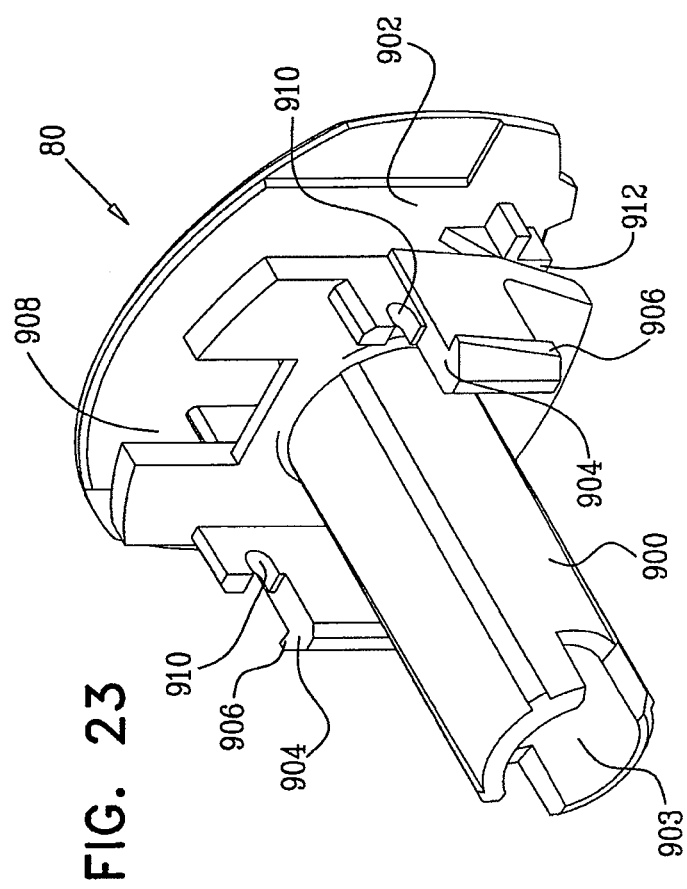
FIG. 23 is a simplified pictorial illustration of a rear end element which forms part of the automatic injection device of FIG. 1.

Reference is now made to FIG. 23, which is a simplified pictorial illustration of rear end element 80 which forms part of the automatic injection device of FIG. 1, to FIGS. 24A and 24B, which are respective top and side view simplified planar illustrations of the rear end element of FIG. 23, and to FIGS. 25A, 25B and 25C, which are sectional illustrations taken along respective section lines and directions XXVA-XXVA, XXVB-XXVB and XXVC-XXVC in FIGS. 24A and 24B.

The rear end element 80 includes a generally cylindrical forward portion 900 terminating rearwardly in a generally planar rearward portion 902. Cylindrical forward portion 900 and rearward portion 902 together define a rearward spring seat for spring 62 (FIG. 1). The cylindrical portion 900 includes a central bore 903 which is adapted to accommodate the plunger 49 (FIG. 1). Extending forwardly from planar rearward portion 902 alongside cylindrical portion 900 are a pair of resilient fingers 904 each including an outwardly facing hook type protrusion 906. The resilient fingers 904 are adapted to engage corresponding rear end element retaining portions 672 in rear housing 60 (FIGS. 14-16C) and to maintain secure engagement of the rear end element 80 thereto. Generally planar rearward portion 902 defines a cut out 908 which accommodates forwardly extending protrusion 808 of the plunger locking element 90.

Adjacent resilient fingers 904 are a pair of partially semi-circular recesses 910, which define the location of axis 810 about which the plunger locking element 90 rotates. Rearward portion 902 also includes a forwardly facing protrusion 912, which is adapted to engage resilient leg 820 (FIGS. 20-22B) of the plunger locking element 90.

Figure 26:
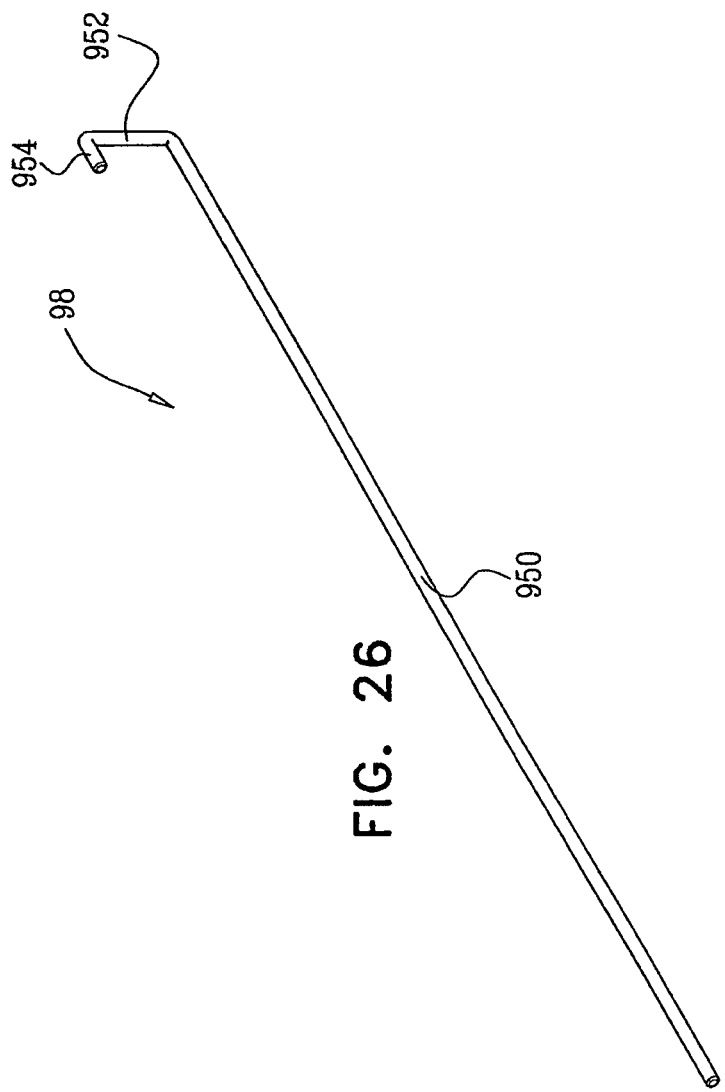
FIG. 26 is a simplified pictorial illustration of a locking rod which forms part of the automatic injection device of FIG. 1.

Reference is now made to FIG. 26, which is a simplified pictorial illustration of locking rod 98 which forms part of the automatic injection device of FIG. 1.

The locking rod 98 includes a first longitudinally extending portion 950, terminating rearwardly at a rearward facing transverse portion 952 which, in turn terminates at a second longitudinally extending portion 954 which is generally parallel to the first longitudinally extending portion 950.

Reference is now made to FIGS. 27A, 27B, 27C, 27D, 27E, 27F, 27G, 27H, 27I, 27J and 27K which are simplified pictorial illustrations of various stages of typical use of the automatic injection device of FIG. 1.

Figure 27A:
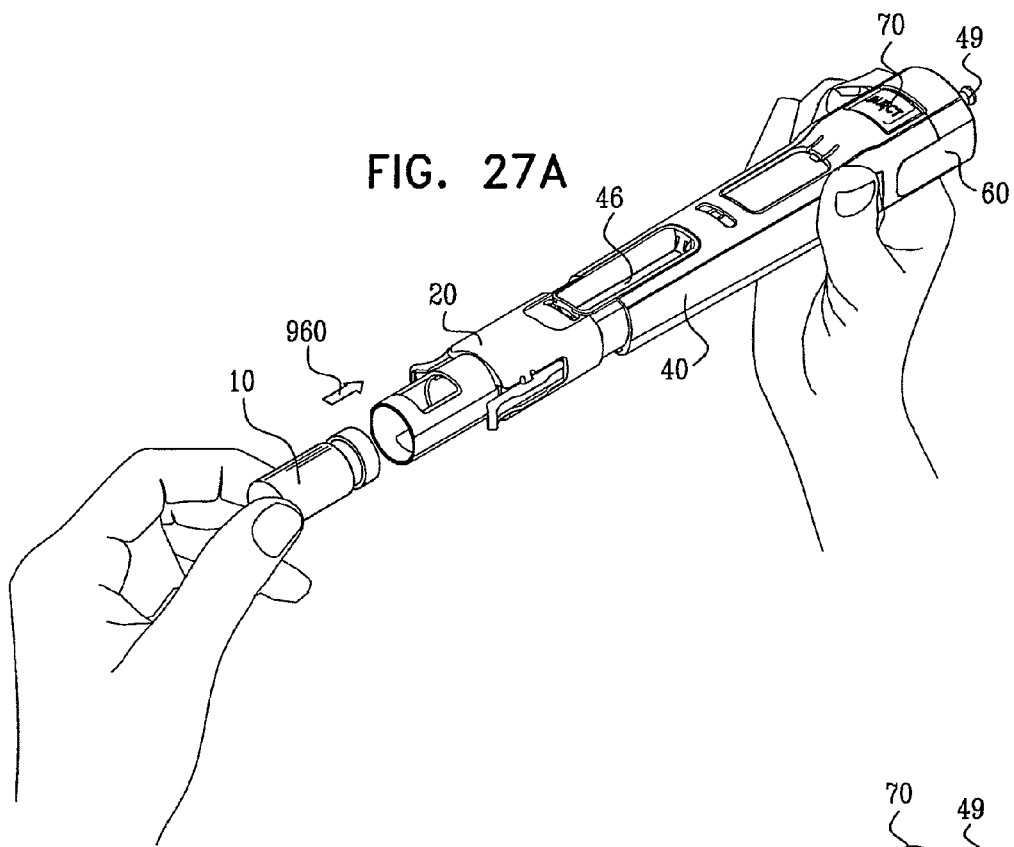
FIGS. 27A, 27B, 27C, 27D, 27E, 27F, 27G, 27H, 27I, 27J and 27K are simplified pictorial illustration of various stages of typical use of the automatic injection device of FIG. 1.
Figure 27B:
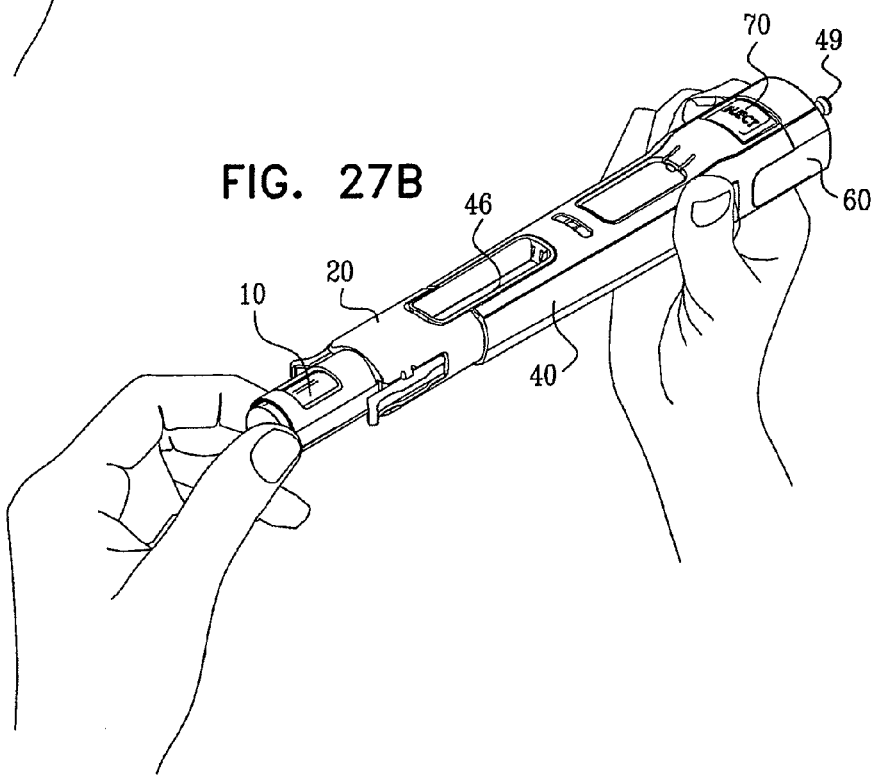

FIG. 27A illustrates insertion of vial 10 into vial adaptor 20, which forms part of the automatic injection device of FIG. 1. FIG. 27B shows the vial 10 fully inserted into vial adaptor 20, it being appreciated that removal of the vial 10 from vial adaptor 20 following full insertion thereof is very difficult or impossible. It is further appreciated that insertion of vial 10 into vial adaptor 20 causes vial adaptor 20 to be displaced in a rearward direction indicated by an arrow 960 in FIG. 27A, with respect to the remainder of the automatic injection device of FIG. 1.

Figure 27C:
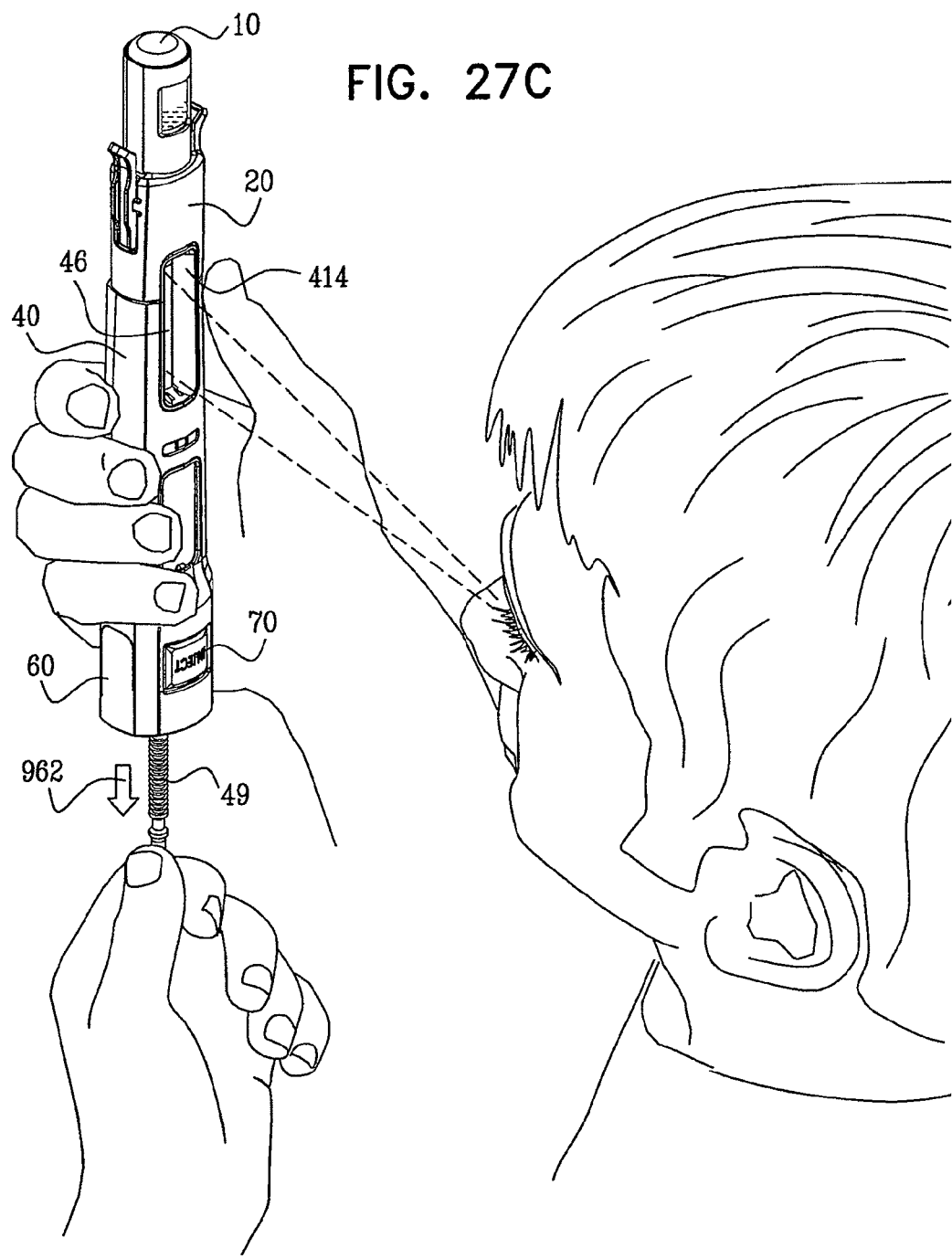

FIG. 27C shows liquid from vial 10 being drawn into syringe 46. This is achieved by a user, holding the automatic injection device of FIG. 1 in a generally vertical orientation as shown, pulling the plunger 49 in a direction indicated by an arrow 962, downward in the sense of FIG. 27C and rearward in the sense of FIG. 1. During this procedure, the user sees the amount of liquid in the syringe 46 via window 414 in forward housing 40. It is appreciated that at this stage, the plunger 49 can be displaced by the user in a direction opposite to that indicated by arrow 962.

Figure 27D:
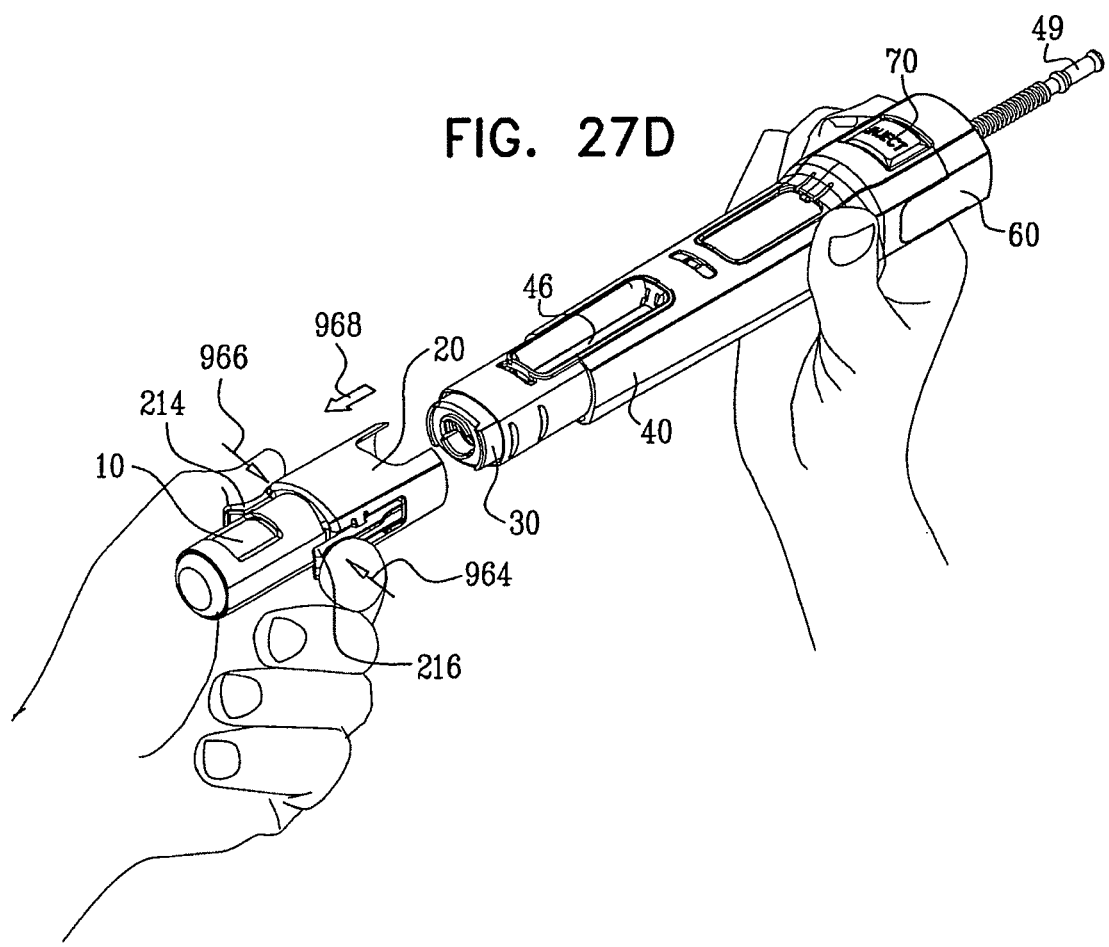

FIG. 27D illustrates removal of the vial adaptor 20, containing vial 10, from the forward housing 40, by first pressing inwardly on finger engagement portions 214 and 216 as indicated by arrows 964 and 966 respectively and then pulling vial adaptor 20 in a direction indicated by an arrow 968. It is appreciated that at this stage, here termed a ready to inject stage, following removal of the vial adaptor 20 from the forward housing 40, the plunger 49 cannot be displaced by the user in a direction opposite to that indicated by arrow 962 (FIG. 27C).

Figure 27E:
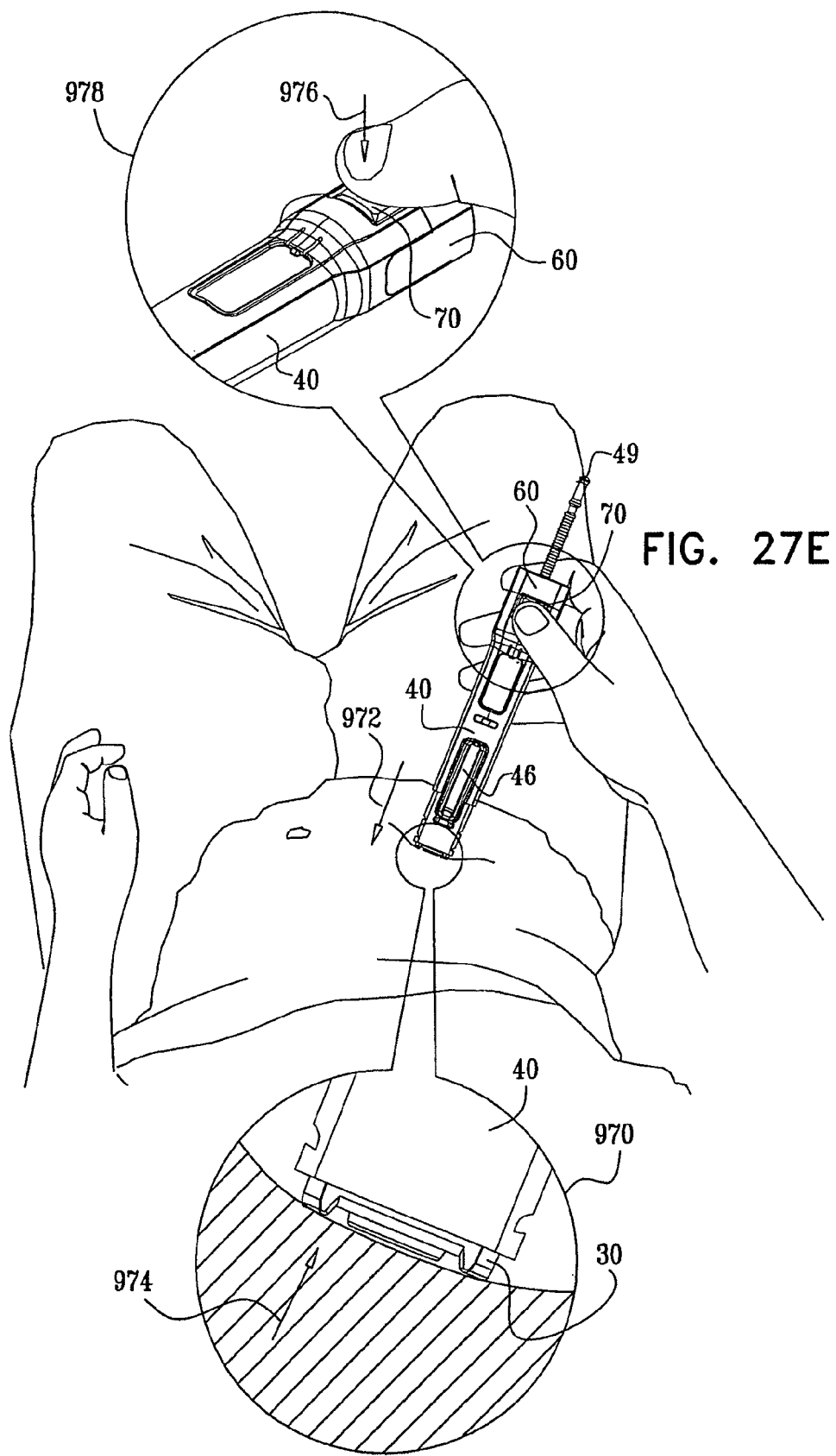

Turning now to FIG. 27E, it is seen that a user is employing the automatic injection device to inject a liquid into his body. As illustrated in enlargement 970, it is seen that by pressing the automatic injection device against his body, in a direction indicated by an arrow 972, the user causes needle guard element 30 to be pushed in a direction indicated by an arrow 974, rearwardly with respect to forward housing 40. This rearward motion unlocks actuation button 70, such that when the user presses on the actuation button 70, as indicated by an arrow 976 in enlargement 978, the actuation button 70 is operative to initiate injection.

Figure 27F:
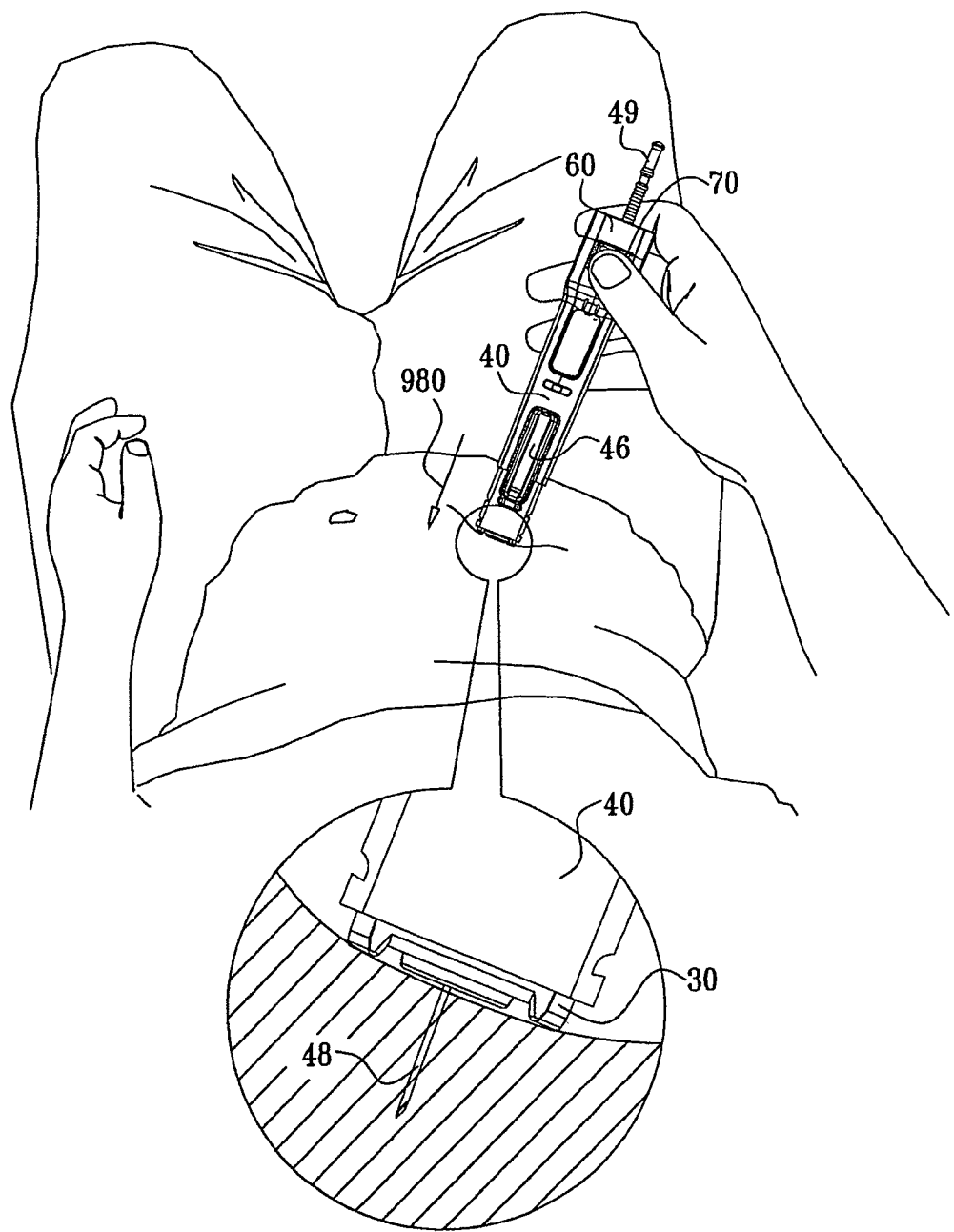
Figure 27G:
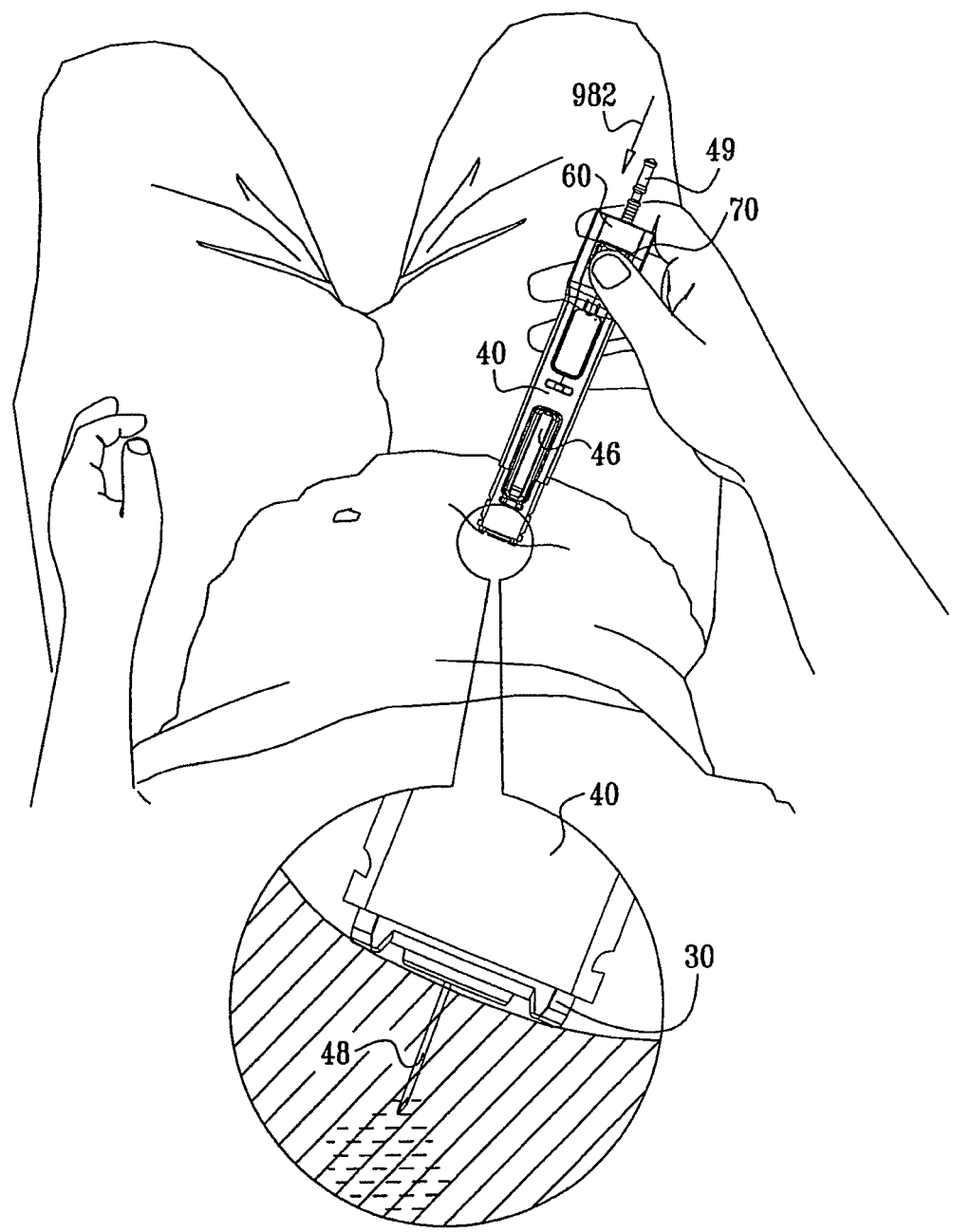
Figure 27H:
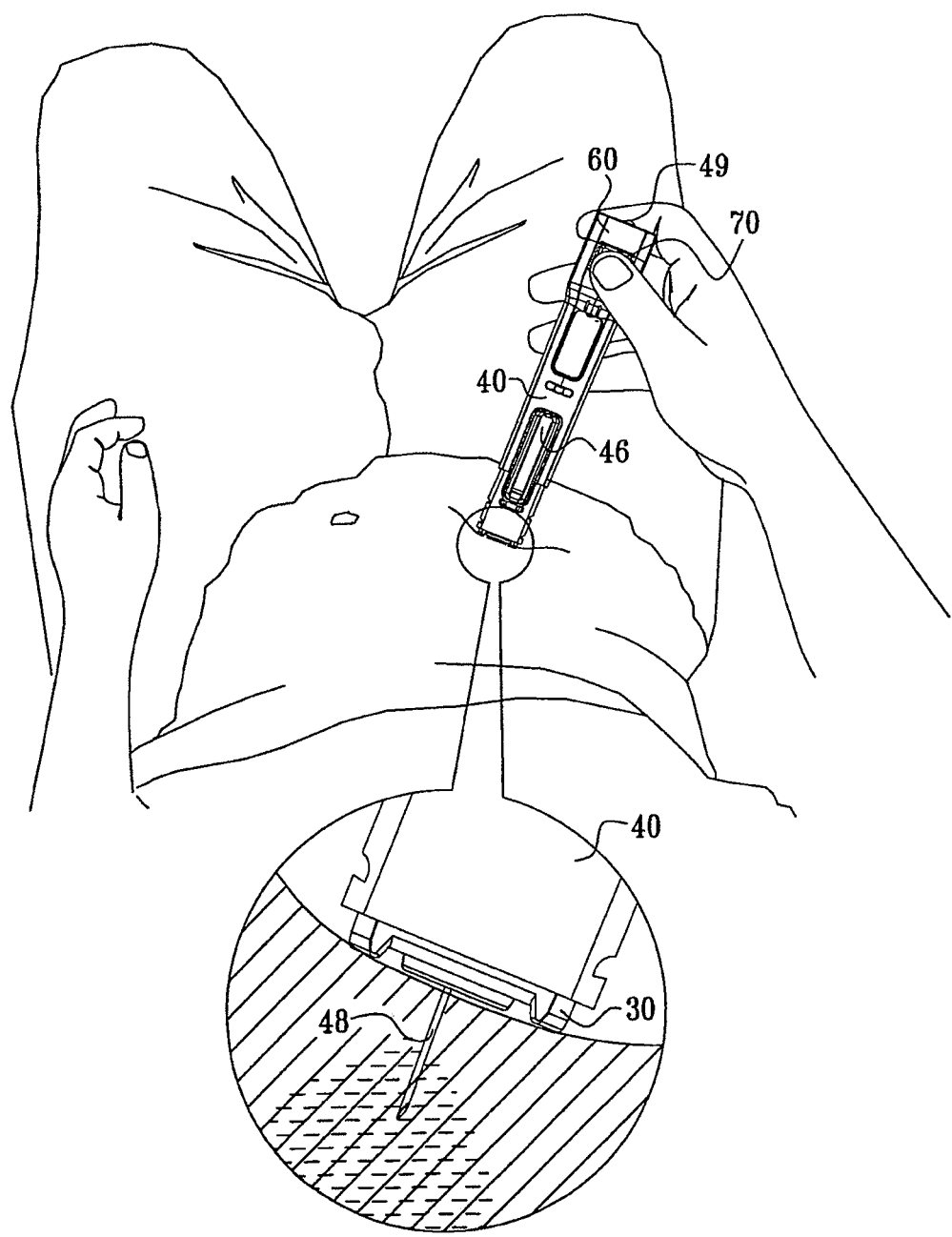

As seen in FIG. 27F, during such injection, responsive to user operation of the actuation button 70, the syringe 46 moves forwardly in a direction indicated by an arrow 980 causing the needle 48 of syringe 46 to penetrate the user's body and subsequently inject liquid into the user's body, as shown in FIG. 27G. It is noted that as the injection of the liquid proceeds, the plunger 49 moves forwardly relative to syringe 46 and to the remainder of the injection device, as indicated by an arrow 982 in FIG. 27G. FIG. 27H shows completion of the injection of the liquid, with the plunger 49 being in a fully forward orientation relative to the remainder of the injection device.

Figure 27I:
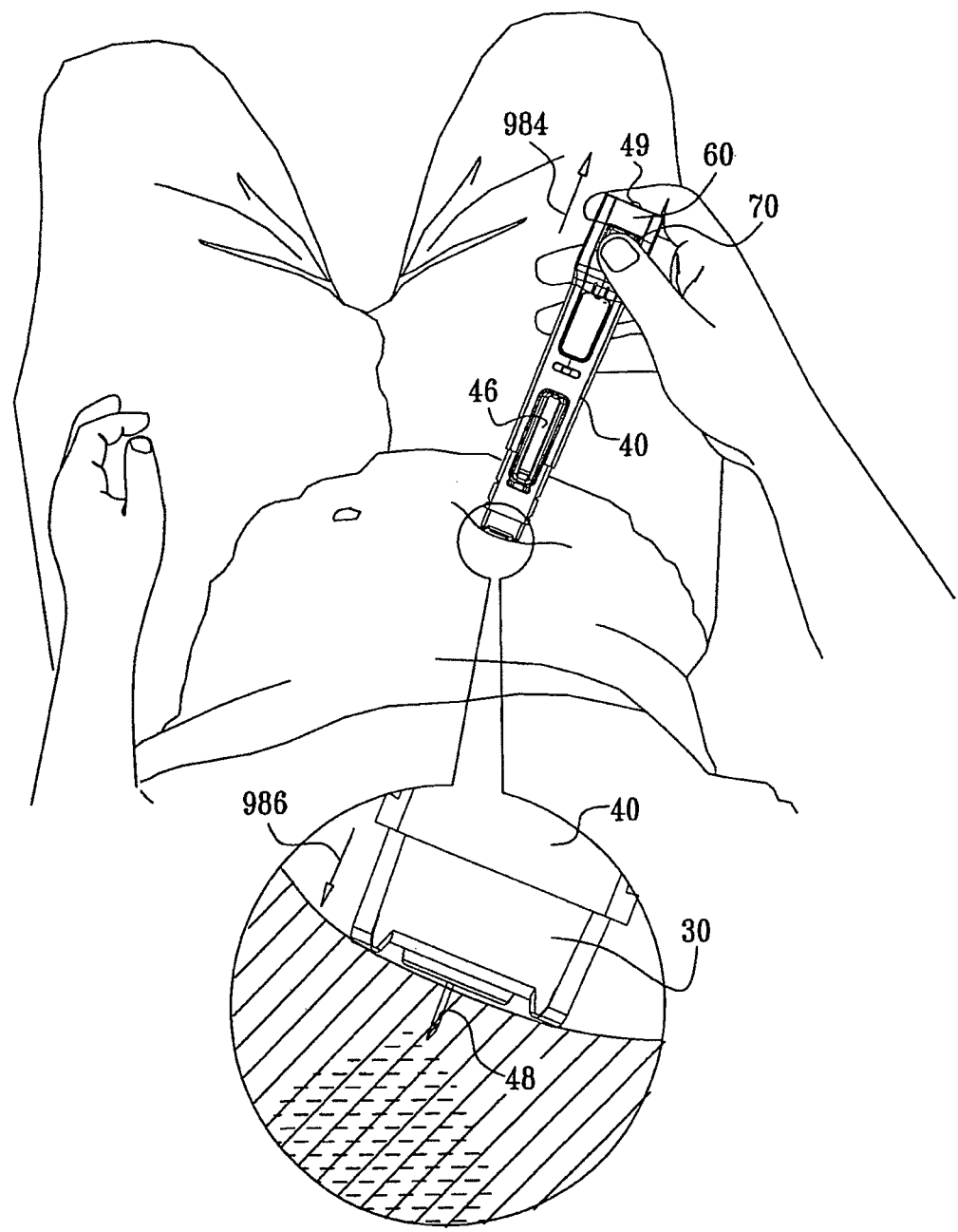
Figure 27J:
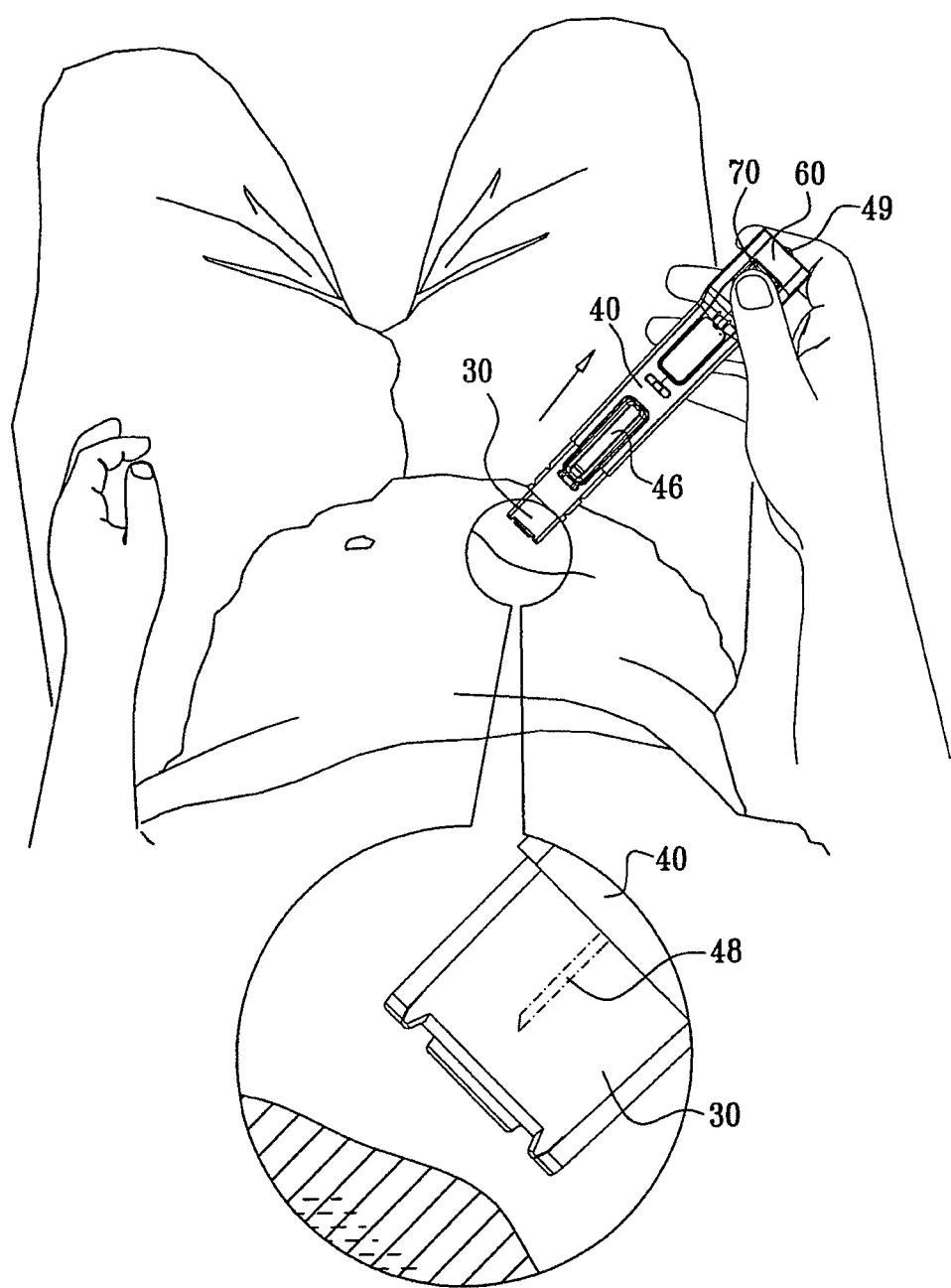

As seen in FIG. 27I, following completion of the injection of the liquid, the user retracts the injection device slightly from his body, as indicated by an arrow 984, causing corresponding retraction of needle 48 from his body and corresponding extension of needle guard element 30 forwardly with respect to the forward housing 40, as indicated by an arrow 986. FIG. 27J shows the injection device fully disengaged from the user's body and the needle guard 30 in a fully extended orientation relative to the forward housing 40, fully covering the needle 48 and generally preventing finger engagement with the needle 48.

Figure 27K:
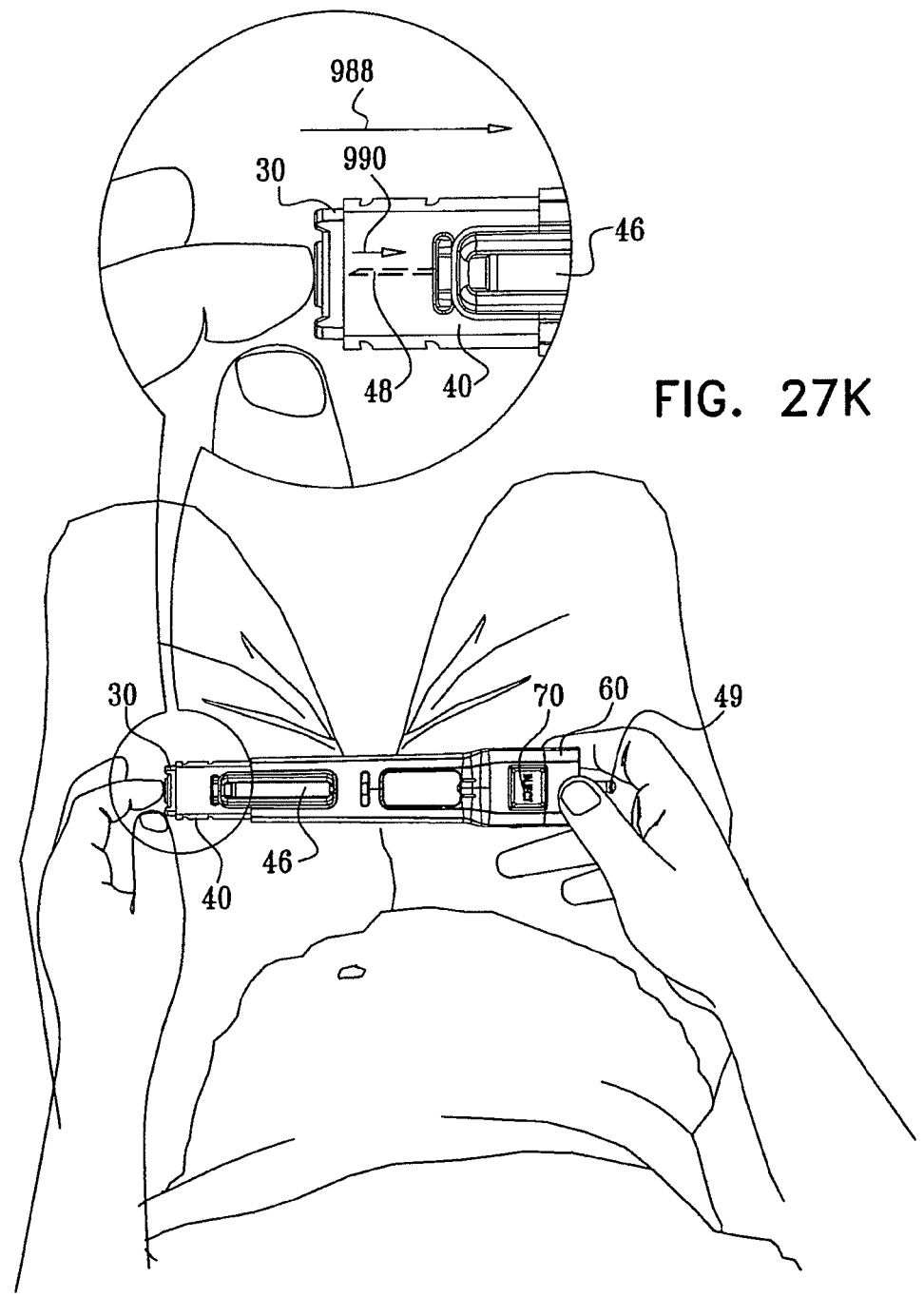

FIG. 27K shows that retraction of the needle guard element 30 is such that even if a user pushes the needle guard element 30 rearwardly as indicated by an arrow 988, the needle guard element 30 causes the needle 48 to be retracted, in a direction indicated by an arrow 990, to the same extent, such that engagement of a user's finger with the tip of needle 48 is prevented.

Figure 28:
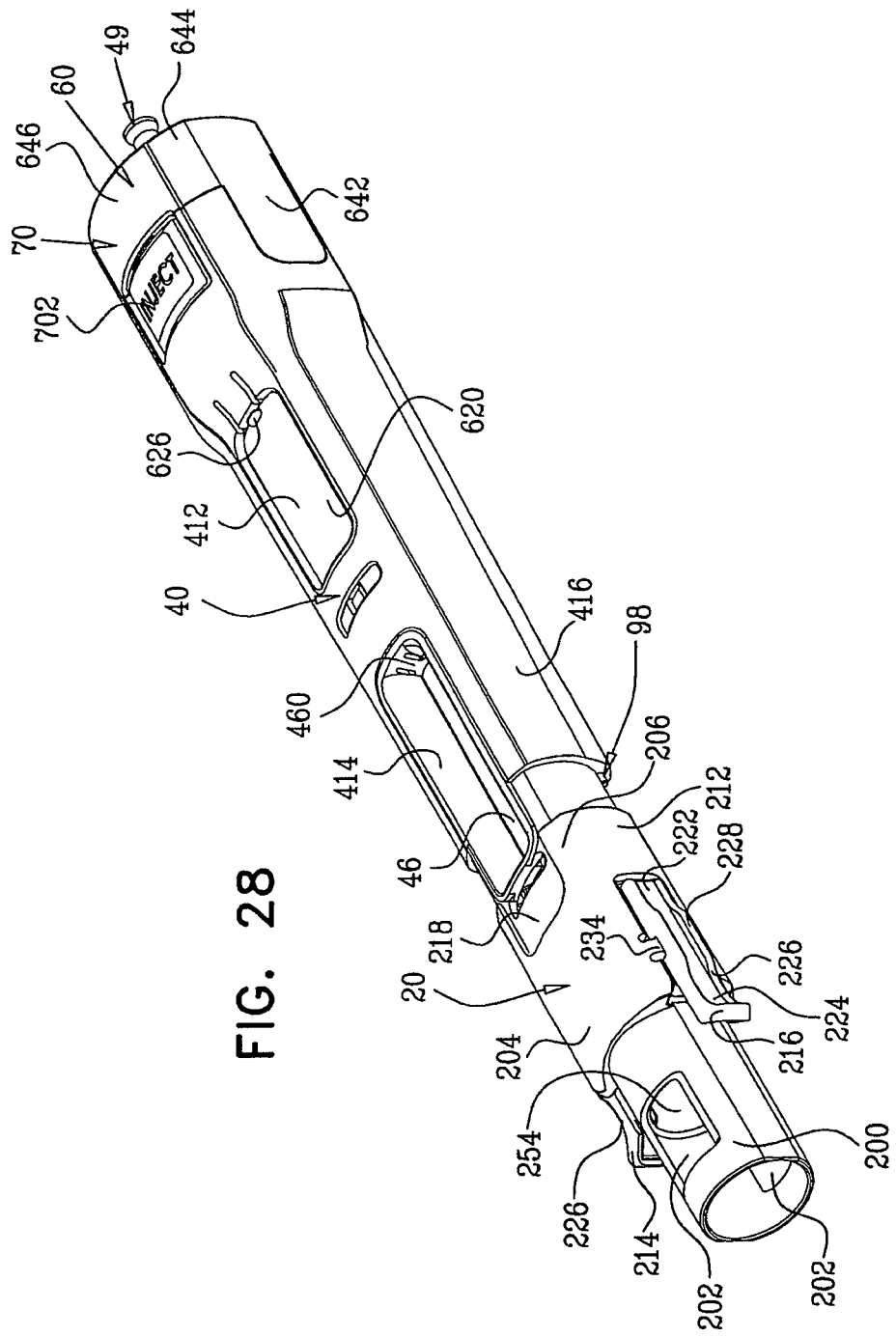
FIG. 28 is a simplified assembled view illustration of the automatic injection device of FIGS. 1 and 27A in a pre-use operative orientation.

Reference is now made to FIG. 28, which is a simplified assembled view illustration of the automatic injection device of FIGS. 1 and 27A in a pre-use and storage operative orientation, to FIGS. 29A and 29B, which are respective side and top view simplified planar illustrations of the automatic injection device of FIG. 28, and to FIGS. 30A, 30B, 30C, 30D and 30E, which are sectional illustrations taken along respective section lines and directions XXXA-XXXA, XXXB-XXXB, XXXC-XXXC, XXXD-XXXD and XXXE-XXXE in FIGS. 29A and 29B.

As seen in FIGS. 27A and 28-30E, the vial adaptor 20 is maintained in engagement with the forward housing 40 by engagement of inwardly facing retaining protrusions 230 with forward recesses 401 and therefore does not rearwardly displace the locking rod 98.

Figure 30A:
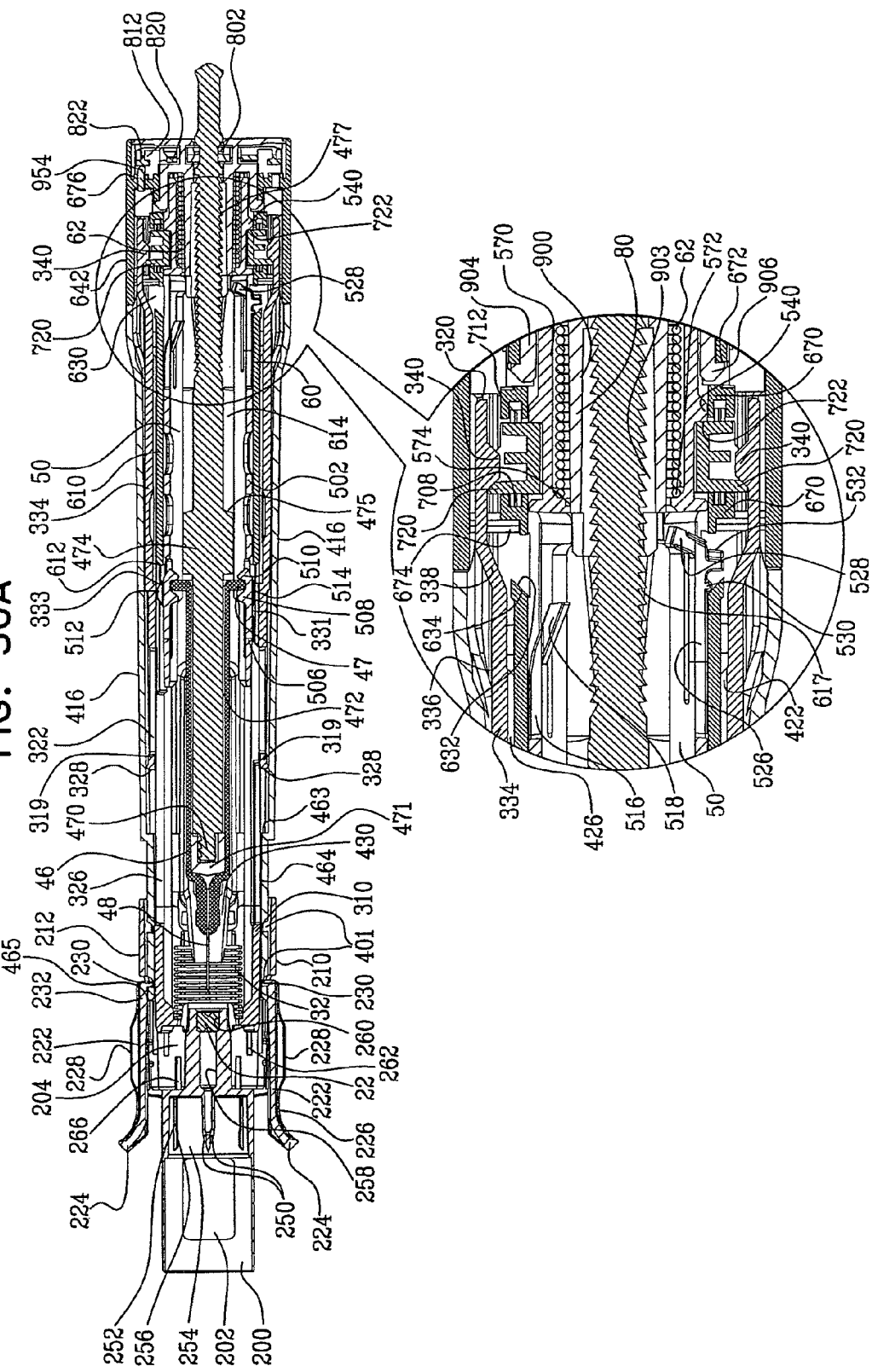

FIGS. 30A and 30C show that the protrusion 720 of the actuation button 70 is oriented, with respect to the generally trapezoidal protrusions 340 of the needle guard element 30, so as to prevent depression of the actuation button 70. Additionally, abutment of protrusion 720 against generally trapezoidal protrusions 340 prevents forward displacement of needle guard element 30 relative to forward housing 40 against the urging of spring 32.

Furthermore, the flexible biasing fingers 673 of the rear housing 60 engage corresponding second outwardly facing recesses 718 of the actuation button 70, and maintain it in the storage orientation shown in FIG. 28.

Figure 30B:
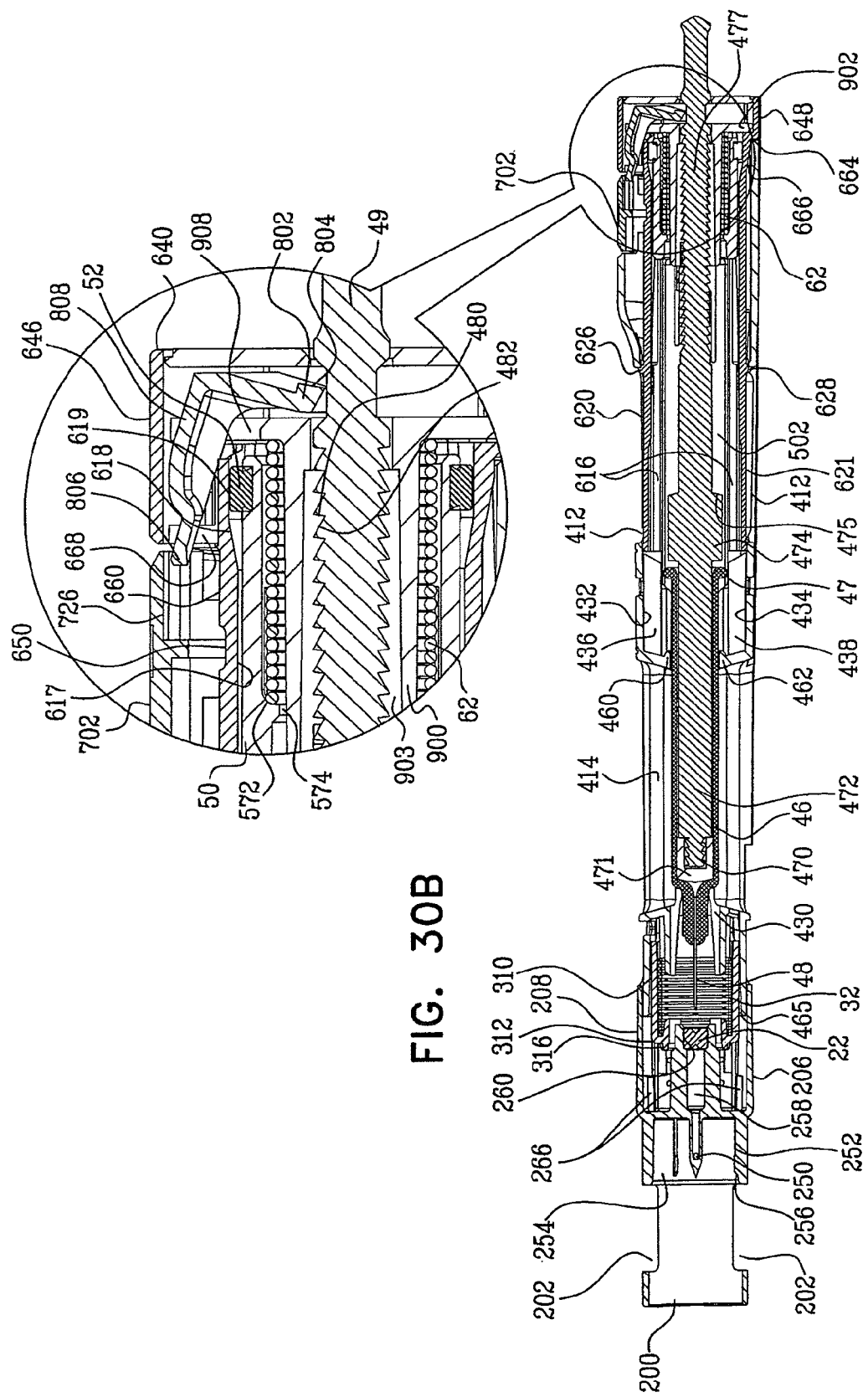

FIG. 30D shows the locking rod 98 abutting against the downward facing protrusions 822 of the plunger locking element 90. The enlarged portion of FIG. 30B shows the plunger engaging protrusion 802 of the plunger locking element 90 in a locking orientation with respect to plunger 49. FIG. 30E shows the resilient leg 820 of the plunger locking element 90 engaging the forwardly facing protrusion 912 of the rear end element 80.

As seen in FIGS. 28-30E, in a pre-use operative orientation of the automatic injection device which is suitable for storage, the rear housing 60 is joined to the forward housing 40 by snap fit engagement of protrusions 626 and 628 of rear housing 60 in the snap fit engagement sockets 412 formed in the forward housing 40.

As seen with particular clarity in the enlarged portion of FIG. 30A, the selectable driving assembly 50 is retained in its axial position by engagement of rearward facing surface 722 with protrusion 540 of the selectable driving assembly 50. In this arrangement, spring 62 is in a relatively compressed state and is held in that state by the selectable driving assembly 50.

The syringe 46 is retained in a retracted orientation by engagement of flange 47 thereof with inwardly facing protrusions 508 and 510 formed in respective first hinged fingers 506 of each of symmetric actuation arms 502 of selectable driving assembly 50 (FIGS. 11-13B).

It is appreciated that when the automatic injection device is in its orientation shown in FIGS. 28-30E, needle 48 does not pierce septum 22.

Figure 31:
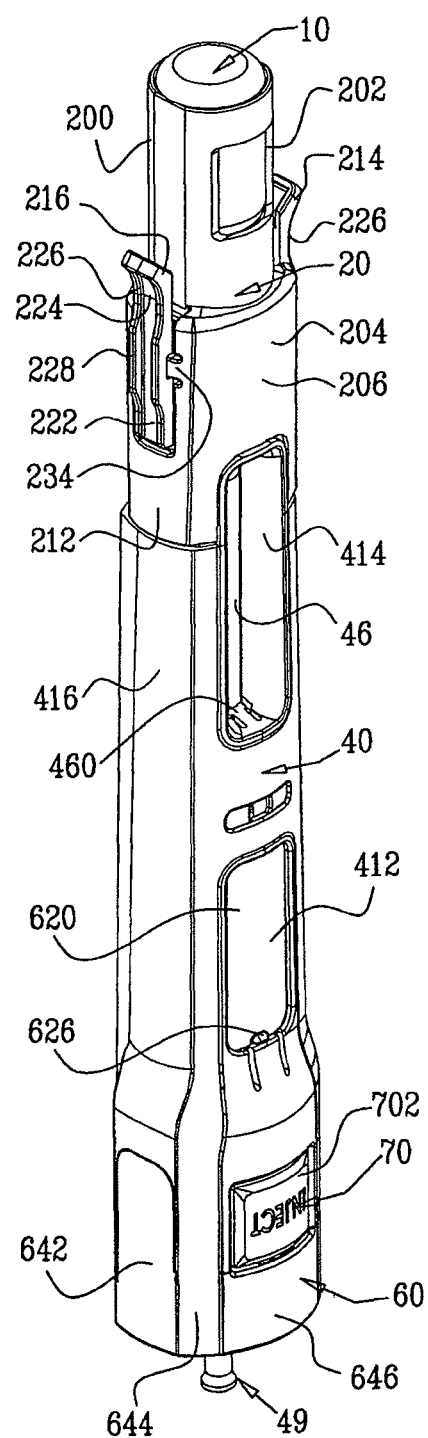
FIG. 31 is a simplified assembled view illustration of the automatic injection device of FIGS. 1 and 27B in a vial connection orientation.

Reference is now made to FIG. 31, which is a simplified assembled view illustration of the automatic injection device of FIGS. 1 and 27B in a vial connection orientation, to FIGS. 32A and 32B, which are respective side and top view simplified planar illustrations of the automatic injection device of FIG. 31, and to FIGS. 33A, 33B, 33C, 33D and 33E, which are sectional illustrations taken along respective section lines and directions XXXIIIA-XXXIIIA, XXXIIIB-XXXIIIB, XXXIIIC-XXXIIIC, XXXIIID-XXXIIID and XXXIIIE-XXXIIIE in FIGS. 32A and 32B.

As seen in FIG. 27B and FIGS. 31-33E, the vial 10 is fully inserted in the vial adaptor 20, causing the vial adaptor 20 to be displaced fully rearwardly relative to the forward housing 40. This displacement causes corresponding rearward displacement of the locking rod 98 relative to, inter alia, the forward housing 40. The vial adaptor 20 is maintained in place by engagement of inwardly facing retaining protrusions 230 with rearward recesses 401. The interior of vial 10 is in fluid flow communication with the interior of syringe 46 via needle 48 which extends through septum 22.

Figure 33B:
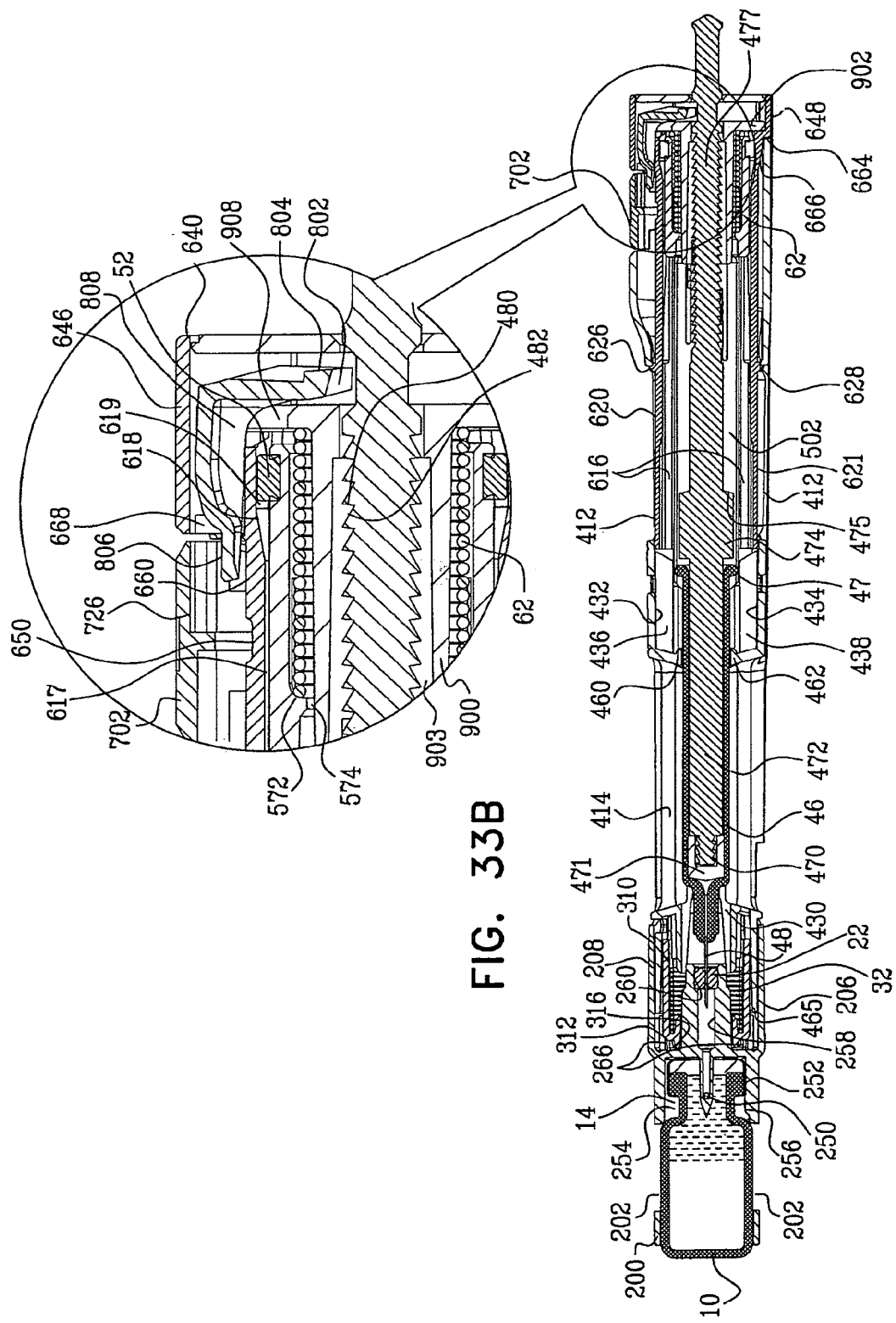

FIG. 33D shows the locking rod 98 rearwardly pushing the downward facing protrusions 822 of the plunger locking element 90 thereby causing rotation of the plunger locking element 90 about axis 810. The enlarged portion of FIG. 33B shows the rotation of the plunger engaging protrusion 802 of the plunger locking element 90 about axis 810 such that it does not engage the plunger 49. FIG. 33E shows a slight bend in the resilient leg 820 of the plunger locking element 90 resulting from rotation thereof about axis 810.

Figure 34:
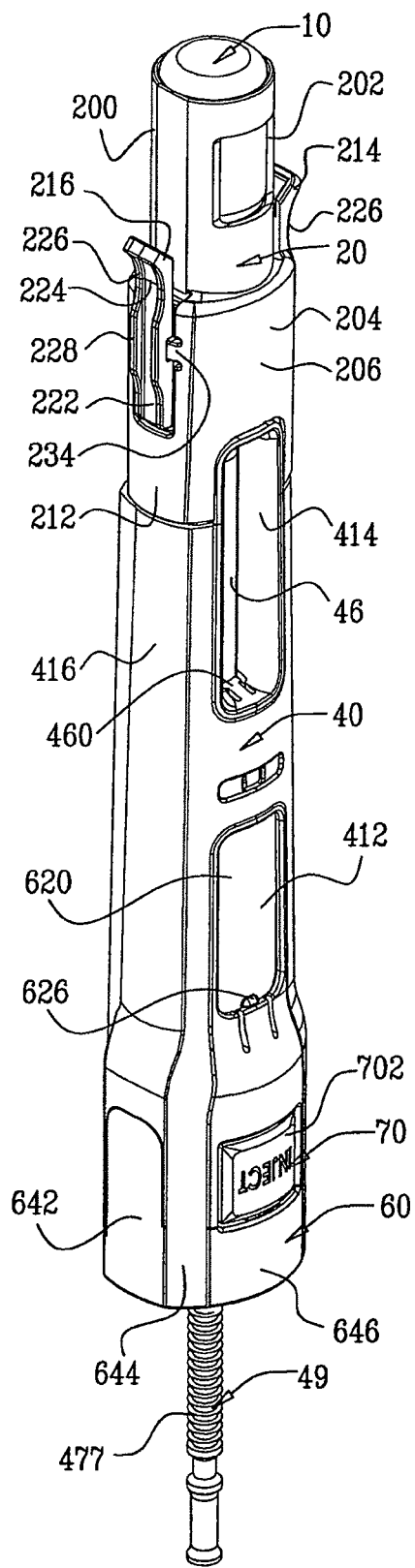
FIG. 34 is a simplified assembled view illustration of the automatic injection device of FIGS. 1 and 27C in a vial pumping orientation.
Figure 36A:
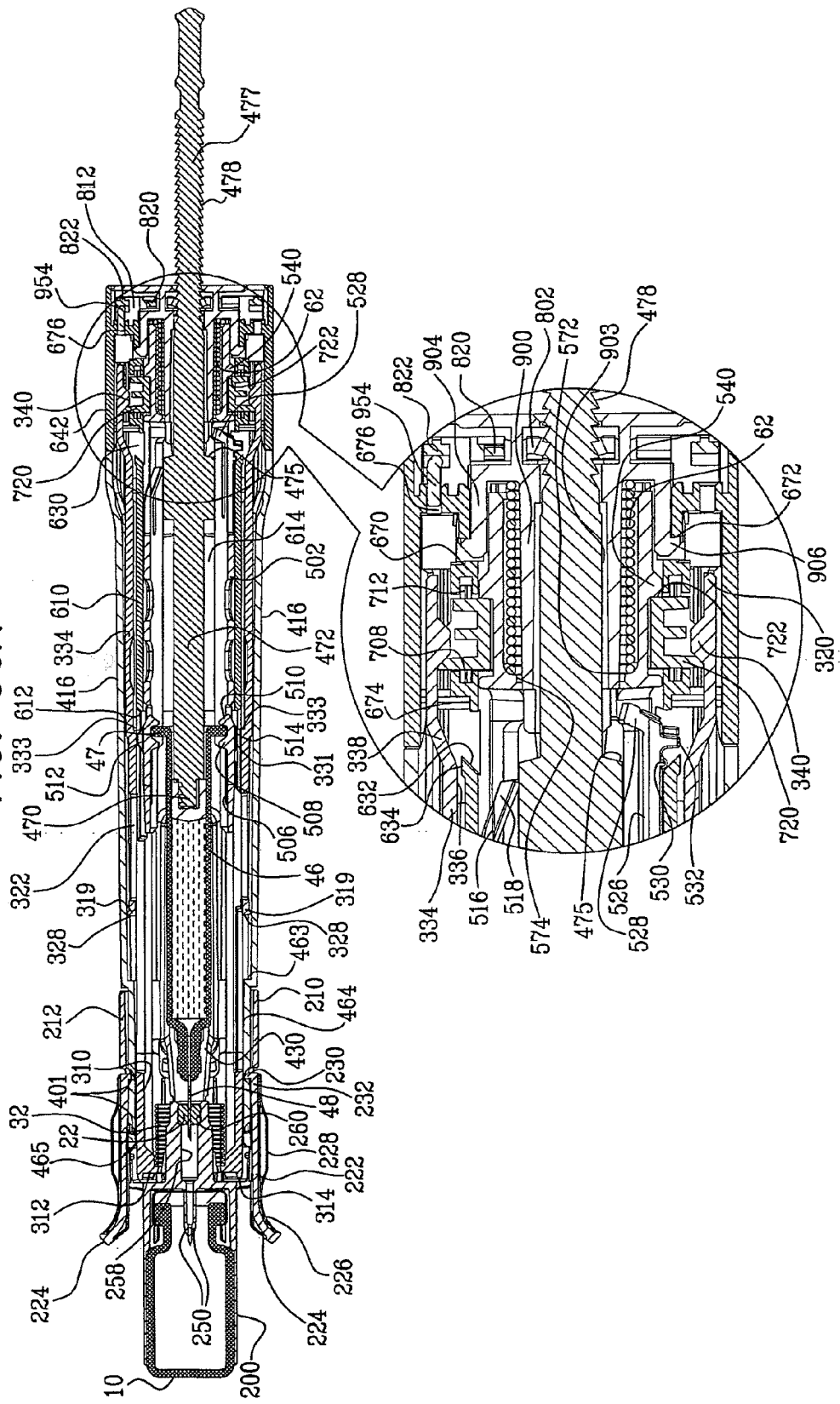
Figure 36B:
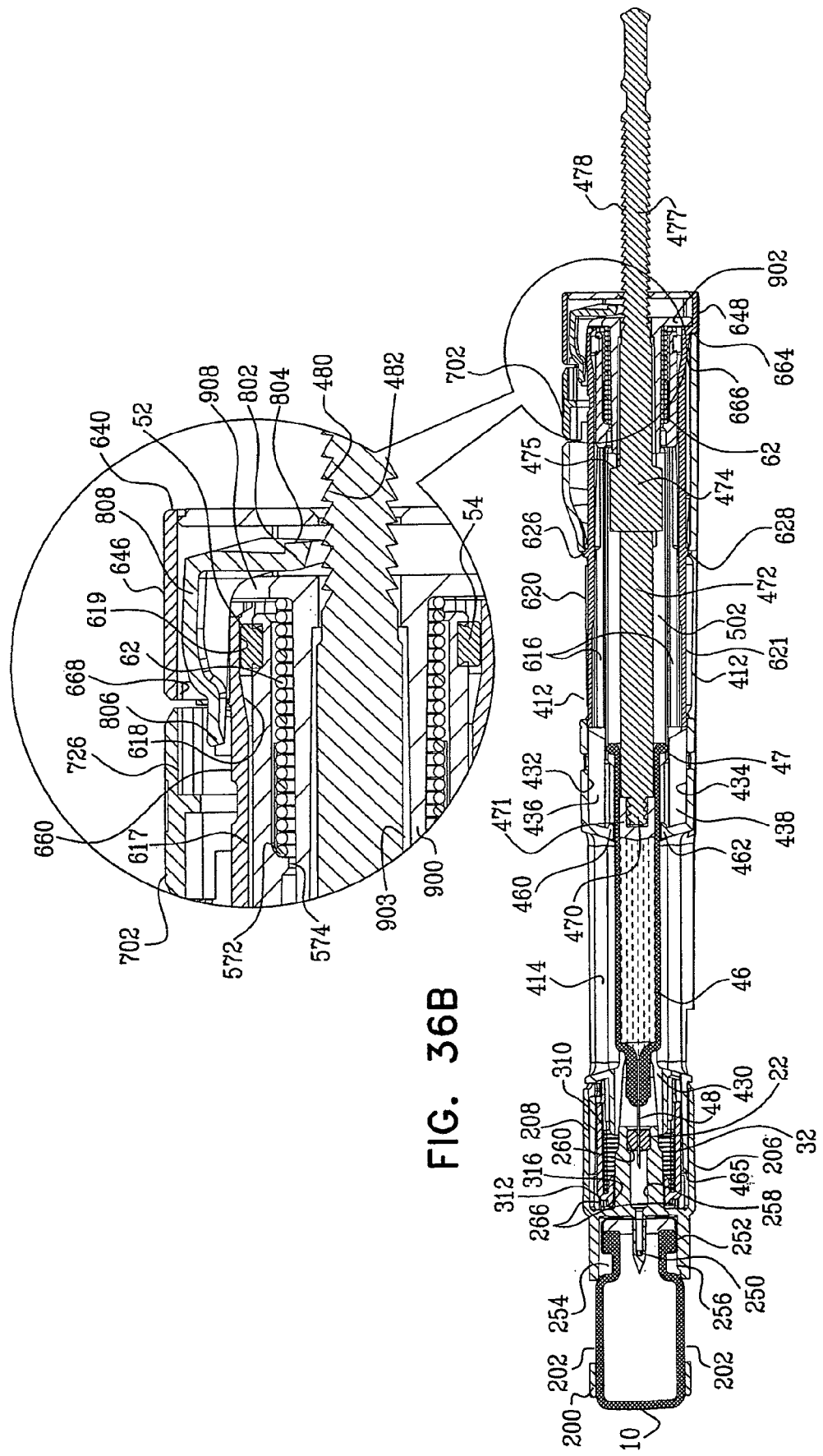

Reference is now made to FIG. 34, which is a simplified assembled view illustration of the automatic injection device of FIGS. 1 and 27C in a vial pumping orientation, to FIGS. 35A and 35B, which are respective side and top view simplified planar illustrations of the automatic injection device of FIG. 34, and to FIGS. 36A, 36B, 36C, 36D and 36E, which are sectional illustrations taken along respective section lines and directions XXXVIA-XXXVIA, XXXVIB-XXXVIB, XXXVIC-XXXVIC, XXXVID-XXXVID and XXXVIE-XXXVIE in FIGS. 35A and 35B.

As seen in FIGS. 27C and 34-36E, the plunger 49 is rearwardly displaced, thereby drawing liquid from the interior of vial 10 into the syringe 46 via needle 48. The enlarged portion of FIG. 36B clearly illustrates that the plunger engaging protrusion 802 of the plunger locking element 90 is located above one of the teeth 478 of the toothed portion 477 of the plunger 49.

Figure 37:
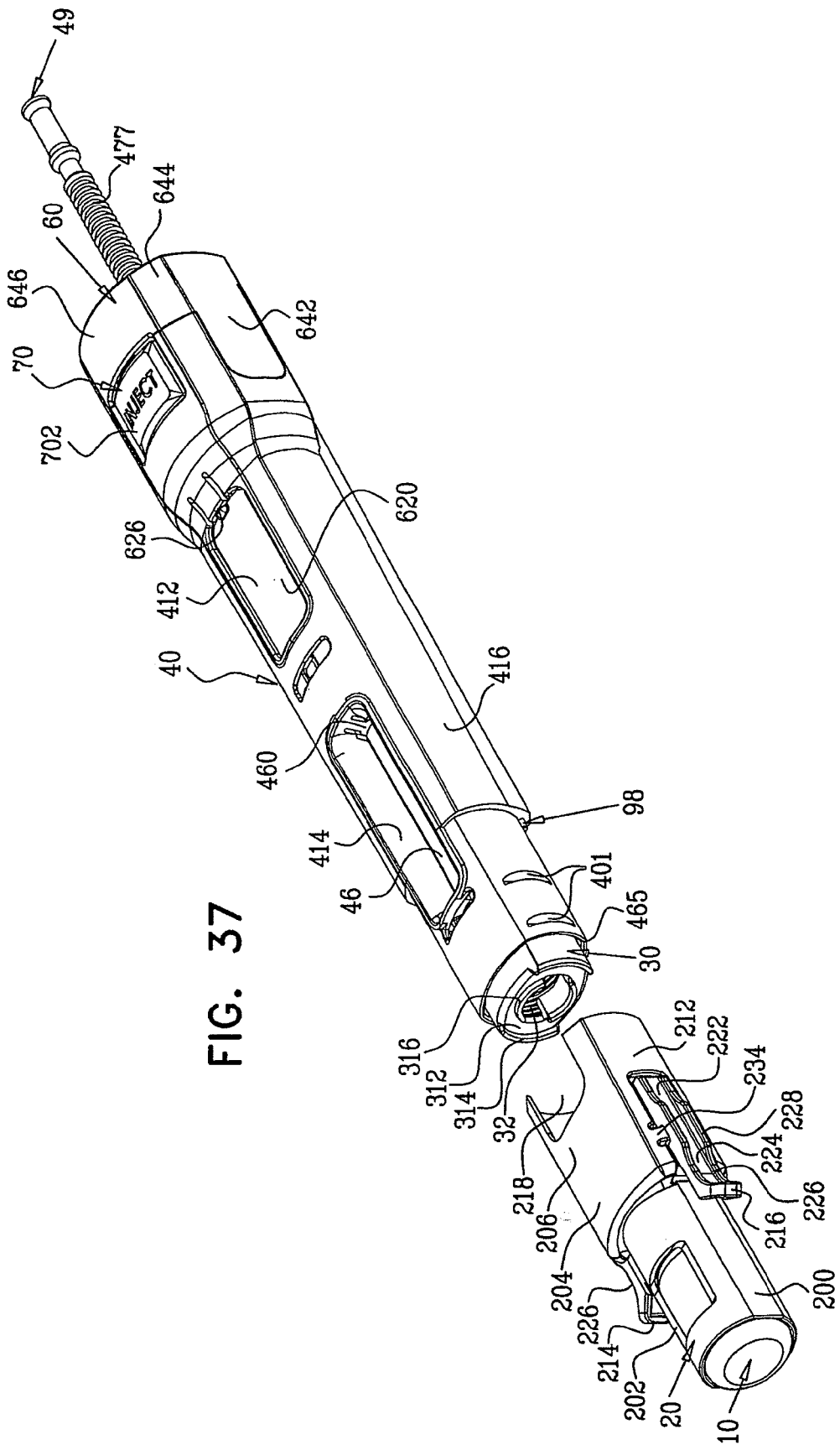
FIG. 37 is a simplified assembled view illustration of the automatic injection device of FIGS. 1 and 27D in a drug vial adaptor removal orientation.

Reference is now made to FIG. 37, which is a simplified assembled view illustration of the automatic injection device of FIGS. 1 and 27D in a drug vial adaptor removal orientation, to FIGS. 38A and 38B, which are respective side and top view simplified planar illustrations of the automatic injection device of FIG. 37, and to FIGS. 39A, 39B, 39C, 39D and 39E, which are sectional illustrations taken along respective section lines and directions XXXIXA-XXXIXA, XXXIXB-XXXIXB, XXXIXC-XXXIXC, XXXIXD-XXXIXD and XXXIXE-XXXIXE in FIGS. 38A and 38B.

As seen in FIGS. 27D and 37-39E, the vial adaptor 20 is removed from the forward housing 40 by a user pressing the finger engagement surfaces 226 of vial adaptor 20 which disengages inwardly facing retaining protrusions 230 from rearward recesses 401. The disengagement of the vial adaptor 20 from the remainder of the injection device enables the locking rod 98 to return to its orientation shown in FIGS. 28-30E. The plunger locking element 90 rotates about axis 810 back to its orientation shown in FIGS. 28-30E under the urging of the resilient leg 820 and thereby forwardly displaces the locking rod 98.

Figure 39A:
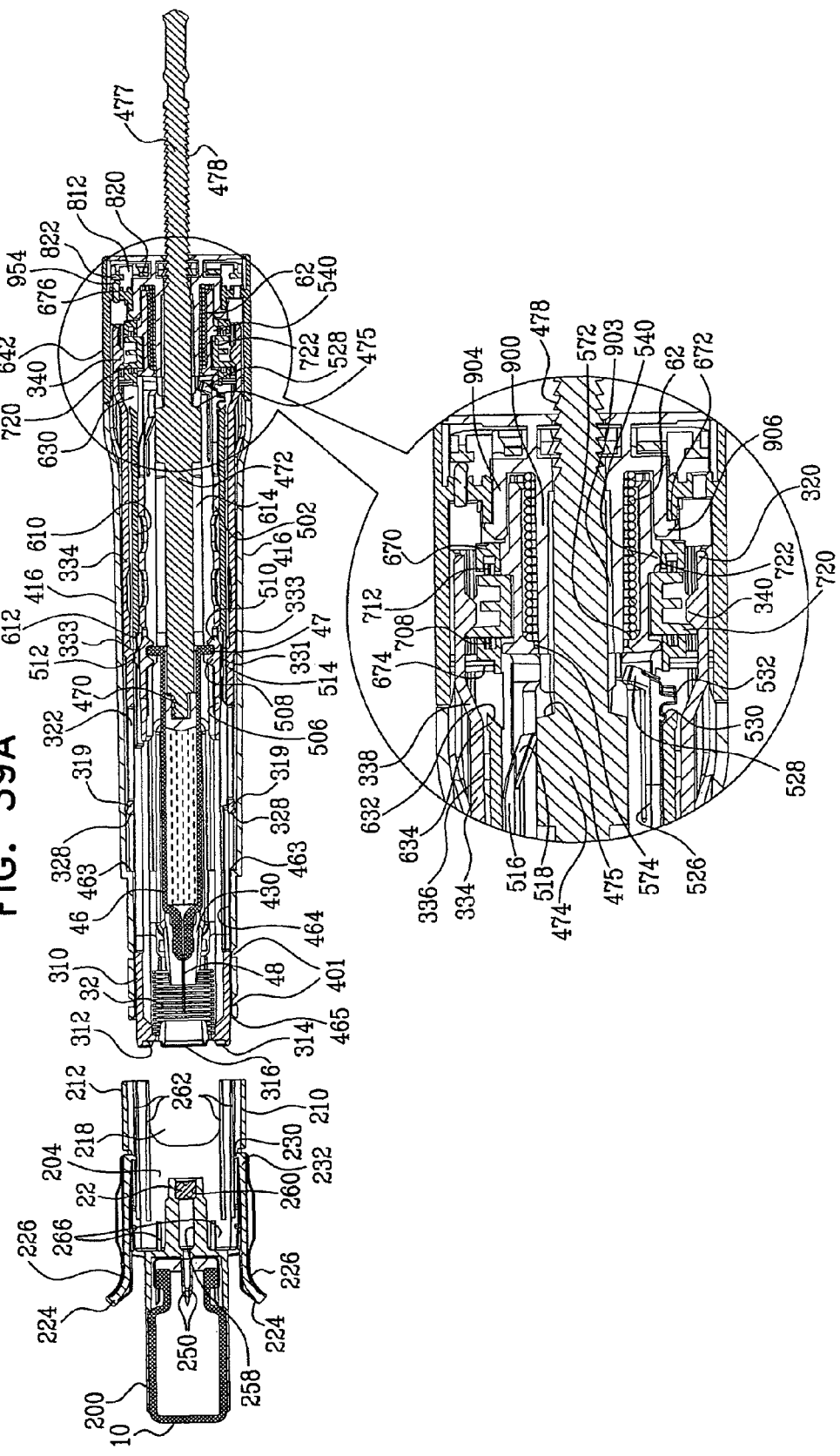
Figure 39B:
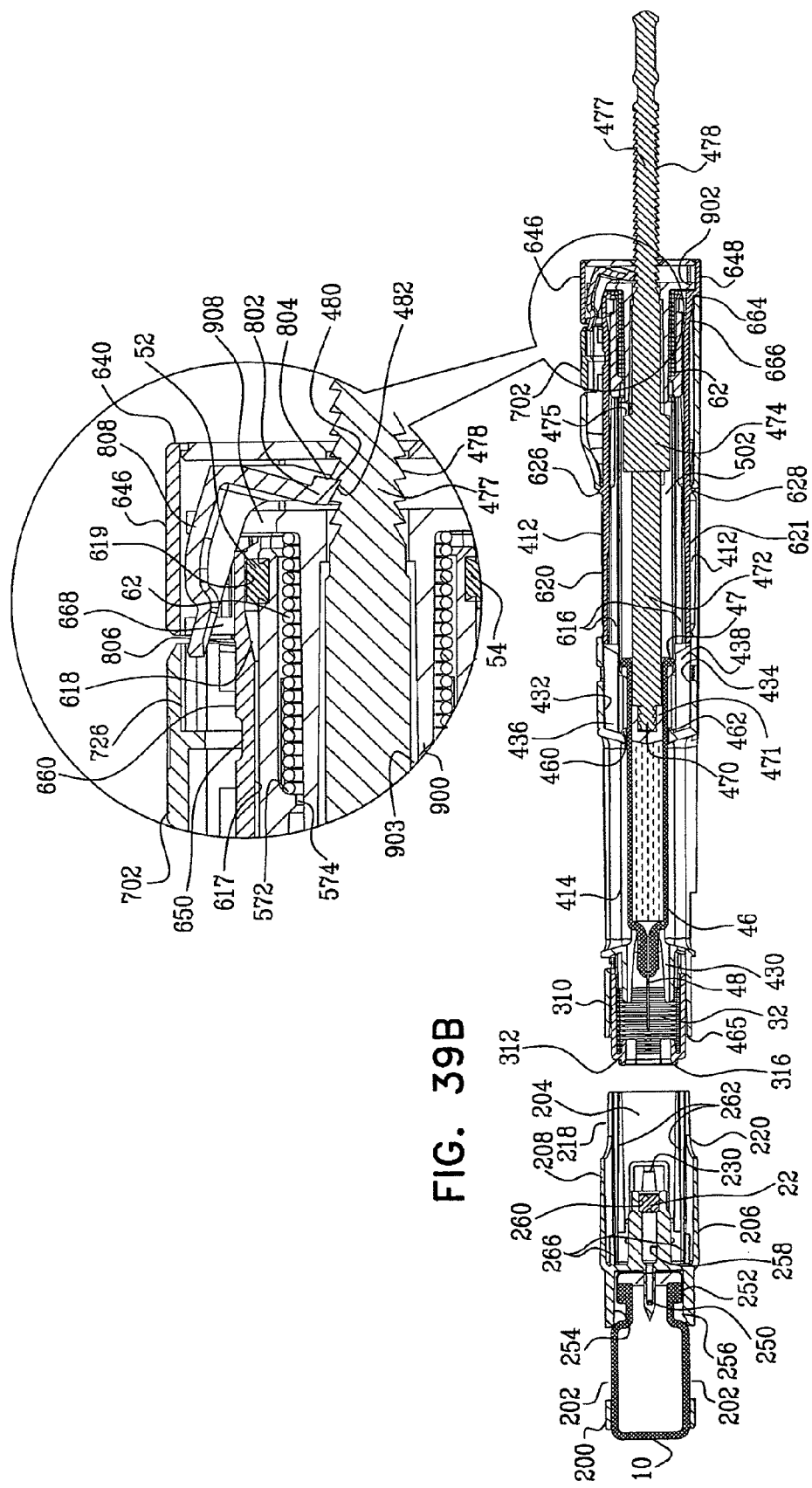

As seen in FIG. 39B, the plunger locking element 90, once returned to its orientation shown in FIGS. 28-30E, locks plunger 49 by engagement of plunger engaging protrusion 802 with teeth 478 of toothed portion 477 of the plunger 49, thereby preventing forward displacement of the plunger 49 by a user. FIG. 39E shows that the resilient leg 820 of the plunger locking element 90 returns to its orientation shown in FIGS. 28-30E in which it is not bent and is located adjacent the forwardly facing protrusion 912 of the rear end element 80.

Figure 40:
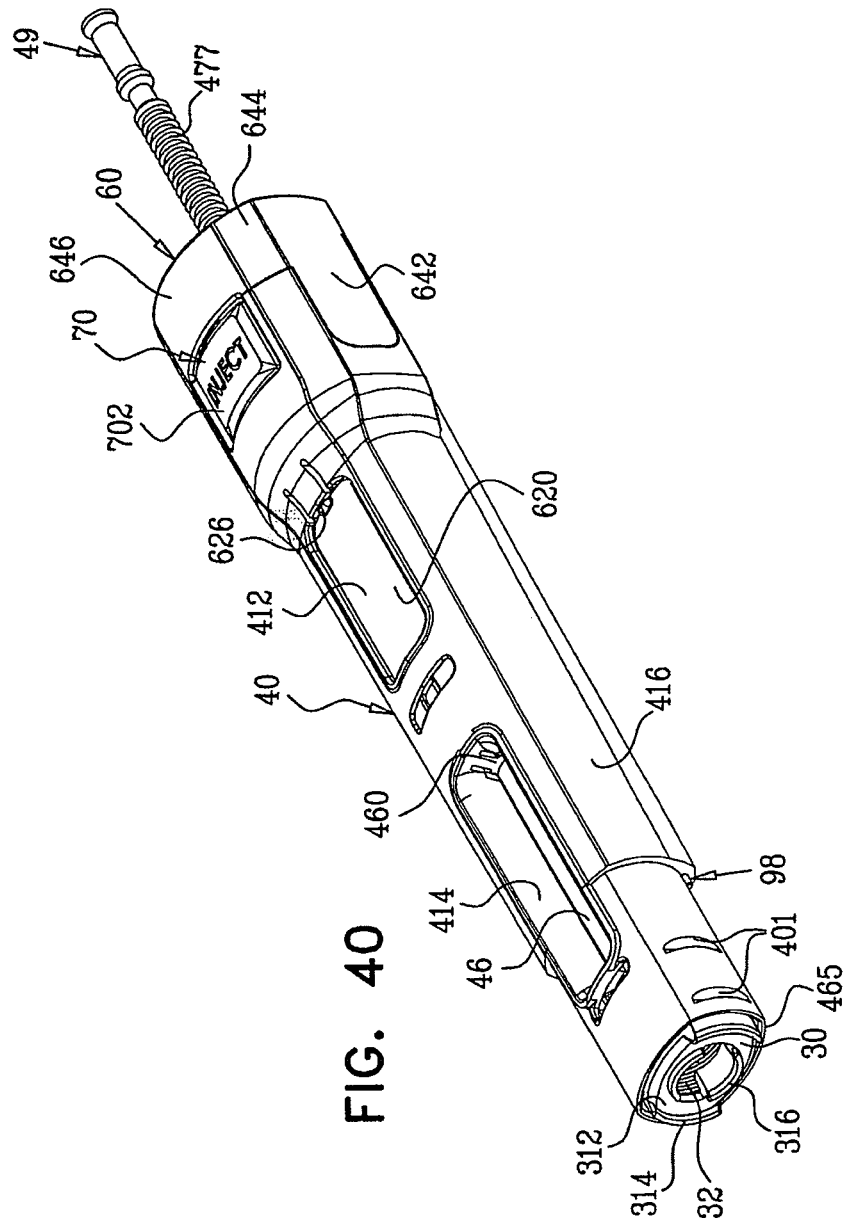
FIG. 40 is a simplified assembled view illustration of the automatic injection device of FIGS. 1 and 27E in an actuated operative orientation.
Figure 42B:
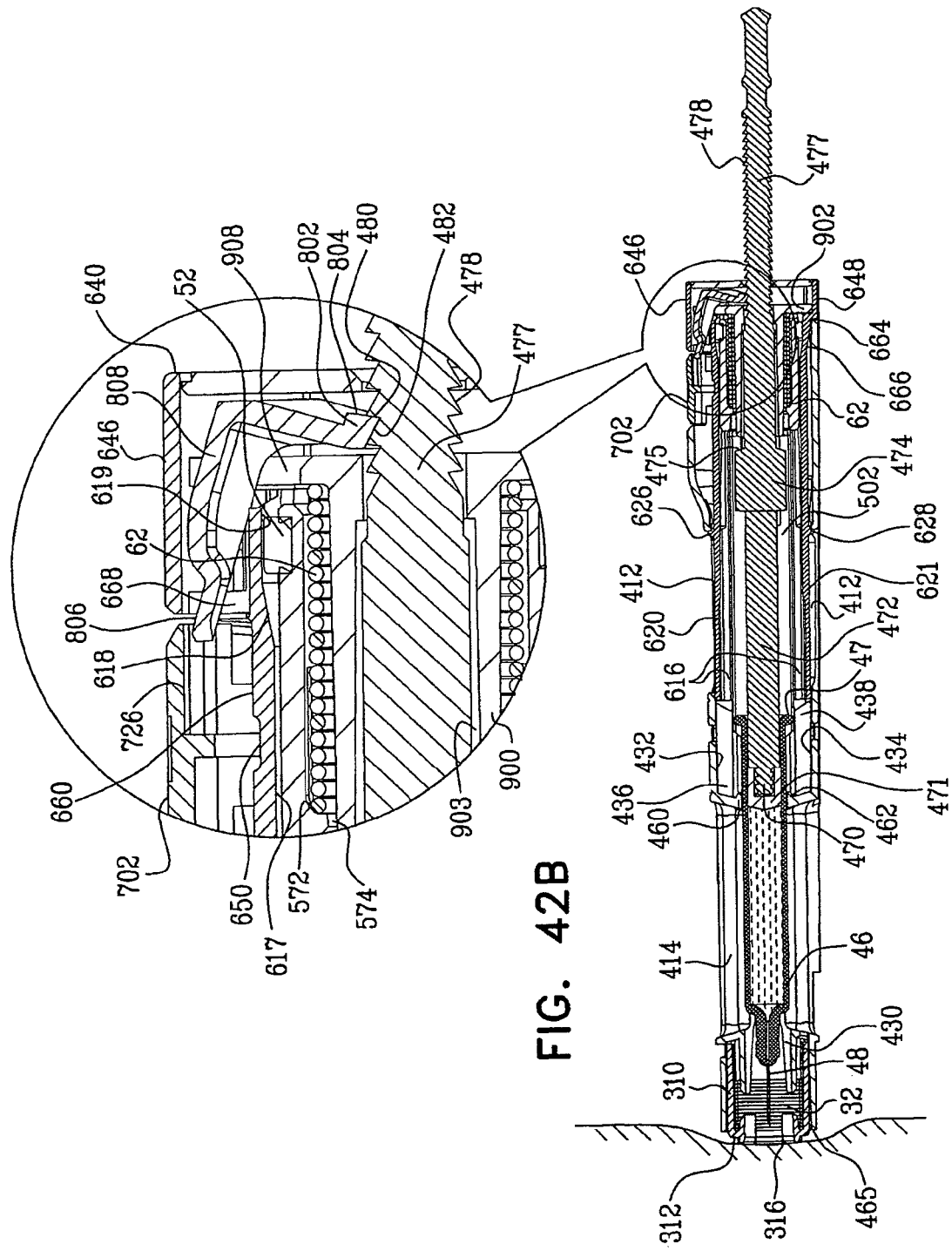
Figure 42E:
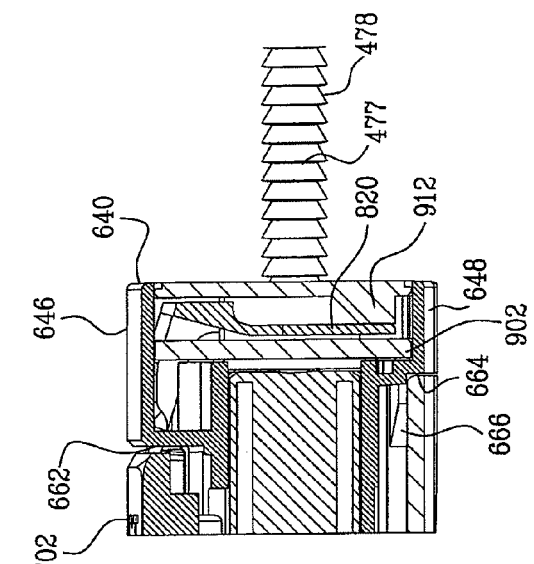
Figure 42D:
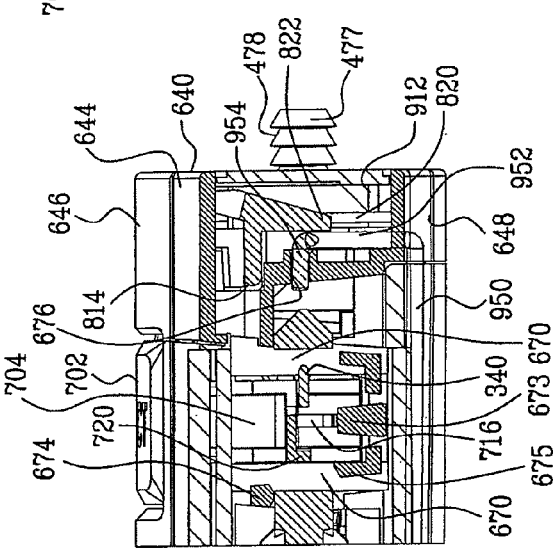
Figure 42C:
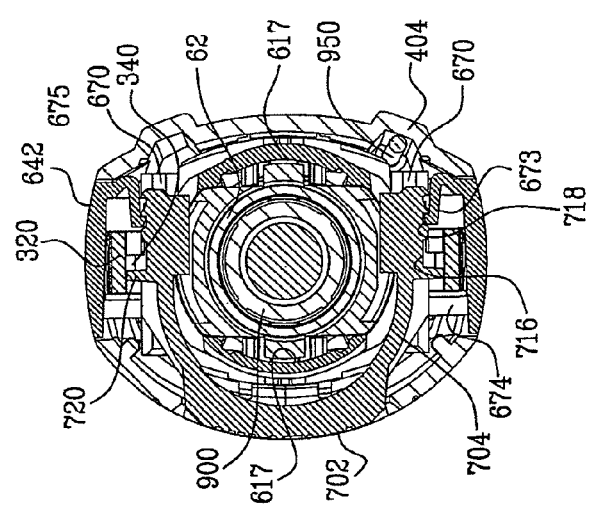

Reference is now made to FIG. 40, which is a simplified assembled view illustration of the automatic injection device of FIGS. 1 and 27E in an actuated operative orientation, to FIGS. 41A and 41B, which are respective side and top view simplified planar illustrations of the automatic injection device of FIG. 40, and to FIGS. 42A, 42B, 42C, 42D and 42E, which are sectional illustrations taken along respective section lines and directions XLIIA-XLIIA, XLIIB-XLIIB, XLIIC-XLIIC, XLIID-XLIID and XLIIE-XLIIE in FIGS. 41A and 41B.

As seen in FIGS. 27E and 40-42E, the user pushes the automatic injection device against his body, thereby rearwardly displacing the needle guard element 30 relative to the forward housing 40. As seen with particular clarity in FIGS. 42A-42D, the rearward displacement of the needle guard element 30 results in rearward displacement of the generally trapezoidal protrusions 340 thereof, which no longer are oriented with respect to the L-shaped transverse outwardly facing protrusions 720 of the arms of the actuation button 70 so as to prevent actuation. Thus, the actuation button 70 is free to be pressed by a user. Until the actuation button 70 is actually pressed by the user, the flexible biasing fingers 673 of the rear housing 60 still engage corresponding second outwardly facing recesses 718 of the legs 704 of the actuation button 70, maintaining it in the "ready to inject" stage.

As seen in FIG. 42A, due to engagement of the needle guard element 30 with an injection site on a body, the resulting rearward displacement of needle guard element 30 with respect to the remainder of the automatic injection device compresses spring 32. The rearward motion of the needle guard element 30 is limited by engagement of the forward facing edge of forward portion 612 of rear housing 60 with shoulders 333 of arms 319 of the needle guard element 30.

In this orientation of the needle guard element 30, pressing of button 70 actuates the automatic injection device.

Reference is now made to FIG. 43, which is a simplified assembled view illustration of the automatic injection device of FIGS. 1 and 27F in a needle penetration, pre-drug delivery operative orientation, to FIGS. 44A and 44B, which are respective side and top view simplified planar illustrations of the automatic injection device of FIG. 43, and to FIGS. 45A, 45B, 45C, 45D and 45E, which are sectional illustrations taken along respective section lines and directions XLVA-XLVA, XLVB-XLVB, XLVC-XLVC, XLVD-XLVD and XLVE-XLVE in FIGS. 44A and 44B.

As seen in FIGS. 27F and 43-45E, the user actuates the automatic injection device by inwardly displacing the actuation button 70. The inward displacement of the actuation button 70 displaces the actuation button engagement surface 806 of forwardly extending protrusion 808 of the plunger locking element 90, thereby rotating the plunger locking element 90 about axis 810 and releasing the plunger 49. Additionally, the protrusions 540 of selectable driving assembly 50 no longer abut against the rearward facing surfaces 722 of the legs 704 of the actuation button 70, and the selectable driving assembly 50 is forwardly displaced under the force of spring 62.

Figure 45B:
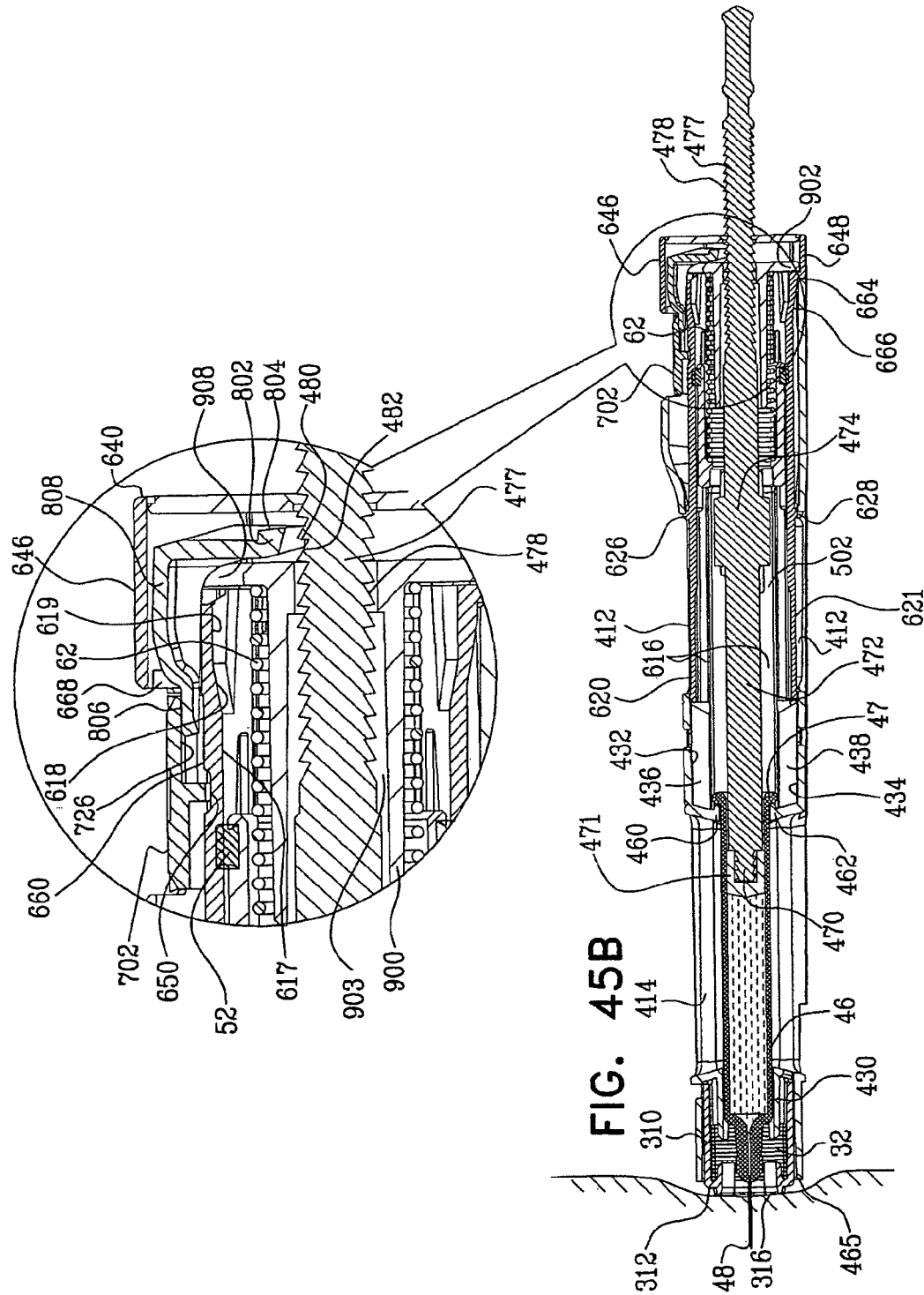
Figure 45E:
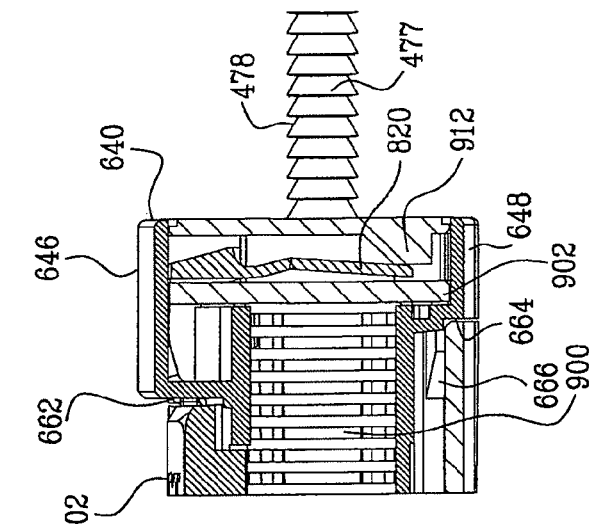
Figure 45D:
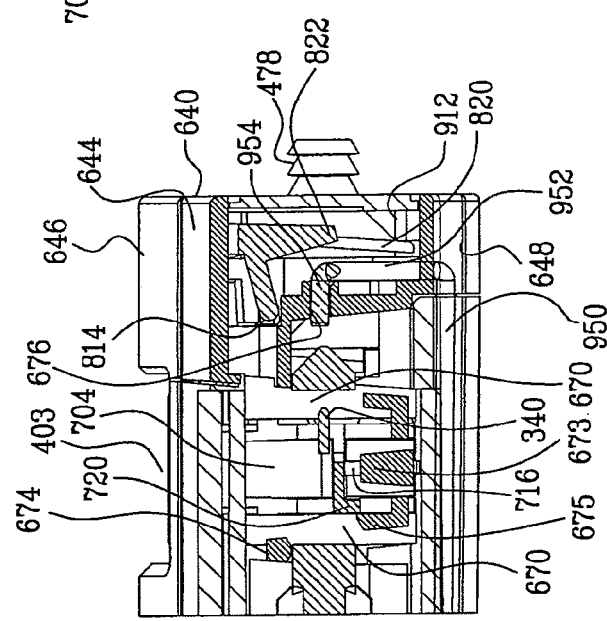
Figure 45C:
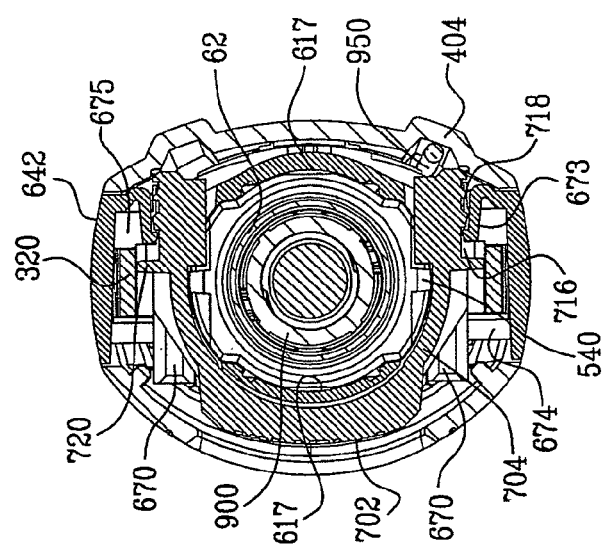
Figure 48A:
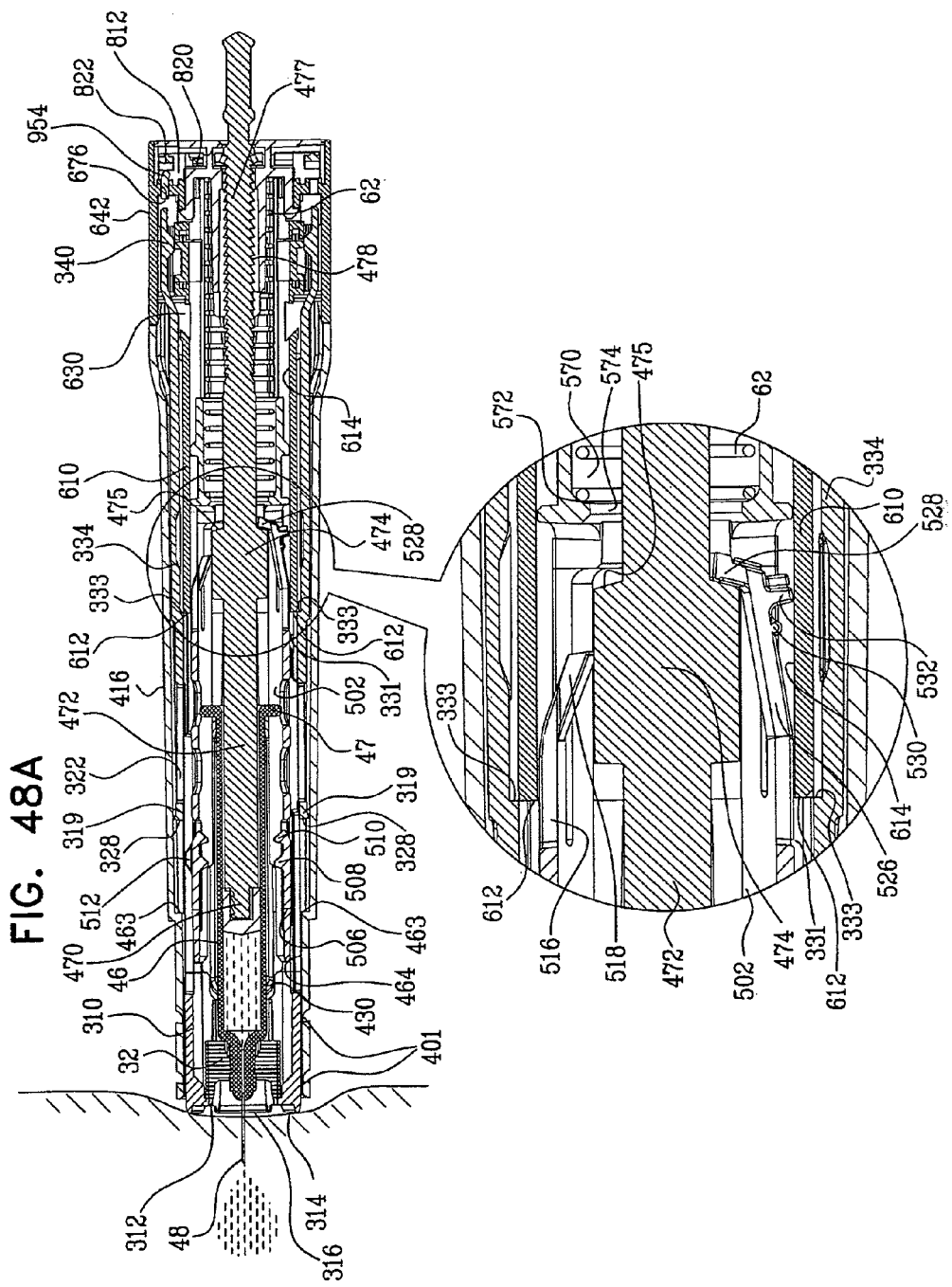
FIGS. 48A, 48B, 48C, 48D and 48E are sectional illustrations taken along respective section lines and directions XLVIIIA-XLVIIIA, XLVIIIB-XLVIIIB, XLVIIIC-XLVIIIC, XLVIIID-XLVIIID and XLVIIIE-XLVIIIE in FIGS. 47A and 47B.
Figure 48B:
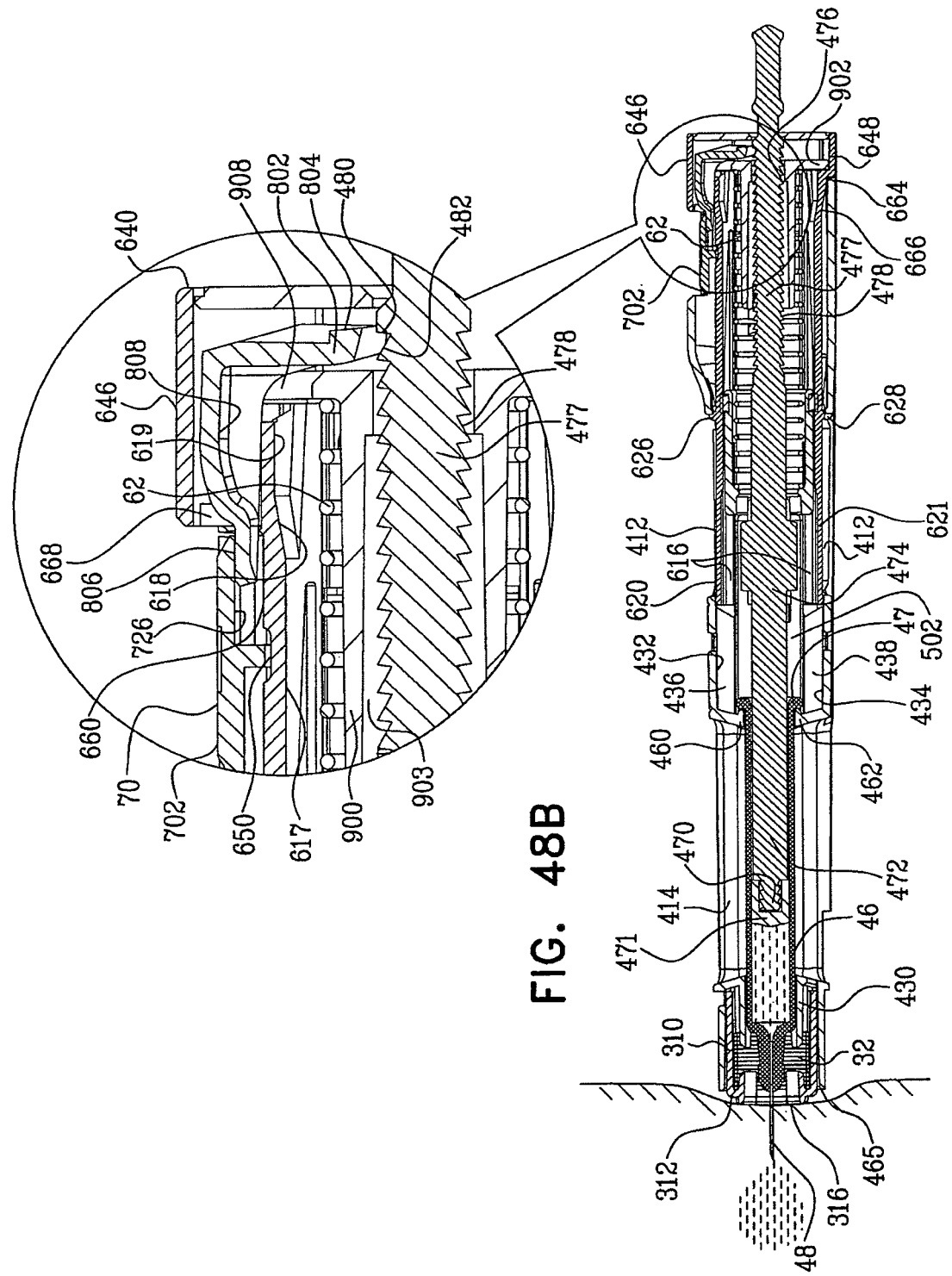
Figure 48E:
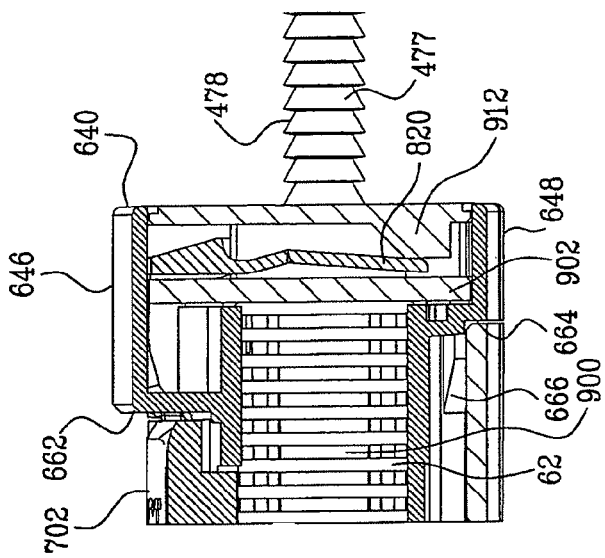
Figure 48D:
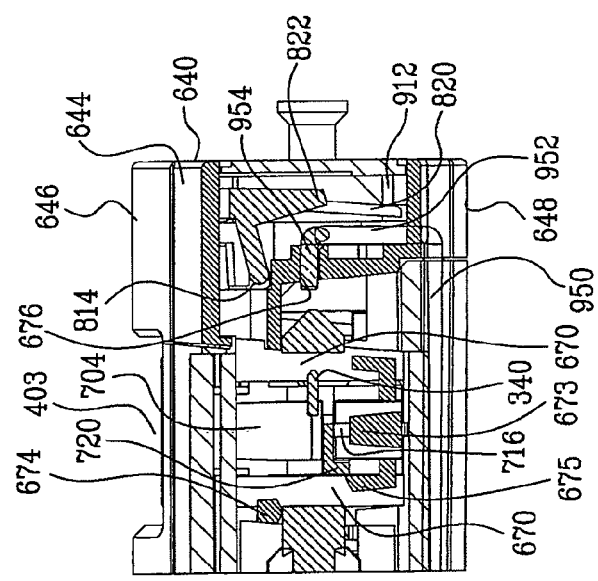
Figure 48C:
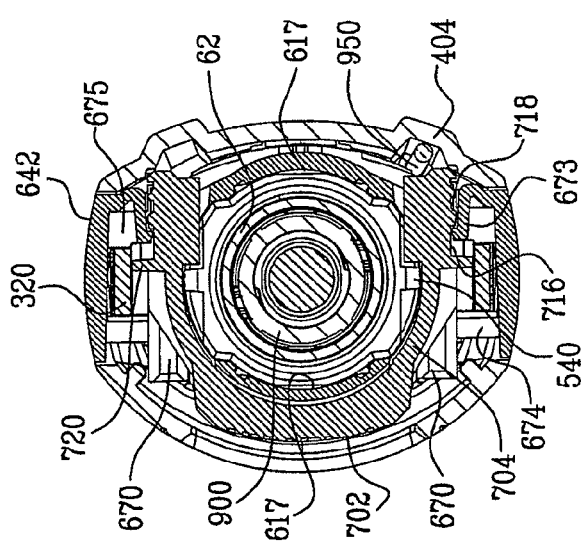

FIG. 45C shows the inward displacement of the actuation button 70, which results in the flexible biasing fingers 673 of the rear housing 60 engaging the first outwardly facing recesses 716 of the legs 704 of the actuation button 70, and maintaining actuation button 70 in an actuated orientation. FIGS. 45B, 45D and 45E show the rotation of the plunger locking element 90, which is caused by the inward displacement of the actuation button 70.

FIGS. 45A and 45B illustrate the forward displacement of the selectable driving assembly 50, accompanied by forward displacement of the syringe 46, which results in needle penetration. As seen in the first enlarged portion of FIG. 45A, when the needle 48 has fully penetrated the body, the forward displacement of the syringe 46 is stopped by engagement of flange 47 with protrusions 460 and 462 of the forward housing 40 (FIG. 45B). The selectable driving assembly 50 continues its forward displacement, thereby outwardly bending the first hinged fingers 506 of the selectable driving assembly 50 into a space formed by rectangular window 322, and releasing fingers 506 from engagement with the flange 47 of the syringe 46.

The third hinged fingers 526 of the selectable driving assembly 50 are inwardly displaced by engagement of protrusions 530 and 532 with undercut forward edge 632, and the inwardly facing slanted protrusions 528 of selectable driving assembly 50 are located adjacent rearwardly facing shoulder 475 of cylindrical portion 474 of the plunger 49. The enlarged portion of FIG. 45B shows the rotation of the plunger engaging protrusion 802 of the plunger locking element 90 such that it no longer prevents the forward movement of plunger 49. FIG. 45E shows a slight bend in the resilient leg 820 of the plunger locking element 90.

During needle penetration, elastomeric motion damping elements 52 and 54 initially engage inclined recesses 618 and then engage interiorly facing protrusions 617. As will be described hereinbelow, drug delivery follows needle penetration.

Reference is now made to FIG. 46, which is a simplified assembled view illustration of the automatic injection device of FIGS. 1 and 27G in a drug delivery operative orientation, to FIGS. 47A and 47B, which are respective side and top view simplified planar illustrations of the automatic injection device of FIG. 46, and to FIGS. 48A, 48B, 48C, 48D and 48E, which are sectional illustrations taken along respective section lines and directions XLVIIIA-XLVIIIA, XLVIIIB-XLVIIIB, XLVIIIC-XLVIIIC, XLVIIID-XLVIIID and XLVIIIE-XLVIIIE in FIGS. 47A and 47B.

As seen in FIGS. 27G and 46-48E, the selectable driving assembly 50 continues its forward displacement, such that the inwardly facing slanted protrusions 528 of the selectable driving assembly 50 engage shoulder 475 of the plunger 49 and forwardly displace the plunger 49. The forward displacement of the plunger 49, which is illustrated with particular clarity in FIG. 48A, results in injection of a drug into the body.

Figure 49:
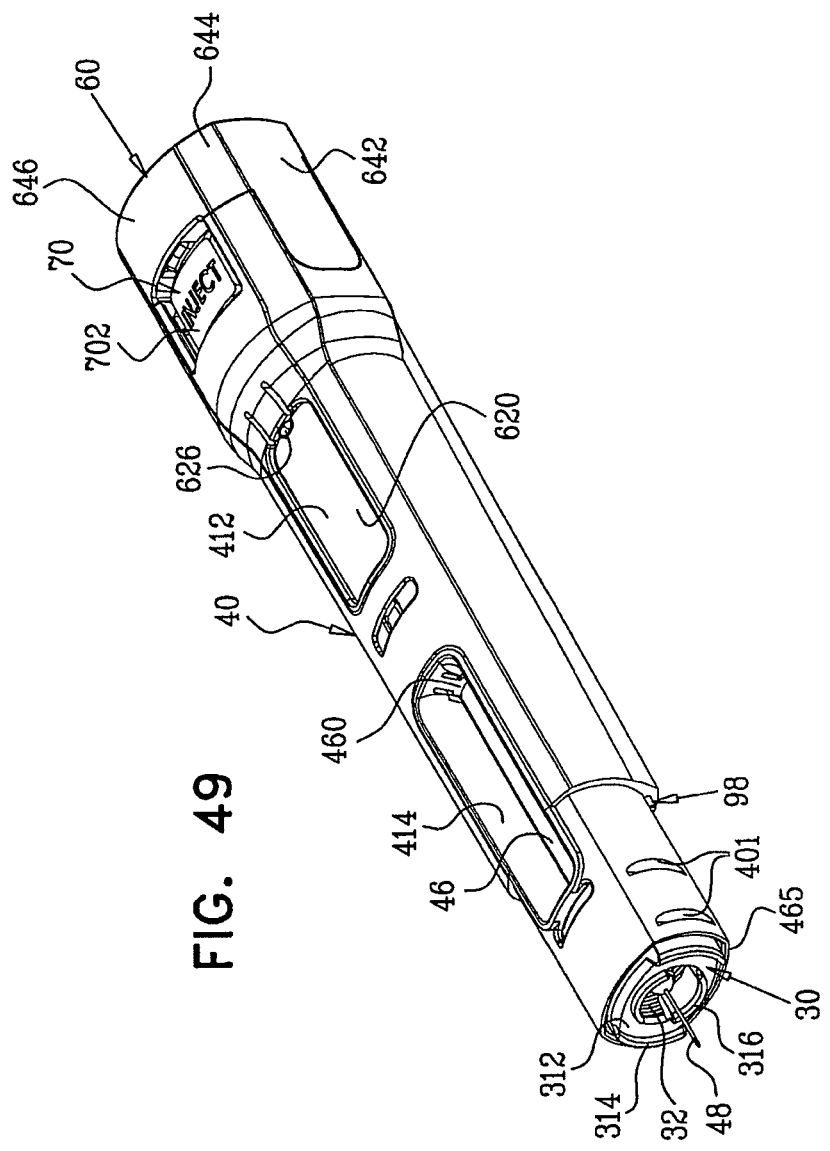
FIG. 49 is a simplified assembled view illustration of the automatic injection device of FIGS. 1 and 27H in an immediate post-drug delivery operative orientation.
Figure 51A:
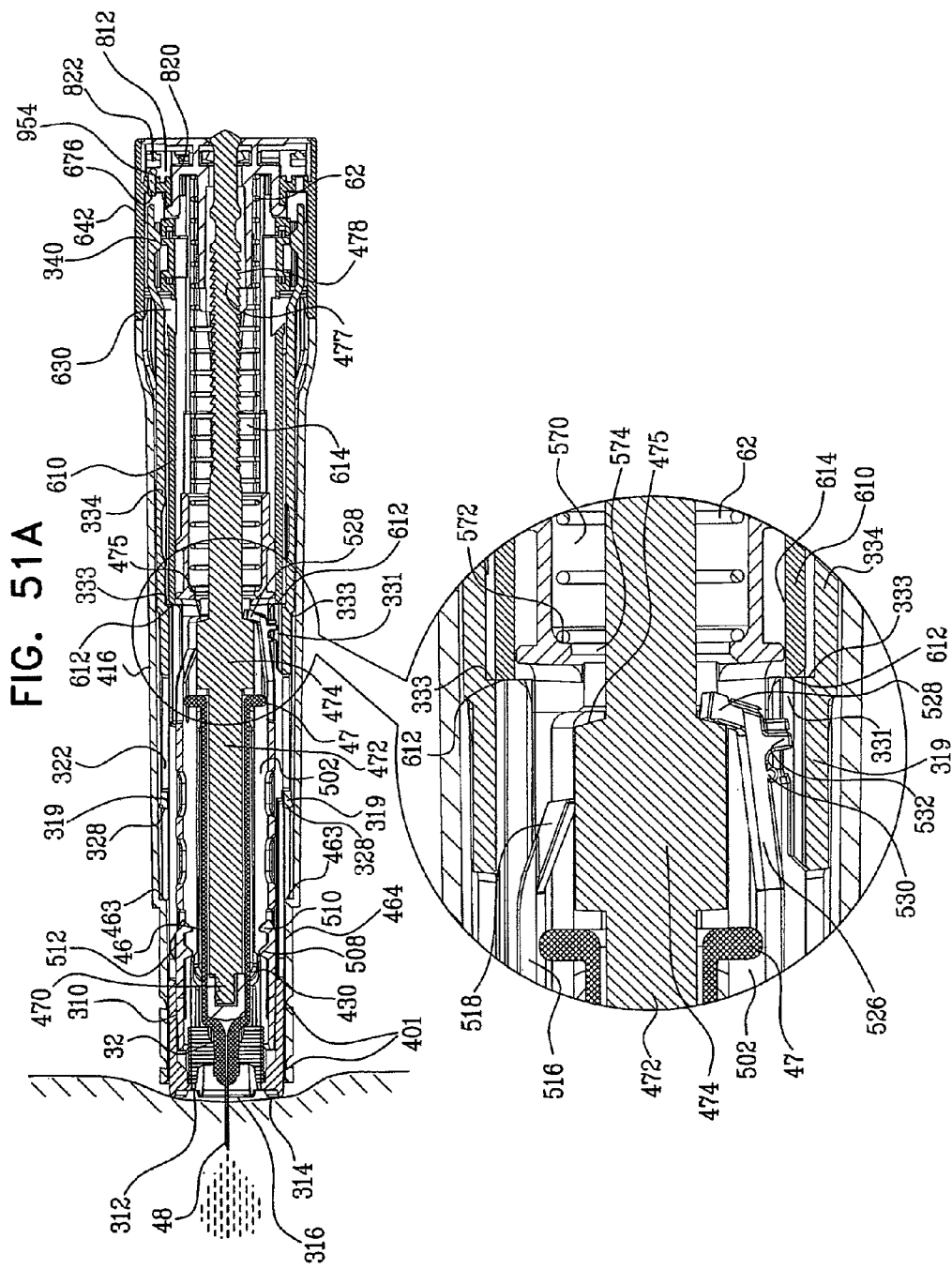
Figure 51B:
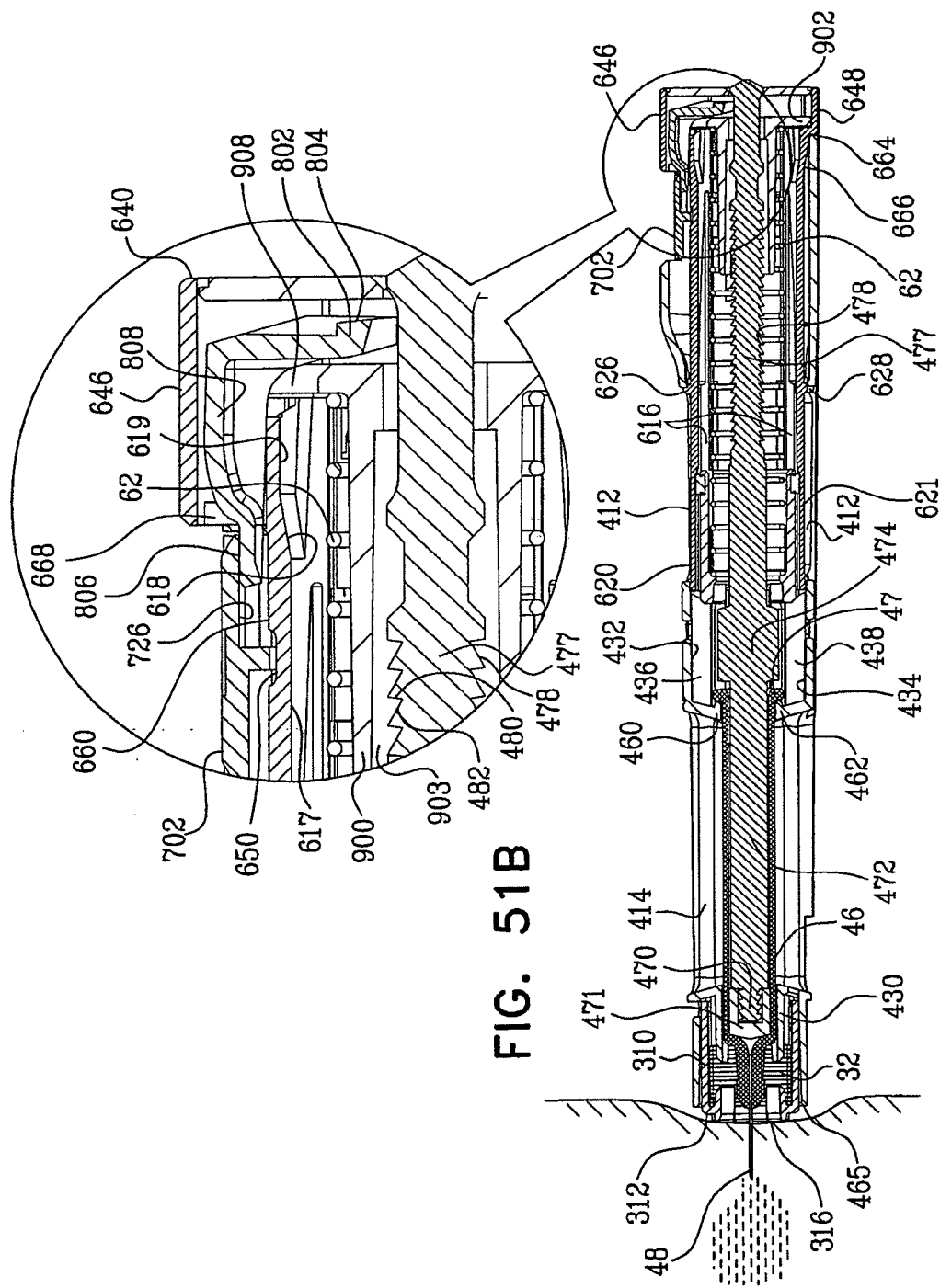

Reference is now made to FIG. 49, which is a simplified assembled view illustration of the automatic injection device of FIGS. 1 and 27H in an immediate post-drug delivery operative orientation, to FIGS. 50A and 50B, which are respective side and top view simplified planar illustrations of the automatic injection device of FIG. 49, and to FIGS. 51A, 51B, 51C, 51D and 51E, which are sectional illustrations taken along respective section lines and directions LIA-LIA, LIB-LIB, LIC-LIC, LID-LID and LIE-LIE in FIGS. 50A and 50B.

As seen in FIGS. 27H and 49-51E, the plunger 49 is fully forwardly displaced and has reached the forward end of the syringe 46. As seen with particular clarity in the enlarged portion of FIG. 51A, the outwardly facing protrusions 532 of the third hinged fingers 526 of the selectable driving assembly 50, which slid along interiorly facing surface 614 of the rear housing 60, now slide along interiorly facing surface 331 of the mounting arms 319 of the needle guard element 30, while the inwardly facing slanted protrusions 528 of the third hinged fingers 526 of the selectable driving assembly 50 continue to engage shoulder 475 of the plunger 49. It is appreciated that forward displacement of both plunger 49 and selectable driving assembly 50 is stopped at this stage. Drug delivery is complete.

Figure 52:
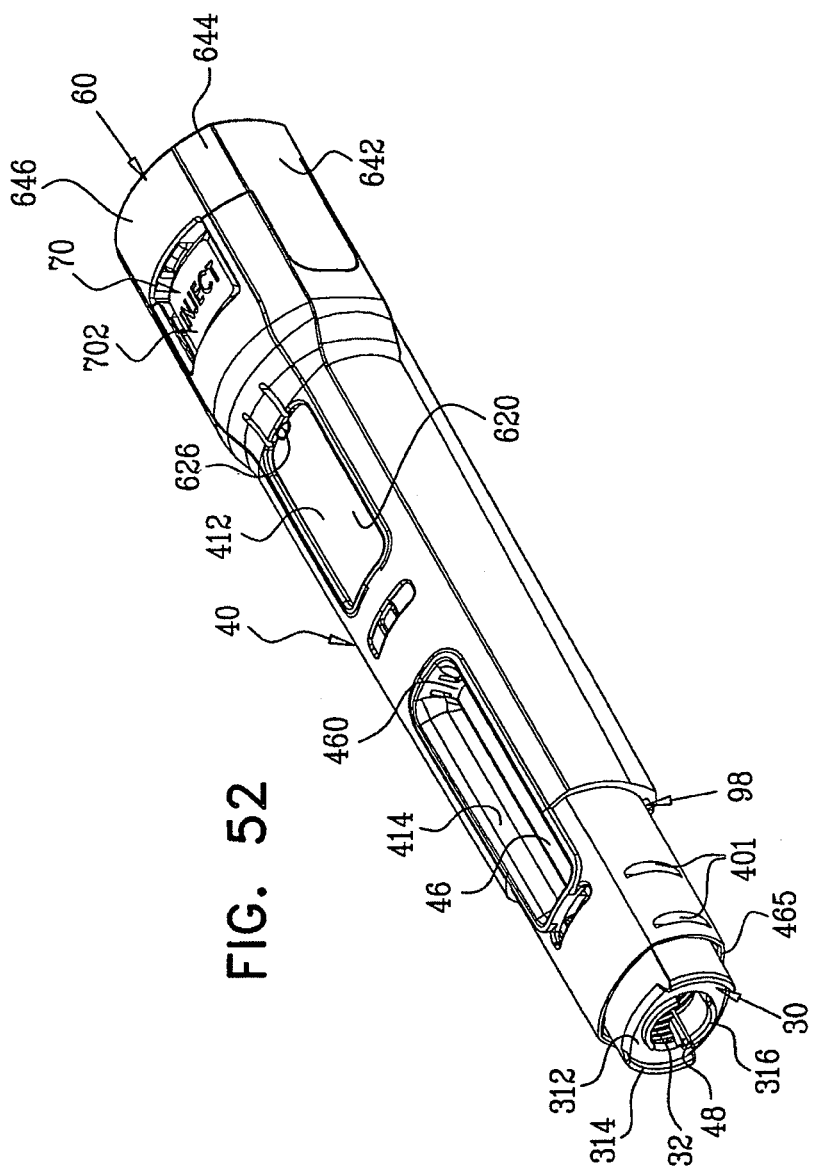
FIG. 52 is a simplified assembled view illustration of the automatic injection device of FIGS. 1 and 27I in its operative orientation as it is being disengaged from the injection site.
Figure 54A:
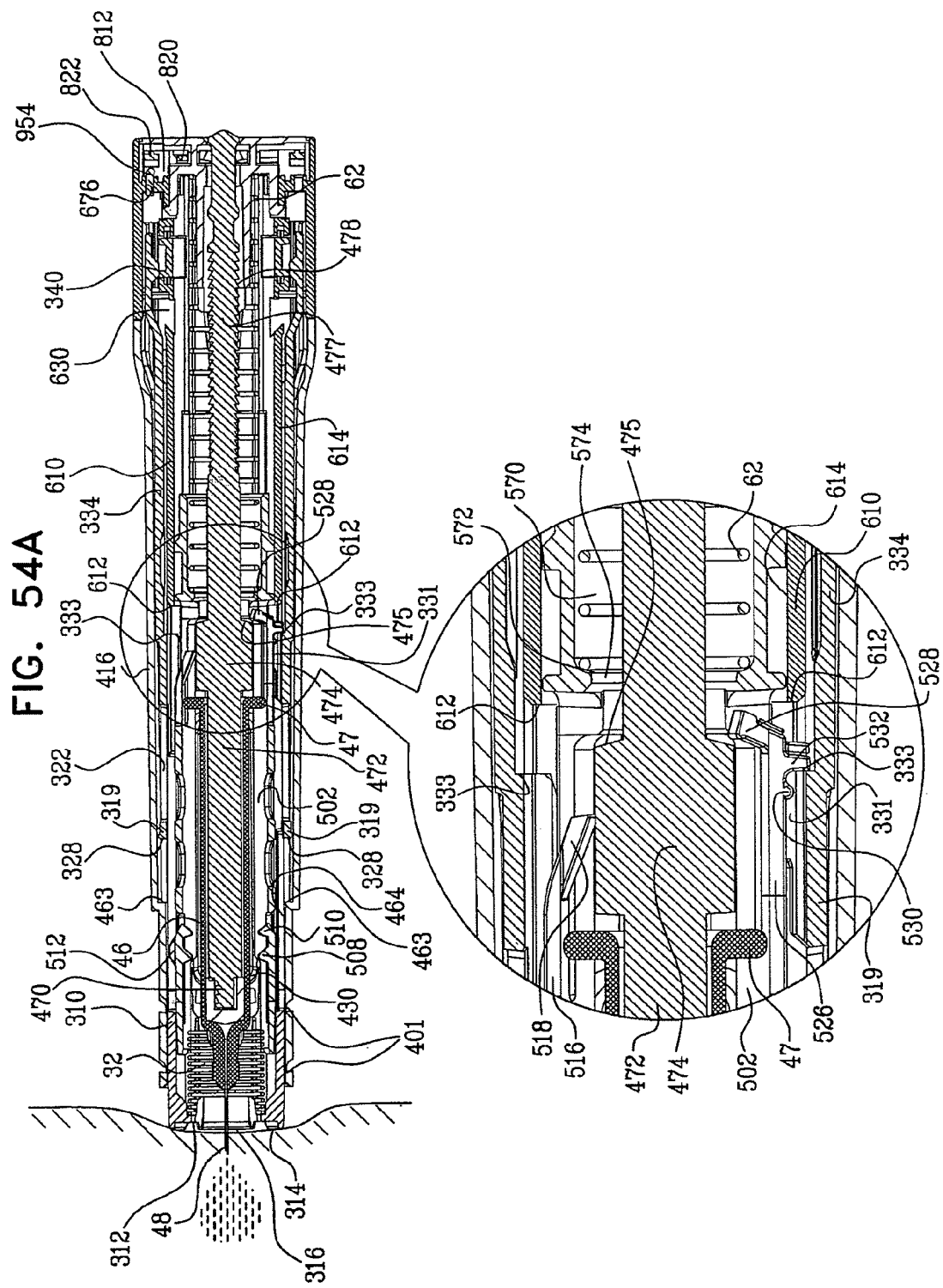
FIGS. 54A, 54B, 54C, 54D and 54E are sectional illustrations taken along respective section lines and directions LIVA-LIVA, LIVB-LIVB, LIVC-LIVC, LIVD-LIVD and LIVE-LIVE in FIGS. 53A and 53B.
Figure 54B:
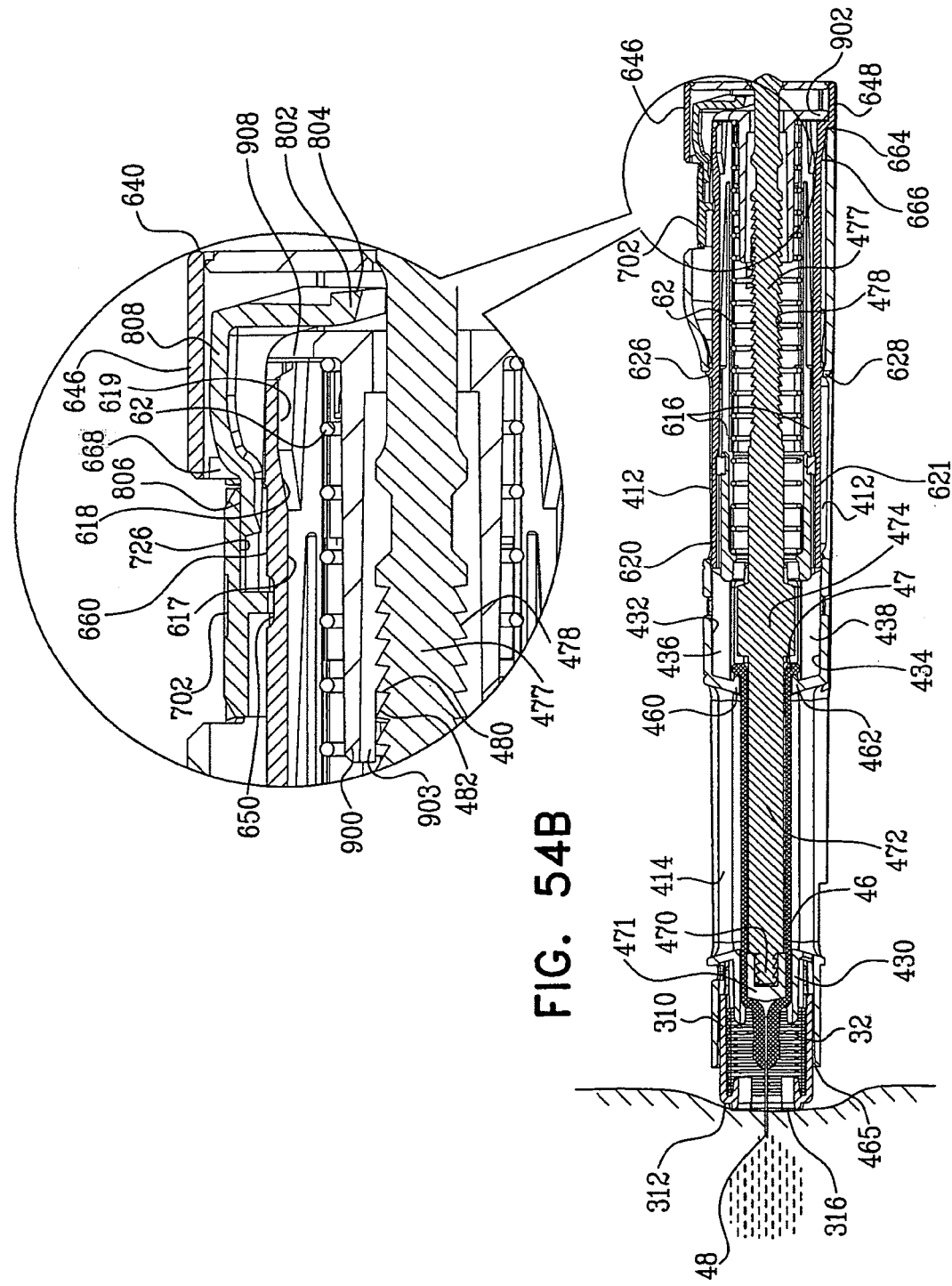
Figure 54E:
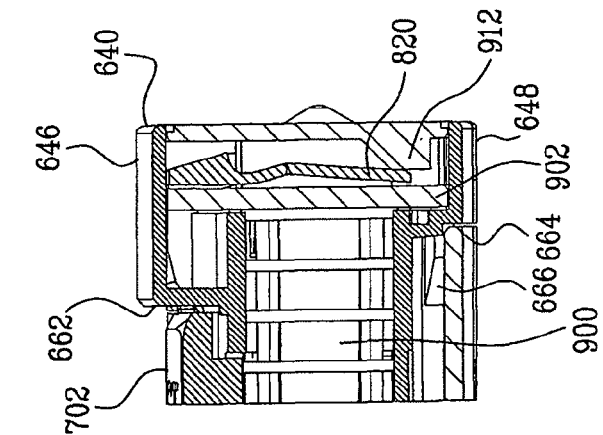
Figure 54D:
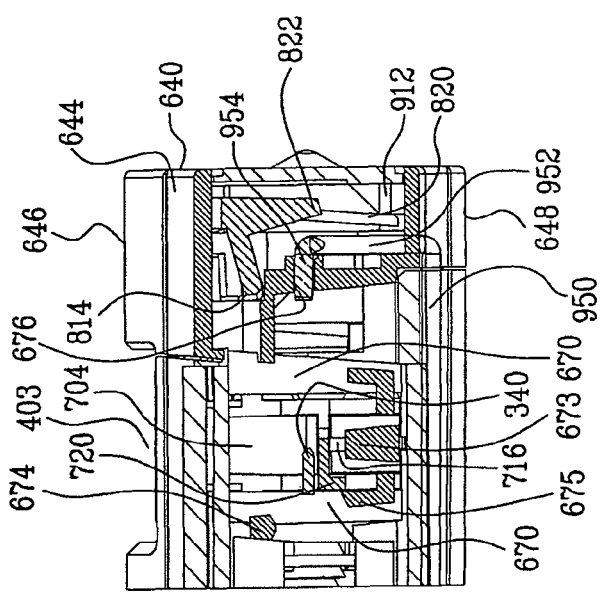
Figure 54C:
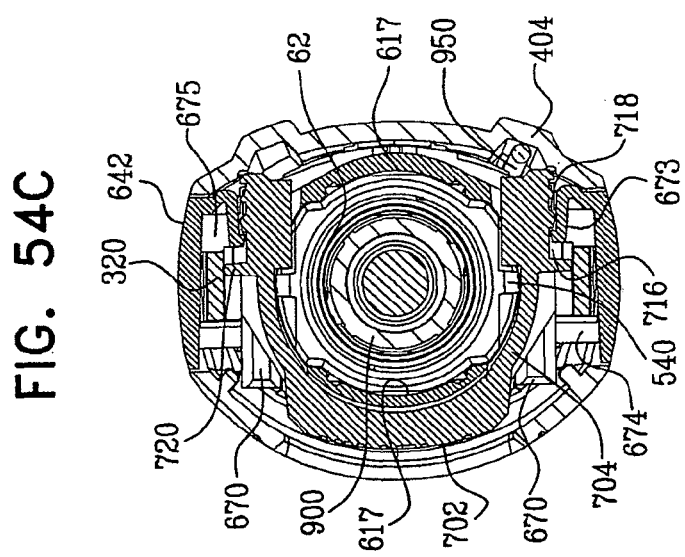

Reference is now made to; FIG. 52, which is a simplified assembled view illustration of the automatic injection device of FIGS. 1 and 27I in its operative orientation as it is being disengaged from the injection site, to FIGS. 53A and 53B, which are respective side and top view simplified planar illustrations of the automatic injection device of FIG. 52, and to FIGS. 54A, 54B, 54C, 54D and 54E, which are sectional illustrations taken along respective section lines and directions LIVA-LIVA, LIVB-LIVB, LIVC-LIVC, LIVD-LIVD and LIVE-LIVE in FIGS. 53A and 53B.

As seen in FIGS. 27I and 52-54E, the user is beginning to disengage the automatic injection device from his body, thereby enabling the needle guard element 30 to be forwardly displaced under the force of spring 32. As seen with particular clarity in the enlarged portion of FIG. 54A, during the forward displacement of the needle guard element 30, the outwardly facing protrusions 532 of the third hinged fingers 526 of the selectable driving assembly 50 move along the interiorly facing surface 331 of the mounting arms 319 of the needle guard element 30, until they pass shoulder 333 in the mounting arms 319 of the needle guard element 30. The third hinged fingers 526 of the selectable driving assembly 50 snap outwardly once the shoulder 333 of the needle guard element 30 has been sufficiently forwardly displaced, thereby causing the disengagement of the inwardly facing slanted protrusions 528 of the third hinged fingers 526 of the selectable driving assembly 50 from the shoulder 475 of the plunger 49. At this stage, the selectable driving assembly 50 does not engage the plunger 49, and selectable driving assembly 50 can continue to be forwardly displaced under the force of spring 62, thereby forwardly displacing needle guard element 30.

Figure 55:
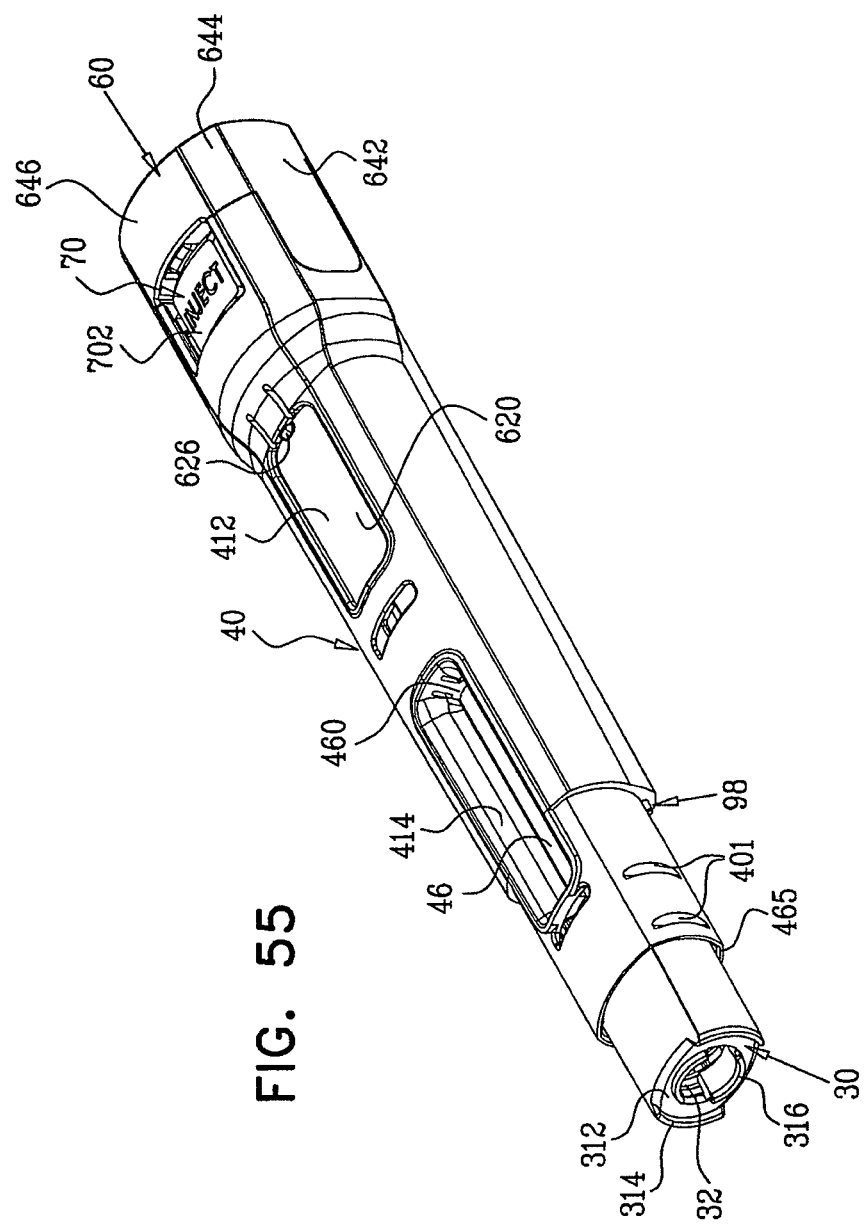
FIG. 55 is a simplified assembled view illustration of the automatic injection device of FIGS. 1 and 27J in a needle protected operative orientation.
Figure 57B:
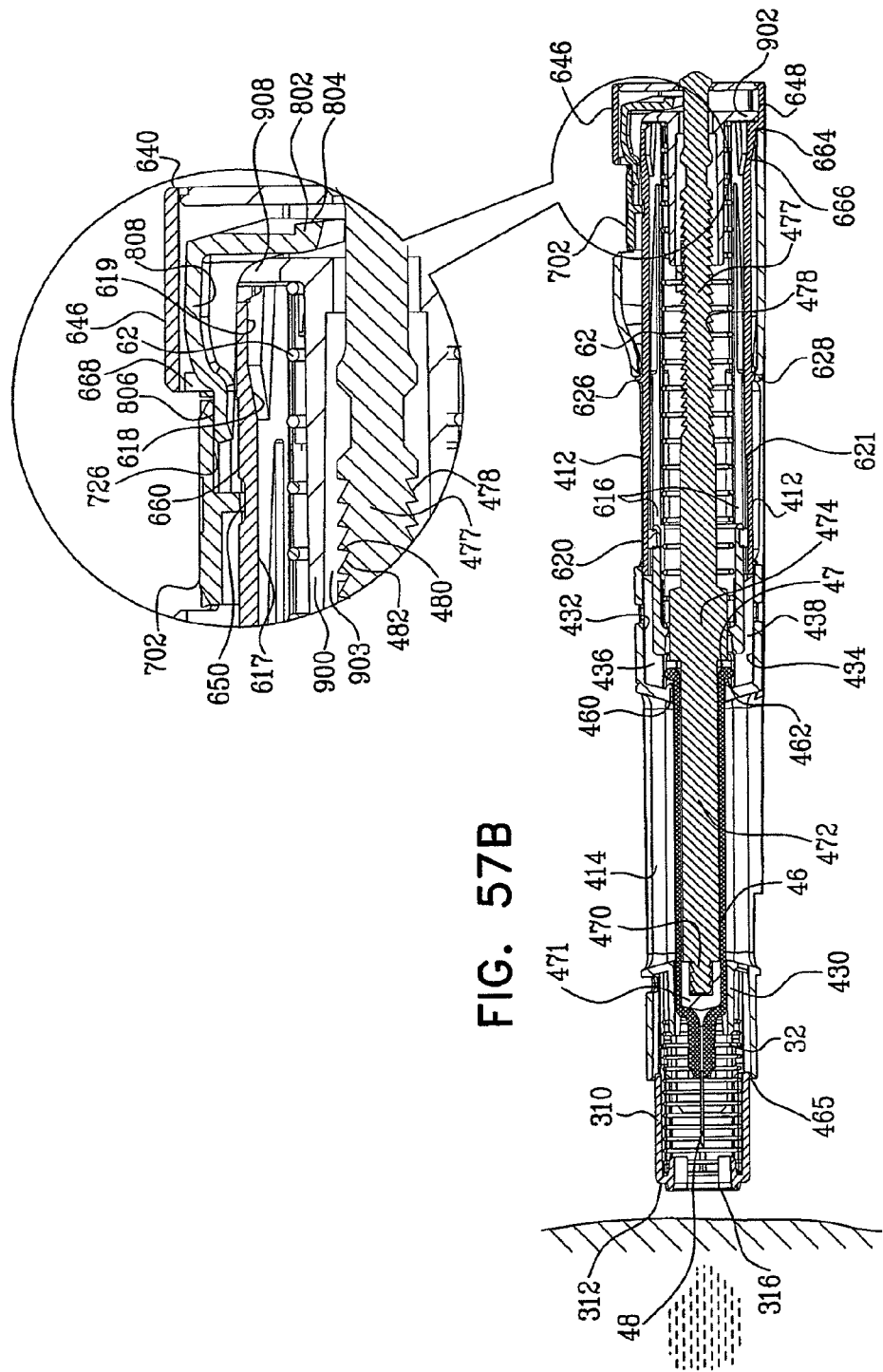
Figure 57E:
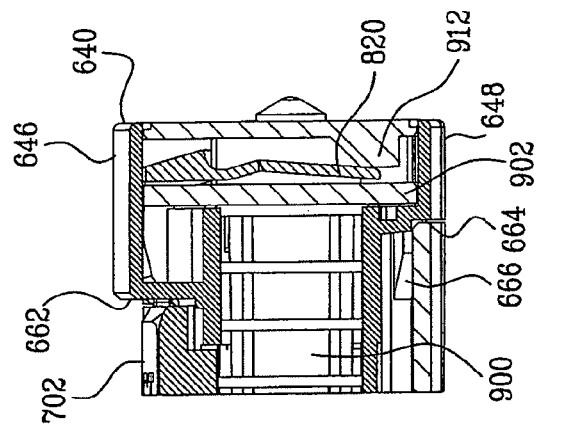
Figure 57D:
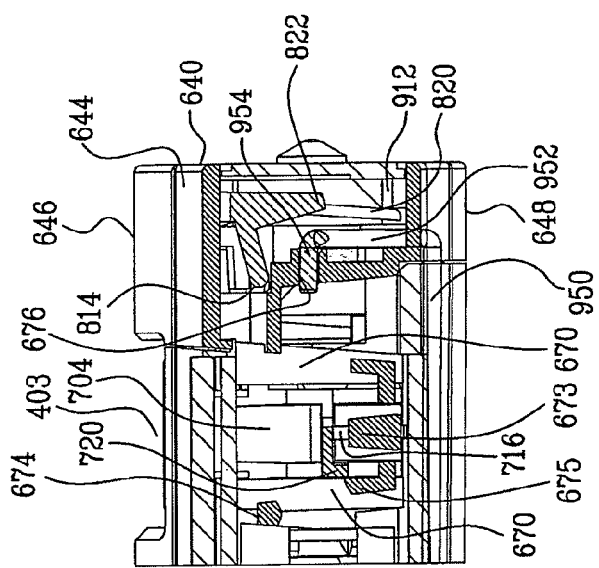
Figure 57C:
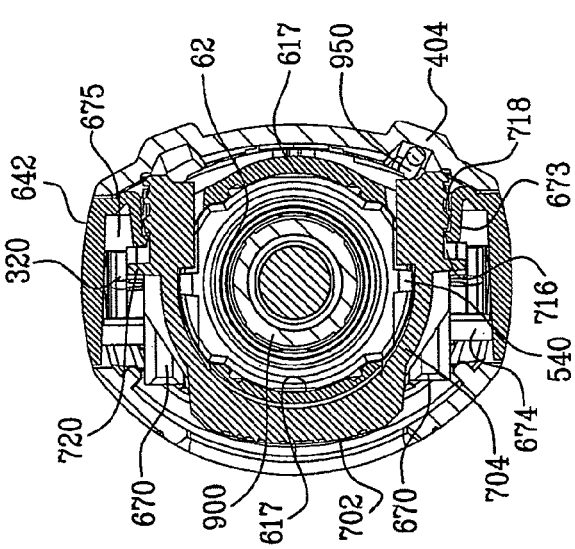

Reference is now made to FIG. 55, which is a simplified assembled view illustration of the automatic injection device of FIGS. 1 and 27J in a needle protected operative orientation, to FIGS. 56A and 56B, which are respective side and top view simplified planar illustrations of the automatic injection device of FIG. 55, and to FIGS. 57A, 57B, 57C, 57D and 57E, which are sectional illustrations taken along respective section lines and directions LVIIA-LVIIA, LVIIB-LVIIB, LVIIC-LVIIC, LVIID-LVIID and LVIIE-LVIIE in FIGS. 56A and 56B.

As seen in FIGS. 27J and 55-57E, the selectable driving assembly 50 continues to be forwardly displaced under the force of spring 62, thereby forwardly displacing the needle guard element 30. The forward displacement of the needle guard element 30 is terminated by engagement of stop surfaces 328 of the needle guard element 30 with corresponding inwardly extending shoulders 463 of forward housing 40, at which stage the needle 48 is fully enclosed by the needle guard element 30 and is locked with respect thereto. As seen with particular clarity in the enlarged portion of FIG. 57A, the forward displacement of the selectable driving assembly 50 results in the second hinged fingers 516 thereof being positioned forwardly of the flange 47 of the syringe 46. This produces the positive locking of the needle 48 with respect to the needle guard element 30. It is noted that the third hinged fingers 526 cannot be bent inwardly at this stage due to engagement of inwardly facing slanted protrusions 528 with cylindrical portion 474.

Figure 58:
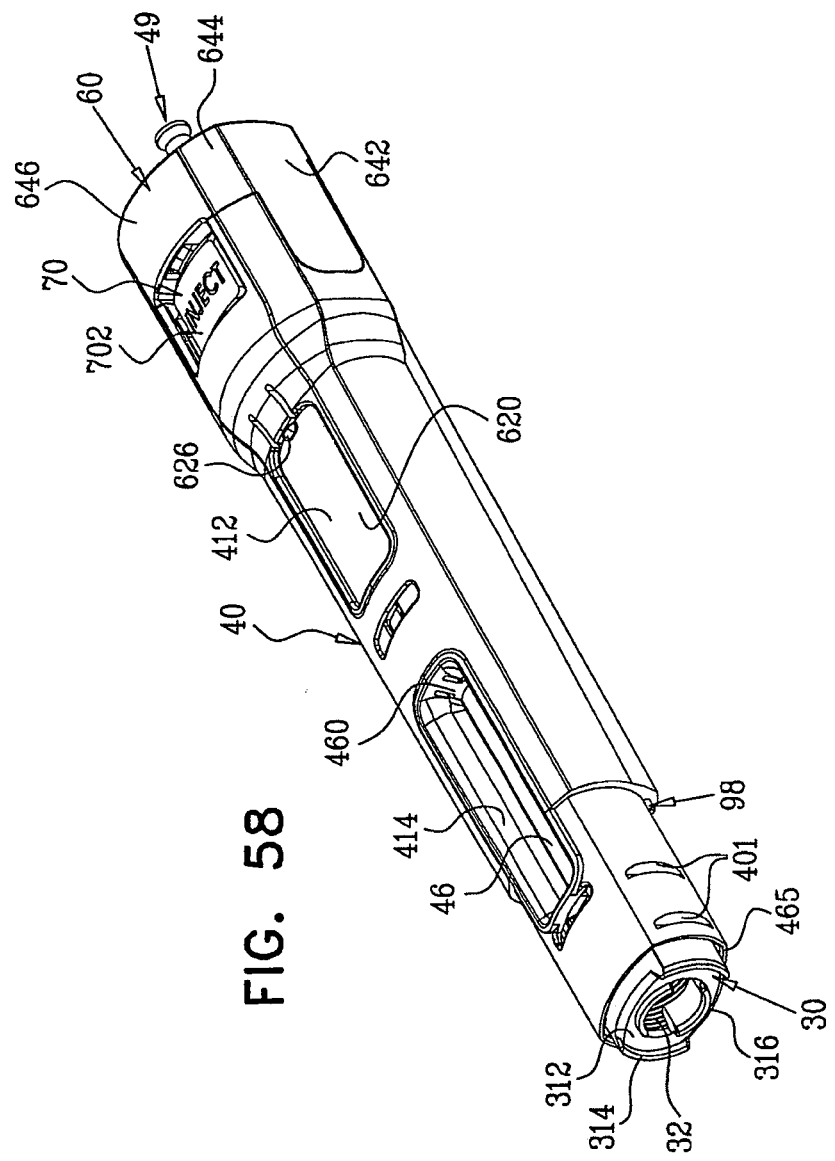
FIG. 58 is a simplified assembled view illustration of the automatic injection device of FIGS. 1 and 27K in a needle-shield push back misuse operative orientation.
Figure 60B:
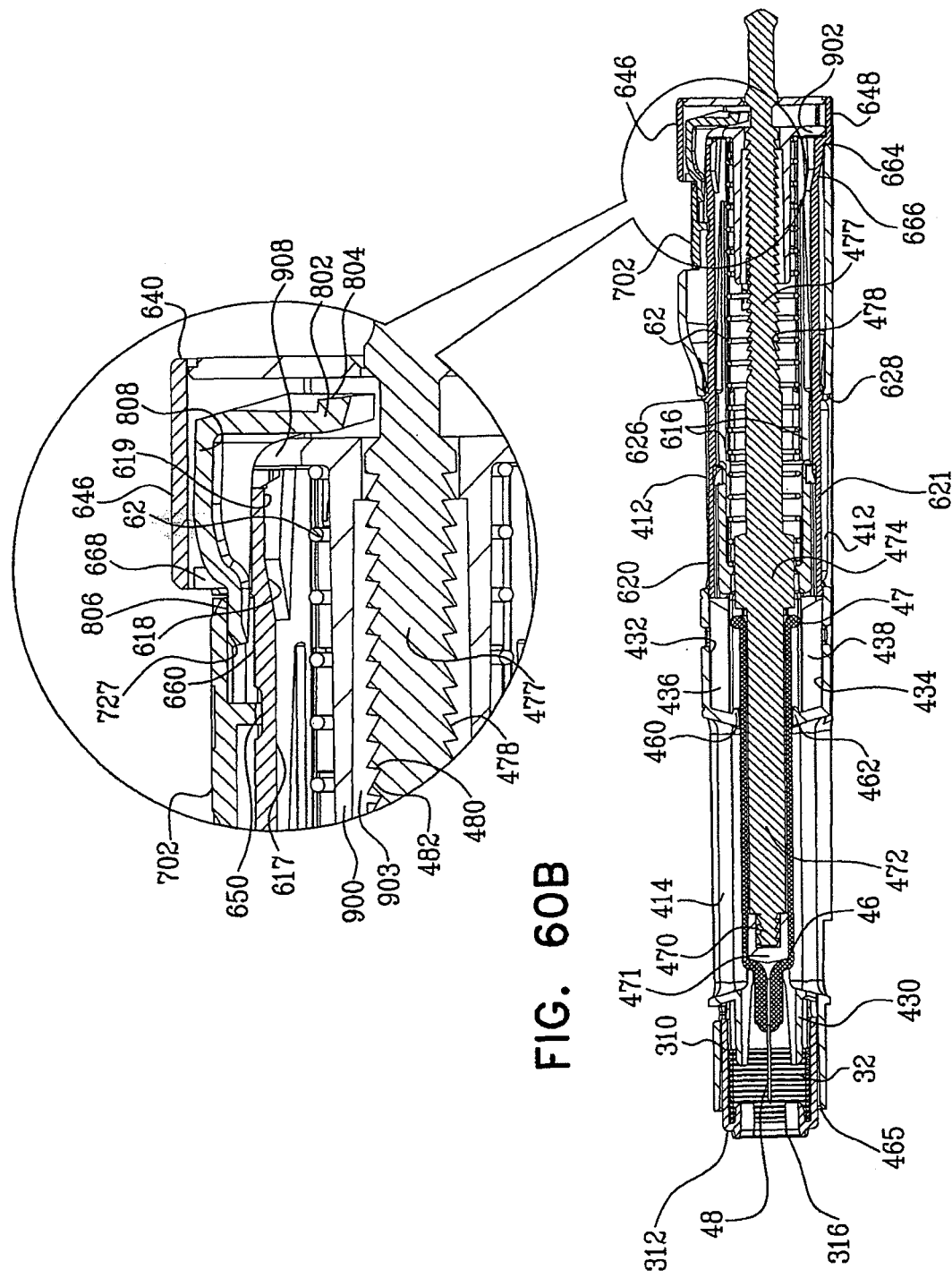
Figure 60C:
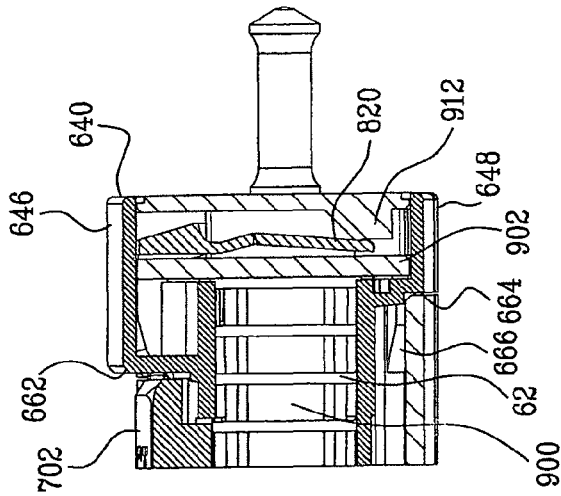
Figure 60D:
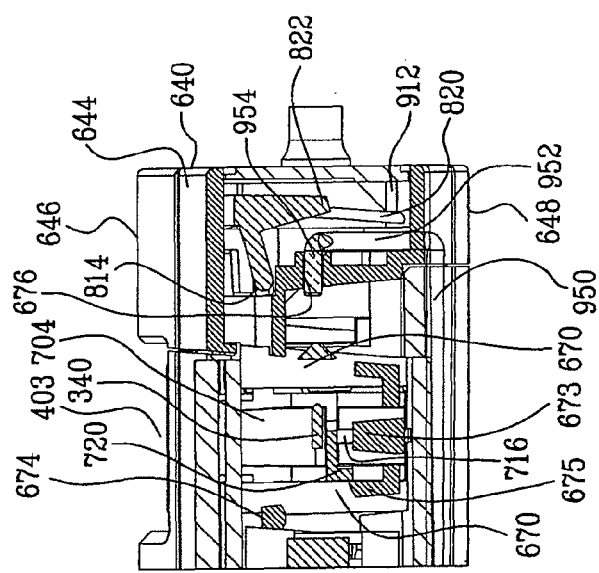
Figure 60E:
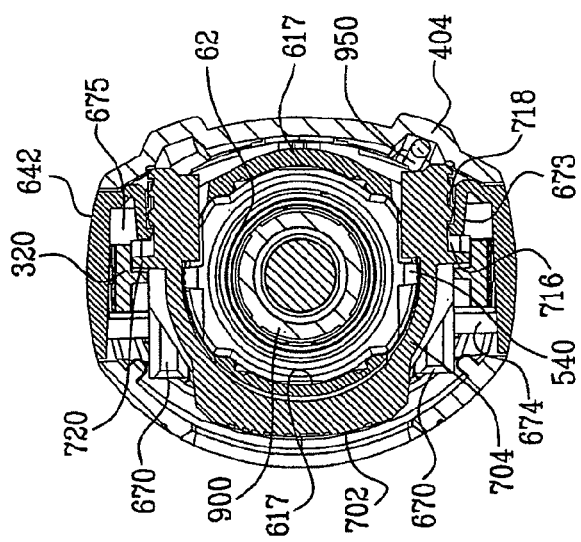

Reference is now made to FIG. 58, which is a simplified assembled view illustration of the automatic injection device of FIGS. 1 and 27K in a needle-shield push back misuse operative orientation, to FIGS. 59A and 59B, which are respective side and top view simplified planar illustrations of the automatic injection device of FIG. 58, and to FIGS. 60A; 60B, 60C, 60D and 60E, which are sectional illustrations taken along respective section lines and directions LXA-LXA, LXB-LXB, LXC-LXC, LXD-LXD and LXE-LXE in FIGS. 59A and 59B.

As seen in FIGS. 27K and 58-60E, when a user misuses the device and rearwardly displaces the needle guard element 30, the rearward displacement of the needle guard element 30 results in rearward displacement of the selectable driving assembly 50. Shoulders 333 of arms 319 of the needle guard 30 push against protrusion 532 of the selectable driving assembly 50. Selectable driving assembly 50 is therefore forced to undergo rearward displacement. Due to this rearward displacement of the selectable driving assembly 50, the second hinged fingers 516 thereof engage the forward facing surface of the flange 47 of the syringe 46. Continued rearward displacement of the selectable driving assembly 50 results in rearward displacement of the syringe 46 and needle 48 together with the selectable driving assembly 50 and the needle guard element 30, thereby ensuring that the needle 48 is not exposed at any stage following injection.

Reference is now made to FIGS. 61-85C, which illustrate the constituent elements of an automatic injection device constructed and operative in accordance with another preferred embodiment of the present invention.

Figure 61:
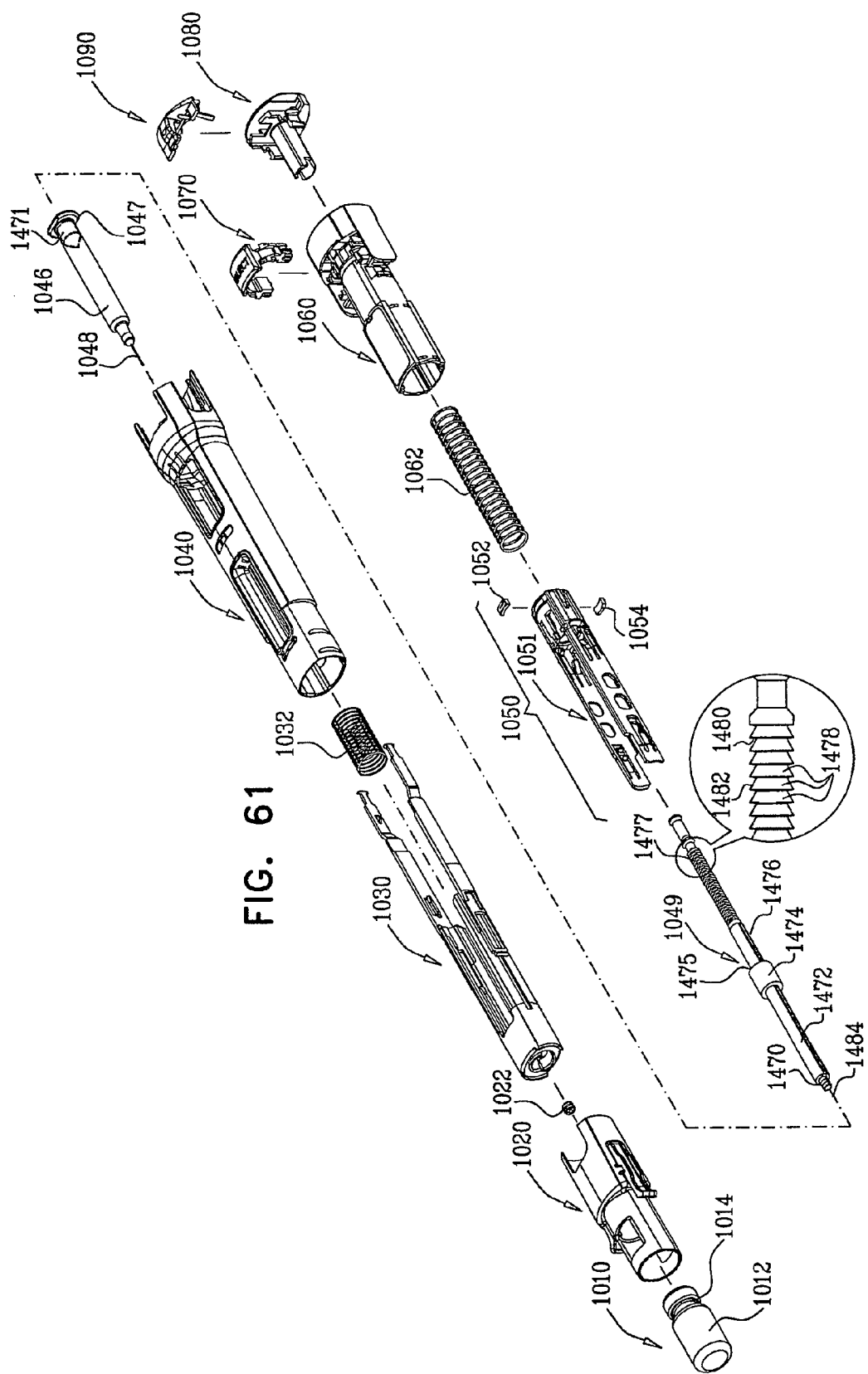
FIG. 61 is a simplified exploded view illustration of an automatic injection device constructed and operative in accordance with another preferred embodiment of the present invention.

As seen with particular clarity in FIG. 61, the automatic injection device comprises a drug vial 1010, including a body portion 1012, a neck portion 1014 and an elastomeric seal (not shown). The drug vial 1010 is seated in a drug vial adaptor 1020 having a septum 1022 associated therewith. A needle guard element 1030, which is positioned by a compression spring 1032 within a forward end of a forward housing 1040, is operative to engage, at a front end thereof, the drug vial adaptor 1020.

A syringe 1046, including a rear flange 1047 and having a hypodermic needle 1048 integrally formed therewith, is operatively engaged by a plunger 1049. Syringe 1046 and plunger 1049 are preferably located within the forward housing 1040. Syringe 1046 may be a conventional syringe, such as a commercially available syringe sold under the catalog designation BD-Hypak™ or may be any other suitable syringe or cartridge.

Plunger 1049 selectably engages a selectable driving assembly 1050, which includes a selectable driving element 1051 and a pair of elastomeric motion damping elements 1052 and 1054. Selectable driving assembly 1050 is preferably at least partially seated within a rear housing 1060, forward of a main compression spring 1062, also seated within rear housing 1060. The main compression spring 1062 provides selectable forward displacement to the selectable driving assembly 1050. Selectable operation of plunger 1049 by selectable driving assembly 1050 causes the plunger 1049 to inject liquid contents of syringe 1046 through hypodermic needle 1048.

The rear housing 1060 has associated therewith an actuation button 1070, operative to selectably actuate operation of selectable driving assembly 1050. Within rear housing 1060 are seated a rear end element 1080, operative to seal the rear end of the rear housing 1060, and a plunger locking element 1090, cooperative with rear end element 1080 and operative to lock the plunger 1049 when liquid contents of the syringe 1046 should not be injected through needle 1048.

Figure 62:
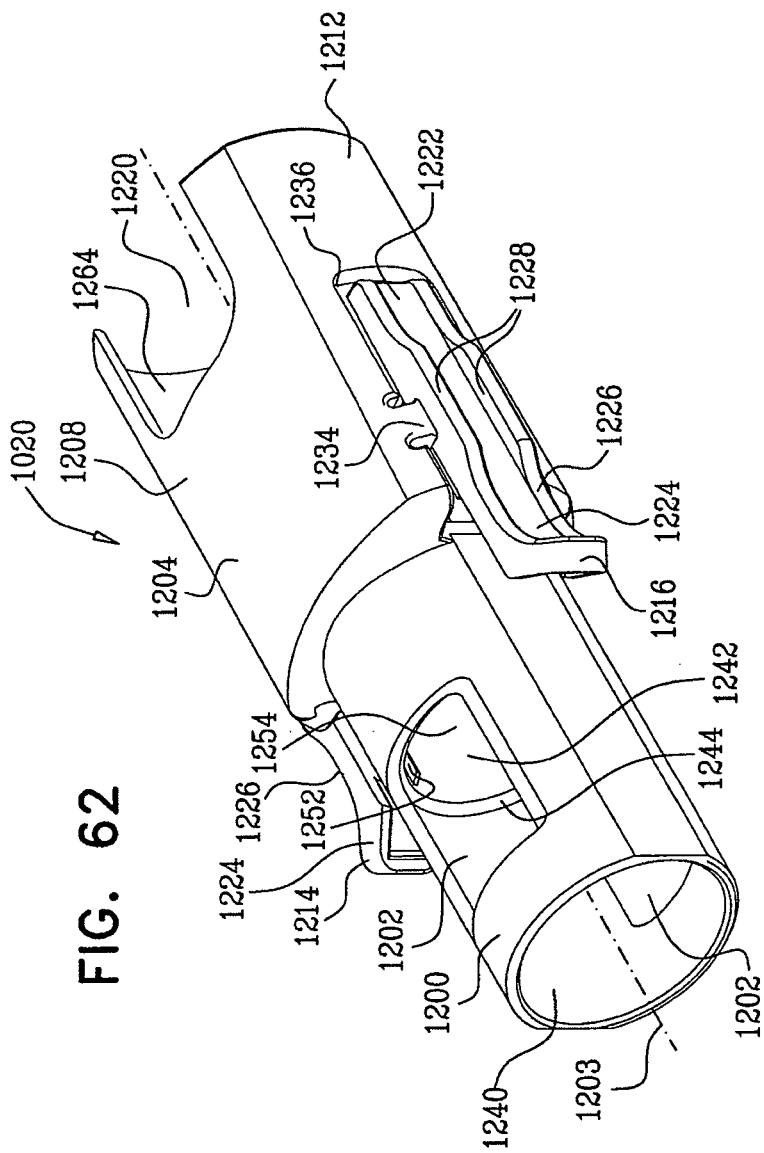
FIG. 62 is a simplified pictorial illustration of a drug vial adaptor which forms part of the automatic injection device of FIG. 61.
Figure 63A:
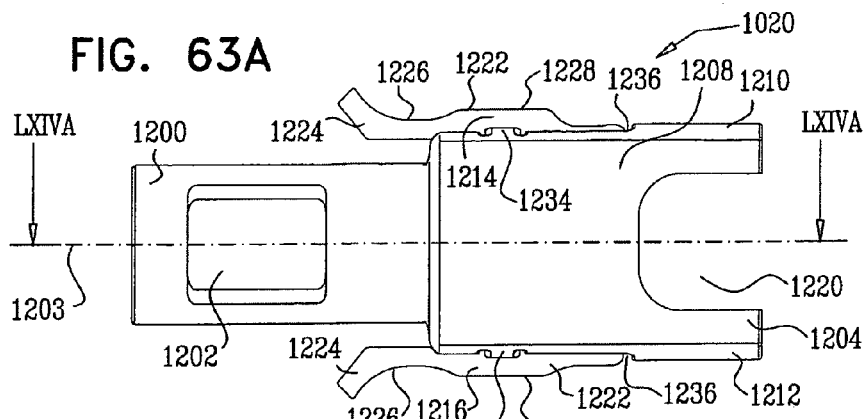
FIGS. 63A and 63B are respective top and side view simplified planar illustrations of the drug vial adaptor of FIG. 62.
Figure 63B:
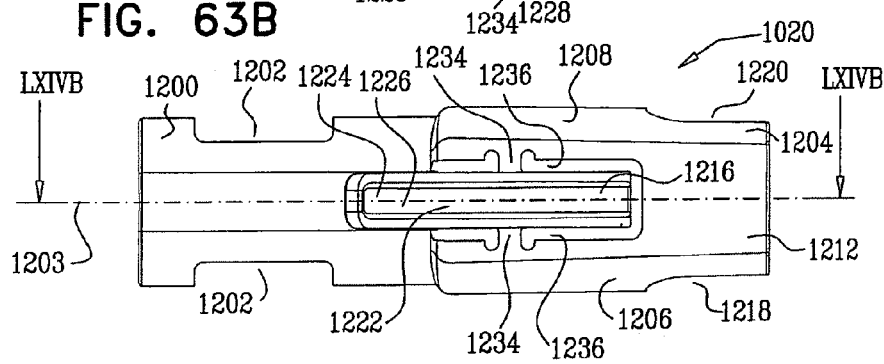
Figure 64A:
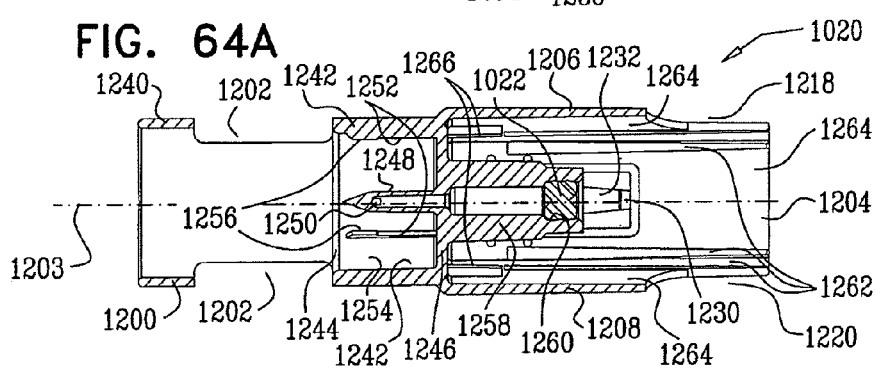
FIGS. 64A and 64B are sectional illustrations taken along respective section lines and directions LXIVA-LXIVA and LXIVB-LXIVB in FIGS. 63A and 63B.
Figure 64B:
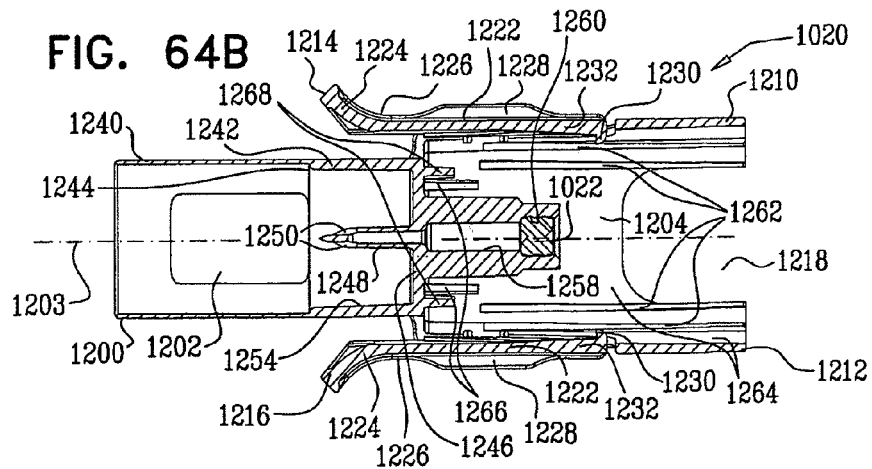

Reference is now made to FIG. 62, which is a simplified pictorial illustration of drug vial adaptor 1020 which forms part of the automatic injection device of FIG. 61, to FIGS. 63A and 63B, which are respective top and side view simplified planar illustrations of the drug vial adaptor of FIG. 62, and to FIGS. 64A and 64B, which are sectional illustrations taken along respective section lines and directions LXIVA-LXIVA and LXIVB-LXIVB in FIGS. 63A and 63B.

As seen in FIGS. 62-64B, the drug vial adaptor 1020 includes a generally circular cylindrical forward facing sleeve 1200, which is configured to generally enclose drug vial 1010 (FIG. 61) and is sized such as to render it difficult, if not impossible, to remove drug vial 1010 from sleeve 1200, following full insertion of the drug vial 1010 into the sleeve 1200. Sleeve 1200 is preferably formed with a pair of oppositely placed windows 1202 to enable a user to view the contents of the vial 1010 following insertion thereof into sleeve 1200.

It is seen that drug vial adaptor 1020 is preferably side-to-side symmetric about a longitudinal axis 1203.

Integrally formed with sleeve 1200 is a generally rectangular cylindrical rearward facing sleeve 1204 having first and second curved side walls 1206 and 1208 and first and second curved edge walls 1210 and 1212. Hinged finger engagement portions 1214 and 1216 are integrally formed with edge walls 1210 and 1212 respectively. Side walls 1206 and 1208 are formed with respective rearward facing cut outs 1218 and 1220.

Hinged finger engagement portions 1214 and 1216 each include a generally planar portion 1222 having an outwardly curved forward end 1224, defining a finger engagement surface 1226, and raised side edges 1228 extending along both sides of portion 1222. An inwardly facing retaining protrusion 1230 is located on an inwardly facing surface of a rearward end 1232 of generally planar portion 1222. A pair of integrally formed side hinges 1234 supports planar portion 1222 in an elongate cut out 1236 formed in each of edge walls 1210 and 1212.

The forward facing sleeve 1200 includes a forward-most portion 1240 having a first inner diameter and rearward thereof an intermediate portion 1242 having a second inner diameter, less than the first inner diameter. A shoulder 1244 is defined between portions 1240 and 1242. Intermediate portion 1242 is defined by a bulkhead 1246 having defined at its center a hollow spike 1248 which extends forwardly nearly to shoulder 1244. In use, spike 1248 punctures the elastomeric seal of drug vial 1010 (FIG. 61), thereby to enable fluid communication between the interior of drug vial 1010 and the interior of syringe 1046 (FIG. 61), via apertures 1250 formed at a forward end of spike 1248. This takes place only after the vial adaptor 1020 moves rearwardly along axis 1203, enabling fluid communication between the interior of syringe 1046 and apertures 1250.

Preferably, a plurality of centering and retaining ribs 1252 are provided along an interior facing surface 1254 of intermediate portion 1242. Ribs 1252 preferably include a forwardly located interiorly facing protrusion 1256 for engaging neck portion 1014 of drug vial 1010 (FIG. 61).

Extending rearwardly from bulkhead 1246 into the interior of rearward facing sleeve 1204 is a generally cylindrical fluid passageway defining lumen 1258 which defines at a rearward end thereof a septum receiving recess 1260 in which septum 1022 is located.

Preferably, a plurality of guiding ribs 1262 are provided along interior facing surfaces 1264 of side walls 1206 and 1208 and edge walls 1210 and 1212. Additionally, a plurality of positioning ribs 1266 extend rearwardly from bulkhead 1246 along surfaces 1264 of side walls 1206 and 1208. A pair of positioning protrusions 1268 extend rearwardly from bulkhead 1246 and are adapted to push the needle guard element 1030 (FIG. 61) rearwardly during pumping of the vial 1010, which in turn disengages the plunger locking element 1090 (FIG. 61) from the plunger 1049 (FIG. 61) to enable forward movement of plunger 1049.

Figure 65:
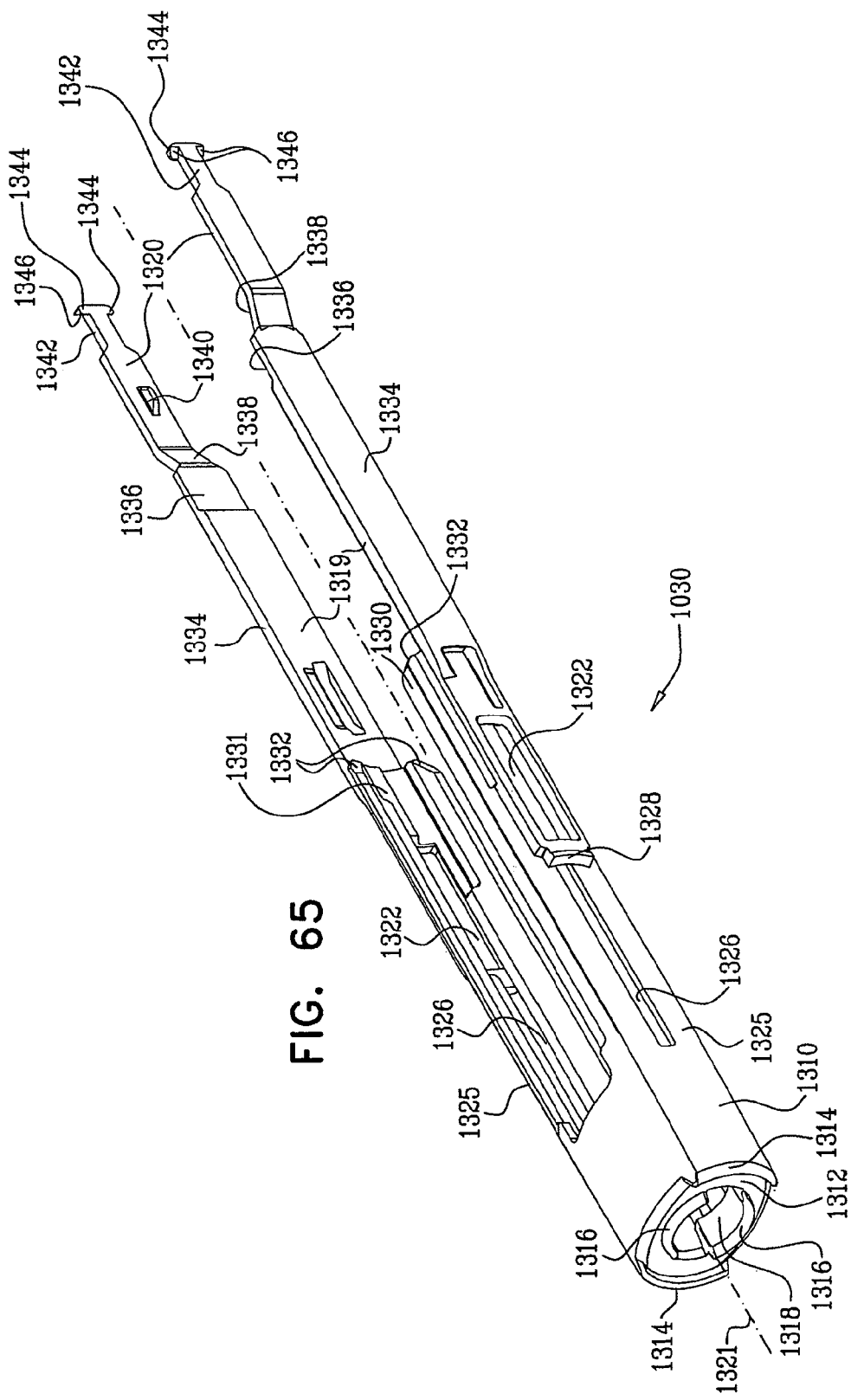
FIG. 65 is a simplified pictorial illustration of a needle guard element which forms part of the automatic injection device of FIG. 61.

Reference is now made to FIG. 65, which is a simplified pictorial illustration of needle guard element 1030 which forms part of the automatic injection device of FIG. 61, to FIGS. 66A and 66B, which are respective top and side view simplified planar illustrations of the needle guard element of FIG. 65, and to FIGS. 67A and 67B, which are sectional illustrations taken along respective section lines and directions LXVIIA-LXVIIA and LXVIIB-LXVIIB in FIGS. 66A and 66B.

As will be described hereinbelow in detail, needle guard element 1030 includes a pair of restriction elements, which prevent actuation of the device when a user presses actuation button 1070 (FIG. 61) when the device is not pressed against the user's body. At a forward part of the needle guard element 1030 there is provided a cylindrical portion having a front end including a generally circular bore, through which the needle passes during injection of the drug. Following injection, the cylindrical portion is displaced forwardly relative to the needle, thereby covering the needle and preventing inadvertent needle pricks.

As seen in FIGS. 65-67B, the needle guard element 1030 is preferably an integrally formed element, preferably injection molded of plastic and preferably has a generally cylindrical configuration including a generally tubular portion 1310, having a forward facing body engaging surface 1312 including pairs of concentrically located ribbed circumferential forward facing ring portions 1314 and 1316. A rearward facing internal surface 1317, facing opposite from body engaging surface 1312, forms a spring-seat for spring 1032 (FIG. 61) in cooperation with rearward extensions 1318 of ring portions 1316 which assist in locating the spring 1032 on surface 1317.

Needle guard element 1030 includes a pair of symmetric mounting arms 1319 having rearwardmost ends 1320, arranged symmetrically about a longitudinal axis 1321, which, when the automatic injection device is assembled, is coaxial with the longitudinal axis 1203 of drug vial adaptor 1020 (FIGS. 62-64B). Mounting arms 1319 are symmetric upon rotation about axis 1321 and extend parallel thereto along and rearwardly of tubular portion 1310. Each of arms 1319 is formed with a rectangular window 1322.

Each of symmetric mounting arms 1319 is formed with a forward portion 1325 having formed therein an elongated slot 1326, which extends rearwardly of generally tubular portion 1310 to a somewhat curved stop surface 1328. Stop surface 1328 is disposed adjacent a forward edge of rectangular window 1322. A widened arm portion 1330, having an interiorly facing surface 1331, is formed on each of arms 1319. The widened arm portion 1330 extends rearwardly along generally tubular portion 1310 to a location rearwardly of rectangular window 1322 and terminates in an inclined surface 1332 adjacent a shoulder 1333.

Extending further rearwardly from a location slightly forwardly of inclined surface 1332, is an intermediate arm portion 1334, having an outer surface which is disposed slightly radially outwardly with respect to longitudinal axis 1321 as compared with forward portion 1325. At a rearward end 1336 of intermediate arm portion 1334, the thickness of intermediate arm portion 1334 is reduced, and arm 1319 continues rearwardly at an outwardly inclined portion 1338. Outwardly inclined portion 1338 is followed by rearwardmost end 1320 of arm 1319, which has an inwardly facing generally trapezoidal protrusion 1340. As will be described hereinbelow, generally trapezoidal protrusion 1340 serves as a restriction element, which prevents actuation of the device when a user presses actuation button 1070 (FIG. 61) when the device is not pressed against the user's body.

Each of rearward most ends 1320 of arms 1319 terminates in a generally T-shaped portion 1342, including a pair of protrusions 1344 having an outwardly inclined surface 1346. The protrusions 1344 are adapted to enable the release of the plunger 1049 (FIG. 61) from its locked orientation when the drug vial adaptor 1020 (FIG. 62-64B) is axially positioned with respect to the forward housing 1040, as shown in FIG. 86B, as will be explained with further detail hereinbelow.

Figure 68:
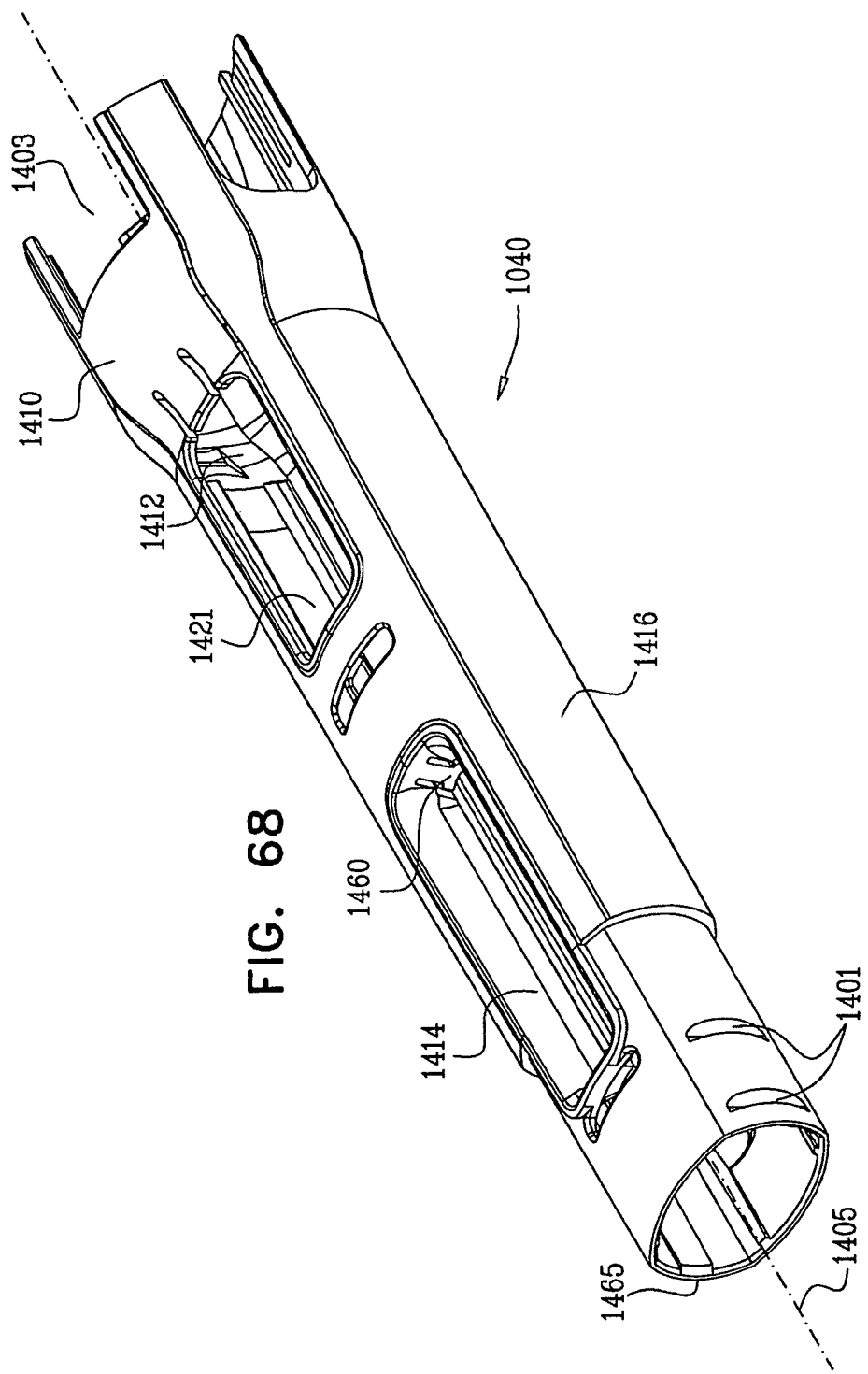
FIG. 68 is a simplified pictorial illustration of a forward housing which forms part of the automatic injection device of FIG. 61.

Reference is now made to FIG. 68, which is a simplified pictorial illustration of forward housing 1040 which forms part of the automatic injection device of FIG. 61, to FIGS. 69A and 69B, which are respective top and side view simplified planar illustrations of the forward housing of FIG. 68, and to FIGS. 70A, 70B and 70C, which are sectional illustrations taken along respective section lines and directions LXXA-LXXA, LXXB-LXXB and LXXC-LXXC in FIGS. 69A and 69B.

As will be described hereinbelow in detail, the forward housing 1040 includes at a forward portion thereof, two pairs of recesses 1401, adapted to receive the retaining protrusions 1230 of the finger engagement portions 1214 and 1216 of the drug vial adaptor 1020 (FIGS. 62-64B). At a rear end of the forward housing 1040 is a cutout portion 1403 adapted to accommodate the actuation button 1070 (FIG. 61).

As seen in FIGS. 68-70C, the forward housing 1040 preferably is an integrally formed element, preferably injection molded of plastic and preferably has a generally cylindrical configuration arranged along a longitudinal axis 1405, which, when the automatic injection device is assembled, is coaxial with longitudinal axes 1203 (FIGS. 62-64B) and 1321 (FIGS. 65-67B). Forward housing 1040 includes a generally tubular rear portion 1410, having an open back and formed with a pair of top-to-bottom symmetric snap fit engagement sockets 1412 which receive protrusions of the rear housing 1060 (FIG. 61) during factory assembly of the automatic injection device.

Forward of tubular rear portion 1410 and rearwardly of the recesses 1401 are formed a pair of top-bottom symmetric windows 1414, which allow the syringe and drug content thereof to be viewed when the automatic injection device is assembled, during use thereof and otherwise. A pair of outer side surfaces 1416 of forward housing 1040 have corresponding inner side surfaces 1421 each of which defines a plurality of longitudinally extending ribs 1422, 1424, 1426 and 1428 which are used to slidably guide the needle guard element 1030 (FIGS. 65-67B) during axial movement thereof.

Inner facing protrusions 1430 define a rearward facing spring seat 1431 for spring 1032 (FIG. 61). Inner facing protrusions 1430 are also operative to slidably support syringe 1046 (FIG. 61) and to slidably guide actuation arms of selectable driving assembly 1050 (FIG. 61).

Inner top and bottom surfaces 1432 and 1434 define respective pairs of ribs 1436 and 1438 which are operative to slidably rotationally orient the syringe 1046 (FIG. 61) about axis 1405 during axial movement of the syringe 1046. As best seen in FIG. 70A, inner facing protrusions 1430 define at rearward facing portions thereof protrusions 1460 and 1462 which form a stop for flange 1047 (FIG. 61), thus limiting the forward movement of the syringe 1046 (FIG. 61).

Inner side surface 1421 extends forwardly to an inwardly extending shoulder 1463 from which extends an inner surface 1464 which extends to a forward edge 1465 of forward housing 1040. Shoulder 1463 defines a stop which limits the forward movement of needle guard element 1030 (FIGS. 65-67B) relative to forward housing 1040.

As seen in FIG. 61, plunger 1049 includes a threaded protrusion 1470, which threadably engages a corresponding threaded socket (not shown) formed in a rear surface of a resilient piston 1471 which sealingly engages the interior of syringe 1046. Rearwardly of threaded protrusion 1470 is a generally circular cylindrical portion 1472 having a first cross sectional radius, followed by a relatively short circular cylindrical portion 1474 having a second cross sectional radius greater than the first radius and defining a rearward facing shoulder 1475.

Rearward of portion 1474 is a third generally circular cylindrical portion 1476 having a third cross sectional radius, generally equal to the first radius. Rearwardly of portion 1476 is formed a toothed portion 1477, each tooth 1478 thereof having a generally transverse forwardly facing portion 1480 and a slanted rearwardly facing portion 1482. The particular shape of the teeth of toothed portion 1477 enables rearward movement of the plunger 1049 at any time, and requires a specific configuration of the device in order to enable forward movement of the plunger 1049.

Plunger 1049 is preferably symmetrically disposed about a longitudinal axis 1484, which, when the automatic injection device is assembled, is coaxial with longitudinal axes 1203 (FIGS. 62-64B), 1321 (FIGS. 65-67B) and 1405 (FIGS. 68-70C).

Figure 71:
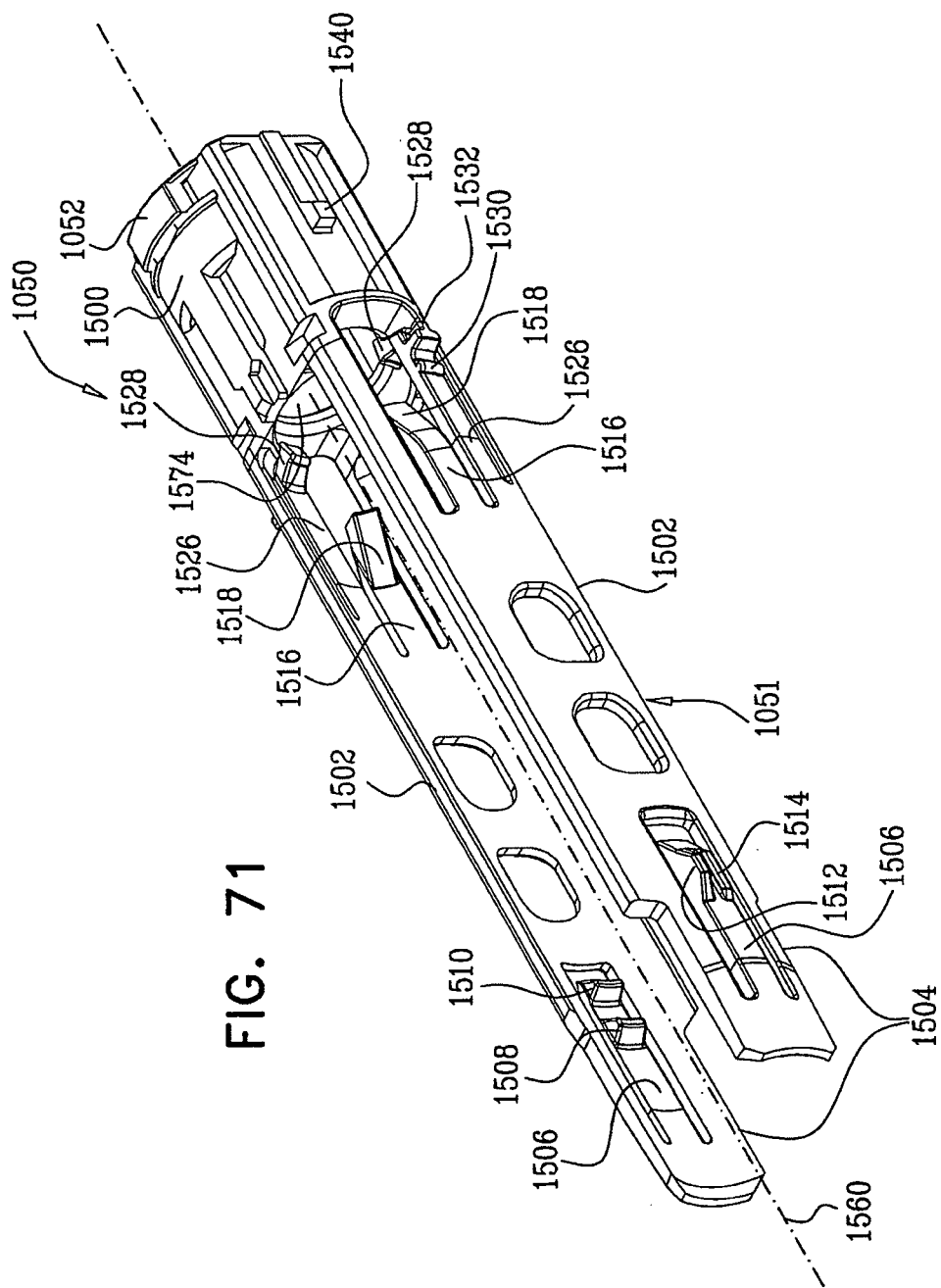
FIG. 71 is a simplified pictorial illustration of a selectable driving assembly which forms part of the automatic injection device of FIG. 61.

Reference is now made to FIG. 71, which is a simplified pictorial illustration of selectable driving assembly 1050 which forms part of the automatic injection device of FIG. 61, to FIGS. 72A and 72B, which are respective top and side view simplified planar illustrations of the selectable driving assembly of FIG. 71, and to FIGS. 73A and 73B, which are sectional illustrations taken along respective section lines and directions LXXIIIA-LXXIIIA and LXXIIIB-LXXIIIB in FIGS. 72A and 72B.

The selectable driving assembly 1050 includes selectable driving element 1051 and elastomeric motion damping elements 1052 and 1054. Selectable driving element 1051 includes a rearward facing generally cylindrical portion 1500 and a pair of longitudinal arms 1502. At a forward end 1504 of each of the longitudinal arms 1502 there is provided a first hinged finger 1506 having formed thereon a pair of inwardly facing protrusions 1508 and 1510. The inwardly facing protrusions 1508 and 1510 are adapted to engage the flange 1047 of syringe 1046 (FIG. 61) to retain it in position during the stages shown in FIGS. 86A-86F and to control its forward movement during actuation of the device. Opposite protrusions 1508 and 1510, on an outer facing surface of first hinged finger 1506, are formed a pair of outwardly facing generally trapezoidal protrusions 1512 and 1514. It is seen that protrusion 1512 extends outwardly to a greater degree than does protrusion 1514.

Rearwardly of first hinged finger 1506 on each of longitudinal arms 1502 is a second hinged finger 1516, having an inwardly facing protrusion 1518, which is adapted to rearwardly displace the syringe 1046 (FIG. 61) following injection, when the needle guard element 1030 (FIGS. 65-67B) is rearwardly displaced.

Generally alongside and parallel to second hinged fingers 1516 there are formed third hinged fingers 1526, each including an inwardly facing slanted protrusion 1528 operative to forwardly displace the plunger 1049 (FIG. 61) during injection, and a pair of outwardly facing protrusions 1530 and 1532, which are operative to inwardly bend the third hinged fingers 1526 during actuation and which engage the needle guard element 1030 (FIGS. 65-67B) and are operative to displace it forwardly as soon as the device disengages the user's body.

The cylindrical portion 1500 of the selectable driving element 1051 includes protrusions 1540 on opposite sides thereof, which are adapted to maintain the selectable driving assembly 1050 in place when the device is in its storage position, by abutting against the actuation button 1070 (FIG. 61). The cylindrical portion 1500 also has seated therein motion damping elements 1052 and 1054 which engage an internal surface of the rear housing 1060 (FIG. 61), and thus are operative to slow the forward movement of the selectable driving assembly 1050, thereby slowing the forward movement of the syringe 1046 (FIG. 61) and plunger 1049 (FIG. 61) during injection.

As seen in FIGS. 71-73B, the selectable driving element 1051 preferably is an integrally formed, element, preferably injection molded of plastic and preferably has a generally cylindrical configuration including generally cylindrical portion 1500, which has an open back. Longitudinal arms 1502 are preferably symmetric actuation arms and extend forwardly of cylindrical portion 1500 parallel to a longitudinal axis 1560, which, when the automatic injection device is assembled, is coaxial with longitudinal axes 1203 (FIGS. 62-64B), 1321 (FIGS. 65-67B), 1405 (FIGS. 68-70C) and 1484 (FIG. 61). Arms 1502 are symmetric upon rotation about axis 1560, and each has a generally curved cross section.

An interior generally cylindrical surface 1570 of cylindrical portion 1500 terminates at a forward end of cylindrical portion 1500 at a shoulder 1572, forwardly of which is an opening 1574 through which extends plunger 1049 (FIG. 61). Shoulder 1572 defines a spring seat for spring 1062 (FIG. 61).

Figure 74:
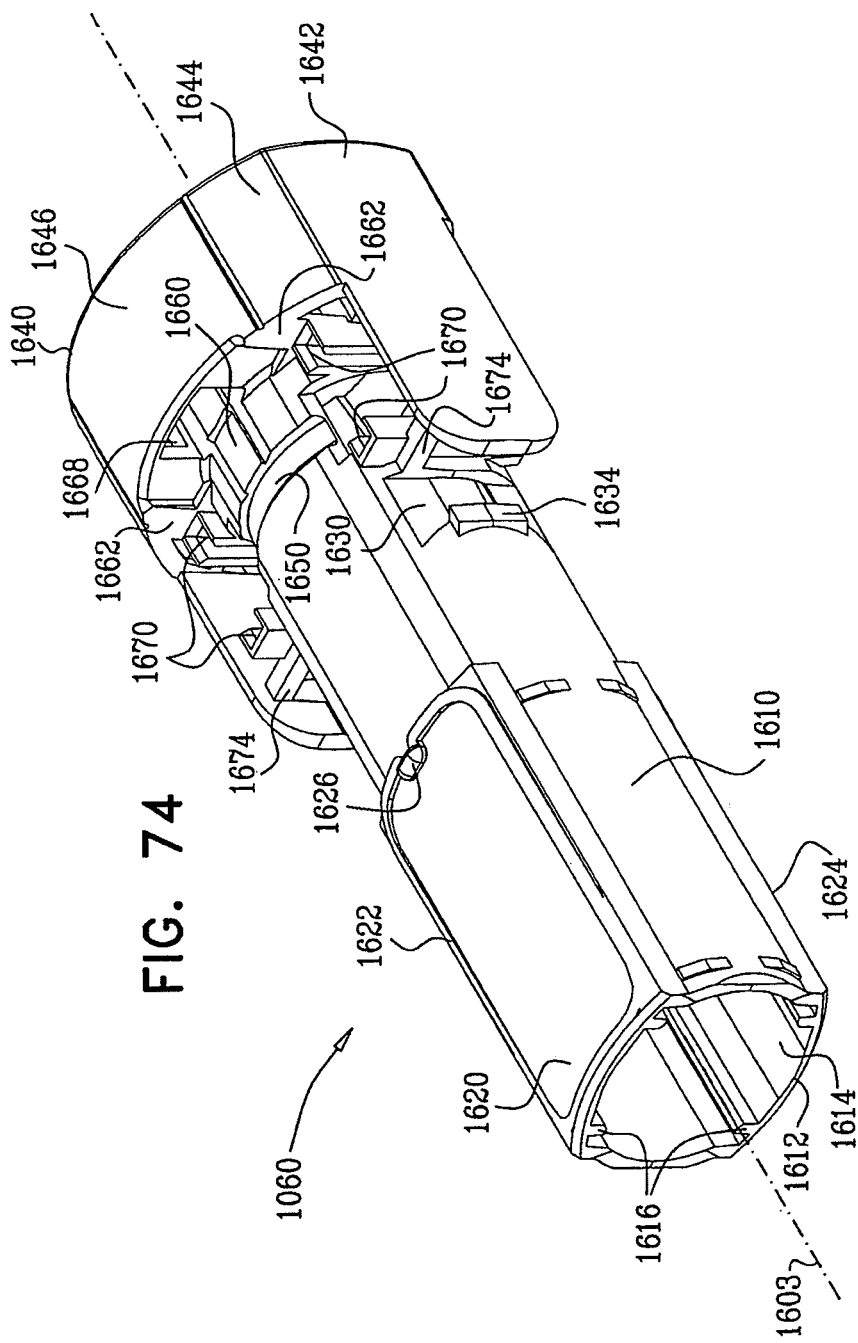
FIG. 74, is a simplified pictorial illustration of a rear housing which forms part of the automatic injection device of FIG. 61.
Figure 75A:
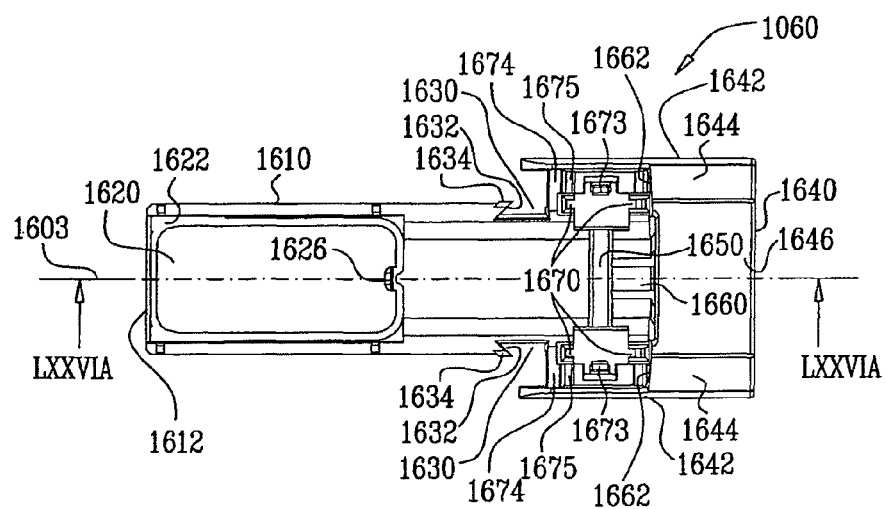
FIGS. 75A and 75B are respective top and side view simplified planar illustrations of the rear housing of FIG. 74.
Figure 75B:
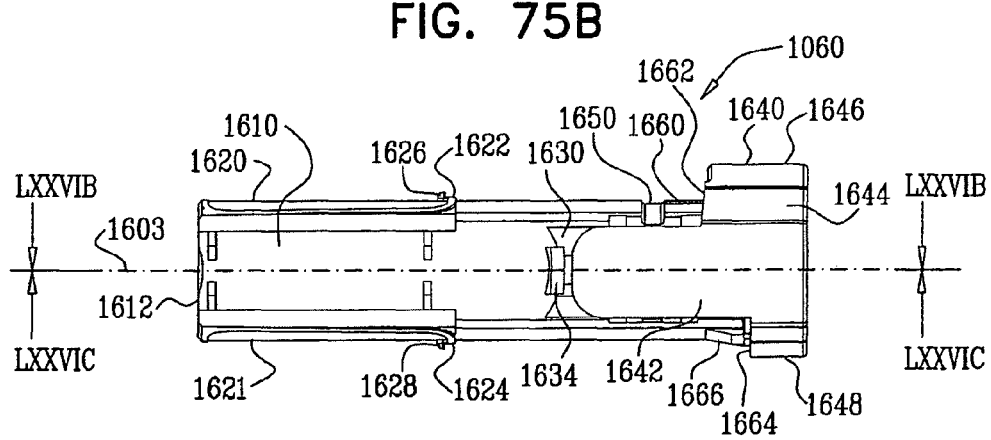
Figure 76A:
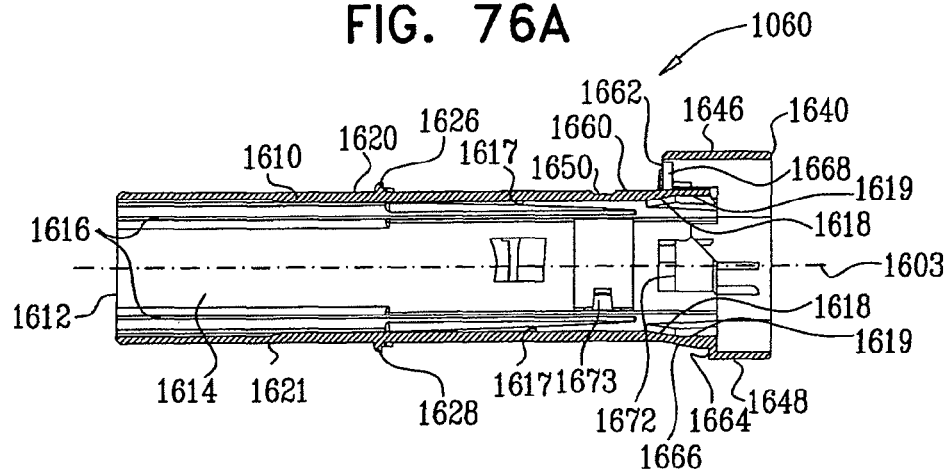
FIGS. 76A, 76B and 76C are sectional illustrations taken along respective section lines and directions LXXVIA-LXXVIA, LXXVIB-LXXVIB and LXXVIC-LXXVIC in FIGS. 75A and 75B.
Figure 76B:
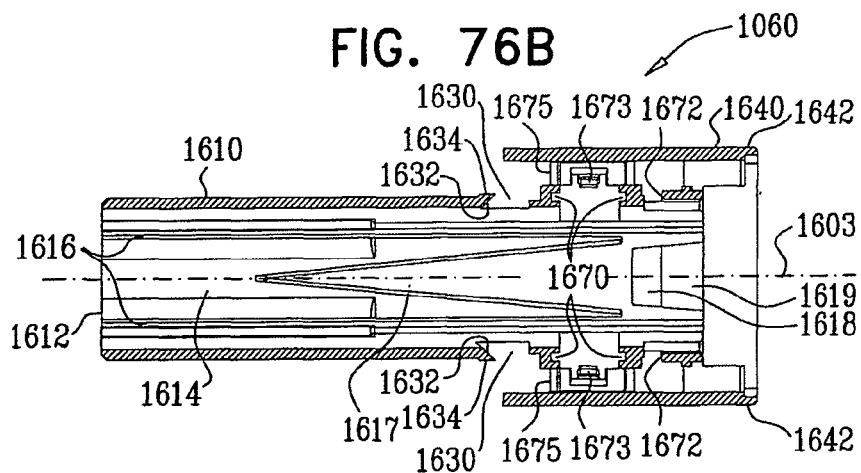
Figure 76C:
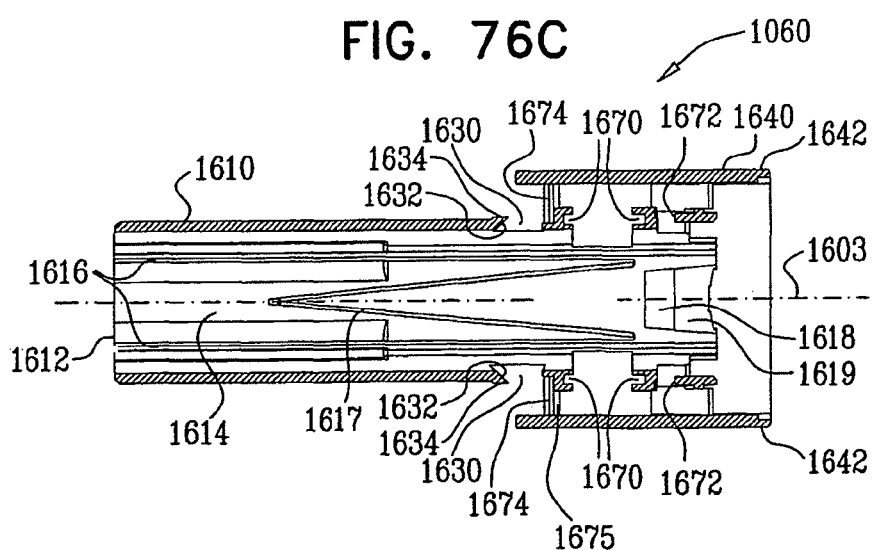

Reference is now made to FIG. 74, which is a simplified pictorial illustration of rear housing 1060 which forms part of the automatic injection device of FIG. 61, to FIGS. 75A and 75B, which are respective top and side view simplified planar illustrations of the rear housing of FIG. 74, and to FIGS. 76A, 76B and 76C, which are sectional illustrations taken along respective section lines and directions LXXVIA-LXXVIA, LXXVIB-LXXVIB and LXXVIC-LXXVIC in FIGS. 75A and 75B.

As seen in FIGS. 74-76C, the rear housing 1060 is preferably an integrally formed element, preferably injection molded of plastic and preferably has a generally cylindrical configuration arranged about a longitudinal axis 1603, which, when the automatic injection device is assembled, is coaxial with longitudinal axes 1203 (FIGS. 62-64B), 1321 (FIGS. 65-67B), 1405 (FIGS. 68-70C), 1484 (FIG. 61) and 1560 (FIGS. 71-73B). The rear housing 1060 includes a tube 1610, which includes a forward portion 1612 having an interiorly facing surface 1614 including four generally equally spaced, longitudinally extending, guiding ribs 1616. Also formed on interiorly facing surface 1614 are a pair of interiorly facing protrusions 1617 whose width tapers in a forwardly facing direction to a point, thus defining a generally triangular engagement surface for elastomeric motion damping elements 1052 and 1054 (FIG. 61). Disposed adjacent the wide end of each of protrusions 1617 are an inclined recess 1618 and a cylindrical recess 1619, which serve to guide elastomeric motion damping elements 1052 and 1054 upstream of their engagement with protrusions 1617.

Formed on a pair of generally equally spaced exteriorly facing surfaces 1620 and 1621 of tube 1610 are respective generally rectangular outwardly protruding frames 1622 and 1624. Further protrusions 1626 and 1628 are located interiorly of frames 1622 and 1624 respectively and centered adjacent rearward ends thereof. Protrusions 1626 and 1628 are accommodated in snap fit engagement sockets 1412 of the forward housing 1040 (FIGS. 68-70C) during factory assembly of the device, and thereby maintain the connection between the rear housing 1060 and the forward housing 1040. Formed in tube 1610 adjacent a rearward end thereof are a pair of side cutouts 1630 each having an undercut forward edge 1632. Disposed forwardly of each of edges 1632 is a generally rectangular outwardly facing protrusion 1634.

Integrally formed with tube 1610 and partially overlapping a rearward portion thereof is a generally cylindrical rearward housing surface portion 1640 including first and second generally rectangular side surface portions 1642, intermediate surface portions 1644, a top surface portion 1646 and a bottom surface portion 1648. At its rearward end, tube 1610 is formed with a transverse curved recess 1650. Rearwardly of recess 1650 is a generally cylindrical portion 1660.

Disposed rearwardly of portion 1660 is a wall 1662 which connects tube 1610 to surface 1646. Adjacent surfaces 1644 and 1646, the wall 1662 is generally perpendicular to tube 1610 and to surfaces 1644 and 1646. Adjacent surface 1648, the wall includes a perpendicular portion 1664 and a tapered portion 1666. An opening 1668 in wall 1662 communicates with a volume disposed between cylindrical portion 1660 and surface 1646.

Four elongate tracks 1670, disposed alongside curved recess 1650 between tube 1610 and surfaces 1642, preferably each having a generally U-shaped cross section, define a pair of guiding tracks for actuation button 1070 (FIG. 61). A pair of rear end element retaining portions 1672 are located rearwardly of tracks 1670 for engagement with rear end element 1080 (FIG. 61).

Between each pair of tracks 1670 there is disposed a flexible biasing finger 1673 for engagement with actuation button 1070 (FIG. 61).

Extending between each of forwardly disposed tracks 1670 and a corresponding rectangular side surface 1642 are a pair of transverse portions 1674 and 1675 which guide a corresponding arm 1319 (FIGS. 65-67B) of needle guard element 1030.

Figure 77A:
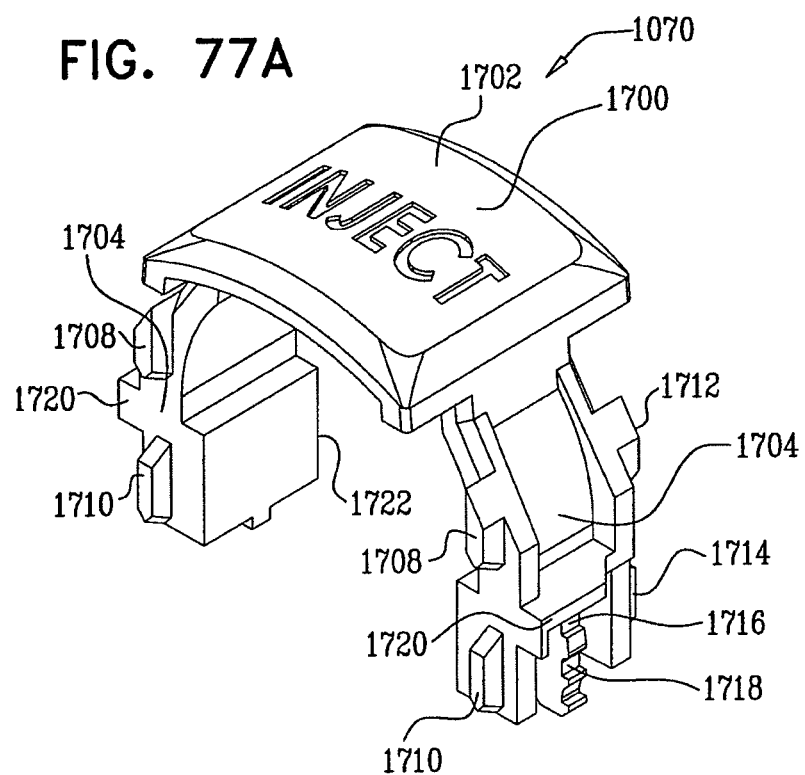
FIGS. 77A and 77B are simplified pictorial illustrations of an actuation button which forms part of the automatic injection device of FIG. 61.
Figure 77B:
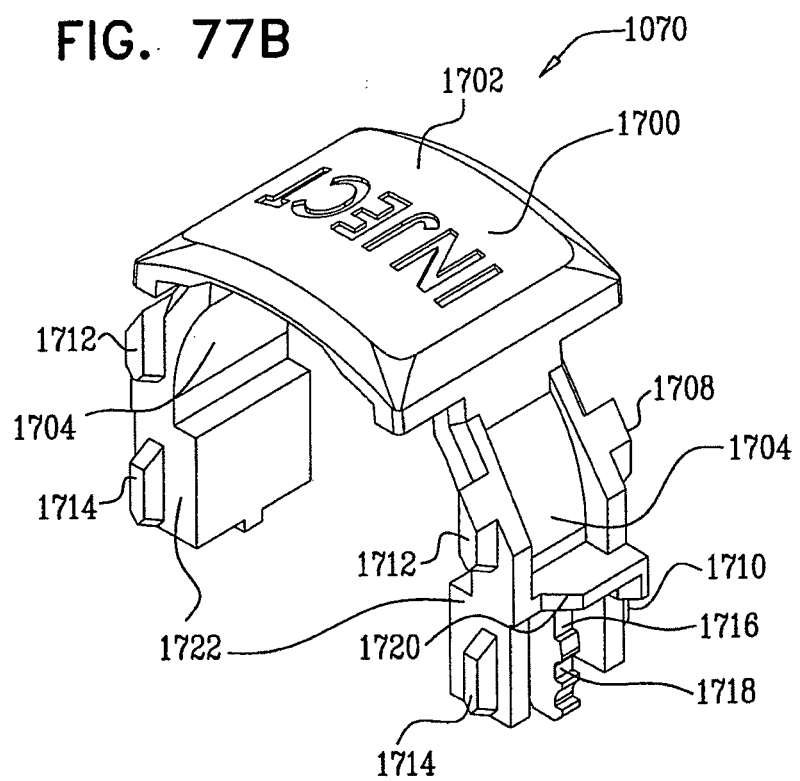

Reference is now made to FIGS. 77A and 77B, which are respective front and back view simplified-pictorial illustrations of actuation button 1070 which forms part of the automatic injection device of FIG. 61, to FIGS. 78A and 78B, which are respective top and side view simplified planar illustrations of the actuation button of FIGS. 77A and 77B, and to FIGS. 79A and 79B, which are sectional illustrations taken along respective section lines and directions LXXIXA-LXXIXA and LXXIXB-LXXIXB in FIGS. 78A and 78B.

The actuation button 1070 has the general configuration of a side-to-side symmetric arch and includes a central portion 1700 having a top finger engagement surface 1702, and a pair of generally rectangular legs 1704. Each of legs 1704 includes first and second generally trapezoidal forwardly directed protrusions 1708 and 1710 and first and second generally trapezoid rearwardly directed protrusions 1712 and 1714, which are adapted to be seated in correspondingly configured tracks 1670 (FIGS. 74-76C) of the rear housing 1060. Intermediate the forwardly directed protrusions 1708 and 1710 and rearwardly directed protrusions 1712 and 1714, each leg 1704 includes first and second outwardly facing recesses 1716 and 1718, which are adapted to engage the flexible biasing fingers 1673 (FIGS. 74-76C) of the rear housing 1060 and thereby maintain the actuation button 1070 in either its storage state or its activated state.

Adjacent the forwardly directed protrusions 1708 and 1710 and rearwardly directed protrusions 1712 and 1714 on each leg 1704 there is provided a generally L-shaped transverse outwardly facing protrusion 1720 with respect to which the generally trapezoidal protrusions 1340 (FIGS. 65-67B) of the needle guard element 1030 are oriented prior to actuation of the device, so as to prevent premature actuation of the device. The L-shaped transverse outwardly facing protrusions 1720 additionally prevent the downward displacement of the actuation button 1070 when the device is not pressed against the user's body and the needle guard element 1030 (FIGS. 65-67B) is not rearwardly displaced.

Each of the legs 1704 additionally includes a rearward facing surface 1722, against which protrusion 1540 (FIG. 71-73B) of the selectable driving assembly 1050 abuts prior to actuation of the device.

During downward displacement of the actuation button 1070 and resulting actuation of the device, the plunger locking element 1090 (FIG. 61) abuts against a bottom surface 1726 of the central portion 1700, generally underlying the top finger engagement surface 1702.

Figure 80:
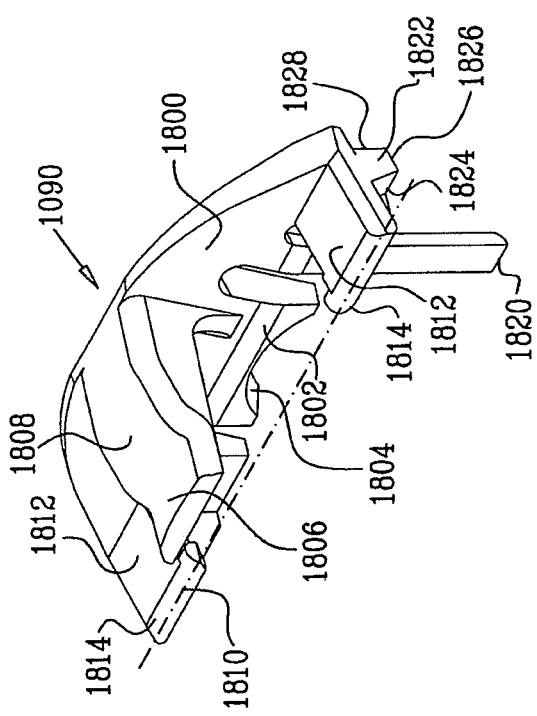
FIG. 80 is a simplified pictorial illustration of a plunger locking element which forms part of the automatic injection device of FIG. 61.

Reference is now made to FIG. 80, which is a simplified pictorial illustration of plunger locking element 1090 which forms part of the automatic injection device of FIG. 61, to FIGS. 81A, 81B, 81C, 81D and 81E, which are respective top, left side, right side, bottom and front view simplified planar illustrations of the plunger locking element of FIG. 80, and to FIGS. 82A and 82B, which are sectional illustrations taken along respective section lines and directions LXXXIIA-LXXXIIA and LXXXIIB-LXXXIIB in FIG. 81A.

The plunger locking element 1090 is preferably an integrally formed element, preferably injection molded of plastic and includes an upright back portion 1800 having at a central bottom region thereof a plunger engaging protrusion 1802 having a curved bottom facing edge surface 1804 which engages the teeth 1478 of toothed portion 1477 (FIG. 61) of the plunger 1049 and thus prevents the plunger 1049 from moving forward.

An actuation button engagement surface 1806 is provided on a forwardly extending protrusion 1808 of the top portion of the plunger locking element 1090. The actuation button engagement surface 1806 is engaged by the actuation button 1070 (FIGS. 77-79B) and is rotated thereby about an axis 1810, extending perpendicular to axis 1603 of rear housing 1060 (FIGS. 74-76B), during actuation of the device, thereby releasing the locking of the plunger 1049 (FIG. 61).

A pair of forwardly facing protrusions 1812, each having a curved forward end 1814, define axis 1810 about which the plunger locking element 1090 rotates during actuation of the device. These protrusions are adapted to be seated in corresponding hemispherical recesses in the rear end element 1080 (FIG. 61).

A resilient leg 1820 extends downwardly from back portion 1800, generally alongside one of the forwardly facing protrusions 1812 and constantly urges the plunger locking element 1090 to rotate about axis 1810 to a configuration in which the plunger 1049 (FIG. 61) is locked. When the plunger locking element 1090 is rotated about axis 1810, the resilient leg 1820 abuts against a forward facing protrusion of the rear end element 1080 (FIG. 61) and the plunger 1049 is released.

A pair of downward facing protrusions 1822, each having a slanted forwardly facing surface 1824, a generally planar bottom surface 1826, and a generally planar rearwardly facing surface 1828, are formed on either of forwardly facing protrusions 1812 of the plunger locking element 1090. During operation of the device, such as during the injection stage, generally T-shaped portions 1342 (FIGS. 65-67B) of needle guard element 1030 abut against slanted forwardly facing surfaces 1824 of protrusions 1822, causing rotation of the plunger locking element 1090 about axis 1810, and thereby releasing the plunger 1049 (FIG. 61).

Figure 83:
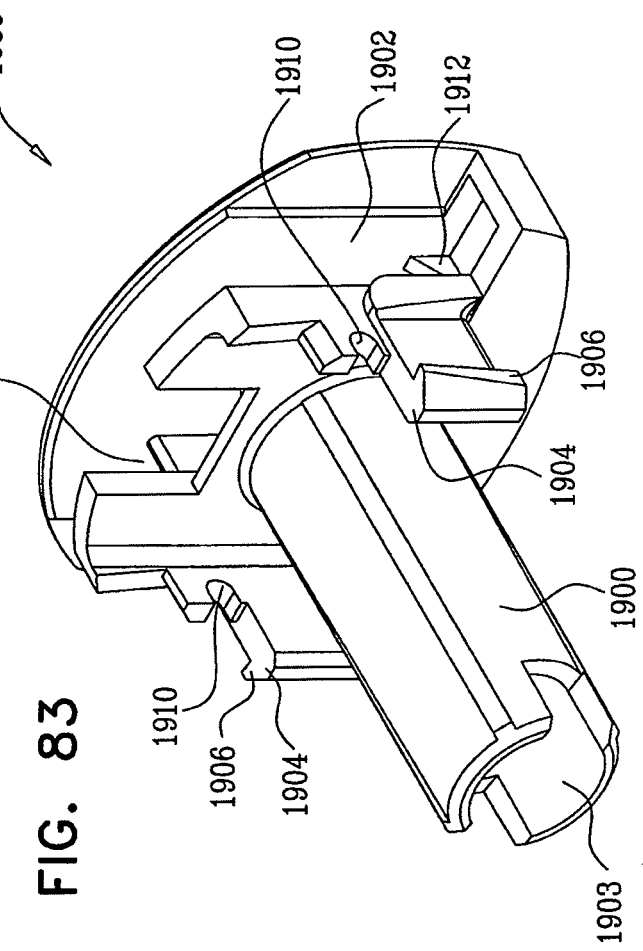
FIG. 83 is a simplified pictorial illustration of a rear end element which forms part of the automatic injection device of FIG. 61.
Figure 84A:
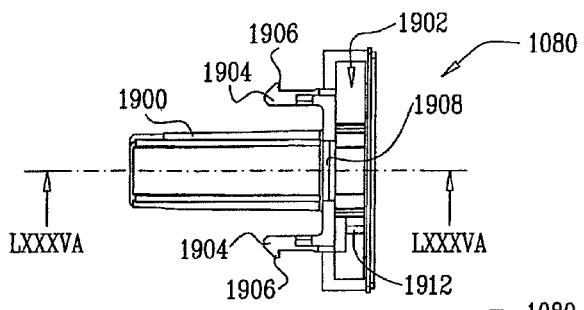
FIGS. 84A and 84B are respective top and side view simplified planar illustrations of the rear end element of FIG. 83.
Figure 84B:
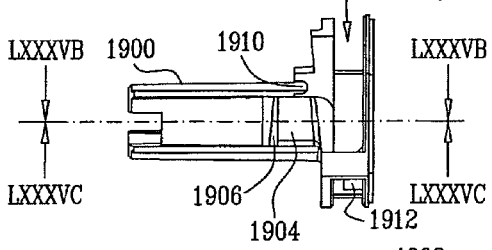
Figure 85A:
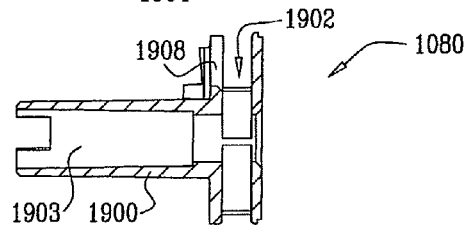
FIGS. 85A, 85B and 85C are sectional illustrations taken along respective section lines and directions LXXXVA-LXXXVA, LXXXVB-LXXXVB and LXXXVC-LXXXVC in FIGS. 84A and 84B.
Figure 85B:
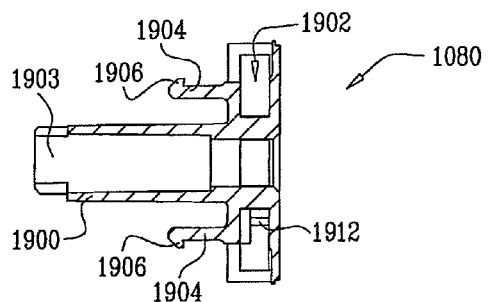
Figure 85C:
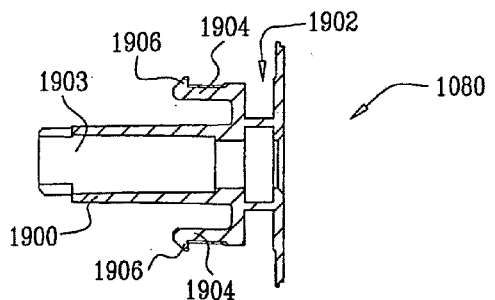

Reference is now made to FIG. 83, which is a simplified pictorial illustration of rear end element 1080 which forms part of the automatic injection device of FIG. 61, to FIGS. 84A and 84B, which are respective top and side view simplified planar illustrations of the rear end element of FIG. 83, and to FIGS. 85A, 85B and 85C, which are sectional illustrations taken along respective section lines and directions LXXXVA-LXXXVA, LXXXVB-LXXXVB and LXXXVC-LXXXVC in FIGS. 84A and 84B.

The rear end element 1080 includes a generally cylindrical forward portion 1900 terminating rearwardly in a generally planar rearward portion 1902. Cylindrical forward portion 1900 and rearward portion 1902 together define a rearward spring seat for spring 1062 (FIG. 61). The cylindrical portion 1900 includes a central bore 1903 which is adapted to accommodate the plunger 1049 (FIG. 61). Extending forwardly from planar rearward portion 1902 alongside cylindrical portion 1900 are a pair of resilient fingers 1904 each including an outwardly facing hook type protrusion 1906. The resilient fingers 1904 are adapted to engage corresponding rear end element retaining portions 1672 (FIG. 74-76C) in rear housing 1060 and to maintain secure engagement of the rear end element 1080 thereto.

Generally planar rearward portion 1902 defines a cut out 1908 which is adapted to accommodate forwardly extending protrusion 1808 of the plunger locking element 1090 (FIGS. 80-82E). Adjacent resilient fingers 1904 are a pair of partially semicircular recesses 1910, which define the location of axis 1810 about which the plunger locking element 1090 (FIG. 61) rotates, and which accommodate curved forward ends 1814 of protrusions 1812 of plunger locking element 1090. Rearward portion 1902 also includes a forwardly facing protrusion 1912 which is adapted to engage the resilient leg 1820 of plunger locking element 1090.

Reference is now made to FIGS. 86A, 86B, 86C, 86D, 86E, 86F, 86G, 86H, 86I, 86J, 86K and 86L, which are simplified pictorial illustration of various stages of typical use of the automatic injection device of FIG. 61.

FIG. 86A illustrates insertion of vial 1010 into vial adaptor 1020, which forms part of the automatic injection device of FIG. 61. FIG. 86B shows the vial 1010 fully inserted into vial adaptor 1020, it being appreciated that removal of the vial 1010 from vial adaptor 1020 following full insertion thereof is very difficult or impossible. It is further appreciated that insertion of vial 1010 into vial adaptor 1020 causes vial adaptor 1020 to be displaced in a rearward direction indicated by an arrow 1960 in FIG. 86A, with respect to the remainder of the automatic injection device of FIG. 61.

Figure 86C:
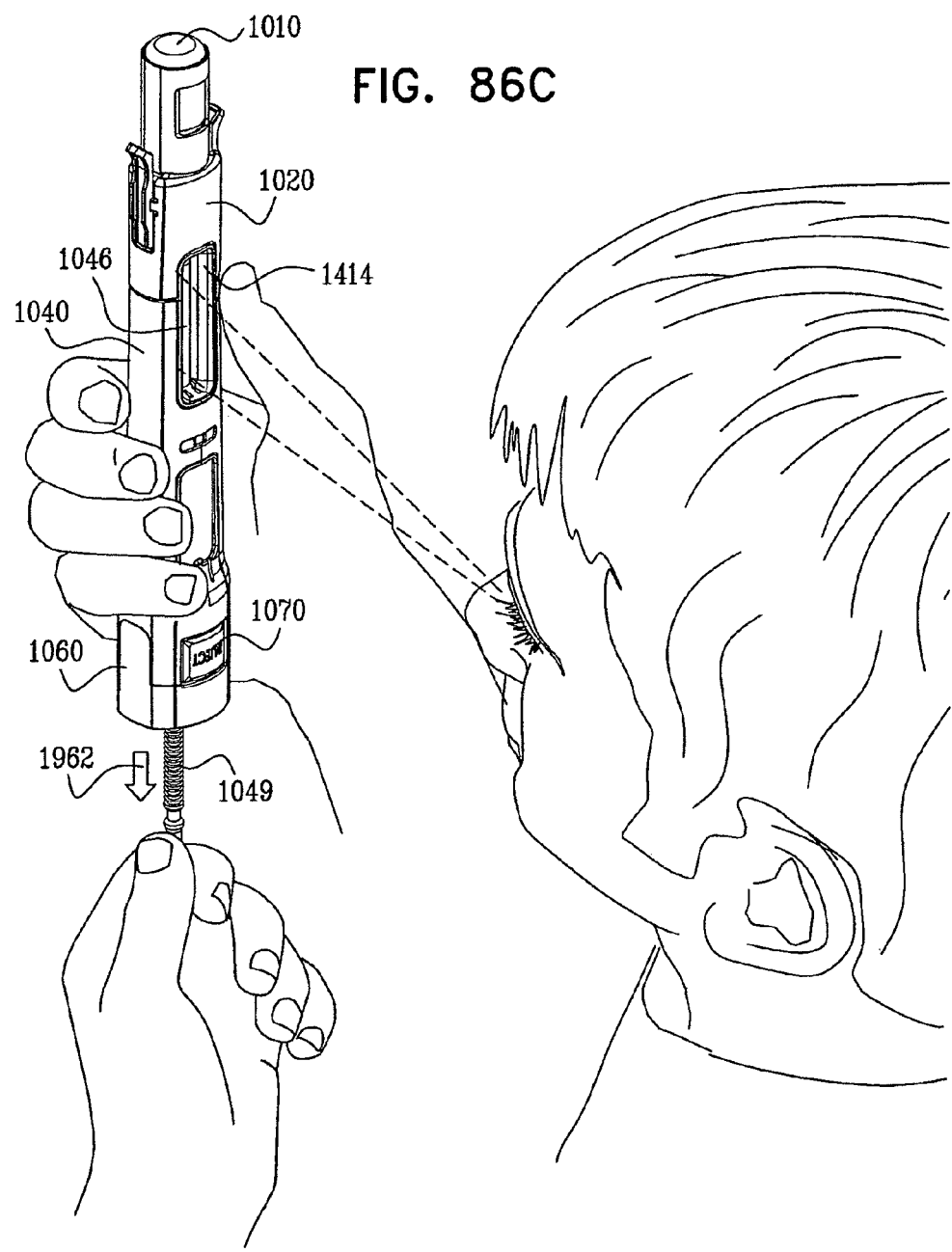

FIG. 86C shows liquid from vial 1010 being drawn into syringe 1046. This is achieved by a user, holding the automatic injection device of FIG. 61 in a generally vertical orientation as shown, pulling the plunger 1049 in a direction indicated by an arrow 1962; downward in the sense of FIG. 86C and rearward in the sense of FIG. 61. During this procedure, the user sees the amount of liquid in the syringe 1046 via windows 1414 in forward housing 1040. It is appreciated that at this stage, the plunger 1049 can be displaced by the user in a direction opposite to that indicated by arrow 1962.

FIG. 86D illustrates removal of the vial adaptor 1020, containing vial 1010, from the forward housing 1040, by first pressing inwardly on finger engagement portions 1214 and 1216 as indicated by arrows 1964 and 1966 respectively and then pulling vial adaptor 1020 in a direction indicated by an arrow 1968. It is appreciated that at this stage, here termed a ready to inject stage, following removal of the vial adaptor 1020 from the forward housing 1040, the plunger 1049 cannot be displaced by the user in a direction opposite to that indicated by arrow 1962 (FIG. 86C).

Figure 86E:
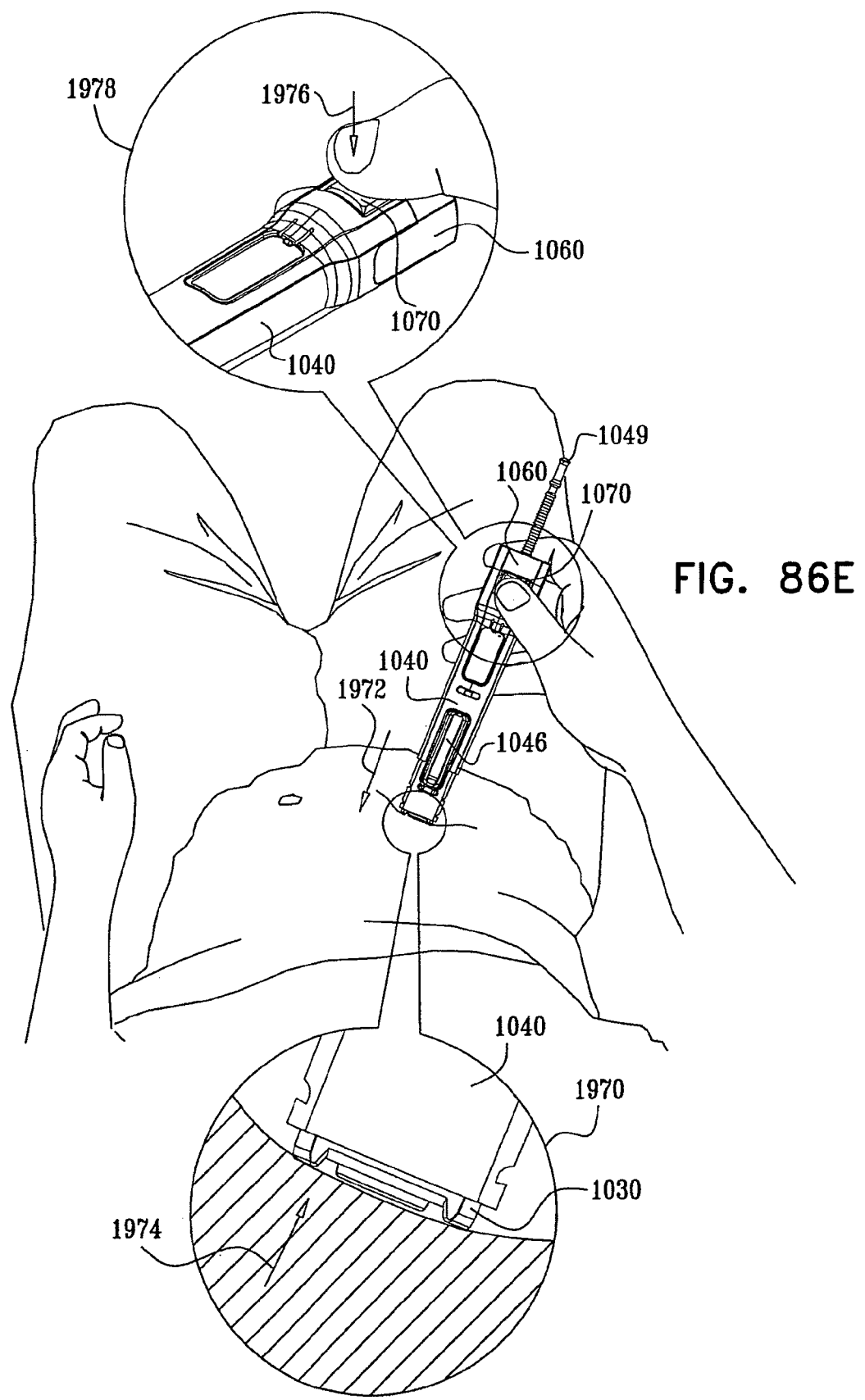

Turning now to FIG. 86E, it is seen that a user is employing the automatic injection device to inject a liquid into his body. As illustrated in enlargement 1970, it is seen that by pressing the automatic injection device against his body, in a direction indicated by an arrow 1972, the user causes needle guard element 1030 to be pushed in a direction indicated by an arrow 1974, rearwardly with respect to forward housing 1040. This rearward motion unlocks actuation button 1070, such that when the user presses on the actuation button 1070, as indicated by an arrow 1976 in enlargement 1978, the actuation button 1070 is operative to initiate injection.

Figure 86F:
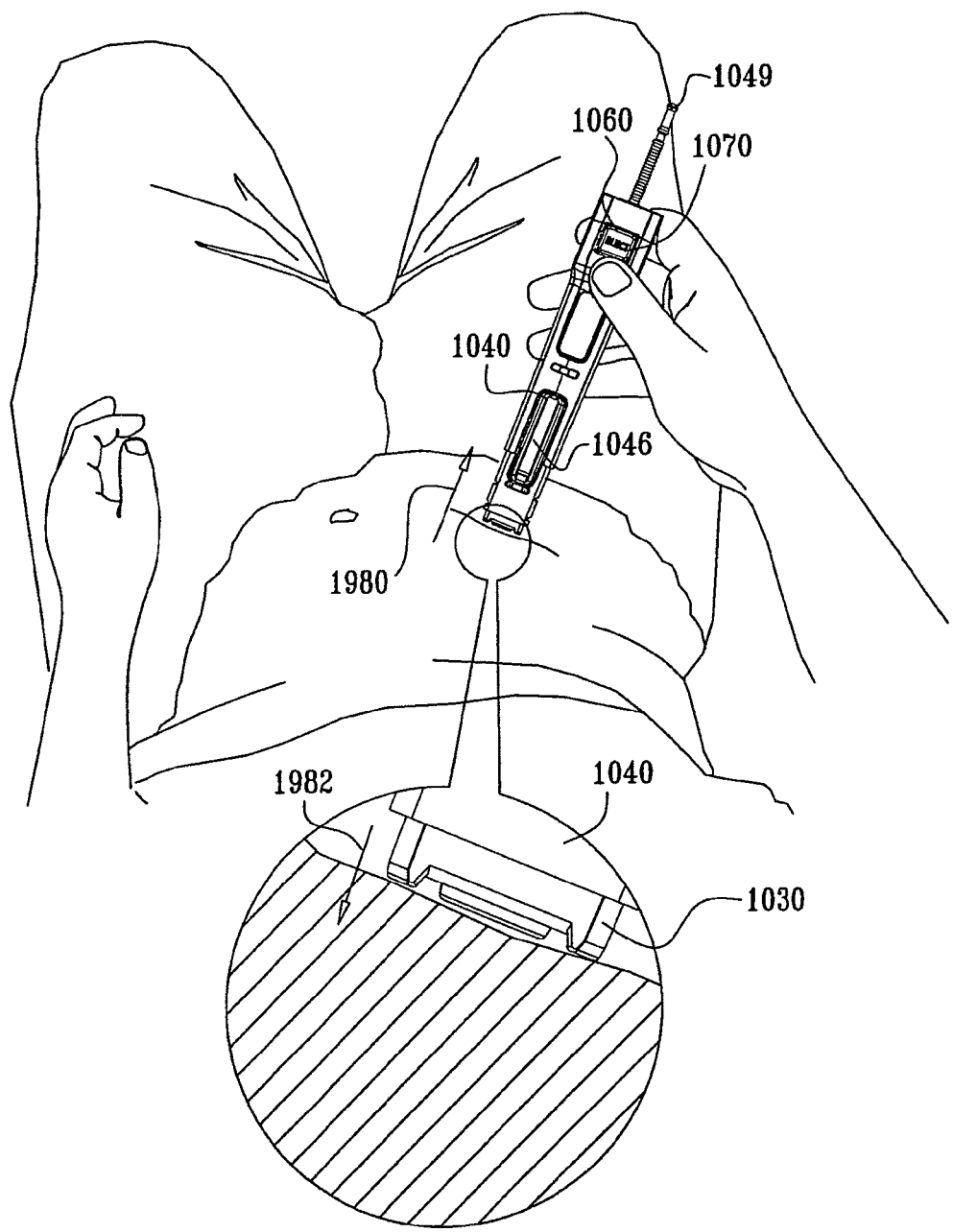

As seen in FIG. 86F, if for any reason the user, prior to pressing the actuation button 1070, removes the automatic injection device from pressed engagement with his body, as indicated by arrow 1980, the needle guard element 1030 is forwardly displaced in the direction indicated by arrow 1982 and returns to its initial position as shown in FIG. 86D. This forward displacement of the needle guard element 1030 relocks the actuation button 1070, such that even if the user were to press on the actuation button 1070 injection would not be initiated until the automatic injection device is again pressed against his body. At this stage, the user can proceed as described hereinabove with reference to FIG. 86E.

Figure 86G:
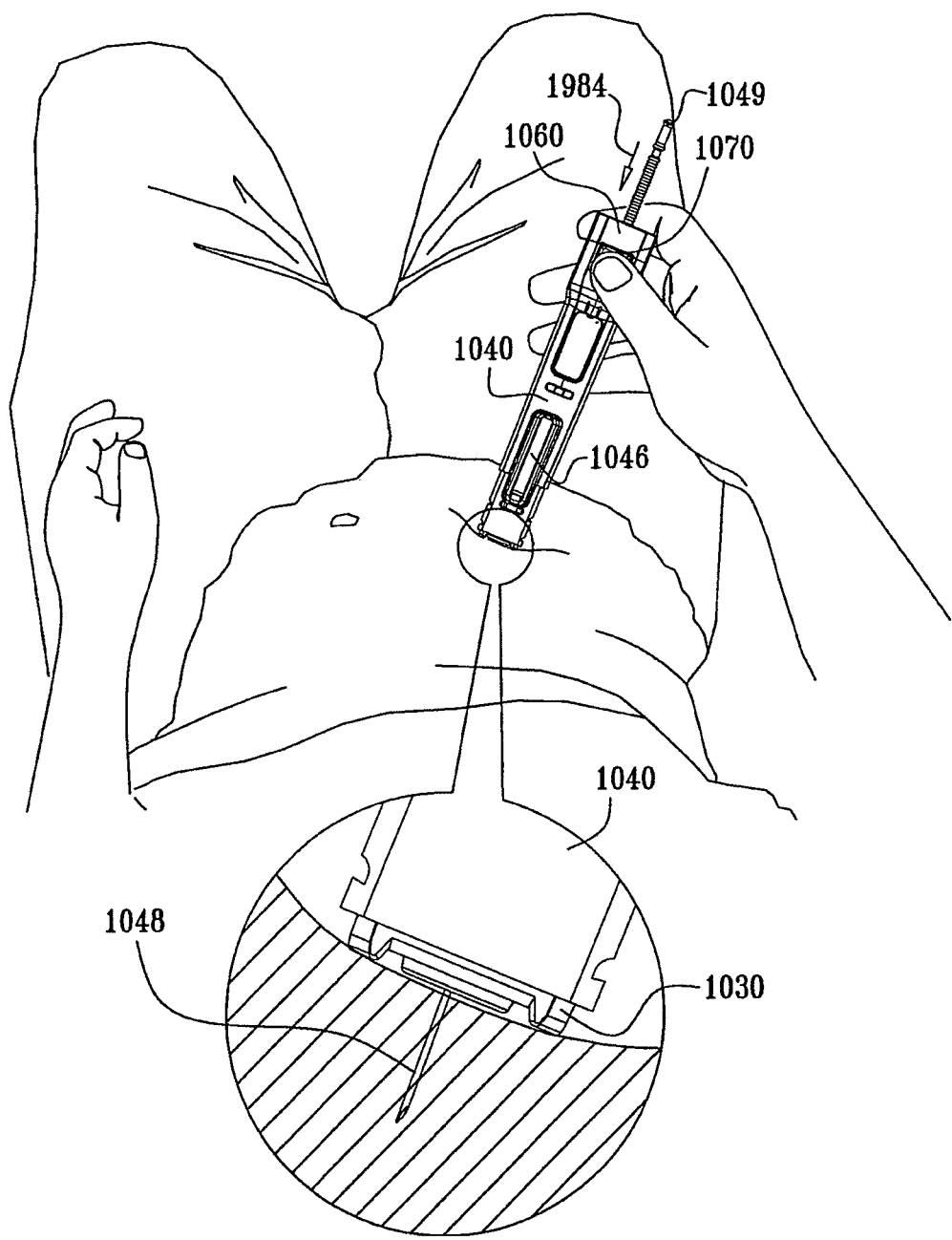
Figure 86H:
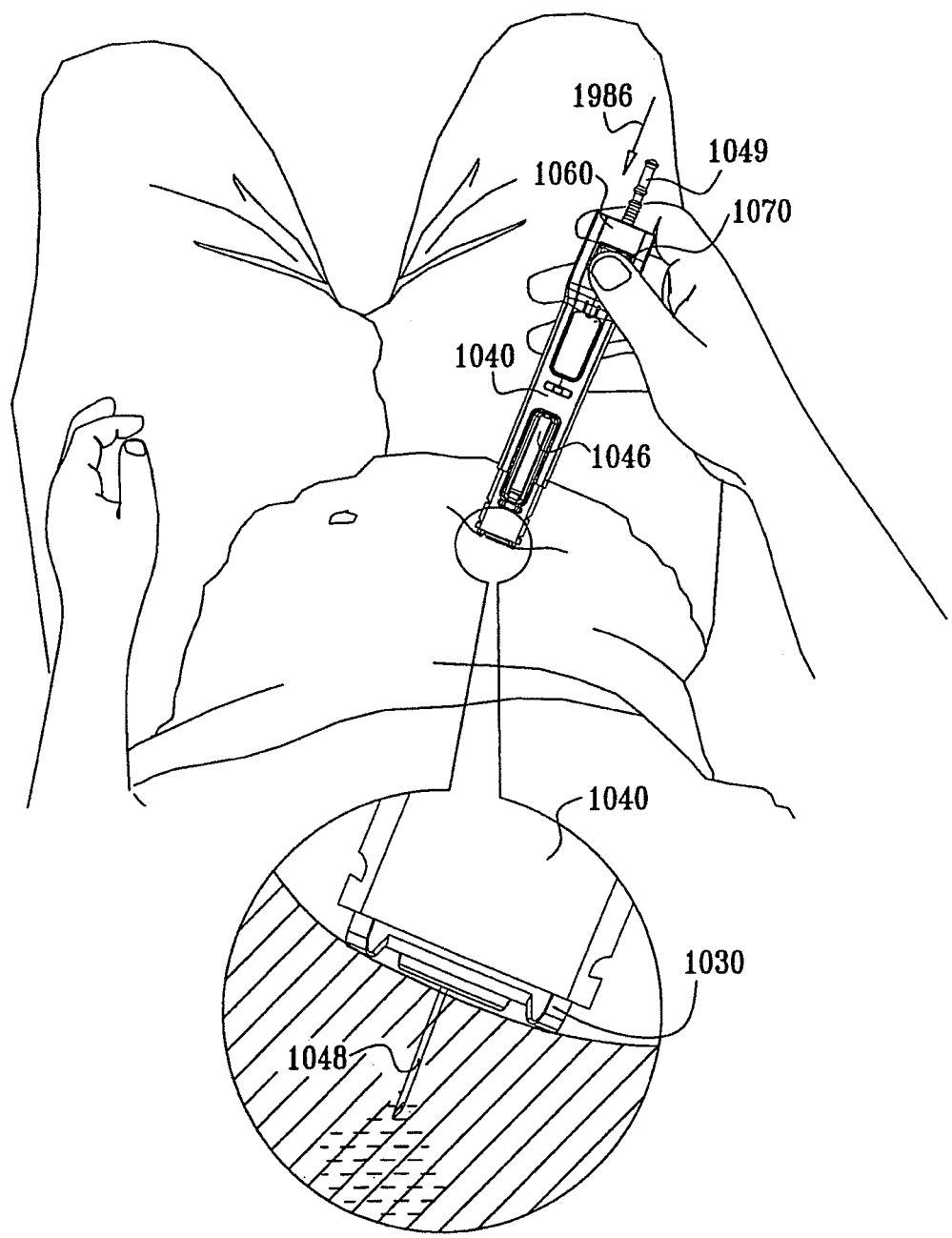
Figure 861:
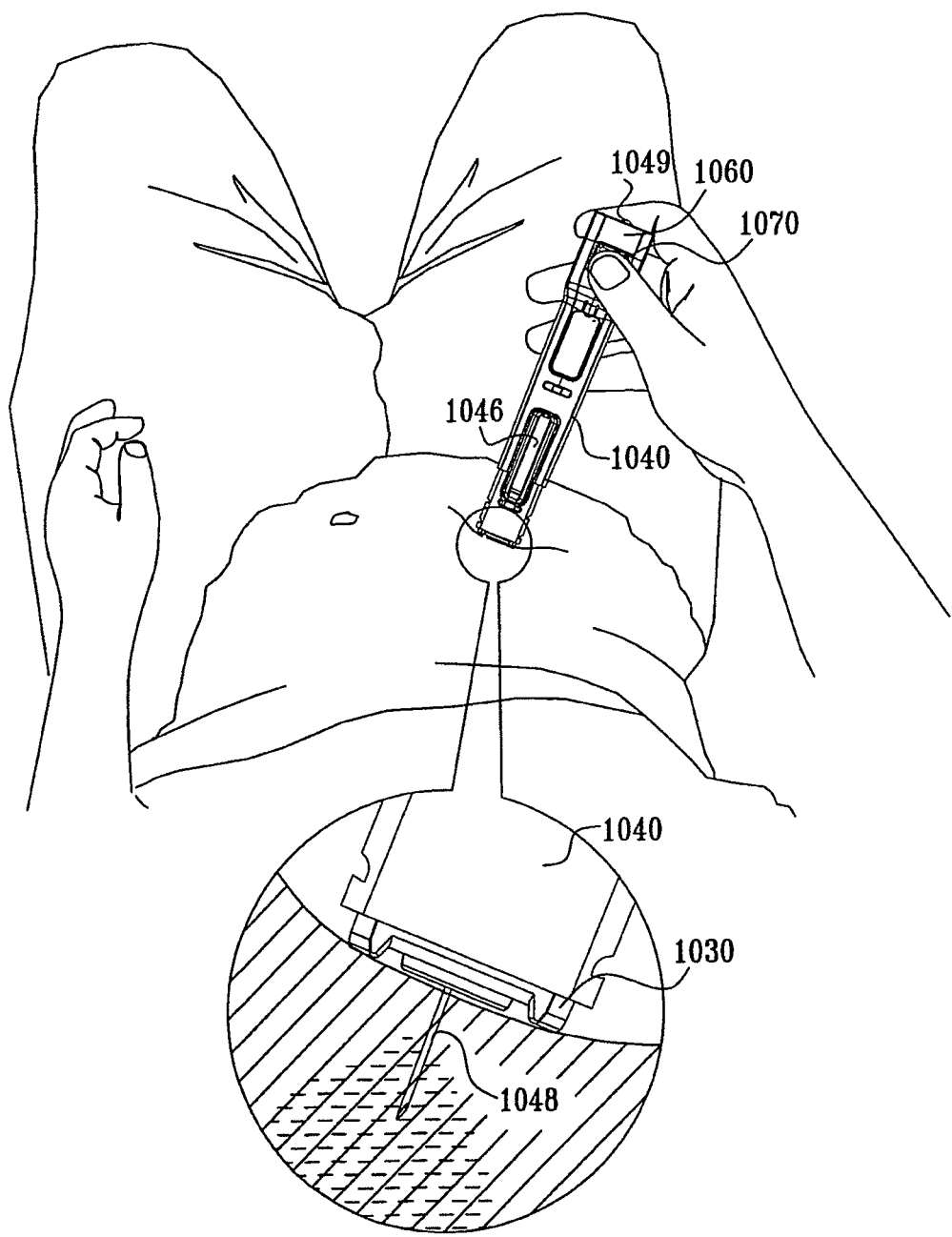

FIG. 86G illustrates that, during injection, responsive to user operation of the actuation button 1070, the syringe 1046 moves forwardly in a direction indicated by an arrow 1984 causing the needle 1048 of syringe 1046 to penetrate the user's body and subsequently inject liquid into the user's body, as shown in FIG. 86H. It is noted that as the injection of the liquid proceeds, the plunger 1049 moves forwardly relative to syringe 1046 and to the remainder of the injection device, as indicated by an arrow 1986 in FIG. 86H. FIG. 86I shows completion of the injection of the liquid, with the plunger 1049 being in a fully forward orientation relative to the remainder of the injection device.

Figure 86J:
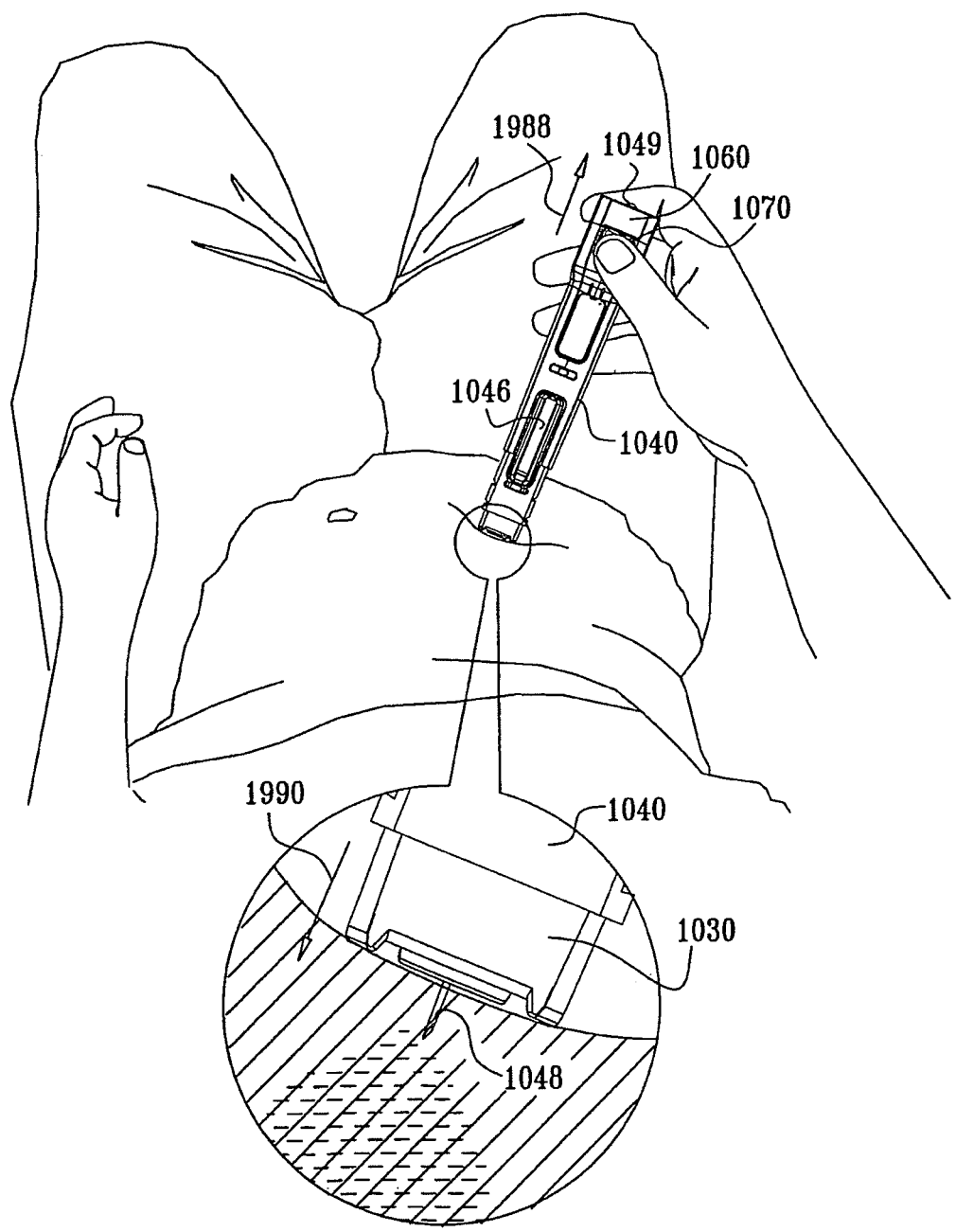
Figure 86K:
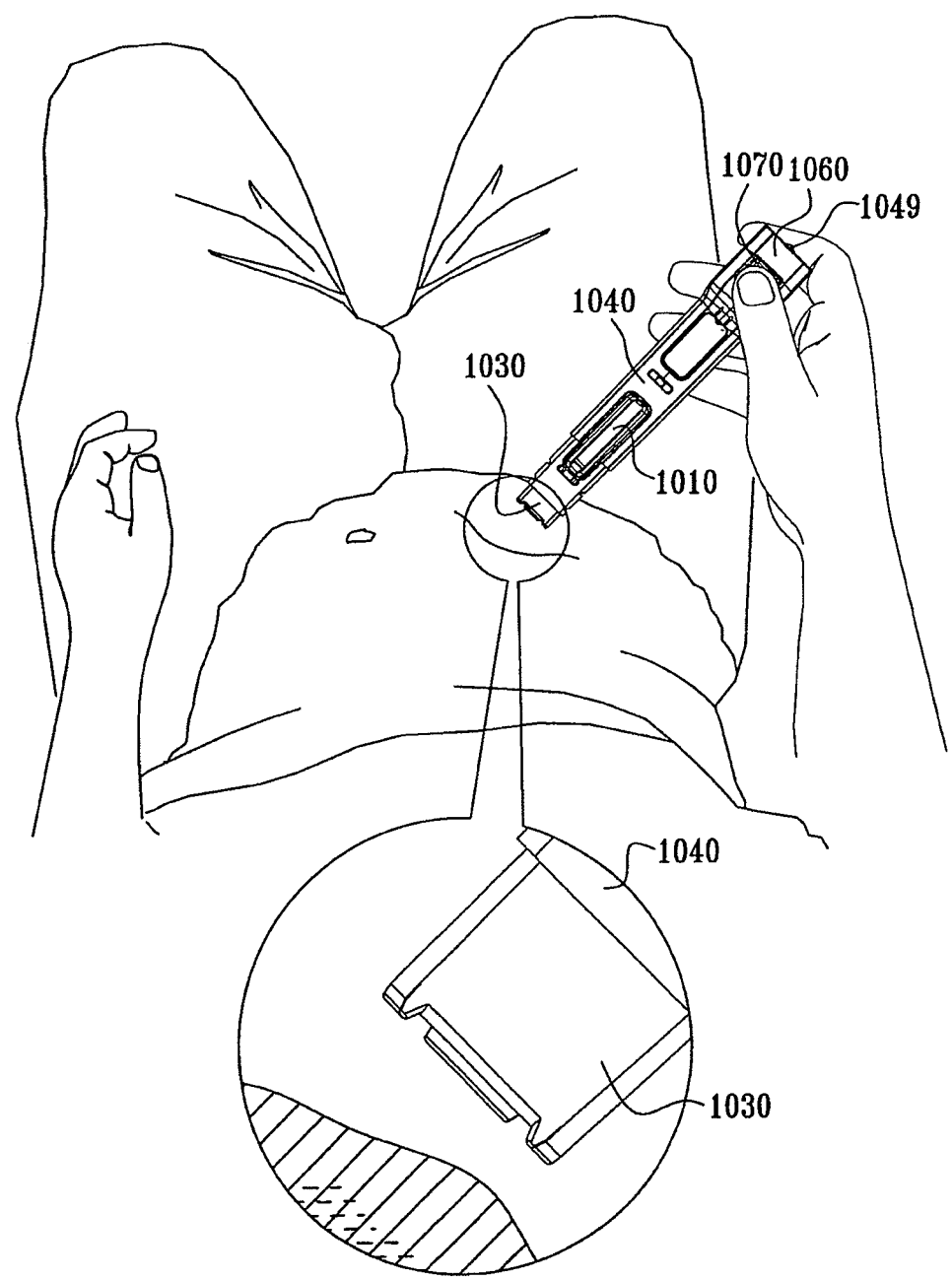

As seen in FIG. 86J, following completion of the injection of the liquid, the user retracts the injection device slightly from his body, as indicated by an arrow 1988, causing corresponding retraction of needle 1048 from his body and corresponding extension of needle guard element 1030 forwardly with respect to the forward housing 1040, as indicated by an arrow 1990. FIG. 86K shows the injection device fully disengaged from the user's body and the needle guard 1030 in a fully extended orientation relative to the forward housing 1040, fully covering the needle 1048 and generally preventing finger engagement with the needle 1048.

Figure 86L:
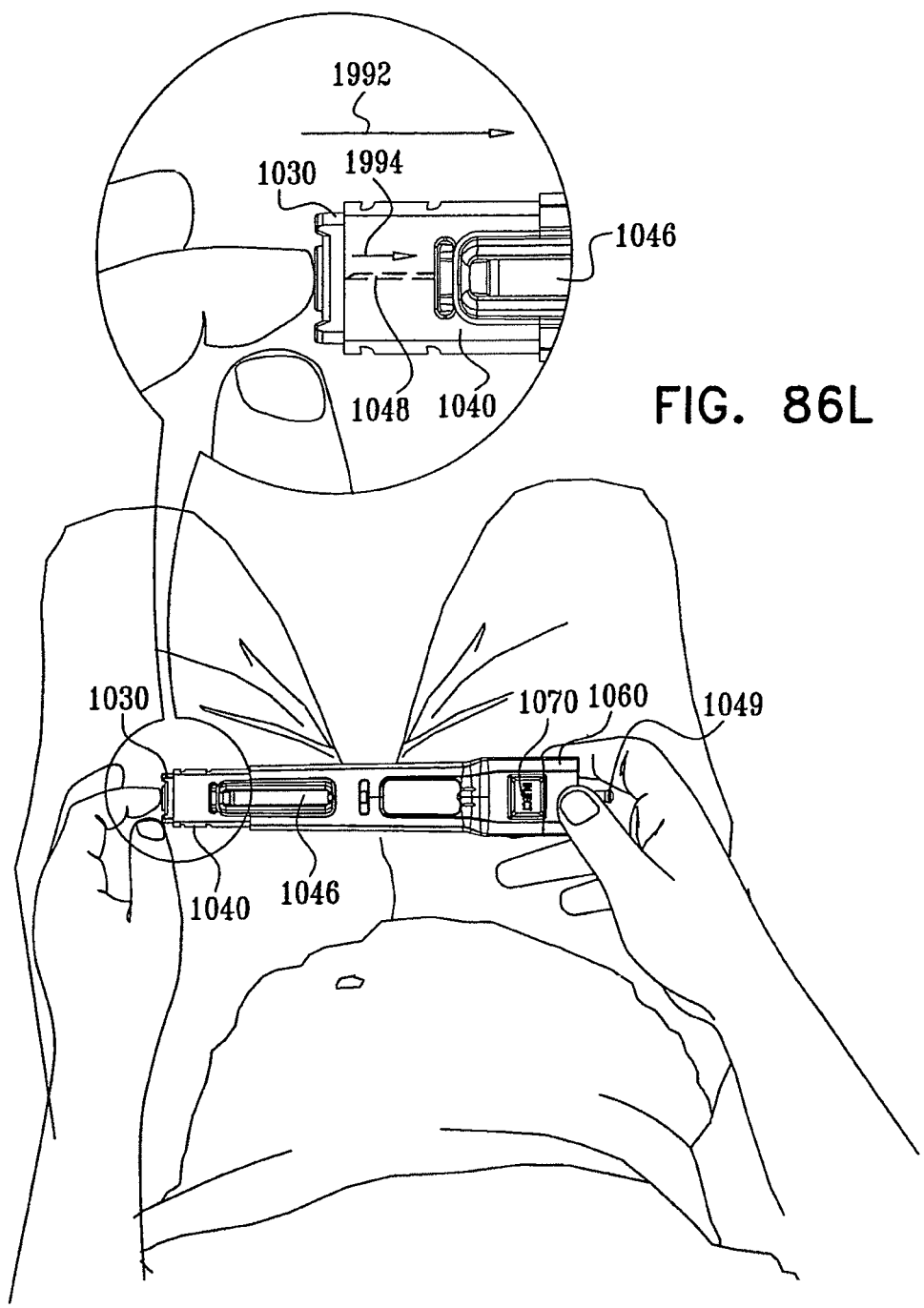

FIG. 86L shows that retraction of the needle guard element 1030 is such that even if a user pushes the needle guard element 1030 rearwardly as indicated by an arrow 1992, the needle guard element 1030 causes the needle 1048 to be retracted, in a direction indicated by an arrow 1994, to the same extent, such that engagement of a user's finger with the tip of needle 1048 is prevented.

Figure 87:
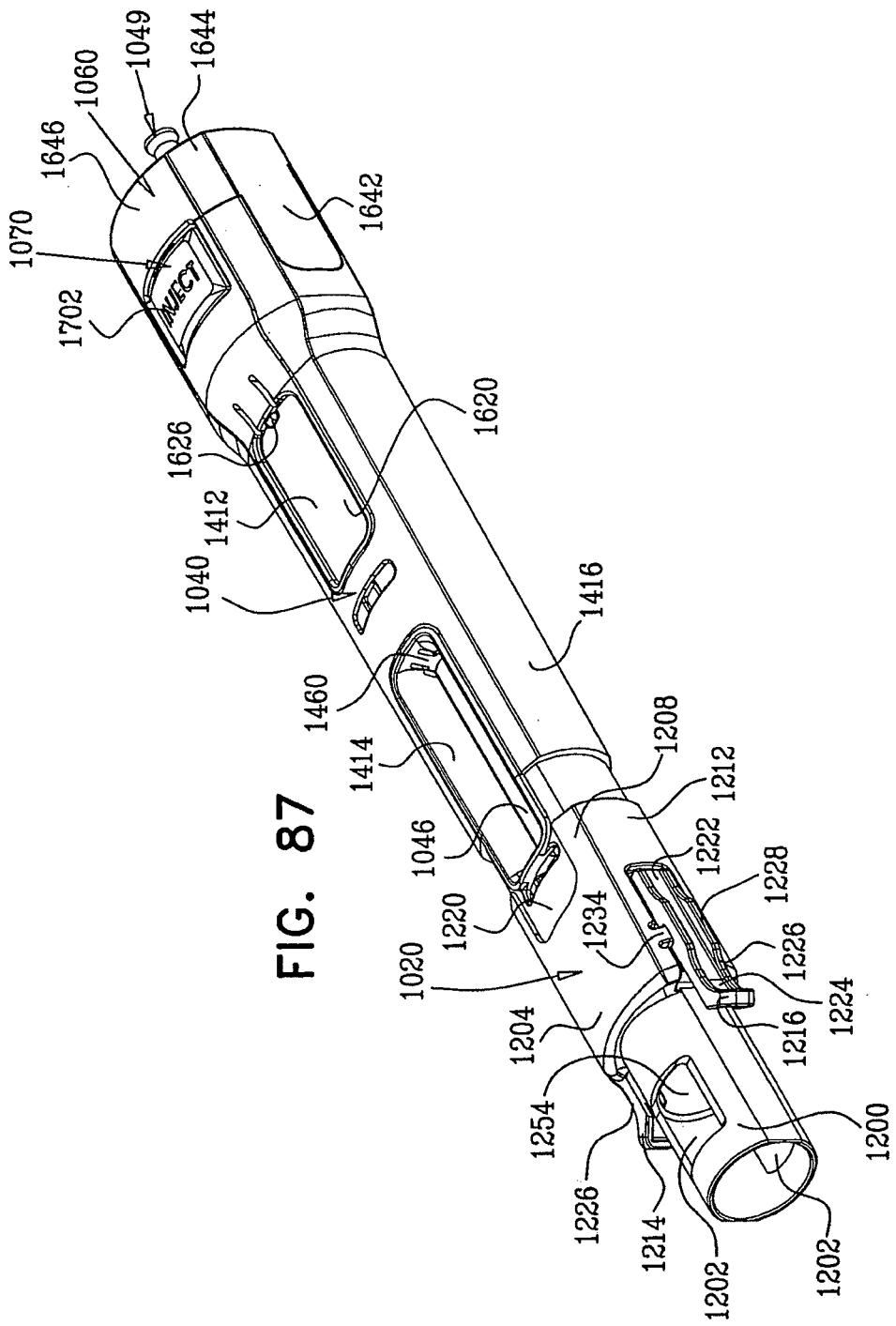
FIG. 87 is a simplified assembled view illustration of the automatic injection device of FIGS. 61 and 86A in a pre-use operative orientation.

Reference is now made to FIG. 87, which is a simplified assembled view illustration of the automatic injection device of FIGS. 61 and 86A in a pre-use operative orientation, to FIGS. 88A and 88B, which are respective side and top view simplified planar illustrations of the automatic injection device of FIG. 87, and to FIGS. 89A, 89B, 89C, 89D and 89E, which are sectional illustrations taken along respective section lines and directions LXXXIXA-LXXXIXA, LXXXIXB-LXXXIXB, LXXXIXC-LXXXIXC, LXXXIXD-LXXXIXD and LXXXIXE-LXXXIXE in FIGS. 88A and 88B.

As seen in FIGS. 86A and 87-89E, the vial adaptor 1020 is maintained in engagement with the forward housing 1040 by engagement of inwardly facing retaining protrusions 1230 with forward recesses 1401.

Figure 89E:
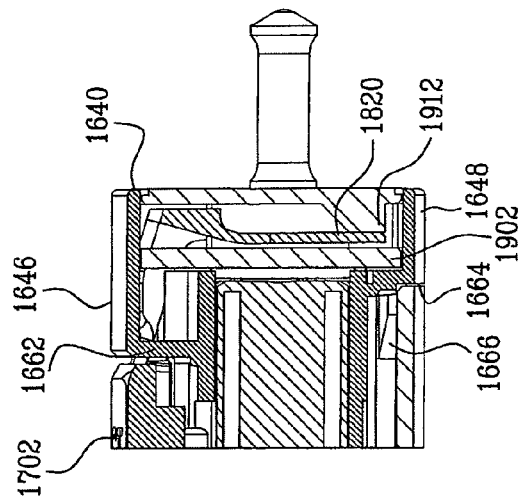
Figure 89D:
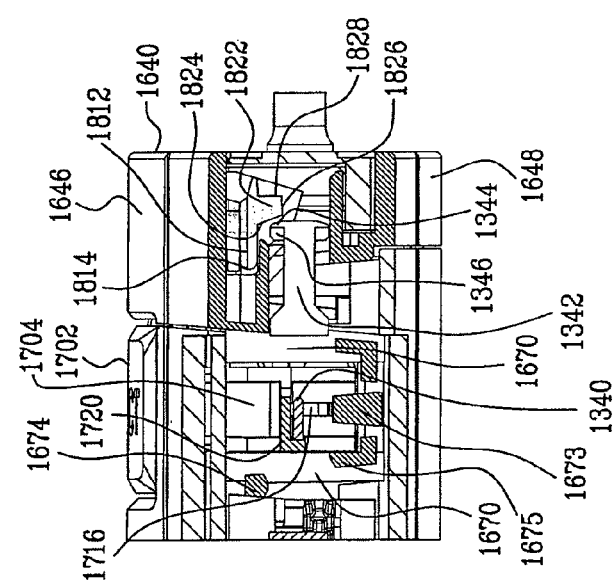
Figure 89C:
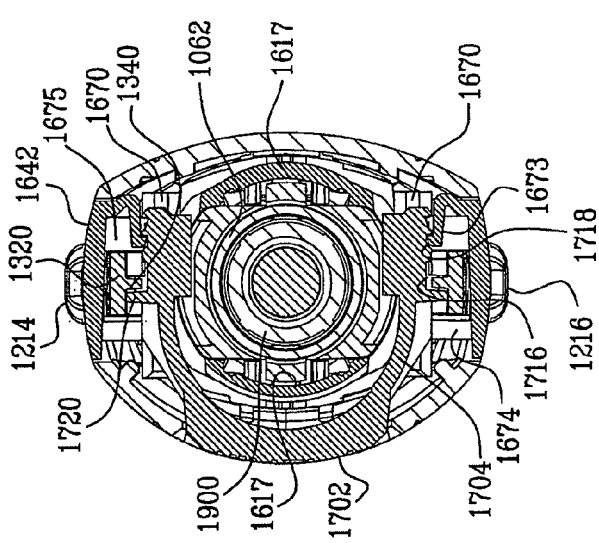

FIGS. 89A and 89C show that the protrusion 1720 of the actuation button 1070, is oriented with respect to the generally trapezoidal protrusions 1340 of the needle guard element 1030, so as to prevent depression of the actuation button 1070. Additionally, abutment of protrusion 1720 against generally trapezoidal protrusions 1340 prevents forward displacement of needle guard element 1030 relative to forward housing 1040 against the urging of spring 1032.

Furthermore, the flexible biasing fingers 1673 of the rear housing 1060 engage corresponding second outwardly facing recesses 1718 of the actuation button 1070, and maintain it in the storage orientation shown in FIG. 87.

FIG. 89D shows the T-shaped protrusions 1342 of the needle guard element 1030 spaced from the slanted forwardly facing surfaces 1824 of the downward facing protrusions 1822 of the plunger locking element 1090.

The enlarged portion of FIG. 89B shows the plunger engaging protrusion 1802 of the plunger locking element 1090 in a locking orientation with respect to plunger 1049. FIG. 89E shows the resilient leg 1820 of the plunger locking element 1090 engaging the forwardly facing protrusion 1912 of the rear end element 1080.

As seen in FIGS. 87-89E, in a pre-use operative orientation of the automatic injection device which is suitable for storage, the rear housing 1060 is joined to the forward housing 1040 by snap fit engagement of protrusions 1626 and 1628 of rear housing 1060 in the snap fit engagement sockets 1412 formed in the forward housing 1040.

As seen with particular clarity in the enlarged portion of FIG. 89A, the selectable driving assembly 1050 is retained in its axial position by engagement of rearward facing surface 1722 of the actuation button 1070 with protrusion 1540 of the selectable driving assembly 1050. In this arrangement, spring 1062 is in a relatively compressed state and is held in that state by the selectable driving assembly 1050.

The syringe 1046 is retained in a retracted orientation by engagement of flange 1047 thereof with inwardly facing protrusions 1508 and 1510 formed in respective first hinged fingers 1506 of each of symmetric actuation arms 1502 of selectable driving assembly 1050.

It is appreciated that when the automatic injection device is in its orientation shown in FIGS. 87-89E, needle 1048 does not pierce septum 1022.

Figure 90:
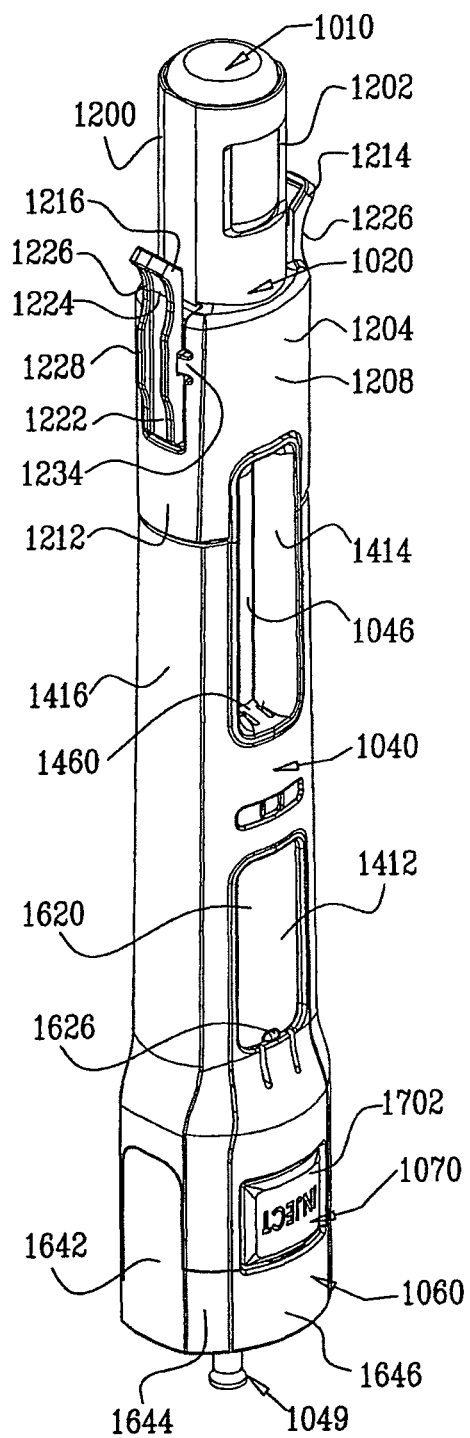
FIG. 90 is a simplified assembled view illustration of the automatic injection device of FIGS. 61 and 86B in a vial connection orientation.

Reference is now made to FIG. 90, which is a simplified assembled view illustration of the automatic injection device of FIGS. 61 and 86B in a vial connection orientation, to FIGS. 91A and 91B are respective side and top view simplified planar illustrations of the automatic injection device of FIG. 90, and to FIGS. 92A, 92B, 92C, 92D and 92E, which are sectional illustrations taken along respective section lines and directions XCIIA-XCIIA, XCIIB-XCIIB, XCIIC-XCIIC, XCIID-XCIID and XCIIE-XCIIE in FIGS. 91A and 91B.

As seen in FIG. 86B and FIGS. 90-92E, the vial 1010 is fully inserted in the vial adaptor 1020, causing the vial adaptor 1020 to be displaced fully rearwardly relative to the forward housing 1040. The vial adaptor 1020 is maintained in place by engagement of inwardly facing retaining protrusions 1230 with rearward recesses 1401. The interior of vial 1010 is in fluid flow communication with the interior of syringe 1046 via needle 1048 which extends through septum 1022.

As seen in FIG. 92A, the rearward displacement of vial adaptor 1020 results in engagement between positioning protrusions 1268 of the vial adaptor 1020 and the body engaging surface 1312 of the needle guard element, which causes the needle guard element 1030 to be rearwardly displaced relative to forward housing 1040.

Figure 92B:
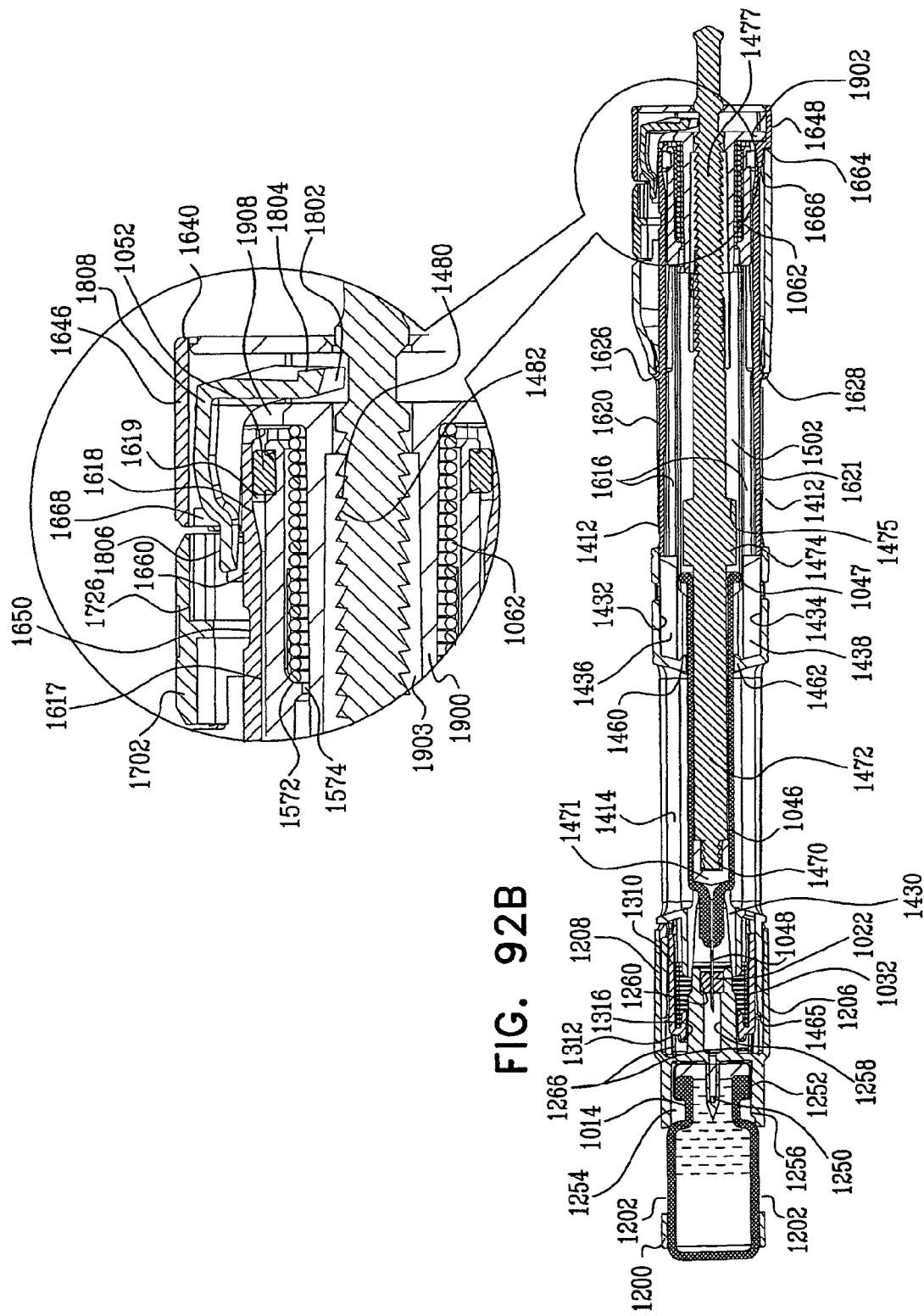

FIG. 92D shows that the rearward displacement of the needle guard element 1030, causes the T-shaped protrusions 1342 thereof to push the downward facing protrusions 1822 of the plunger locking element 1090 thereby causing rotation of the plunger locking element 1090 about axis 1810. The enlarged portion of FIG. 92B shows the rotation of the plunger engaging protrusion 1802 of the plunger locking element 1090 about axis 1810 such that it does not engage the plunger 1049. FIG. 92E shows a slight bend in the resilient leg 1820 of the plunger locking element 1090 resulting from rotation thereof about axis 1810.

As seen in FIG. 92A and FIGS. 92C-92D, the extent of rearward displacement of the needle guard element 1030 is selected such that the protrusion 1720 of the actuation button 1070 is still oriented with respect to the generally trapezoidal protrusions 1340 of the needle guard element 1030, so as to prevent depression of the actuation button 1070.

Figure 93:
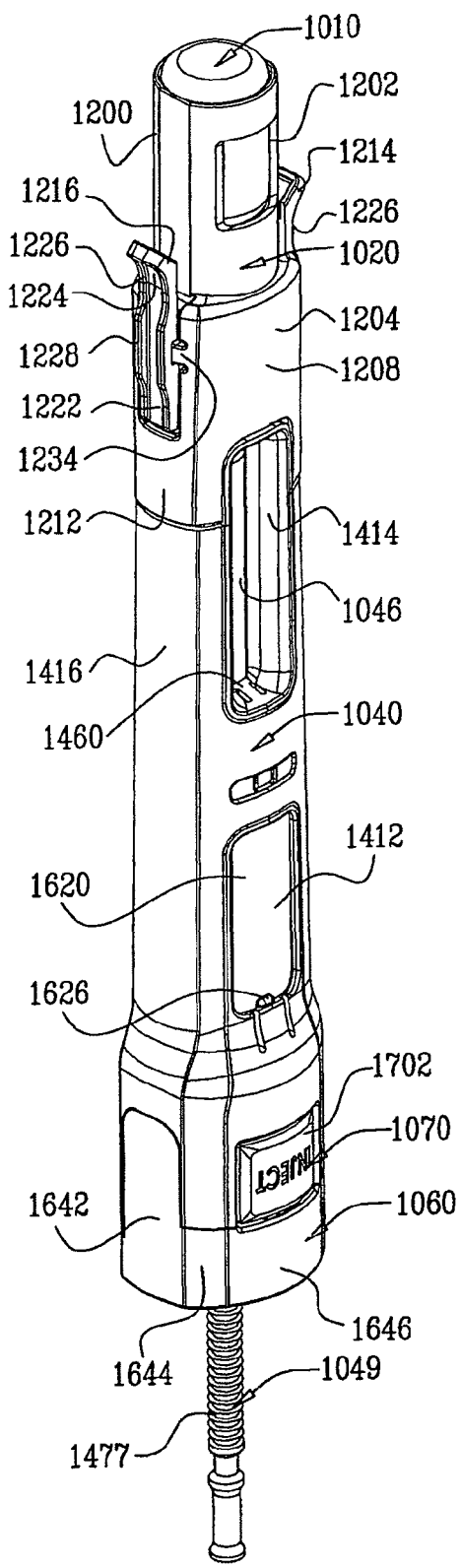
FIG. 93 is a simplified assembled view illustration of the automatic injection device of FIGS. 61 and 86C in a vial pumping orientation.

Reference is now made to FIG. 93, which is a simplified assembled view illustration of the automatic injection device of FIGS. 61 and 86C in a vial pumping orientation, to FIGS. 94A and 94B, which are respective side and top view simplified planar illustrations of the automatic injection device of FIG. 93, and to FIGS. 95A, 95B, 95C, 95D and 95E, which are sectional illustrations taken along respective section lines and directions XCVA-XCVA, XCVB-XCVB, XCVC-XCVC, XCVD-XCVD and XCVE-XCVE in FIGS. 94A and 94B.

As seen in FIGS. 86C and 93-95E, the plunger 1049 is rearwardly displaced, thereby drawing liquid from the interior of vial 1010 into the syringe 1046 via needle 1048. The enlarged portion of FIG. 95B clearly illustrates that the plunger engaging protrusion 1802 of the plunger locking element 1090 is located above one of the teeth 1478 of the toothed portion 1477 of the plunger 1049.

Figure 96:
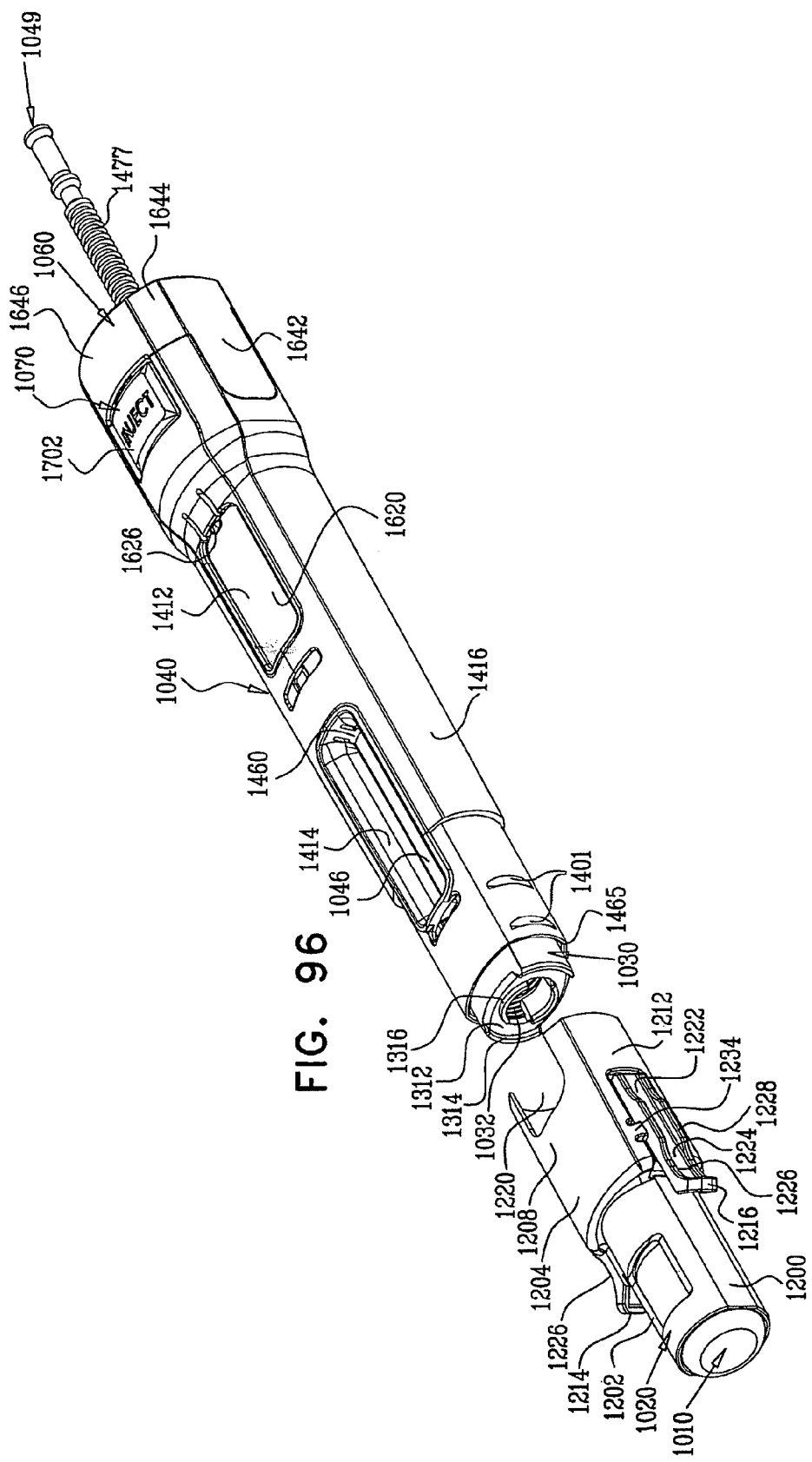
FIG. 96 is a simplified assembled view illustration of the automatic injection device of FIGS. 61 and 86D in a drug vial adaptor removal orientation.

Reference is now made to FIG. 96, which is a simplified assembled view illustration of the automatic injection device of FIGS. 61 and 86D in a drug vial adaptor removal orientation, to FIGS. 97A and 97B, which are respective side and top view simplified planar illustrations of the automatic injection device of FIG. 96, and to FIGS. 98A, 98B, 98C, 98D and 98E, which are sectional illustrations taken along respective section lines and directions XCVIIIA-XCVIIIA, XCVIIIB-XCVIIIB, XCVIIIC-XCVIIIC, XCVIIID-XCVIIID and XCVIIIE-XCVIIIE in FIGS. 97A and 97B.

As seen in FIGS. 86D and 96-98E, the vial adaptor 1020 is removed from the forward housing 1040 by a user pressing the finger engagement surfaces 1226 of vial adaptor 1020 which disengages inwardly facing retaining protrusions 1230 from rearward recesses 1401. The disengagement of the vial adaptor 1020 from the remainder of the injection device enables the needle guard element 1030 be forwardly displaced under the urging of spring 1032, and the T-shaped protrusions 1342 stop pushing the downward facing protrusions 1822 of the plunger locking element 1090. The plunger locking element 1090 rotates about axis 1810 back to its orientation shown in FIGS. 87-89E under the urging of the resilient leg 1820.

Figure 98B:
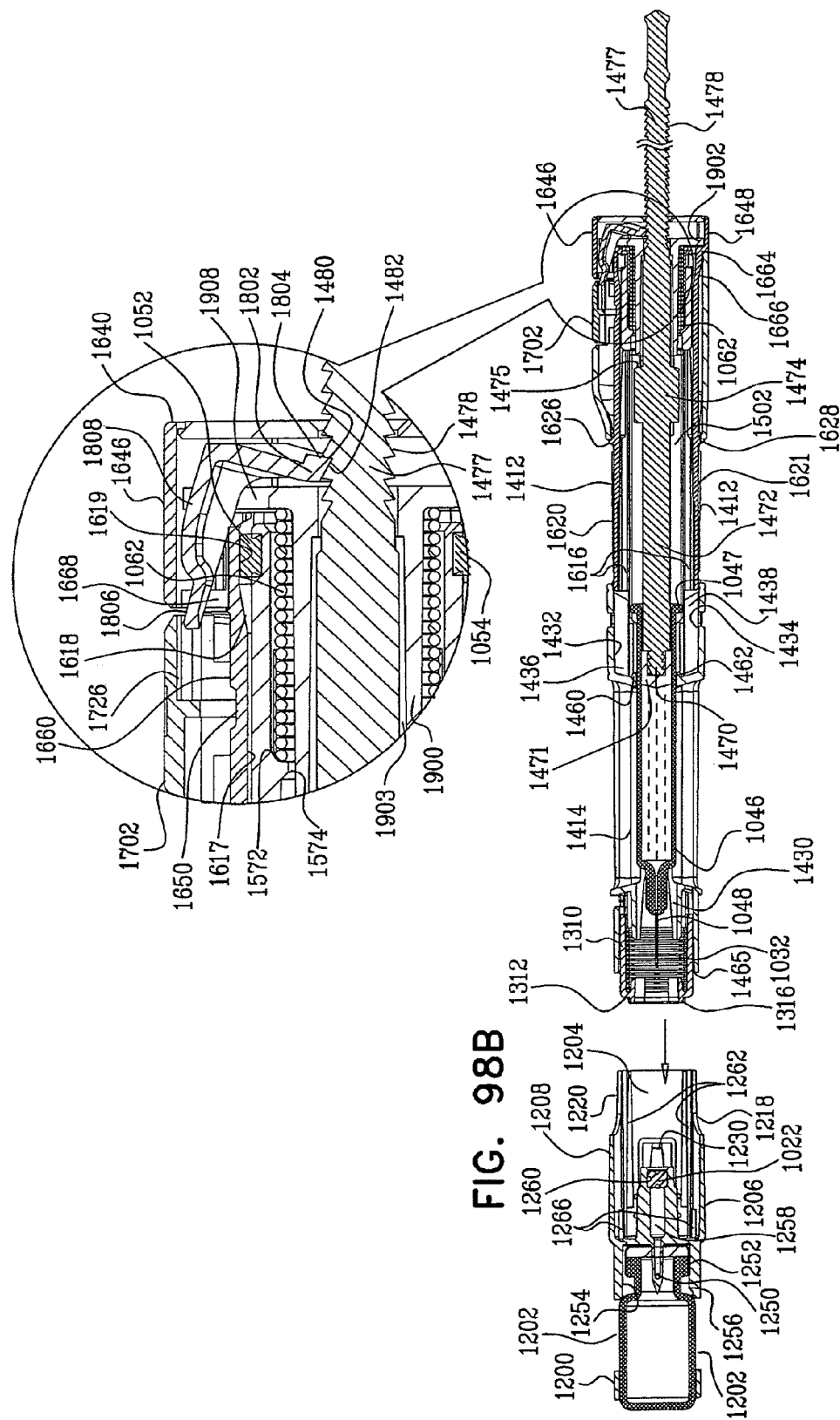

As seen in FIG. 98B, the plunger locking element 1090, once returned to its orientation shown in FIGS. 87-89E, locks plunger 1049 by engagement of plunger engaging protrusion 1802 with teeth 1478 of toothed portion 1477 of the plunger 1049, thereby preventing forward displacement of the plunger 1049 by a user. FIG. 98E shows that the resilient leg 1820 of the plunger locking element 1090 returns to its orientation shown in FIGS. 96-98E in which it is not bent and is located adjacent the forwardly facing protrusion 1912 of the rear end element 1080.

Figure 99:
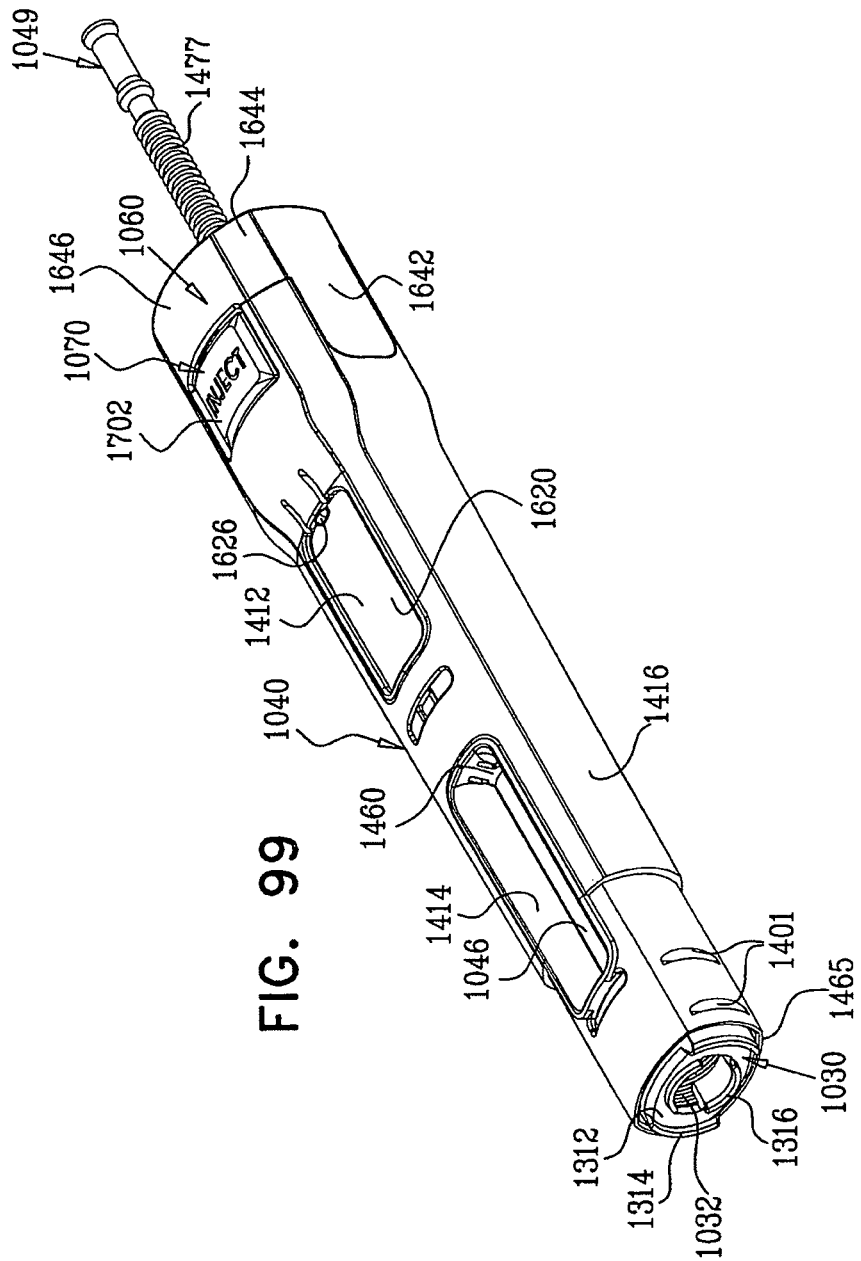
FIG. 99 is a simplified assembled view illustration of the automatic injection device of FIGS. 61 and 86E in an actuated operative orientation.

Reference is now made to FIG. 99, which is a simplified assembled view illustration of the automatic injection device of FIGS. 61 and 86E in an actuated operative orientation, to FIGS. 100A and 100B, which are respective side and top view simplified planar illustrations of the automatic injection device of FIG. 99, and to FIGS. 101A, 101B, 101C, 101D and 101E, which are sectional illustrations taken along respective section lines and directions CIA-CIA, CIB-CIB, CIC-CIC, CID-CID and CIE-CIE in FIGS. 100A and 100B.

As seen in FIGS. 86E and 99-101E, the user pushes the automatic injection device against his body, thereby rearwardly displacing the needle guard element 1030 relative to the forward housing 1040. As seen with particular clarity in FIGS. 101A-101D, the rearward displacement of the needle guard element 1030 results in rearward displacement of the generally trapezoidal protrusions 1340 thereof, which no longer are oriented with respect to the L-shaped transverse outwardly facing protrusions 1720 of the arms of the actuation button 1070 so as to prevent actuation. Thus, the actuation button 1070 is free to be pressed by a user. Until the actuation button 1070 is actually pressed by the user, the flexible biasing fingers 1673 of the rear housing 1060 still engage corresponding second outwardly facing recesses 1718 of the legs 1704 of the actuation button 1070, maintaining it in the "ready to inject" stage.

Figure 95A:
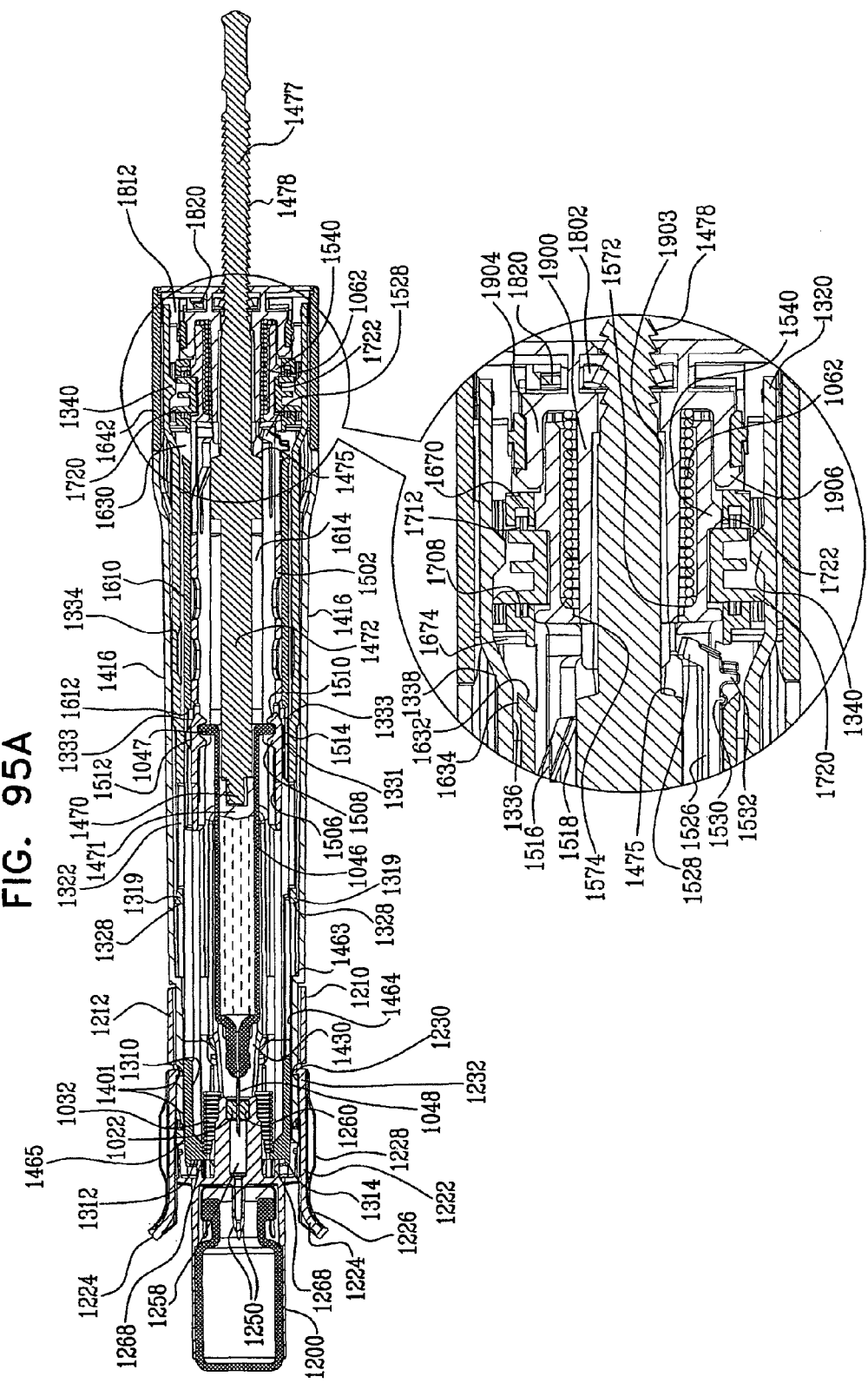
FIGS. 95A, 95B, 95C, 95D and 95E are sectional illustrations taken along respective section lines and directions XCVA-XCVA, XCVB-XCVB, XCVC-XCVC, XCVD-XCVD and XCVE-XCVE in FIGS. 94A and 94B.
Figure 95B:
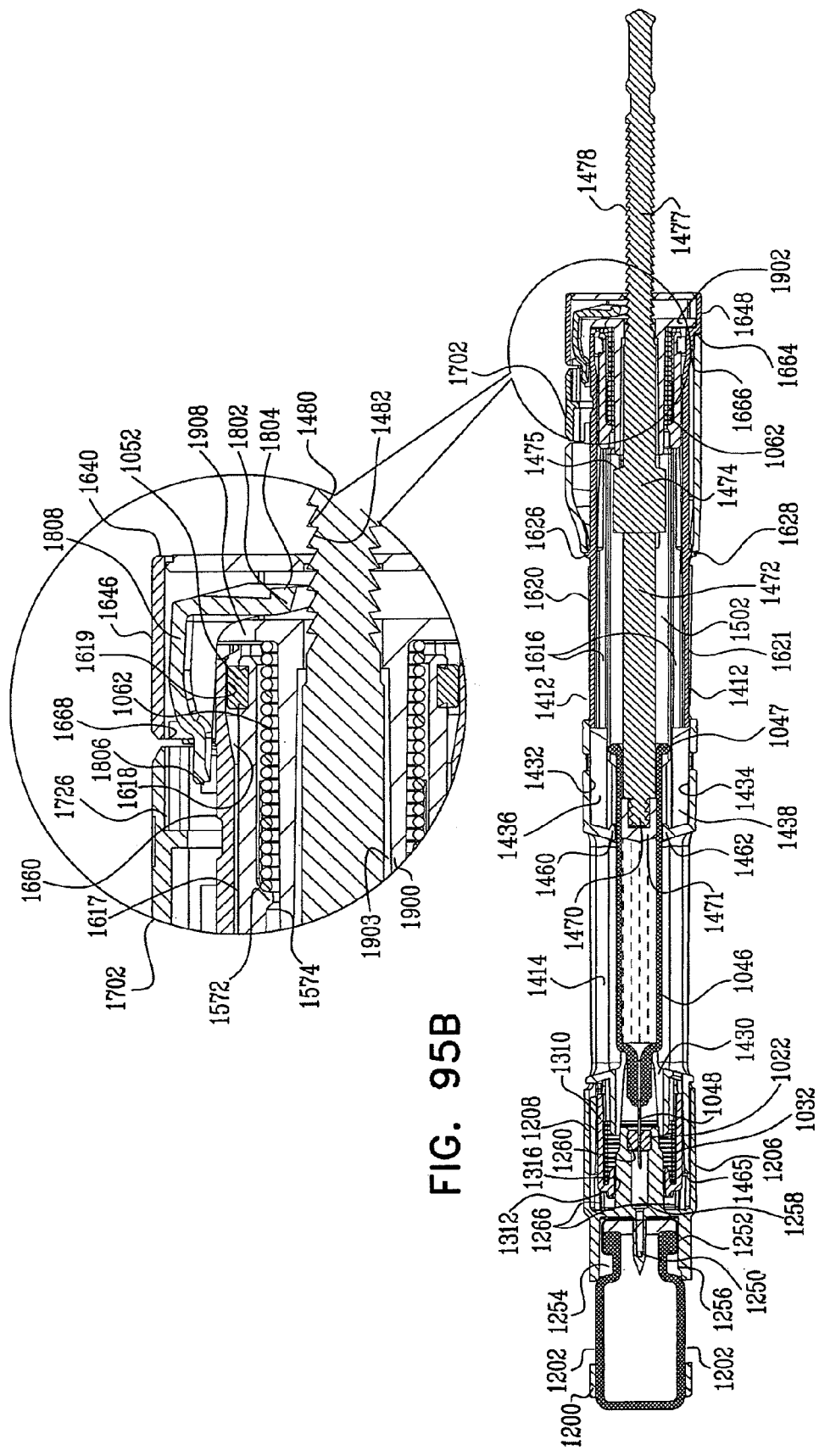
Figure 95E:
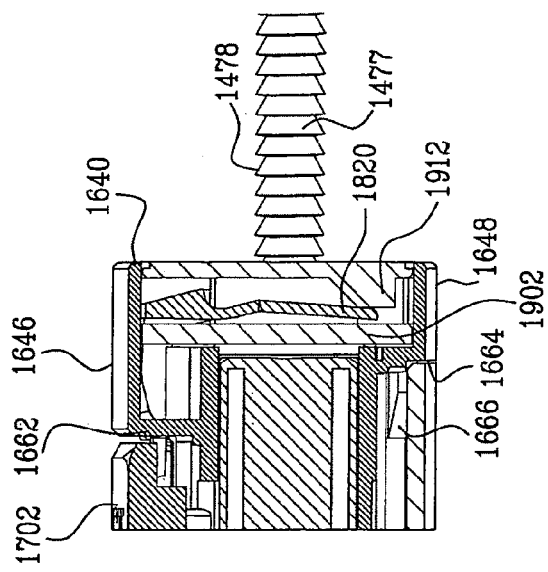
Figure 95D:
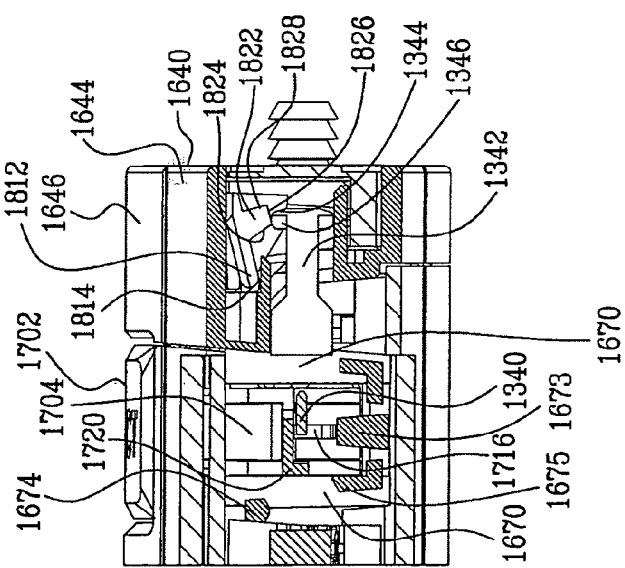
Figure 95C:
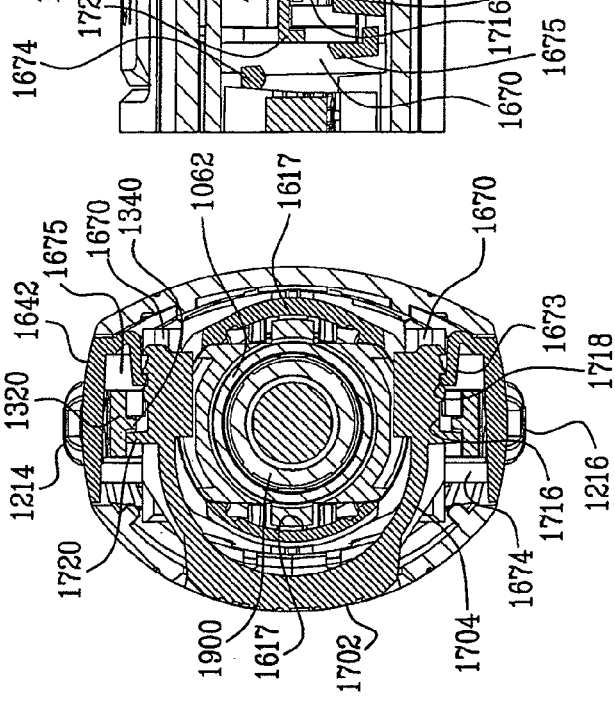
Figures 101C, 101D, 101E:
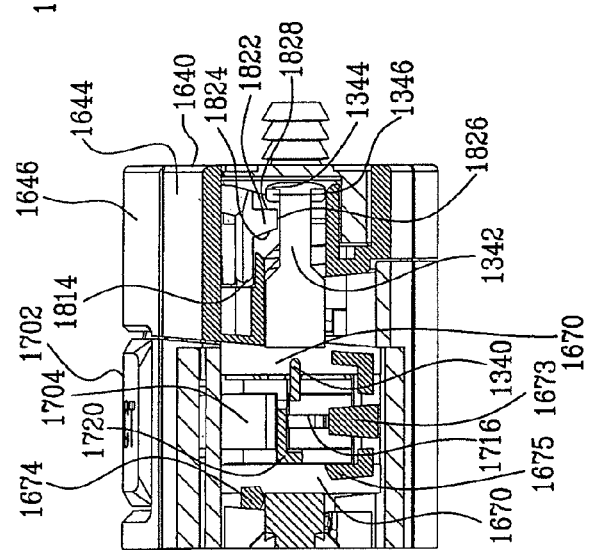

As seen particularly in the enlarged portion of FIG. 101A, the rearward displacement of needle guard element 1030 with respect to the remainder of the automatic injection device, resulting from engagement of the needle guard element 1030 with an injection site on a body, compresses spring 1032. The rearward displacement of the needle guard element 1030 is limited by engagement of the forward facing edge of forward portion 1612 of rear housing 1060 with shoulders 1333 of arms 1319 of the needle guard element 1030. As seen in FIG. 101D, the rearward displacement of the needle guard element 1030 causes the T-shaped protrusions 1342 thereof to be further rearwardly displaced, such that they now are placed rearwardly of planar rearwardly facing surface 1828 of downward facing protrusions 1822 of the plunger locking element 1090. It is noted that during this rearward displacement from the orientation of FIG. 98D to the orientation of FIG. 101D, the plunger locking element 1090 is temporarily rotated out of locking engagement with the plunger 1049, as illustrated in FIG. 95D and described hereinabove in the context of vial pumping. This transitional disengagement is normally imperceptible to the user. In the orientation of the needle guard element 1030 shown in FIGS. 99-101E, pressing of button 1070 actuates the automatic injection device.

Figure 102:
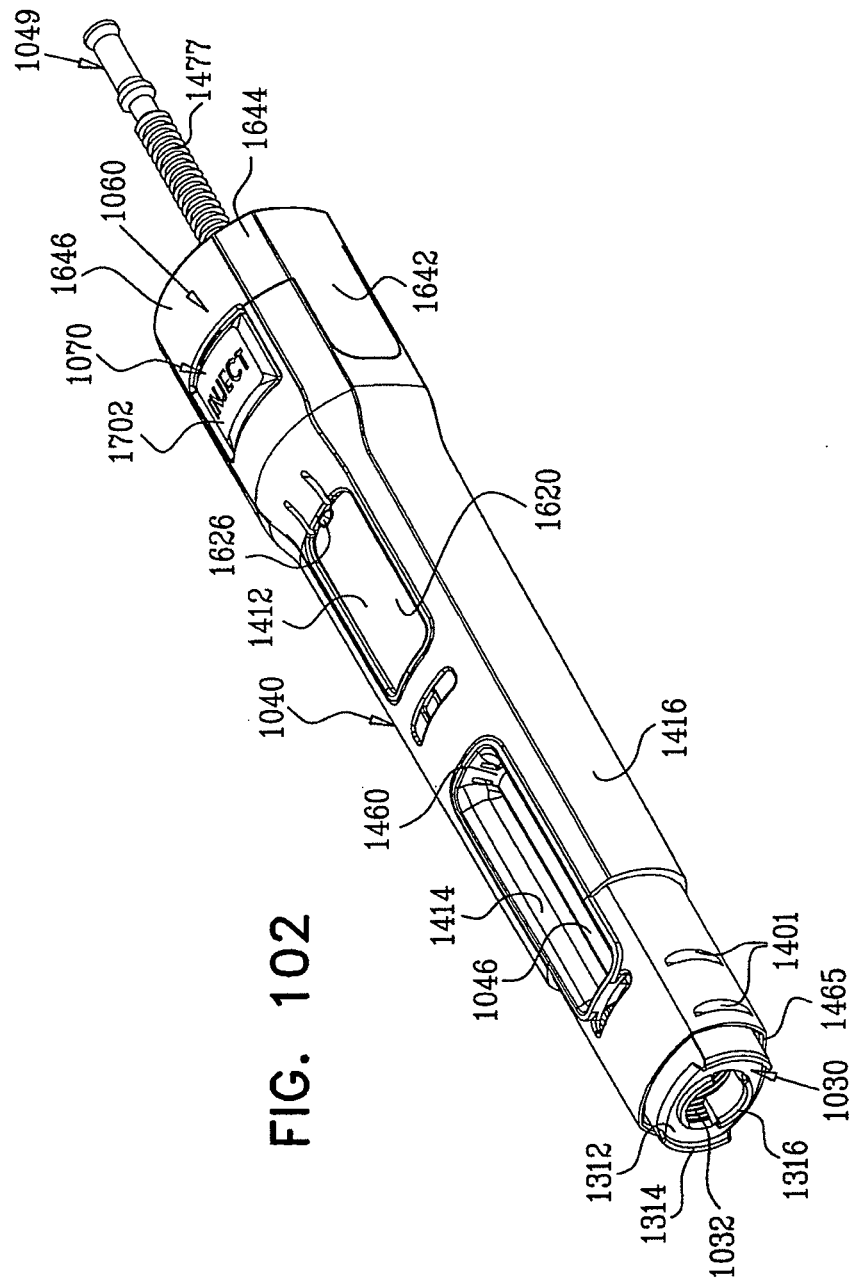
FIG. 102 is a simplified assembled view illustration of the automatic injection device of FIGS. 61 and 86F in an unactuated operative orientation.
Figure 103A:
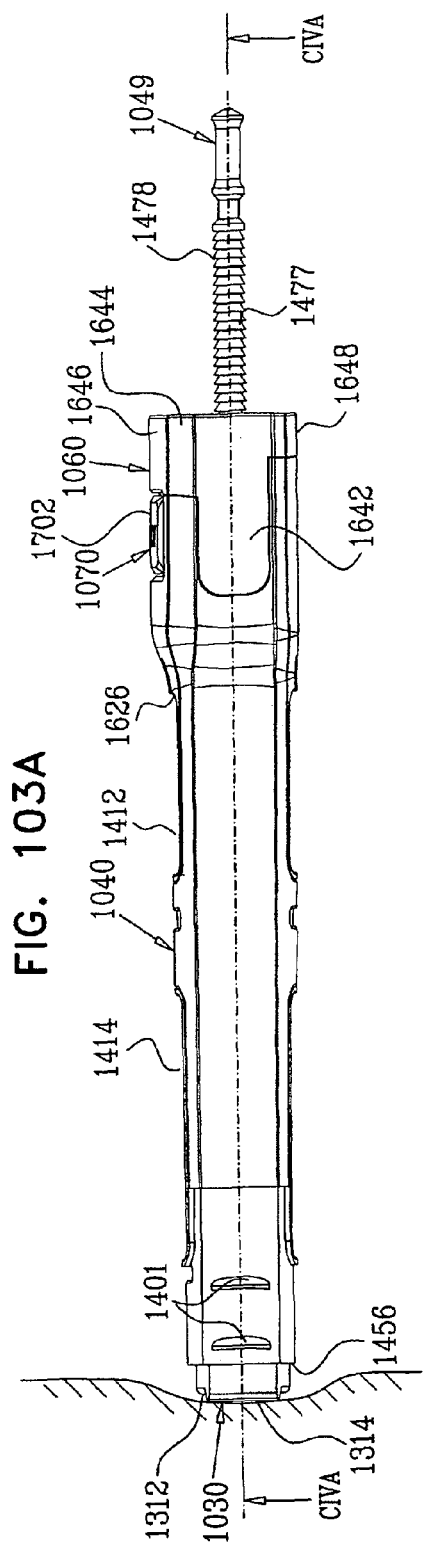
FIGS. 103A and 103B are respective side and top view simplified planar illustrations of the automatic injection device of FIG. 102.
Figure 103B:
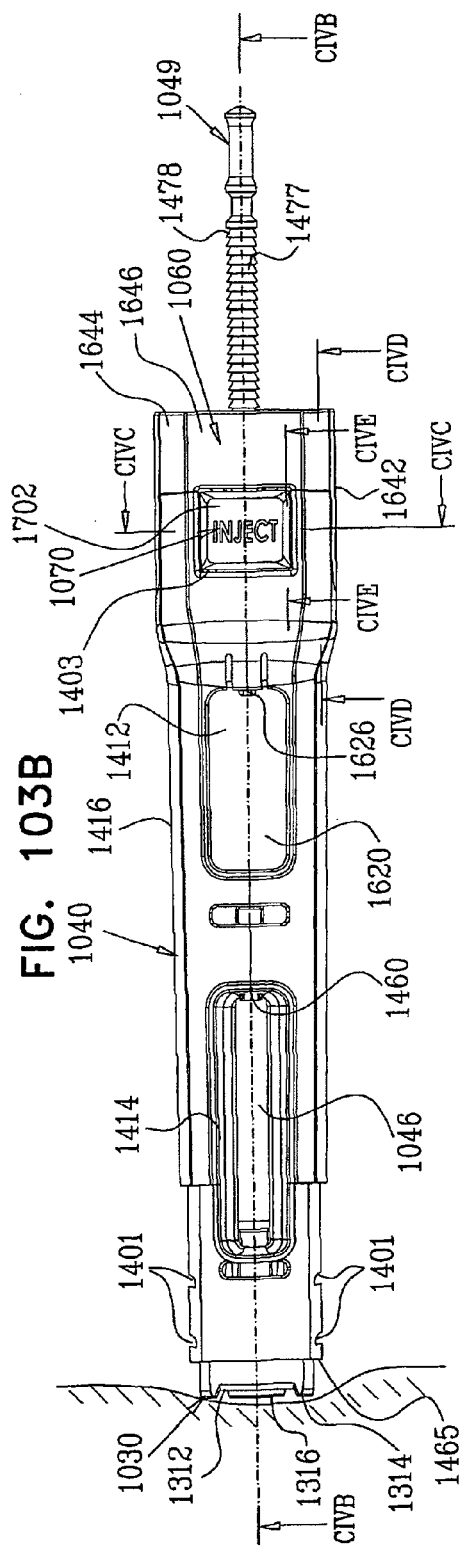

Reference is now made to FIG. 102, which is a simplified assembled view illustration of the automatic injection device of FIG. 61 in the orientation described hereinabove with reference to FIG. 86F, where prior to pressing the actuation button 1070, the user removes the automatic injection device from pressed engagement with his body, as indicated by arrow 1980 (FIG. 86F), to FIGS. 103A and 103B, which are respective side and top view simplified planar illustrations of the automatic injection device of FIG. 102, and to FIGS. 104A, 104B, 104C, 104D and 104E, which are sectional illustrations taken along respective section lines and directions CIVA-CIVA, CIVB-CIVB, CIVC-CIVC, CIVD-CIVD and CIVE-CIVE in FIGS. 103A and 103B.

As seen in FIGS. 86F and 102-104E, as the user displaces the automatic injection device away from his body, spring 1032 forwardly displaces the needle guard element 1030 relative to the forward housing 1040. As seen with particular clarity in FIGS. 104A and 104D, the forward displacement of the needle guard element 1030 results in forward displacement of the generally trapezoidal protrusions 1340 thereof, which are now closer to the L-shaped transverse outwardly facing protrusions 1720 of the legs 1704 of the actuation button 1070 than in the orientation shown in FIG. 86E.

If the user fully removes the automatic injection device from engagement with his body, the generally trapezoidal protrusions 1340 of the needle guard element are oriented with respect to the L-shaped transverse outwardly facing protrusions 1720 of the actuation button 1070 so as to prevent actuation. Thus, the actuation button 1070 is no longer free to be pressed by a user. This orientation is the same as shown and described hereinabove with reference to FIG. 86D.

Figure 104A:
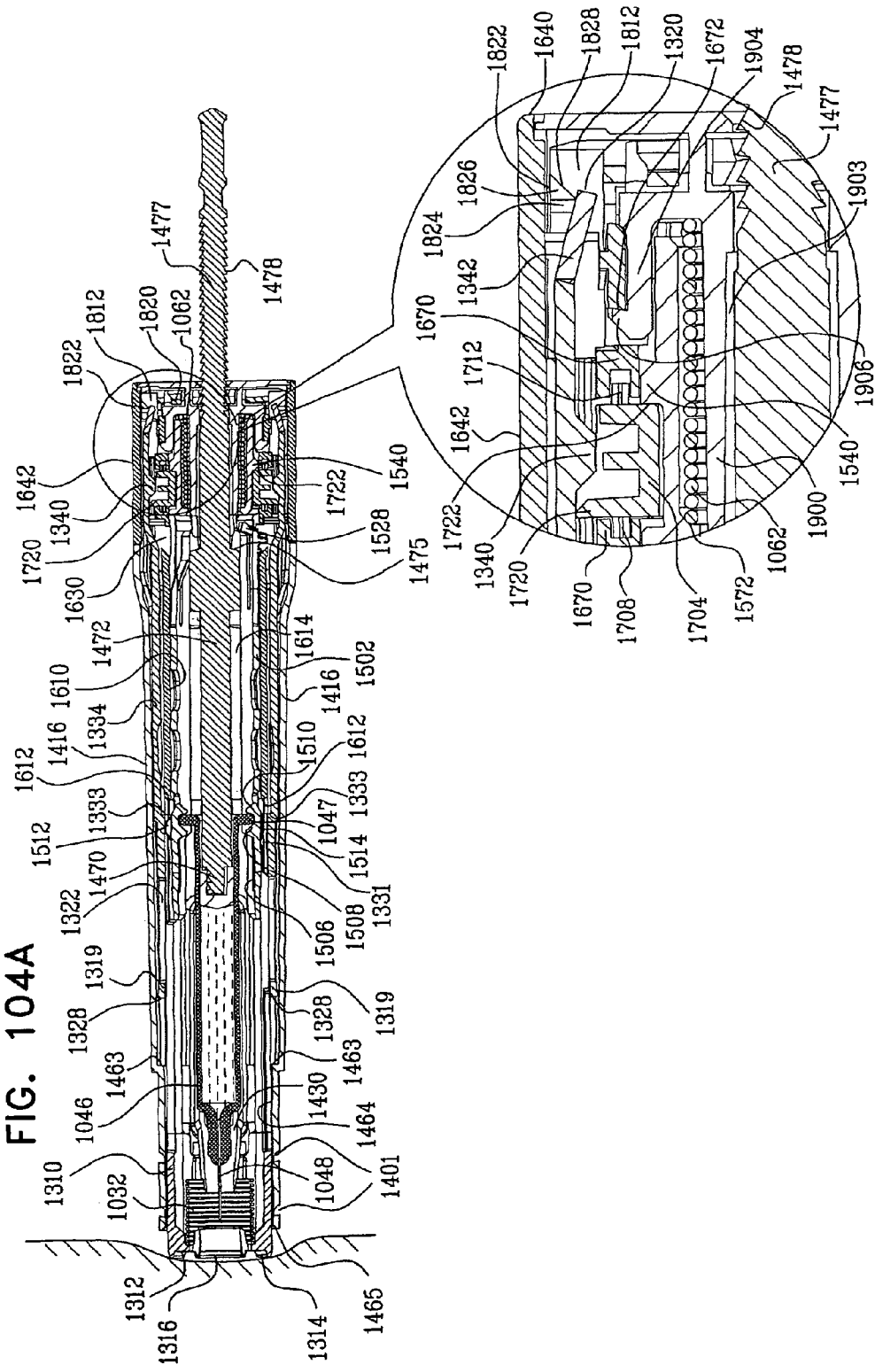
Figure 104B:
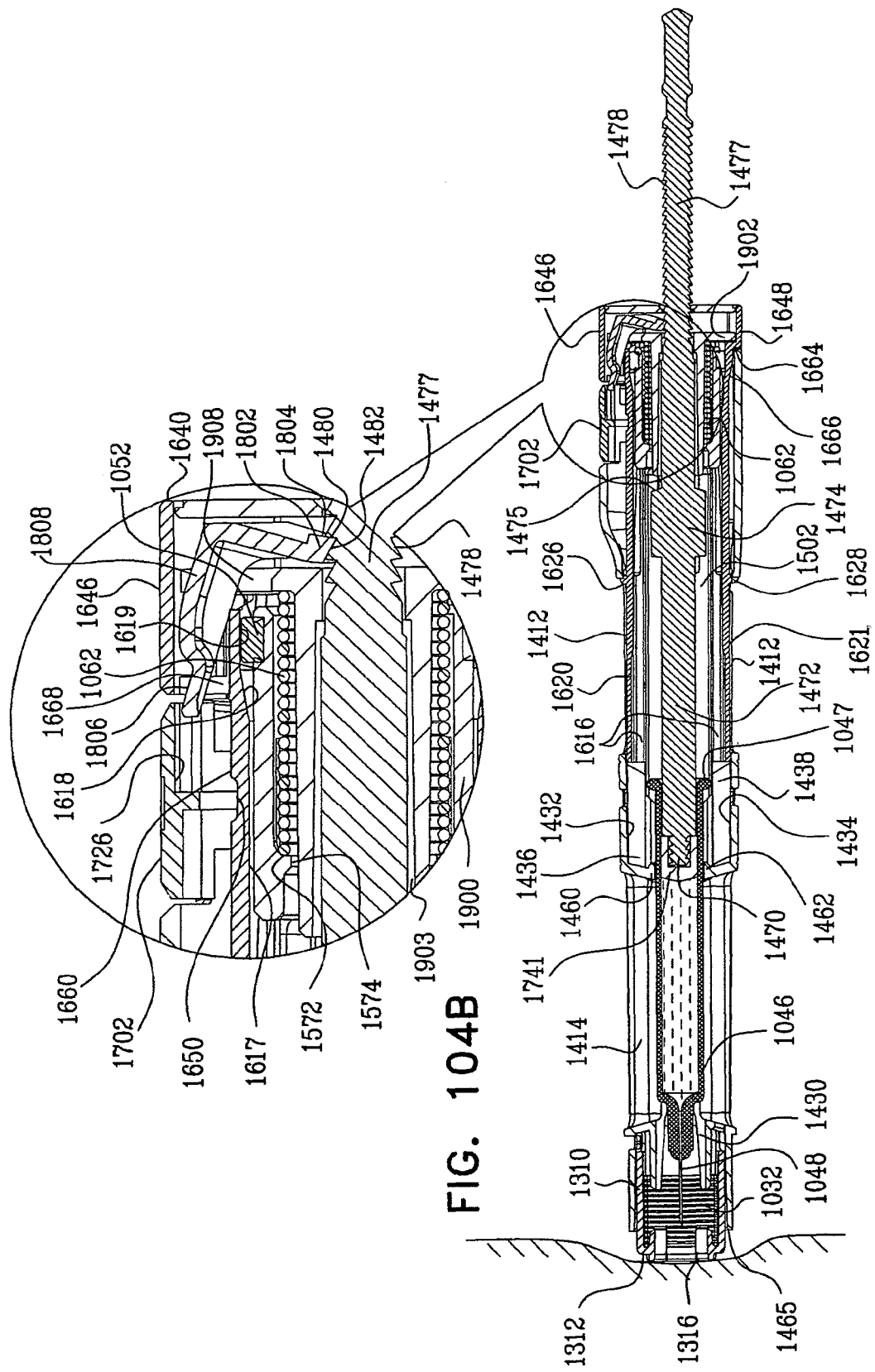

Considering the transition from the orientation of FIG. 86E back to the orientation of FIG. 86D via the orientation of FIG. 86F, it is seen particularly in the enlarged portion of FIG. 104A that during disengagement of the needle guard element 1030 with the body, the resulting forward displacement of needle guard element 1030 with respect to the remainder of the automatic injection device decompresses spring 1032. As seen in FIG. 104D, the forward displacement of the needle guard element 1030 causes the outwardly inclined surface 1346 of the T-shaped protrusions 1342 of the needle guard element 1030 to slide inwardly and forwardly alongside slanted backwardly facing surfaces 1828 of the downward facing protrusions 1822, such that the forward facing protrusions 1344 now are placed alongside of downward facing protrusions 1822 of the plunger locking element 1090, thus maintaining the plunger 1049 in a locked state.

It is a particular feature of this embodiment of the present invention that throughout the transition from the orientation of FIG. 86E back to the orientation of FIG. 86D via the orientation of FIG. 86F, pressing of button 1070 is prevented and thus ejection of fluid from syringe 1046 is prevented when the forward end of needle 1048 is not in the body.

Figure 105:
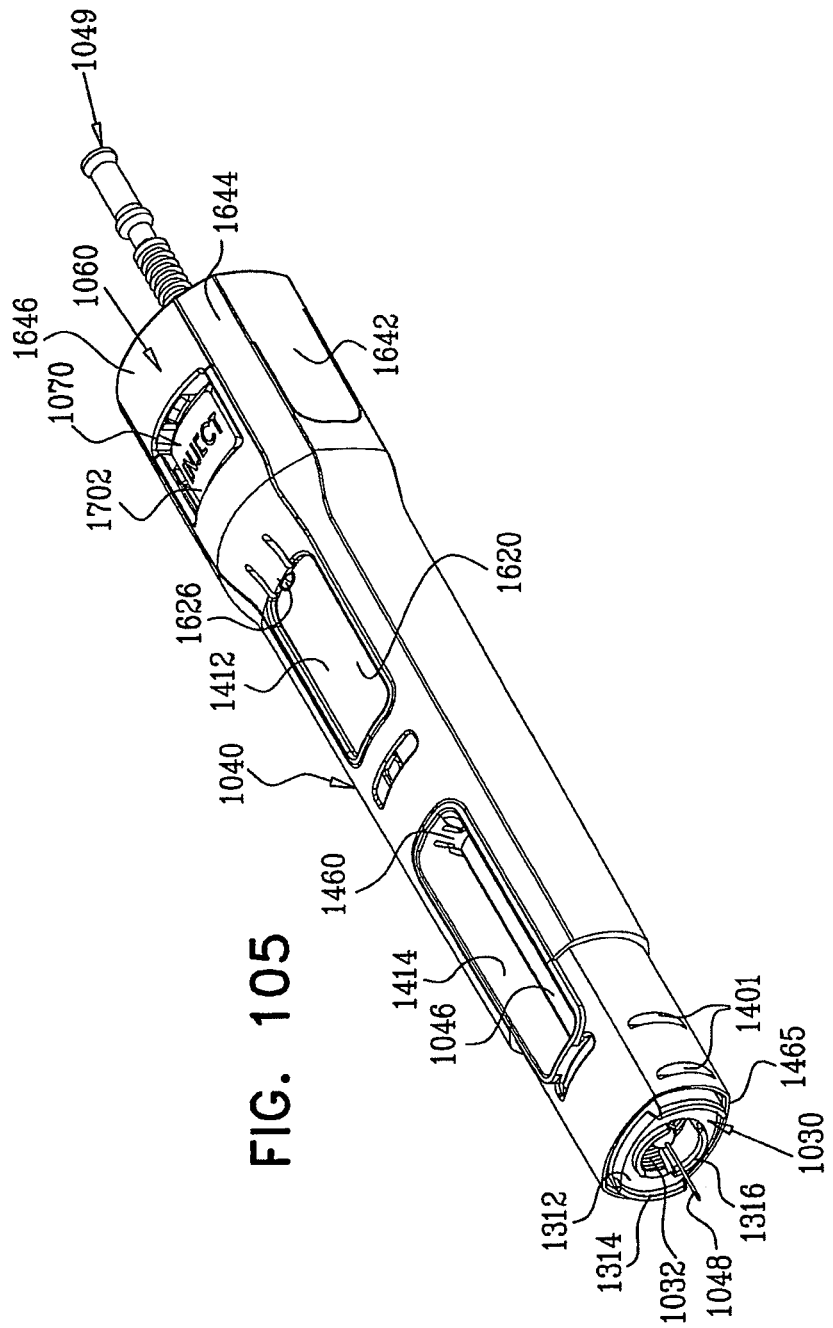
FIG. 105 is a simplified assembled view illustration of the automatic injection device of FIGS. 61 and 86G in a needle penetration, pre-drug delivery operative orientation.

Reference is now made to FIG. 105, which is a simplified assembled view illustration of the automatic injection device of FIGS. 61 and 86G in a needle penetration, pre-drug delivery operative orientation, to FIGS. 106A and 106B, which are respective side and top view simplified planar illustrations of the automatic injection device of FIG. 105, and to FIGS. 107A, 107B, 107C, 107D and 107E, which are sectional illustrations taken along respective section lines and directions CVIIA-CVIIA, CVIIB-CVIIB, CVIIC-CVIIC, CVIID-CVIID and CVIIE-CVIIE in FIGS. 106A and 106B.

As seen in FIGS. 86G and 105-107E, the user actuates the automatic injection device by once again pressing it against an injection site on his body, and inwardly displacing the actuation button 1070.

Figure 107B:
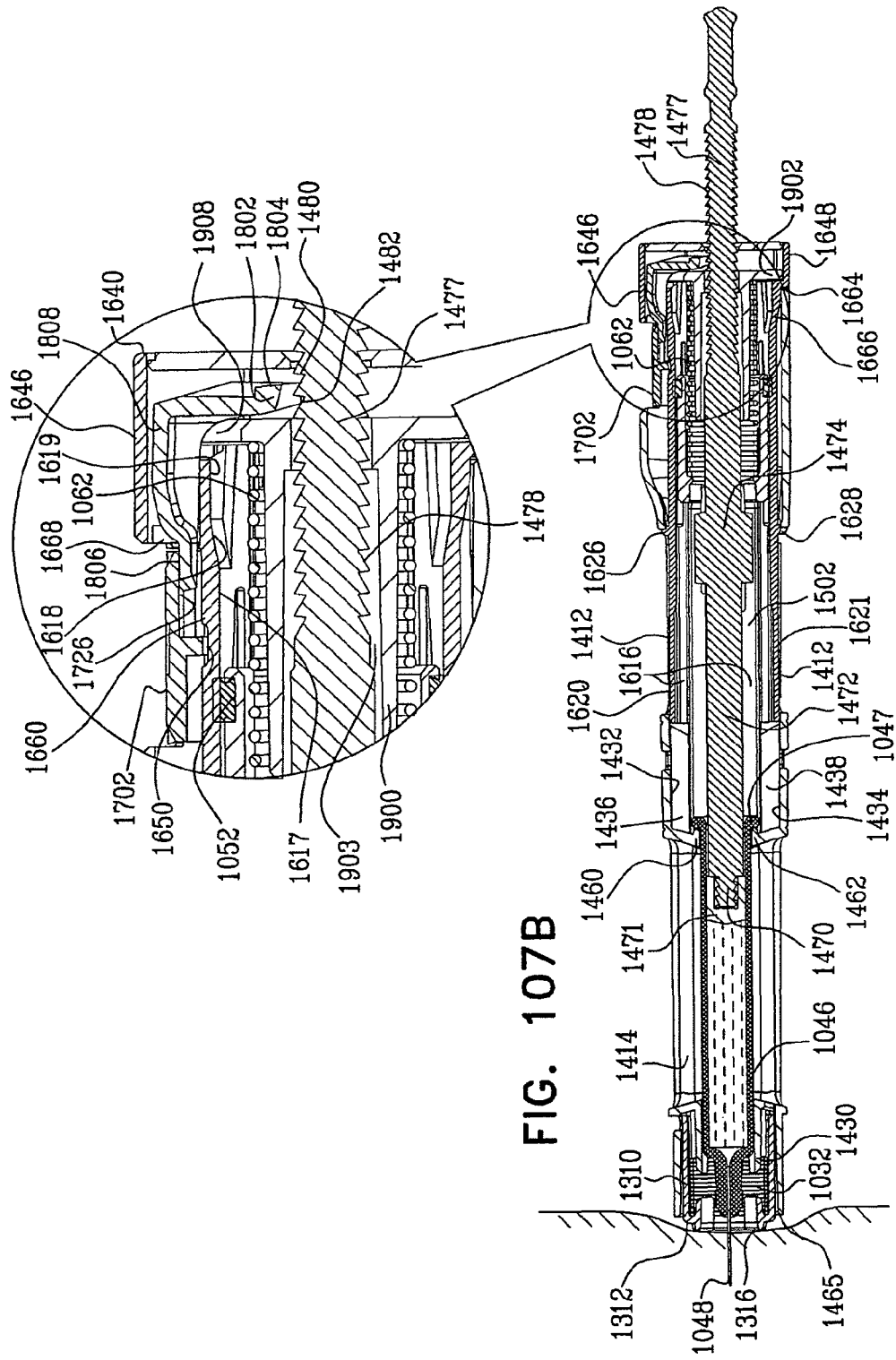

As seen with particular clarity in the enlarged portion of FIG. 107B, the inward displacement of the actuation button 1070 displaces the actuation button engagement surface 1806 of forwardly extending protrusion 1808 of the plunger locking element 1090, thereby rotating the plunger locking element 1090 about axis 1810 and releasing the plunger 1049. Additionally, the protrusions 1540 of selectable driving assembly 1050 no longer abut against the rearward facing surfaces 1722 of the legs 1704 of the actuation button 1070, and the selectable driving assembly 1050 is forwardly displaced under the force of spring 1062.

FIG. 107C shows the inward displacement of the actuation button 1070, which results in the flexible biasing fingers 1673 of the rear housing 1060 engaging the first outwardly facing recesses 1716 of the legs 1704 of the actuation button 1070, and maintaining actuation button 1070 in an actuated orientation. FIGS. 107B, 107D and 107E show the rotation of the plunger locking element 1090, which is caused by the inward displacement of the actuation button 1070.

FIGS. 107A and 107B illustrate the forward displacement of the selectable driving assembly 1050, accompanied by forward displacement of the syringe 1046, which results in needle penetration. As seen in the first enlarged portion of FIG. 107A, when the needle 1048 has fully penetrated the body, the forward displacement of the syringe 1046 is stopped by engagement of flange 1047 with protrusions 1460 and 1462 of the forward housing 1040. The selectable driving assembly 1050 continues its forward displacement, thereby outwardly bending the first hinged fingers 1506 of the selectable driving assembly 1050 into a space formed by rectangular window 1322, and releasing fingers 1506 from engagement with the flange 1047 of the syringe 1046.

The third hinged fingers 1526 of the selectable driving assembly 1050 are inwardly displaced by engagement of protrusions 1530 and 1532 with undercut forward edge 1632, and the inwardly facing slanted protrusions 1528 of selectable driving assembly 1050 are located adjacent rearwardly facing shoulder 1475 of cylindrical portion 1474 of the plunger 1049. The enlarged portion of FIG. 107B shows the rotation of the plunger engaging protrusion 1802 of the plunger locking element 1090 such that it no longer prevents the forward movement of plunger 1049. FIG. 107E shows a slight bend in the resilient leg 1820 of the plunger locking element 1090.

During needle penetration, elastomeric motion damping elements 1052 and 1054 initially engage inclined recesses 1618 and then engage interiorly facing protrusions 1617. As will be described hereinbelow, drug delivery follows needle penetration.

Figure 108:
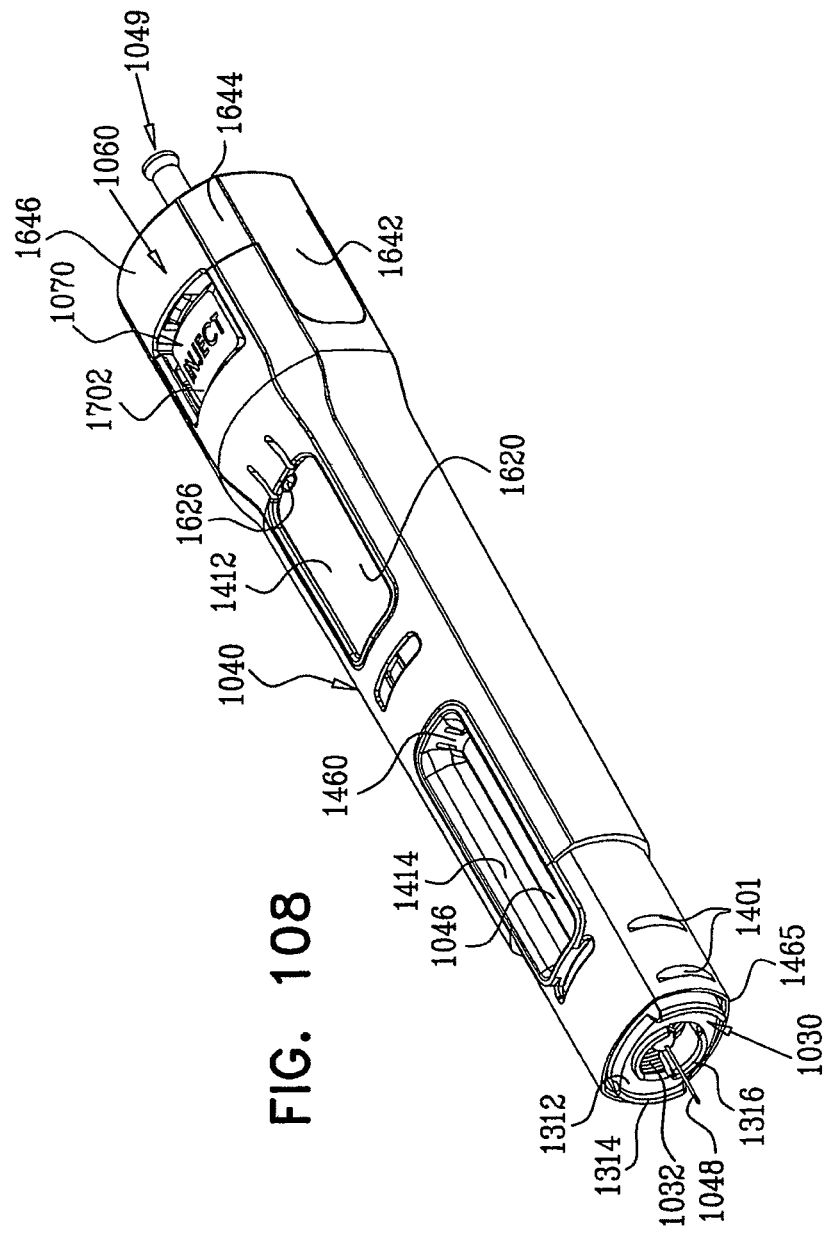
FIG. 108 is a simplified assembled view illustration of the automatic injection device of FIGS. 61 and 86H in a drug delivery operative orientation.
Figure 110A:
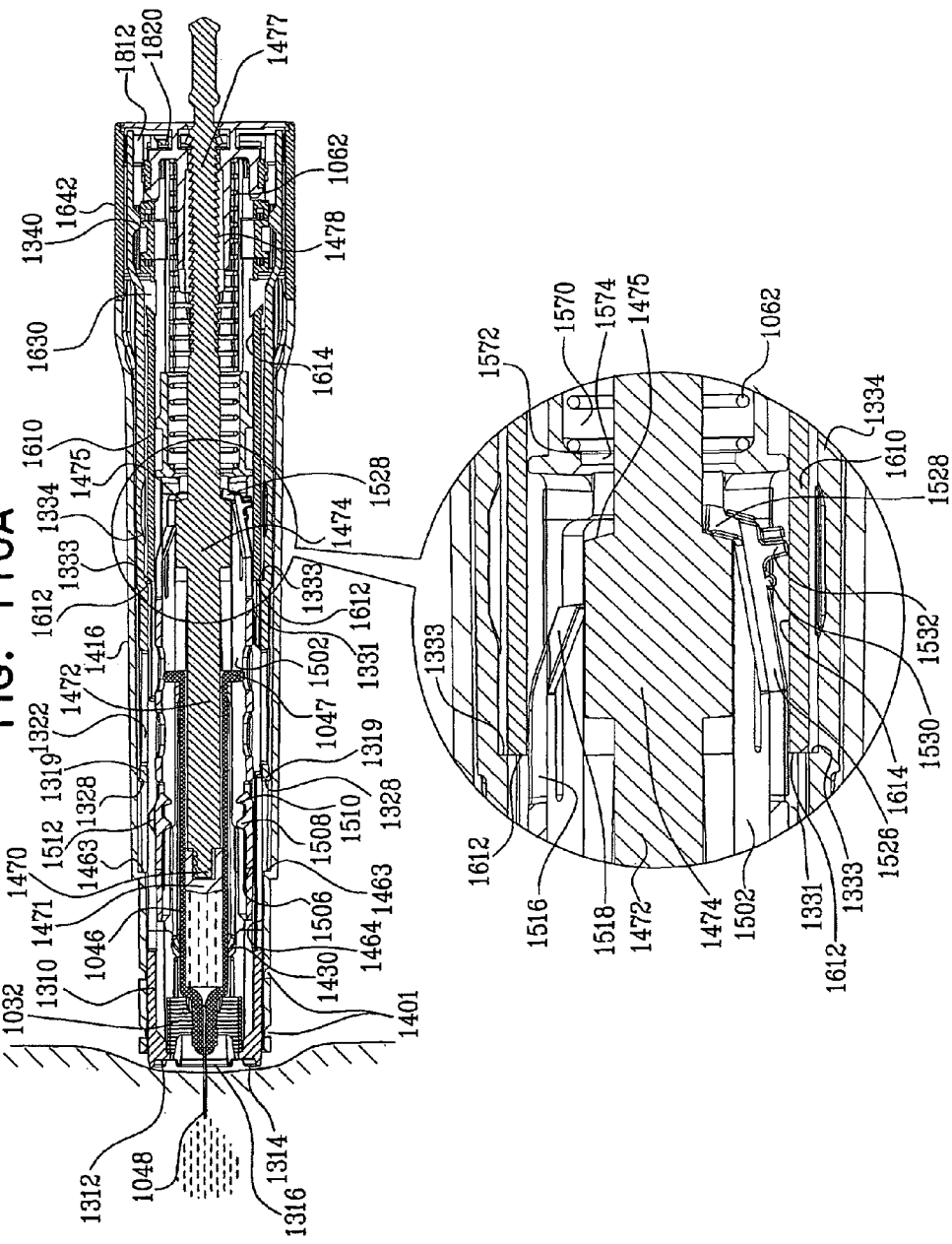
FIGS. 110A, 110B, 110C, 110D and 110E are sectional illustrations taken along respective section lines and directions CXA-CXA, CXB-CXB, CXC-CXC, CXD-CXD and CXE-CXE in FIGS. 109A and 109B.
Figure 110B:
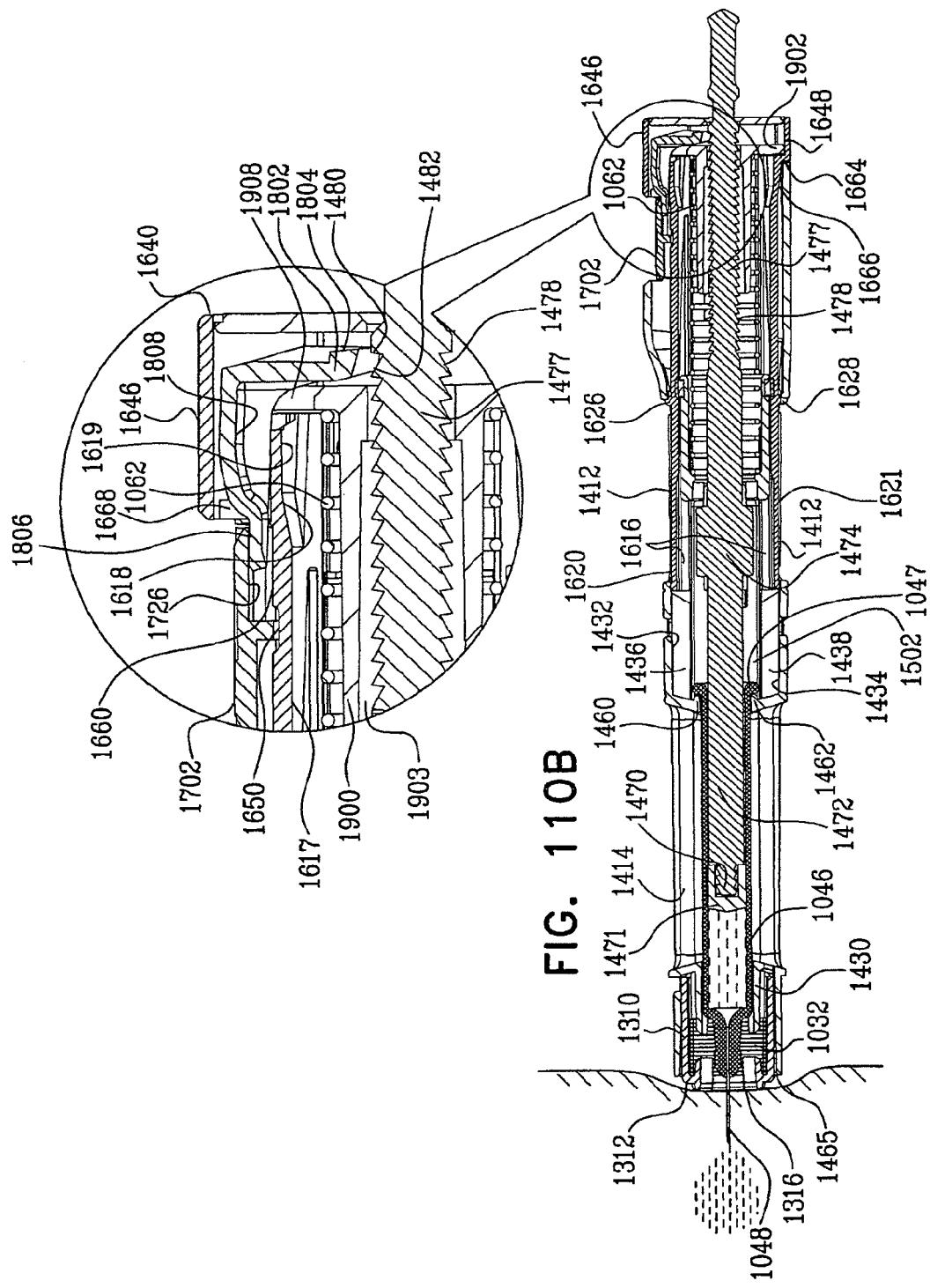
Figure 110E:
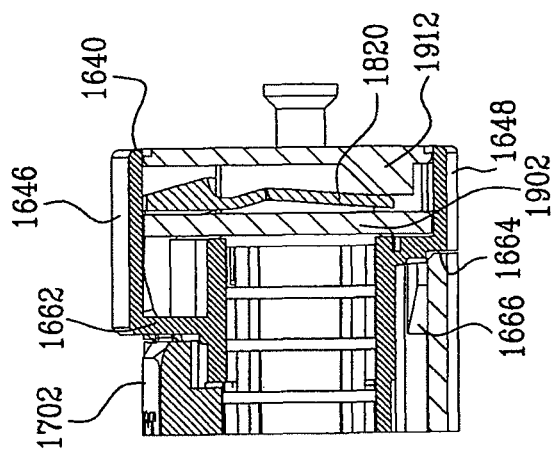
Figure 110D:
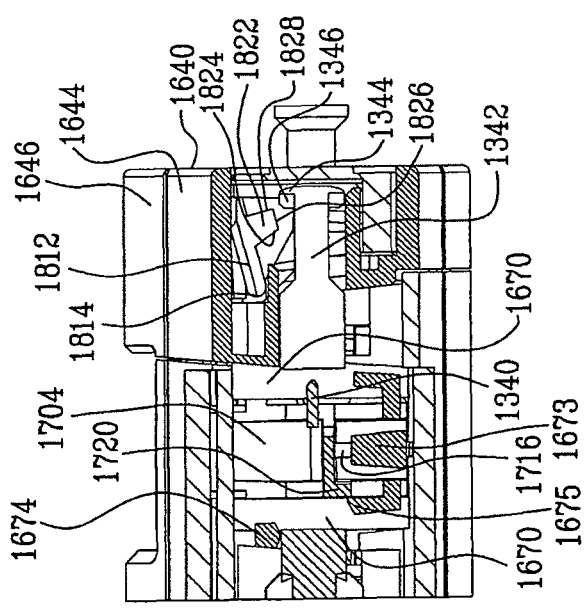
Figure 110C:
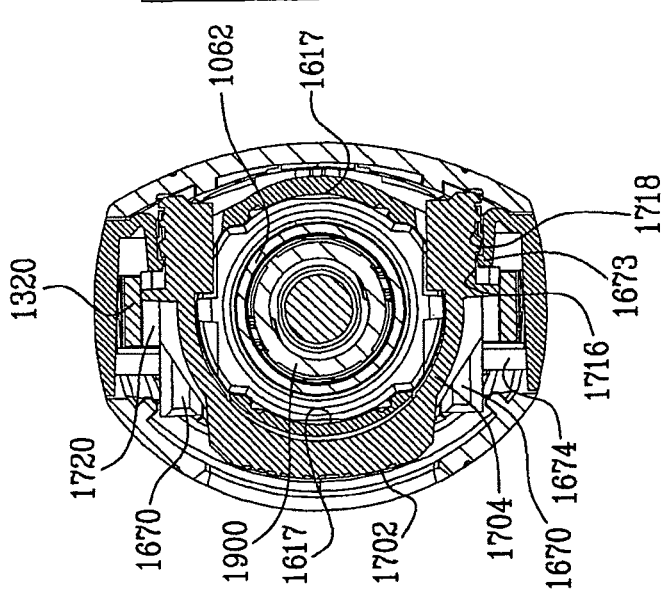

Reference is now made to FIG. 108, which is a simplified assembled view illustration of the automatic injection device of FIGS. 61 and 86H in a drug delivery operative orientation, to FIGS. 109A and 109B, which are respective side and top view simplified planar illustrations of the automatic injection device of FIG. 108, and to FIGS. 110A, 110B, 110C, 110D and 110E, which are sectional illustrations taken along respective section lines and directions CXA-CXA, CXB-CXB, CXC-CXC, CXD-CXD and CXE-CXE in FIGS. 109A and 109B.

As seen in FIGS. 86H and 108-110E, the selectable driving assembly 1050 continues its forward displacement, such that the inwardly facing slanted protrusions 1528 of the selectable driving assembly 1050 engage shoulder 1475 of the plunger 1049 and forwardly displace the plunger 1049. The forward displacement of the plunger 1049, which is illustrated with particular clarity in FIG. 11A, results in injection of a drug into the body.

Figure 111:
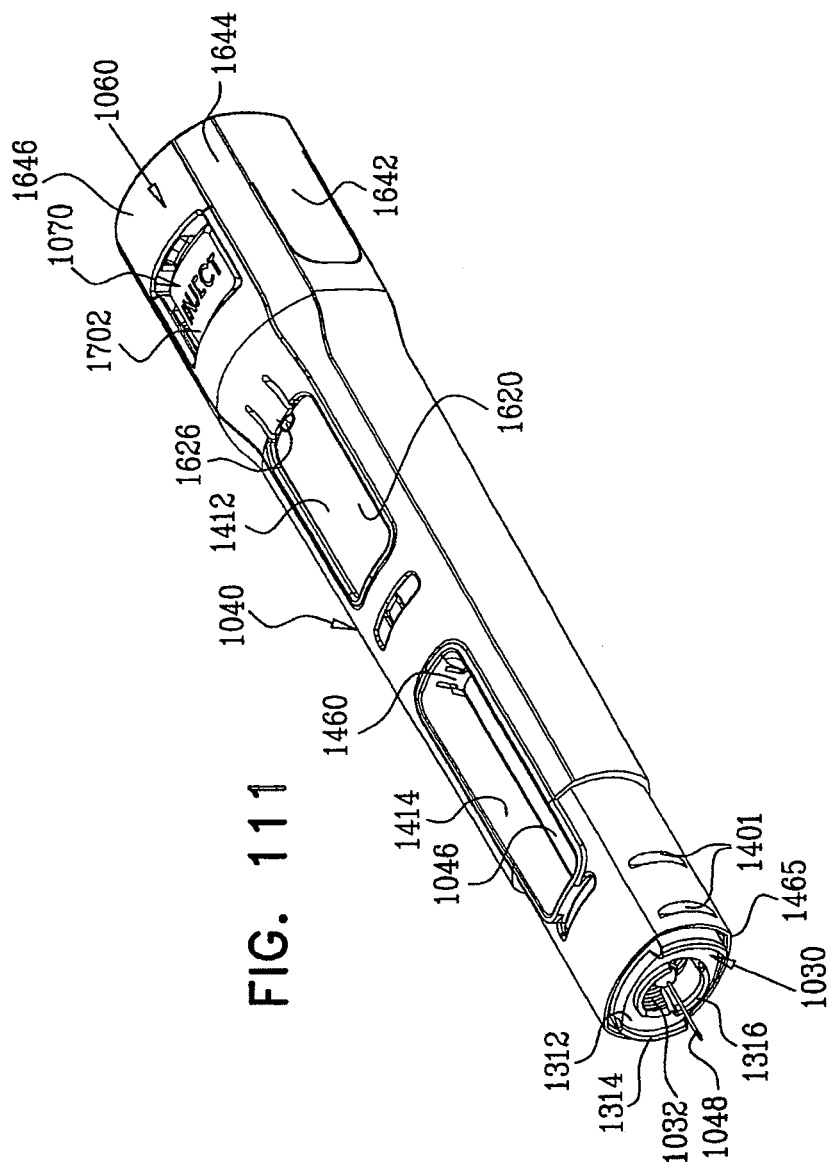
FIG. 111 is a simplified assembled view illustration of the automatic injection device of FIGS. 61 and 86I in an immediate post-drug delivery operative orientation.
Figure 113A:
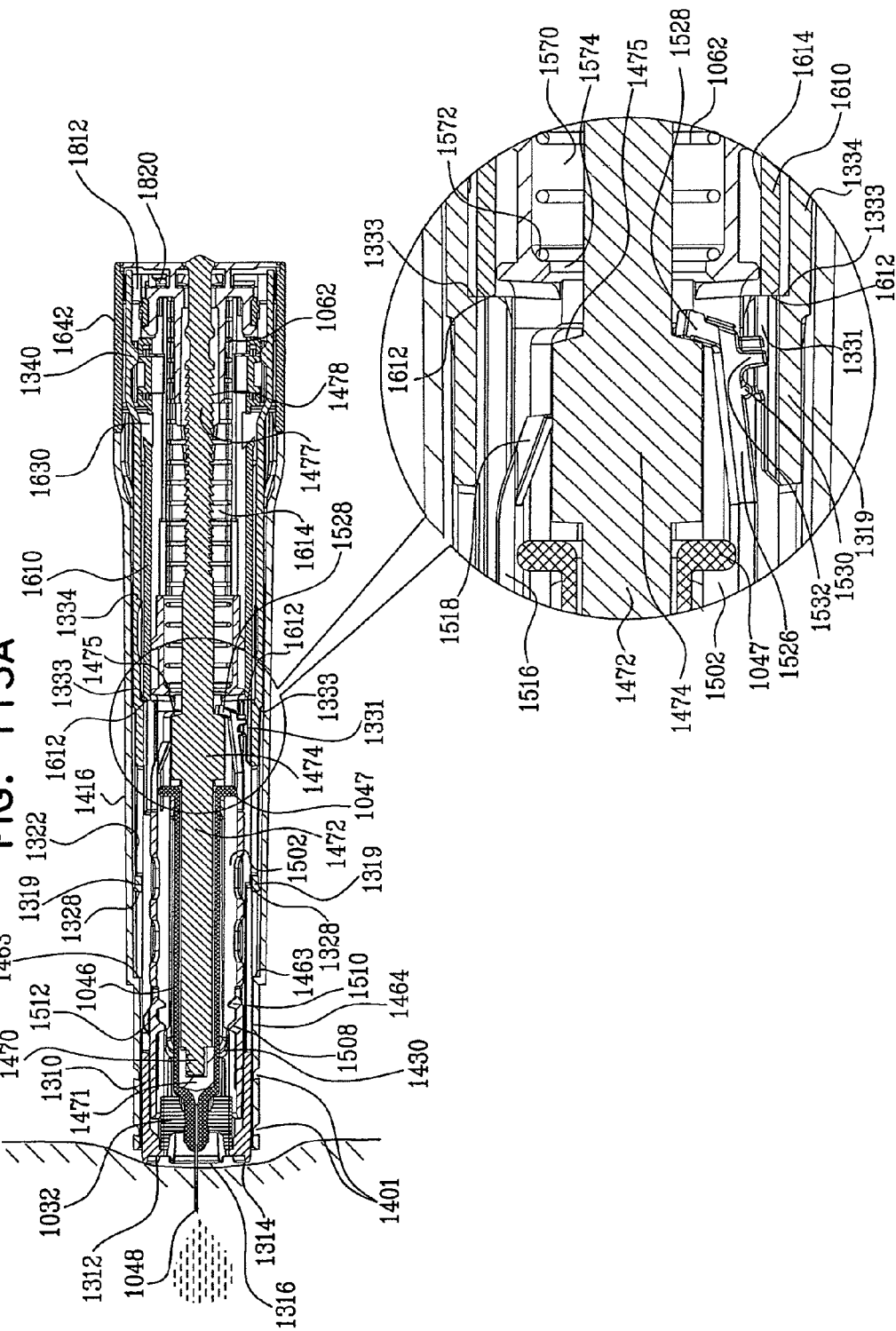
FIGS. 113A, 113B, 113C, 113D and 113E are sectional illustrations taken along respective section lines and directions CXIIIA-CXIIIA, CXIIIB-CXIIIB, CXIIIC-CXIIIC, CXIIID-CXIIID and CXIIIE-CXIIIE in FIGS. 112A and 112B.
Figure 113B:
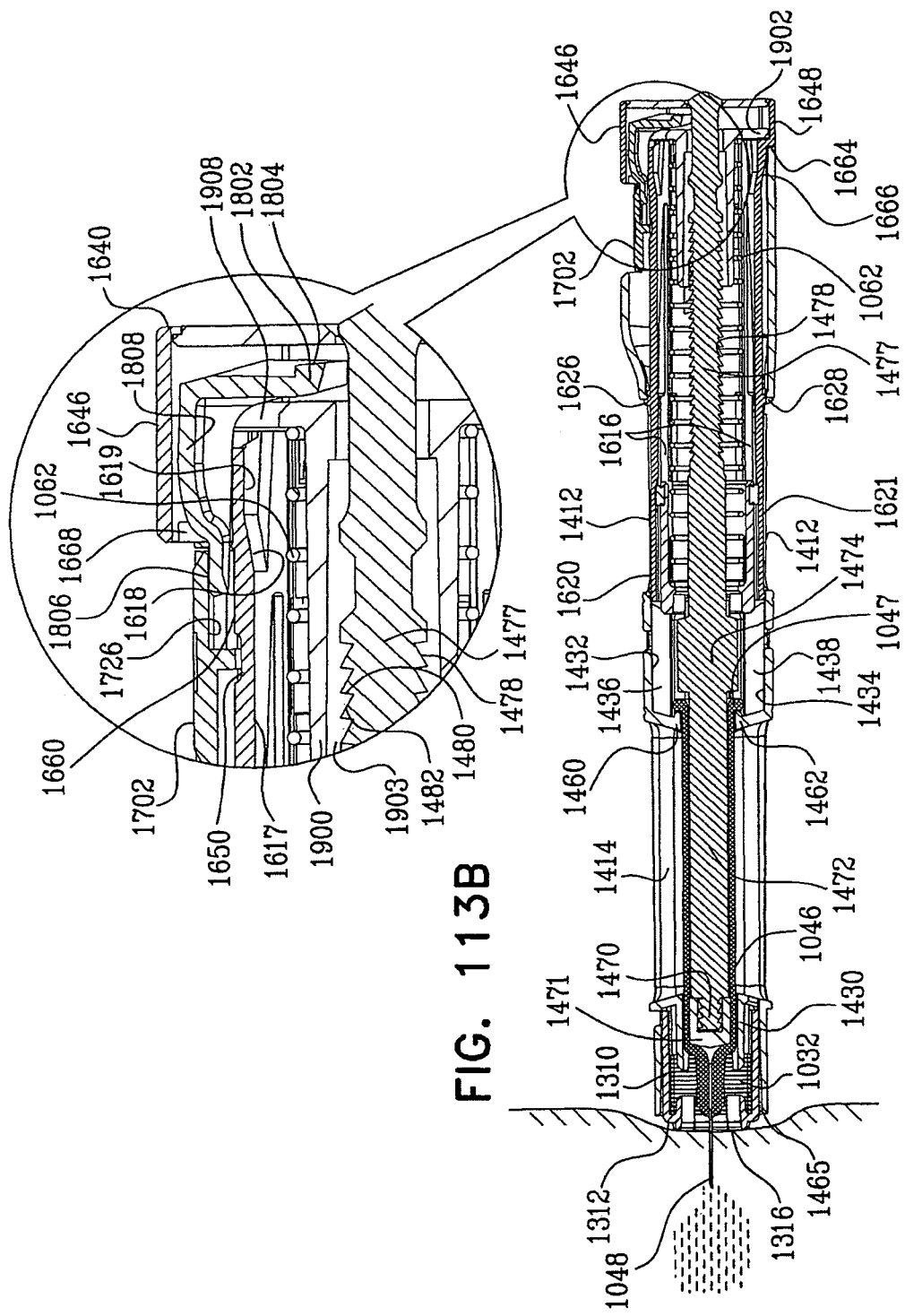
Figure 113E:
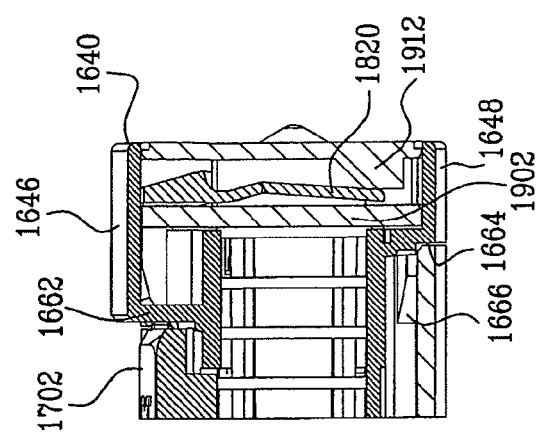
Figure 113D:
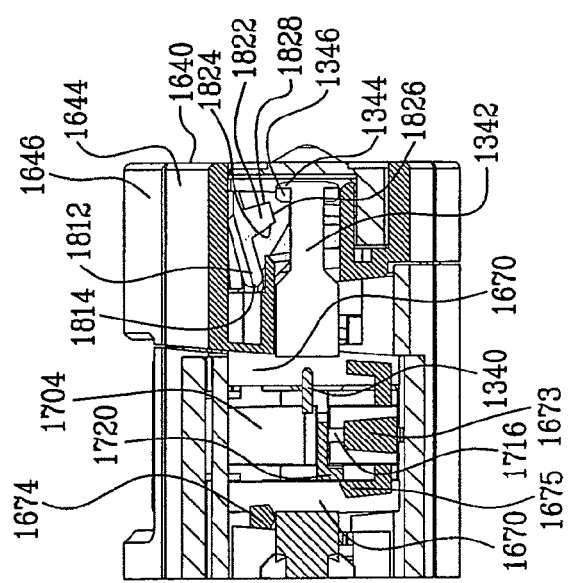
Figure 113C:
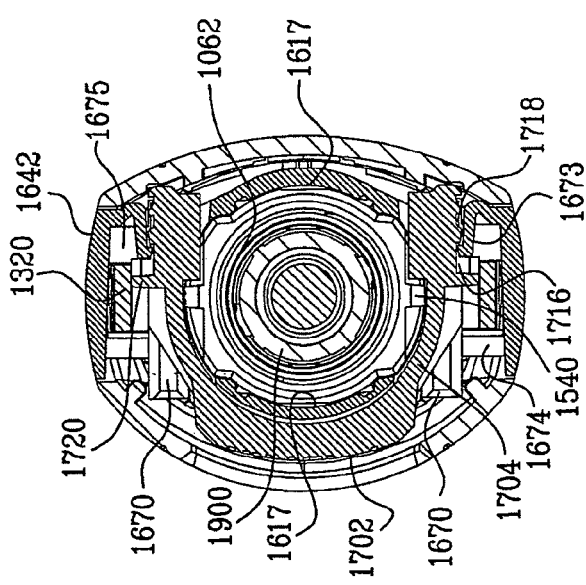

Reference is now made to FIG. 111, which is a simplified assembled view illustration of the automatic injection device of FIGS. 61 and 86I in an immediate post-drug delivery operative orientation, to FIGS. 112A and 112B, which are respective side and top view simplified planar illustrations of the automatic injection device of FIG. 111, and to FIGS. 113A, 113B, 113C, 113D and 113E, which are sectional illustrations taken along respective section lines and directions CXIIIA-CXIIIA, CXIIIB-CXIIIB, CXIIIC-CXIIIC, CXIIID-CXIIID and CXIIIE-CXIIIE in FIGS. 112A and 112B.

As seen in FIGS. 86I and 111-113E, the plunger 1049 is fully forwardly displaced and has reached the forward end of the syringe 1046. As seen with particular clarity in the enlarged portion of FIG. 113A, the outwardly facing protrusions 1532 of the third hinged fingers 1526 of the selectable driving assembly 1050, which slid along interiorly facing surface 1614 of the rear housing 1060, now slide along interiorly facing surface 1331 of the mounting arms 1319 of the needle guard element 1030, while the inwardly facing slanted protrusions 1528 of the third hinged fingers 1526 of the selectable driving assembly 1050 continue to engage shoulder 1475 of the plunger 1049. It is appreciated that forward displacement of both plunger 1049 and selectable driving assembly 1050 is stopped at this stage. Drug delivery is complete.

Figure 114:
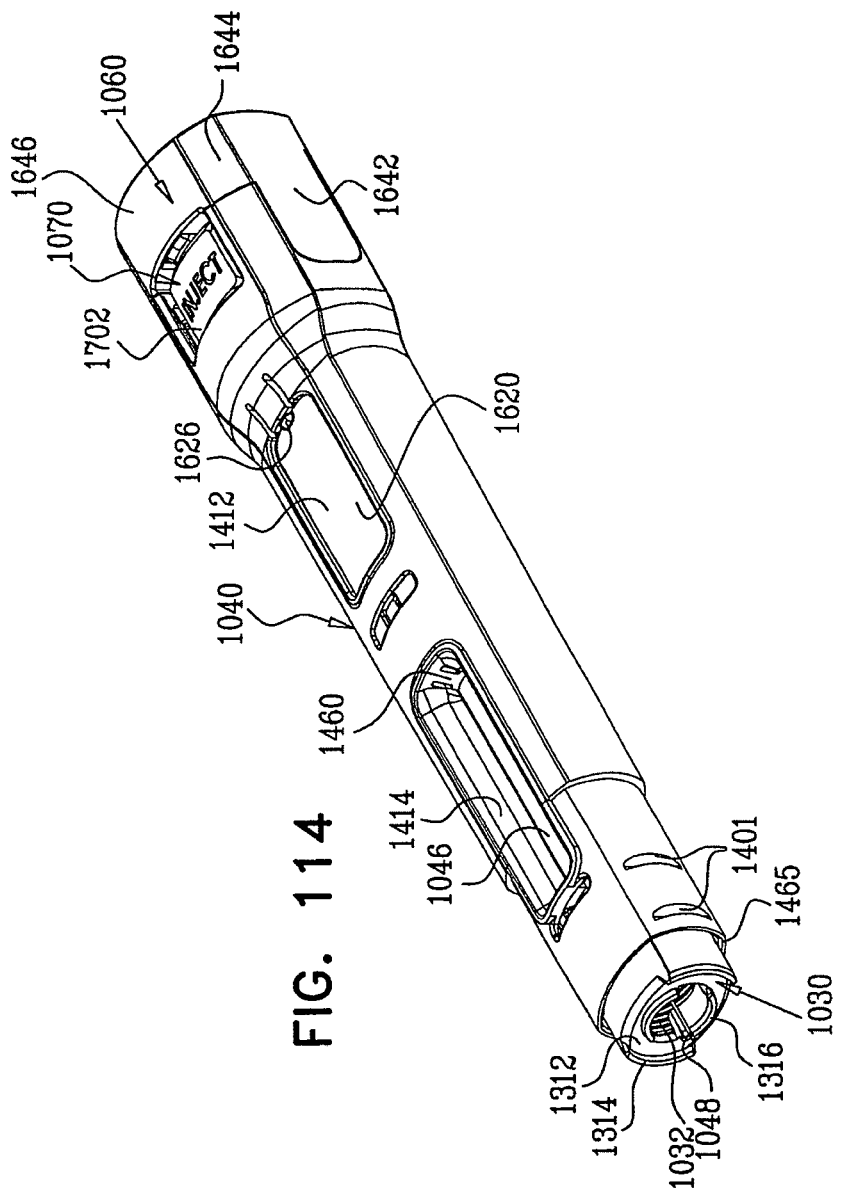
FIG. 114 is a simplified assembled view illustration of the automatic injection device of FIGS. 61 and 86J in its operative orientation as it is being disengaged from the injection site.
Figure 116A:
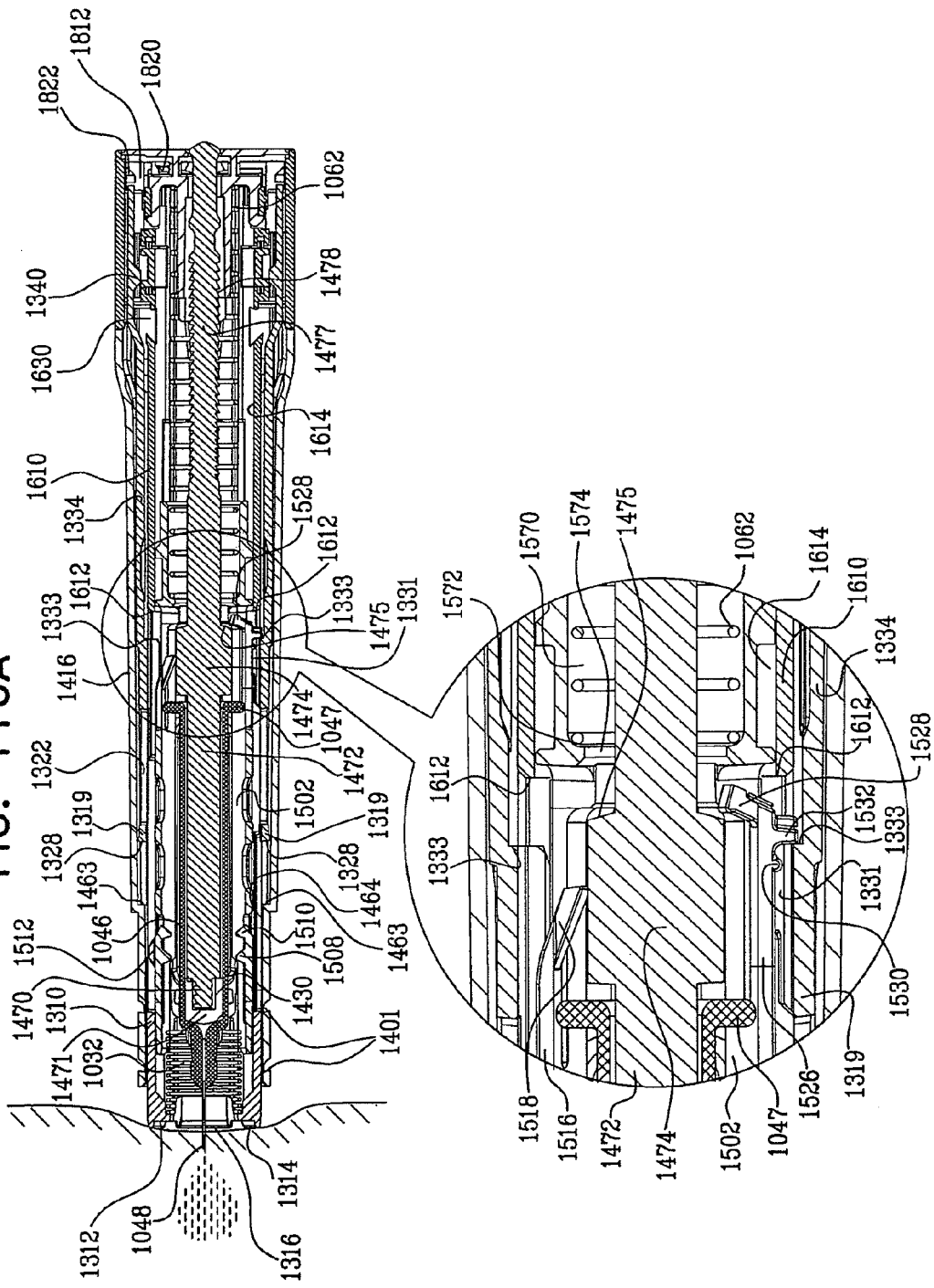
FIGS. 116A, 116B, 116C, 116D and 116E are sectional illustrations taken along respective section lines and directions CXVIA-CXVIA, CXVIB-CXVIB, CXVIC-CXVIC, CXVID-CXVID and CXVIE-CXVIE in FIGS. 115A and 115B.
Figure 116B:
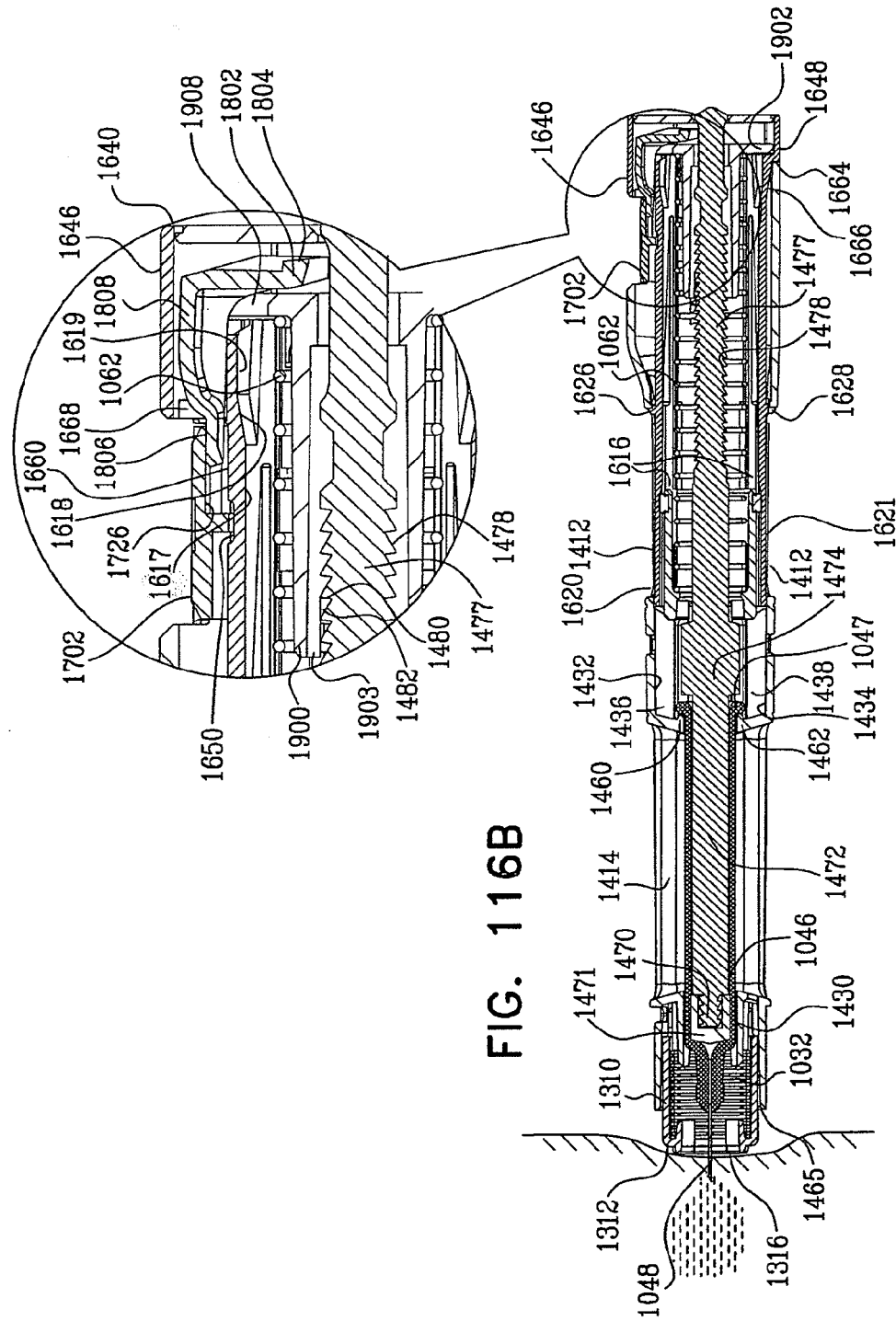
Figure 116E:
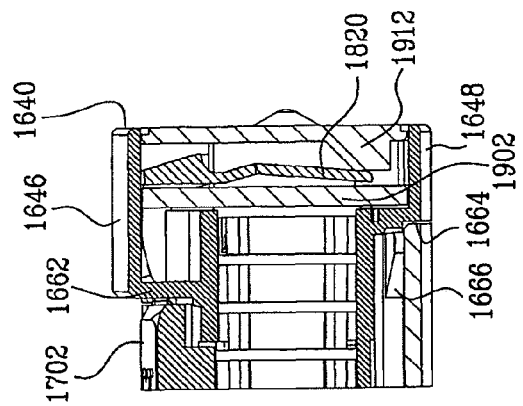
Figure 116D:
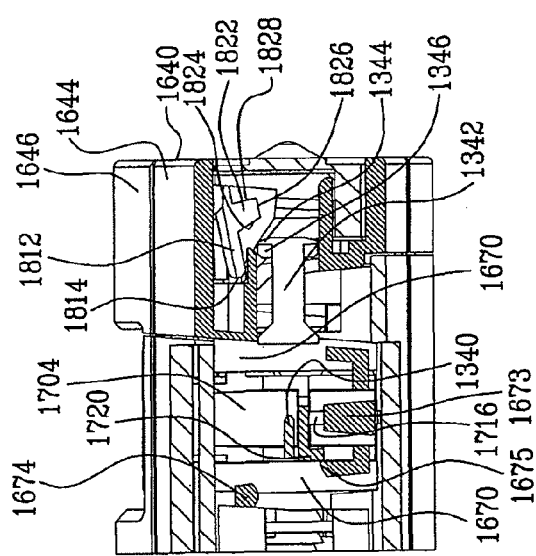
Figure 116C:
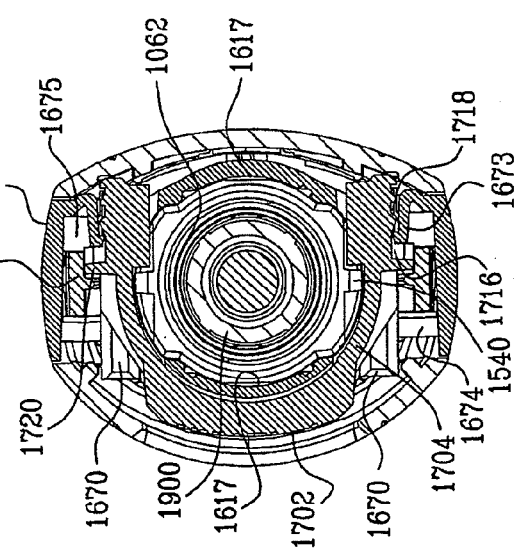

Reference is now made to FIG. 114, which is a simplified assembled view illustration of the automatic injection device of FIGS. 61 and 86J in its operative orientation as it is being disengaged from the injection site, to FIGS. 115A and 1-15B, which are respective side and top view simplified planar illustrations of the automatic injection device of FIG. 114, and to FIGS. 116A, 116B, 116C, 116D and 116E, which are sectional illustrations taken along respective section lines and directions CXVIA-CXVIA, CXVIB-CXVIB, CXVIC-CXVIC, CXVID-CXVID and CXVIE-CXVIE in FIGS. 115A and 115B.

As seen in FIGS. 86J and 114-116E, the user is beginning to disengage the automatic injection device from his body, thereby enabling the needle guard element 1030 to be forwardly displaced under the force of spring 1032. As seen with particular clarity in the enlarged portion of FIG. 116A, during the forward displacement of the needle guard element 1030, the outwardly facing protrusions 1532 of the third hinged fingers 1526 of the selectable driving assembly 1050 move along the interiorly facing surface 1331 of the mounting arms 1319 of the needle guard element 1030, until they pass shoulder 1333 in the mounting arms 1319 of the needle guard element 1030. The third hinged fingers 1526 of the selectable driving assembly 1050 snap outwardly once the shoulder 1333 of the needle guard element 1030 has been sufficiently forwardly displaced, thereby causing the disengagement of the inwardly facing slanted protrusions 1528 of the third hinged fingers 1526 of the selectable driving assembly 1050 from the shoulder 1475 of the plunger 1049. At this stage, the selectable driving assembly 1050 does not engage the plunger 1049, and selectable driving assembly 1050 can continue to be forwardly displaced under the force of spring 1062, thereby forwardly displacing needle guard element 1030.

Figure 117:
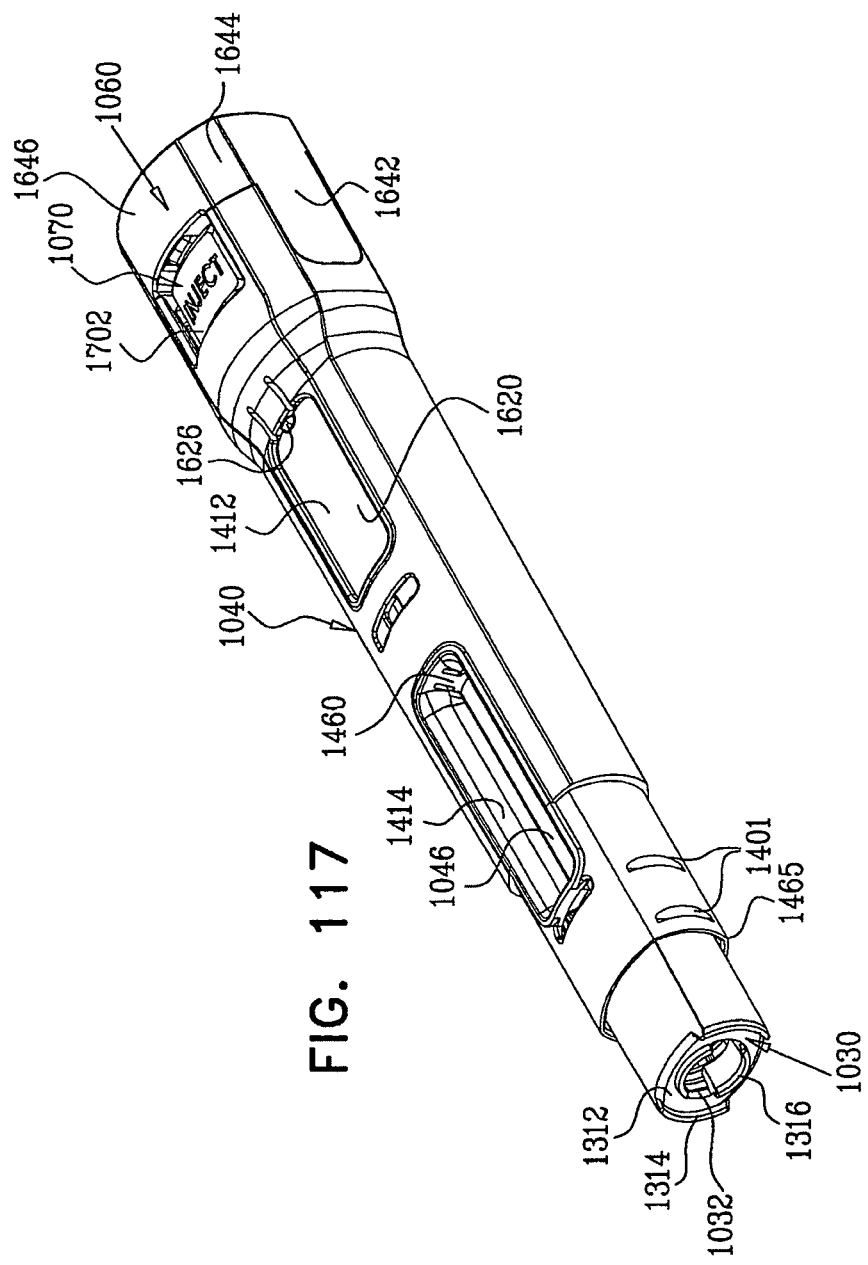
FIG. 117 is a simplified assembled view illustration of the automatic injection device of FIGS. 61 and 86K in a needle protected operative orientation.

Reference is now made to FIG. 117, which is a simplified assembled view illustration of the automatic injection device of FIGS. 61 and 86K in a needle protected operative orientation, to FIGS. 118A and 118B, which are respective side and top view simplified planar illustrations of the automatic injection device of FIG. 117, and to FIGS. 119A, 119B, 119C, 119D and 119E, which are sectional illustrations taken along respective section lines and directions CXIXA-CXIXA, CXIXB-CXIXB, CXIXC-CXIXC, CXIXD-CXIXD and CXIXE-CXIXE in FIGS. 118A and 118B.

As seen in FIGS. 86K and 117-119E, the selectable driving assembly 1050 continues to be forwardly displaced under the force of spring 1062, thereby forwardly displacing the needle guard element 1030. The forward displacement of the needle guard element 1030 is terminated by engagement of stop surfaces 1328 of the needle guard element 1030 with corresponding inwardly extending shoulders 1463 of forward housing 1040, at which stage the needle 1048 is fully enclosed by the needle guard element 1030 and is locked with respect thereto.

Figure 119A:
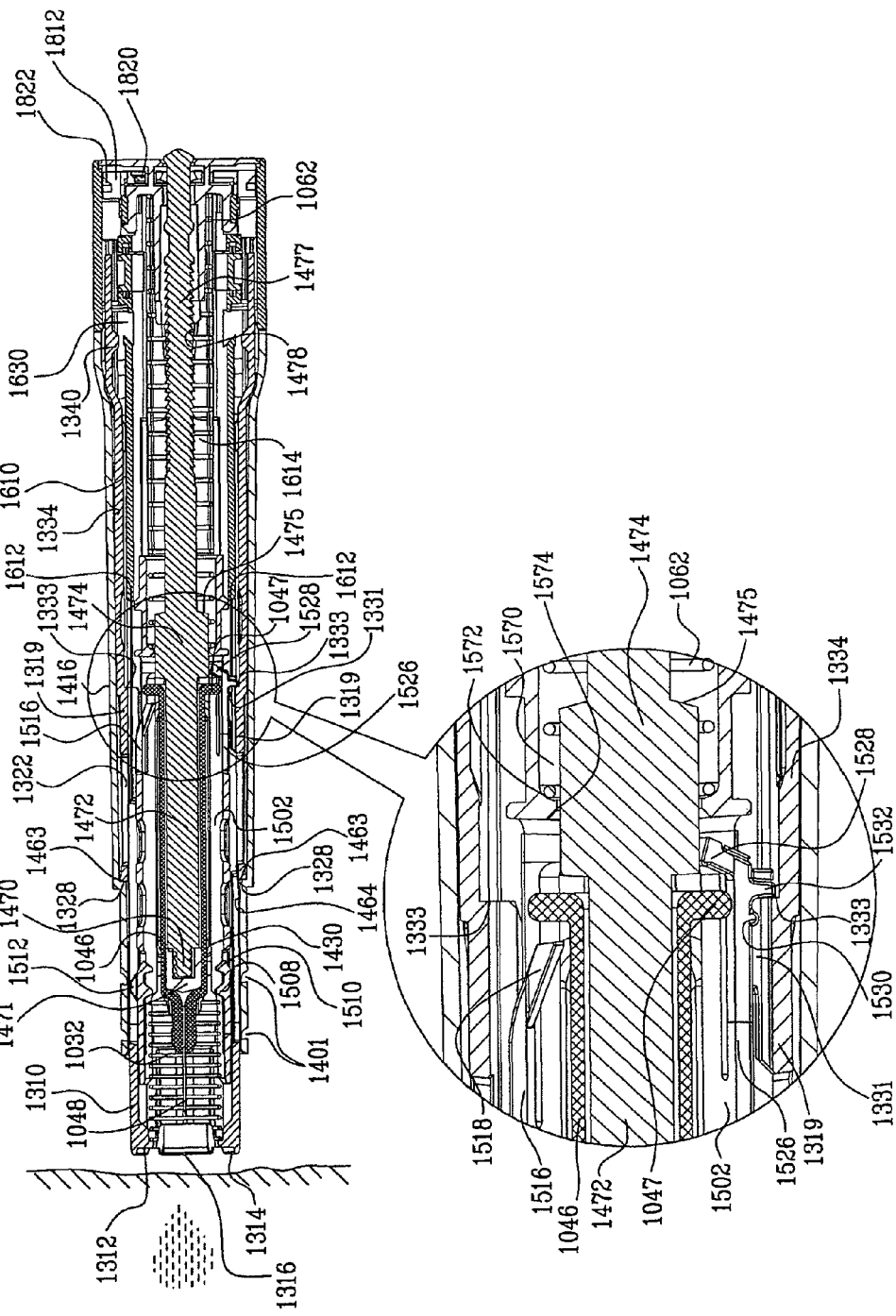
Figure 119B:
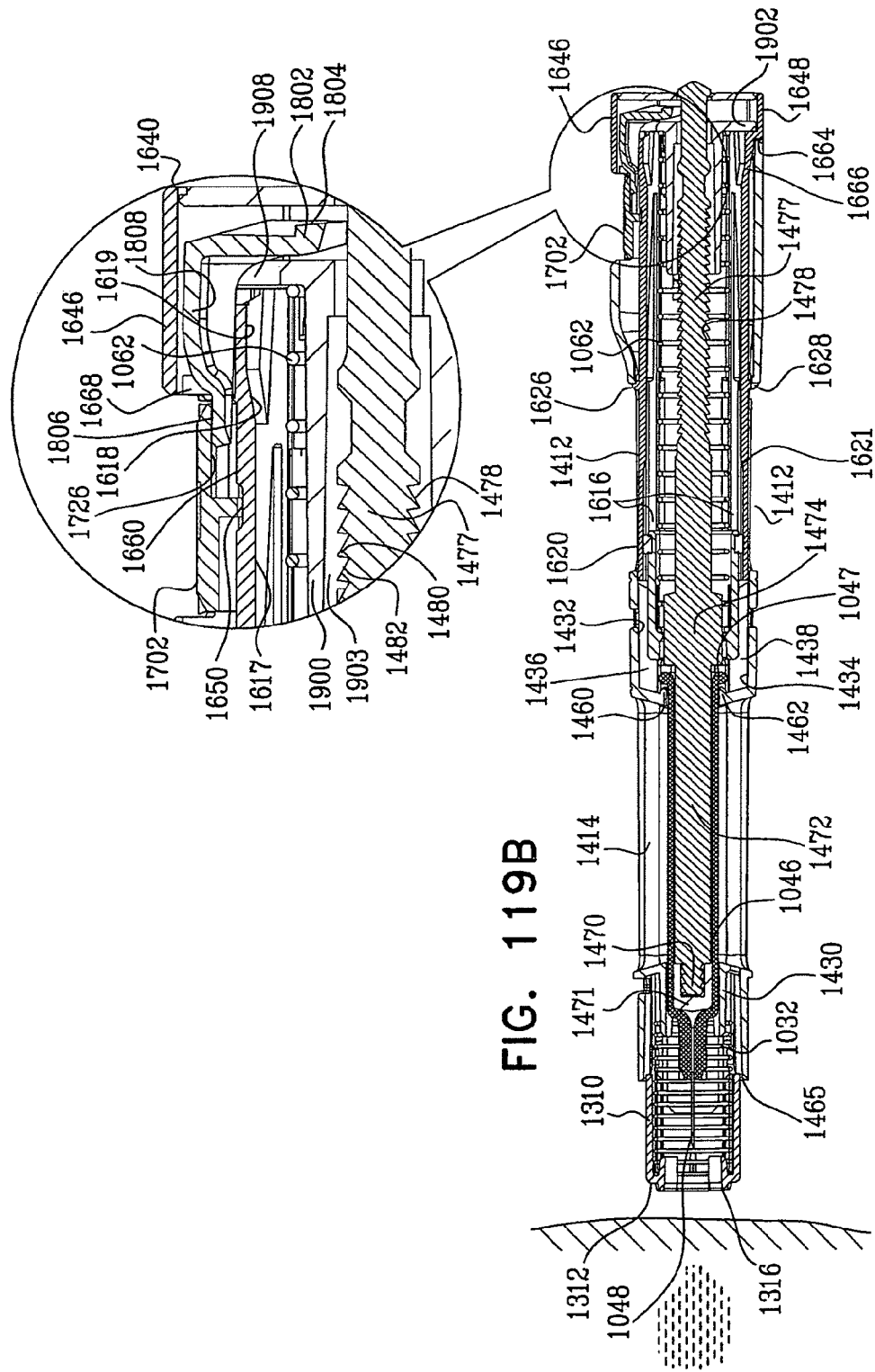

As seen with particular clarity in the enlarged portion of FIG. 119A, the forward displacement of the selectable driving assembly 1050 results in the second fingers 1516 thereof being positioned forwardly of the flange 1047 of the syringe 1046. This produces the positive locking of the needle 1048 with respect to the needle guard element 1030. It is noted that the third hinged fingers 1526 cannot be bent inwardly at this stage due to engagement of inwardly facing slanted protrusions 1528 with cylindrical portion 1474.

Figure 120:
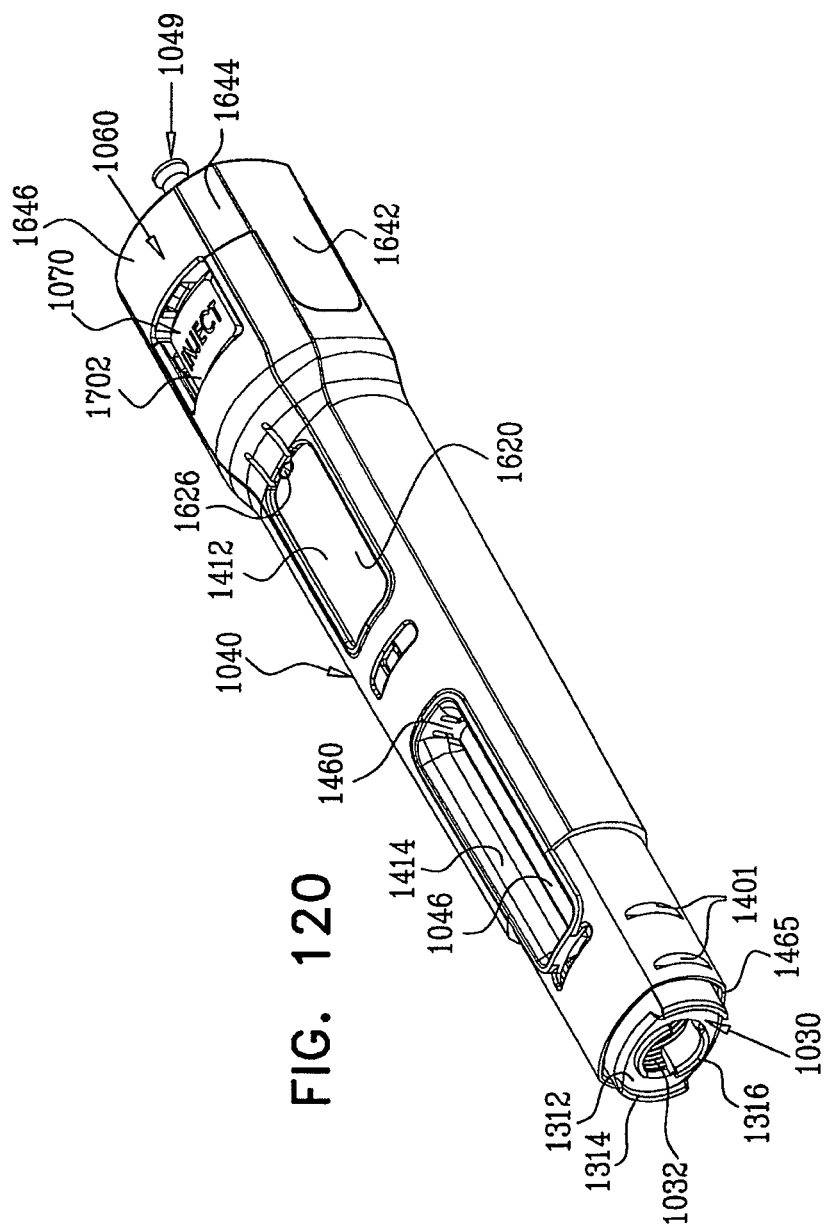
Figure 122A:
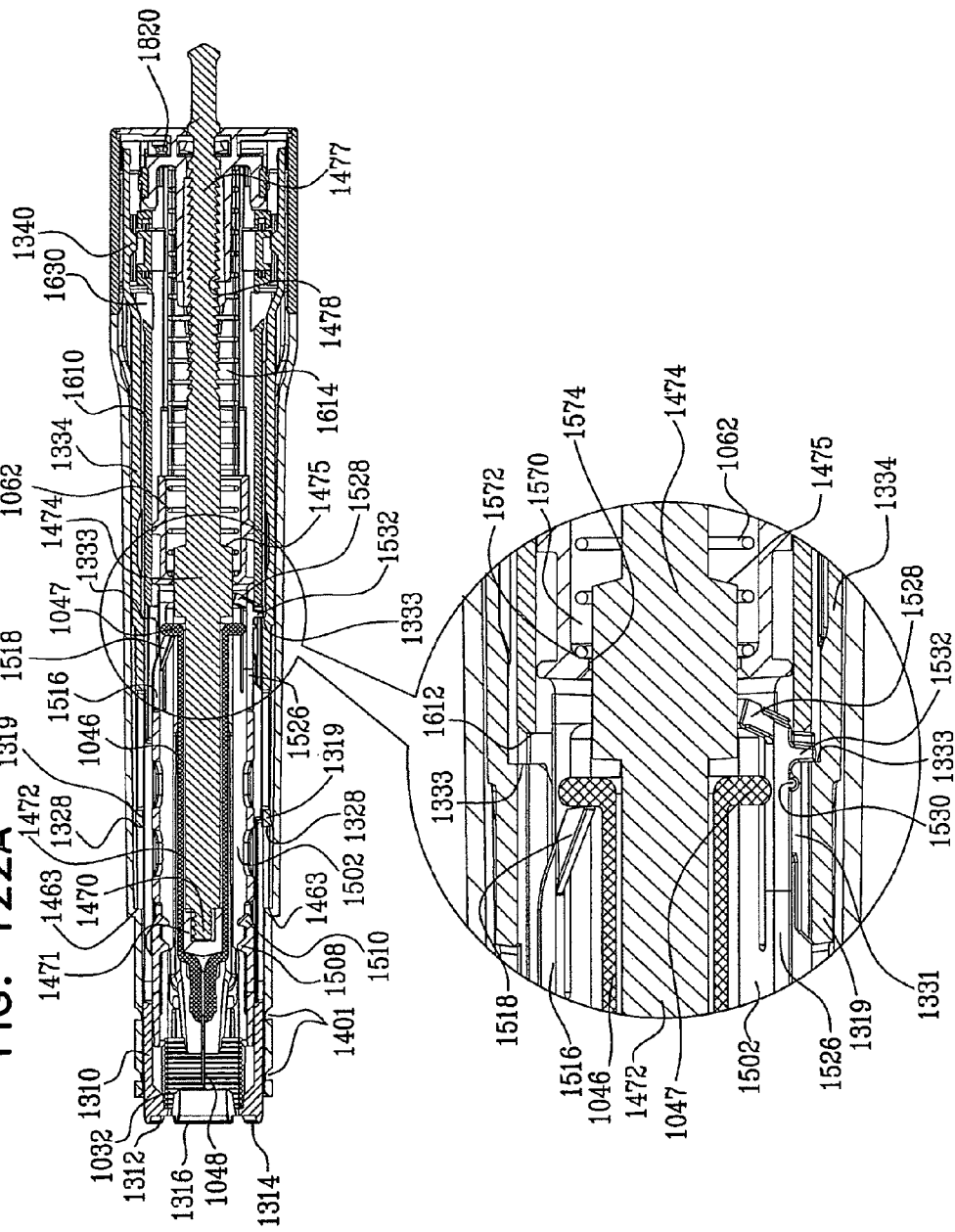
Figure 122B:
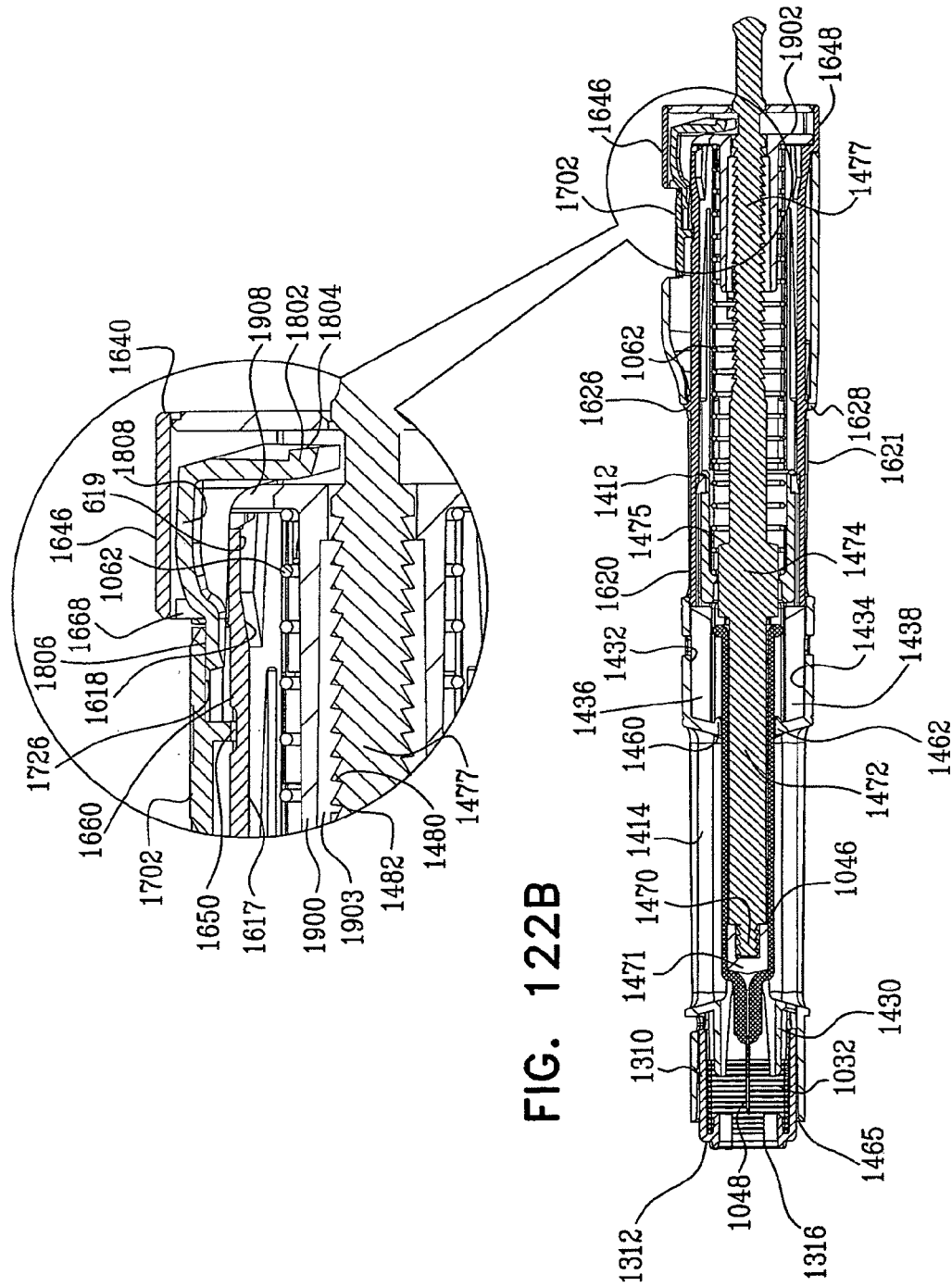
Figure 122C:
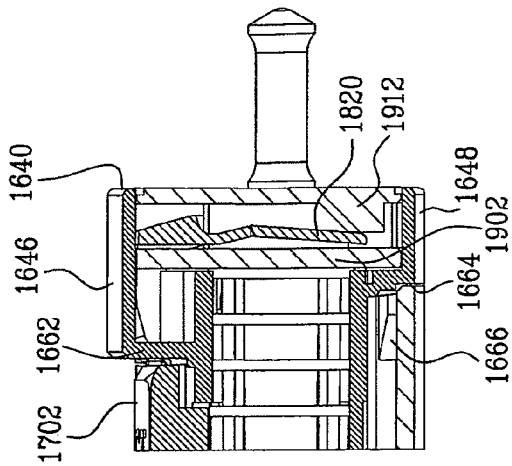
Figure 122D:
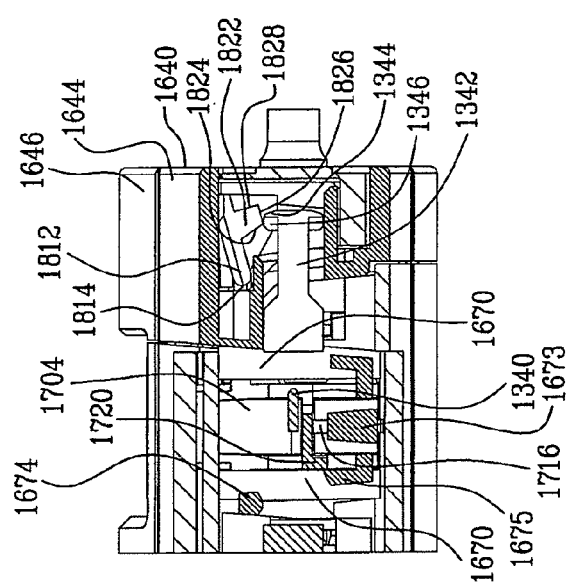
Figure 122E:
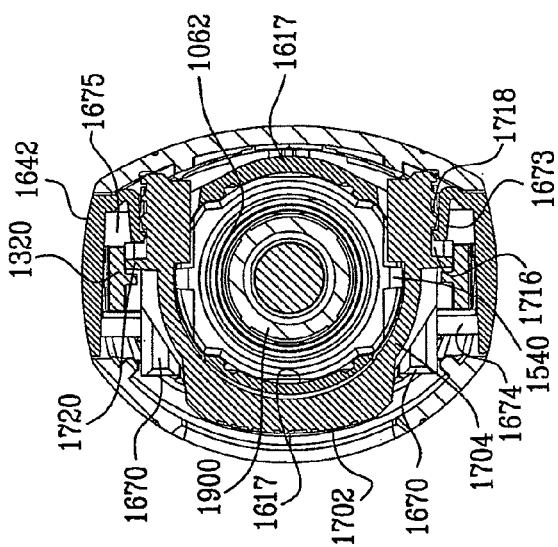

Reference is now made to FIG. 120, which is a simplified assembled view illustration of the automatic injection device of FIGS. 61 and 86L in a needle-shield push back misuse operative orientation, to FIGS. 121A and 121B, which are respective side and top view simplified planar illustrations of the automatic injection device of FIG. 120, and to FIGS. 122A, 122B, 122C, 122D and 122E, which are sectional illustrations taken along respective section lines and directions CXXIIA-CXXIIA, CXXIIB-CXXIIB, CXXIIC-CXXIIC, CXXIID-CXXIID and CXXIIE-CXXIIE in FIGS. 121A and 121B.

As seen in FIGS. 86L and 120-122E, when a user misuses the device and rearwardly displaces the needle guard element 1030, the rearward displacement of the needle guard element 1030 results in rearward displacement of the selectable driving assembly 1050. Shoulders 1333 of arms 1319 of the needle guard 1030 push against protrusion 1532 of the selectable driving assembly 1050. Selectable driving assembly 1050 is therefore forced to undergo rearward displacement. Due to this rearward displacement of the selectable driving assembly 1050, the second hinged fingers 1516 thereof engage the forward facing surface of the flange 1047 of the syringe 1046.

Continued rearward displacement of the selectable driving assembly 1050 results in rearward displacement of the syringe 1046 and needle 1048 together with the selectable driving assembly 1050 and the needle guard element 1030, thereby ensuring that the needle 1048 is not exposed at any stage following injection.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. An automatic injection device for injecting a fluid into an object, said automatic injection device comprising:
   a plunger assembly for operative engagement with a syringe adapted to contain said fluid and permit ejection of said fluid therefrom via a syringe outlet, said plunger assembly being displaceable relative to said syringe in a first direction which causes at least some of said fluid contained in said syringe to be ejected from said syringe via said syringe outlet;

a vial adaptor engagement assembly adapted for engagement with a vial adaptor, said vial adaptor engagement assembly comprising a needle guard; and a user operable actuator button which, when displaced in a button displacement direction, is operable to cause displacement of said plunger assembly relative to said syringe in said first direction, said user operable actuator button being mechanically locked against displacement in said button displacement direction by said vial adaptor preventing access to said needle guard at all times that said syringe outlet is in operative engagement with said vial adaptor.

2. An automatic injection device according to claim 1 and wherein said user operable actuator button is displaceable in said button displacement direction only when said syringe outlet is in operative engagement with an injection site.

3. An automatic injection device according to claim 1 and wherein said plunger assembly is adapted for displacement also in a second direction opposite to said first direction.

4. An automatic injection device according to claim 1 and wherein said vial adaptor engagement assembly is displaceable responsive to operative engagement with said vial adaptor to an operative orientation which enables said plunger assembly to be displaced in said first direction.

5. An automatic injection device according to claim 1 and also comprising:

a selectable driving assembly operative, when actuated by a user, to drive said plunger assembly in said first direction; and an inadvertent fluid ejection prevention assembly comprising:

a locking assembly operative to lock said plunger assembly against displacement in said first direction and to permit displacement of said plunger assembly in a second direction, opposite to said first direction.

6. An automatic injection device according to claim 5 and wherein said user operable actuation button is operative, when displaced in said button displacement direction to generally simultaneously unlock said plunger assembly and unlock said selectable driving assembly.

7. An automatic injection device according to claim 5 and wherein said vial adaptor engagement assembly comprises a connector rod which provides mechanical interaction between said vial adaptor and said locking assembly.

8. An automatic injection device according to claim 5 and wherein said needle guard provides mechanical interaction between said vial adaptor and said locking assembly.

* * * * *